United States Patent
Grue-Sørensen et al.

(10) Patent No.: US 9,708,286 B2
(45) Date of Patent: Jul. 18, 2017

(54) INGENOL-3-ACYLATES III AND INGENOL-3-CARBAMATES

(71) Applicant: LEO Laboratories Limited, Dublin (IE)

(72) Inventors: Gunnar Grue-Sørensen, Ballerup (DK); Xifu Liang, Ballerup (DK); Thomas Högberg, Ballerup (DK); Kristoffer Månsson, Ballerup (DK); Per Vedsø, Ballerup (DK); Thomas Vifian, Ballerup (DK)

(73) Assignee: LEO LABORATORIES LIMITED, Dublin (IE)

( * ) Notice: Subject to any disclaimer, the term of this patent is extended or adjusted under 35 U.S.C. 154(b) by 0 days.

(21) Appl. No.: 14/748,925

(22) Filed: Jun. 24, 2015

(65) Prior Publication Data
US 2015/0291551 A1   Oct. 15, 2015

Related U.S. Application Data

(62) Division of application No. 13/996,989, filed as application No. PCT/DK2011/000154 on Dec. 22, 2011, now Pat. No. 9,102,687.
(Continued)

(51) Int. Cl.
C07C 271/34 (2006.01)
C07D 333/38 (2006.01)
(Continued)

(52) U.S. Cl.
CPC .......... *C07D 333/38* (2013.01); *A61K 31/365* (2013.01); *A61K 31/381* (2013.01); *A61K 31/404* (2013.01); *A61K 31/415* (2013.01); *A61K 31/416* (2013.01); *A61K 31/4192* (2013.01); *A61K 31/42* (2013.01); *A61K 31/472* (2013.01); *A61K 31/502* (2013.01); *A61K 31/538* (2013.01); *A61K 31/5375* (2013.01); *C07C 271/34* (2013.01); *C07C 271/36* (2013.01); *C07C 271/38* (2013.01); *C07D 209/42* (2013.01); *C07D 217/26* (2013.01); *C07D 231/14* (2013.01); *C07D 231/56* (2013.01); *C07D 237/28* (2013.01); *C07D 249/04* (2013.01); *C07D 249/06* (2013.01); *C07D 261/18* (2013.01); *C07D 265/36* (2013.01); *C07D 271/08* (2013.01); *C07D 277/32* (2013.01); *C07D 277/587* (2013.01); *C07D 295/205* (2013.01); *C07D 295/21* (2013.01); *C07D 307/00* (2013.01); *C07D 307/94* (2013.01); *C07D 309/08* (2013.01); *C07D 401/04* (2013.01); *C07D 405/06* (2013.01); *C07D 471/04* (2013.01);
(Continued)

(58) Field of Classification Search
CPC . C07C 271/34; C07C 271/38; C07C 2103/86; A61K 31/538; C07D 249/06; C07D 261/18; C07D 277/32; C07D 295/21; C07D 309/08; C07D 333/38; C07D 401/04
See application file for complete search history.

(56) References Cited

U.S. PATENT DOCUMENTS 5,891,870 A   4/1999 Driedger et al.
5,891,906 A   4/1999 Driedger et al.
(Continued)

FOREIGN PATENT DOCUMENTS

AU   2010200429 A1   8/2010
CA   2 541 903 A1   10/2007
(Continued)

OTHER PUBLICATIONS

Stella, Valentino J, Expert Opinion of Therapeutic Patents, Prodrugs as therapeutics, 2004 14(3): 277-280.*
(Continued)

*Primary Examiner* — Savitha Rao
*Assistant Examiner* — Angela Brown-Pettigrew
(74) *Attorney, Agent, or Firm* — Birch, Stewart, Kolasch & Birch, LLP

(57) ABSTRACT

The invention relates to compounds of general formula I

I

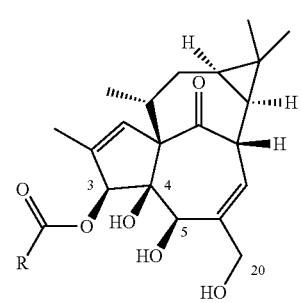

wherein R is heteroaryl optionally substituted by R7; or R is heterocycloalkyl or heterocycloalkenyl, optionally substituted by R8; or R is X wherein X is —NR11R12; and pharmaceutically acceptable salts, hydrates, or solvates thereof, for use—alone or in combination with one or more other pharmaceutically active compounds—in therapy, for preventing, treating or ameliorating diseases or conditions responsive to stimulation of neutrophil oxidative burst, responsive to stimulation of keratinocyte IL-8 release or responsive to induction of necrosis.

20 Claims, No Drawings

Related U.S. Application Data

(60) Provisional application No. 61/426,378, filed on Dec. 22, 2010, provisional application No. 61/448,350, filed on Mar. 2, 2011, provisional application No. 61/534,055, filed on Sep. 13, 2011.

(51) Int. Cl.

| | |
|---|---|
| C07C 271/36 | (2006.01) |
| C07C 271/38 | (2006.01) |
| C07D 249/06 | (2006.01) |
| C07D 261/18 | (2006.01) |
| C07D 277/32 | (2006.01) |
| C07D 295/21 | (2006.01) |
| C07D 309/08 | (2006.01) |
| C07D 401/04 | (2006.01) |
| C07D 471/04 | (2006.01) |
| C07D 495/04 | (2006.01) |
| C07D 265/36 | (2006.01) |
| C07D 271/08 | (2006.01) |
| C07D 277/587 | (2006.01) |
| C07D 295/205 | (2006.01) |
| C07D 307/00 | (2006.01) |
| C07D 307/94 | (2006.01) |
| C07D 405/06 | (2006.01) |
| C07D 513/04 | (2006.01) |
| A61K 31/365 | (2006.01) |
| A61K 31/381 | (2006.01) |
| A61K 31/404 | (2006.01) |
| A61K 31/415 | (2006.01) |
| A61K 31/416 | (2006.01) |
| A61K 31/4192 | (2006.01) |
| A61K 31/42 | (2006.01) |
| A61K 31/472 | (2006.01) |
| A61K 31/502 | (2006.01) |
| A61K 31/5375 | (2006.01) |
| A61K 31/538 | (2006.01) |
| C07D 209/42 | (2006.01) |
| C07D 217/26 | (2006.01) |
| C07D 231/14 | (2006.01) |
| C07D 231/56 | (2006.01) |
| C07D 237/28 | (2006.01) |
| C07D 249/04 | (2006.01) |

(52) U.S. Cl.
CPC ......... *C07D 495/04* (2013.01); *C07D 513/04* (2013.01); *C07C 2103/86* (2013.01)

(56) References Cited

U.S. PATENT DOCUMENTS

| 5,955,501 A | 9/1999 | Driedger et al. |
| 2009/0163587 A1 | 6/2009 | Xu et al. |

FOREIGN PATENT DOCUMENTS

| CN | 101742996 A | 6/2010 |
| EA | 009669 B1 | 2/2008 |
| JP | 7-165600 A | 6/1995 |
| JP | 8-245379 A | 9/1996 |
| JP | 8-245505 A | 9/1996 |
| WO | WO 87/07599 A2 | 12/1987 |
| WO | WO 92/02484 A1 | 2/1992 |
| WO | WO 95/11036 A1 | 4/1995 |
| WO | WO 99/08994 A1 | 2/1999 |
| WO | WO 2005/065696 A1 | 7/2005 |
| WO | WO 2006/116897 A1 | 11/2006 |
| WO | WO 2008/131491 A1 | 11/2008 |

OTHER PUBLICATIONS

Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Abo, "Irritancy of Ingenol Esters from Euphorbia Kamerunica", Fitoterapia, vol. LIX, No. 3, 1988, pp. 244-246.
Beeby, Angeloyl Chloride:Synthesis and Utilisation in the Partial Synthesis of Lantadene a (Rehmannic Acid), Tetrahedron Letters, No. 38, 1977, pp. 3379-3382.
Bohlmann et al., "Struktur and Synthese eines aus Bellis perennis L. Isolierten Diesters", Chem. Ber., 103, 1970, pp. 561-563.
CDC (http://www.cdc.gov/std/treatment/2010/genital-warts.htm, accessed Dec. 17, 2014).
Challacombe et al., Neutrophils are a Key Component of the Antitumor Efficacy of Topical Chemotherapy with Ingenol-3-Angelate:, J. Immunol, 177, 2006, pp. 8123-8132.
Cozzi, et al., "Induction of Senescene in Diterpene Ester-Treated Melanoma Cells via Protein Kinase C-Dependent Hyperactivation of the Mitogen-Activated Protein Kinase Pathway", Cancer Research, 66, 2006, pp. 10083-10091.
English translation of the Chinese Office Action issued in Chinese Application No. 201180068162.3, dated Jul. 21, 2013.
Ersvaer et al., The Protein Kinase C Agonist PEP005 (Ingenol 3-Angelate) in the Treatment of Human Cancer: A Balance Between Efficacy and Toxicity, Toxins, 2, 2010, pp. 174-194.
Gotta et al., On the Active Principles of the Euphorbiaceae, IXa Ingenane Type Diterpene Esters from Five *Euphorbia* Species, Z. Naturforsch. 39b, 1984, pp. 683-694.
Hampson et al., "PEP005, a Selective Small-Molecule Activator of Protein Kinase C, has Potent Antileukemic Activity Mediated Via the Delta Isoform of PKC", Blood, 106, 2005, pp. 1362-1368.
Hamspon et al., "The anti-tumor agent, ingenol-3-angelate (PEP005), promotes the recruitment of cytotoxic neutrophils by activation of vascular endothelial cells in a PKC-8 dependent manner", Cancer Immunol Immunother, 57, 2008, pp. 1241-1251.
Hoskins et al., Pyrrolizidine Alkaloid Analogues. Preparation of Semisynthetic Esters of Retronecine, J. Chem. Soc. Perkin Trans., 1, 1977, pp. 538-544.
Le et al., "Immunostimulatory cancer chemotheraphy using local ingenol-3-angelate and synergy with immunotherapies", Vaccine, 27, 2009, pp. 3053-3062.
Marston et al., "On the Active Principles of the Euphorbiaceae", Planta Medica, vol. 47, 1983, pp. 141-147.
Ogbourne et al., "Antitumor Activity of 3-Ingenyl Angelate: Plasma Membrane and Mitochondrial Disruption and Necrotic Cell Death", Cancer Research, 64, 2004, pp. 2833-2839.
Rosen et al., "Dual Mechanism of Action of Ingenol Mebutate Gel for Topical Treatment of Actinic Keratoses: Rapid Lesion Necrosis Followed by Lesion-Specific Immune Response", J Am Acad Derm, 2012, 66, pp. 486-493.
Skin Care Foundation (http://www.skincancer.org/skin-cancer-information/squamous-cell-carcinoma/scc-treatment-options, accessed: Dec. 17, 2014).
Sorg et al., "Structure/Activity Realtionships of Polyfunctional Diterpenes of the Ingenane Type. I. Tumor-Promoting Activity of Homologous, Aliphatic 3-esters of Ingenol and of 7.8-isoingenol-3-Tetradecanoate", Carcinogenesis vol. 8, No. 1, 1987, pp. 1-4.
Sorg et al., Zur Chemie des Ingenols, II [1] Ester des Ingenols and des-Isoingenols, Z. Naturforsch. 37b, 1982, pp. 748-756.
Zayed et al., Dietary Cancer Risk from Conditional Cancerogens (Tumor Promoters) in Produce of Livestock Fed on Species of Spurge (Euphorbiaceae), J. Cancer Res. Clin. Oncol, 127, 2001, pp. 40-47.
English translation of the Chinese Office Action dated Jun. 1, 2015, for Chinese Application No. 201180068162.3.
English translation of the Japanese Office Action dated Aug. 4, 2015, for Chinese Application No. 2013-545050.

(56) References Cited

OTHER PUBLICATIONS

English translation of the Russian Decision on grant of patent for invention dated Aug. 5, 2015, for Russian Application No. 2013133874.
English translation of the Tawainese Search Report dated Aug. 20, 2015, for Tawainese Application No. 100148201.
Japanese Office Action (with English Translation) dated Oct. 4, 2016 issued in Application No. 2015-201428.

* cited by examiner

INGENOL-3-ACYLATES III AND INGENOL-3-CARBAMATES

CROSS REFERENCE TO RELATED APPLICATIONS

The present application is a 37 C.F.R. §1.53(b) divisional of, and claims priority to, U.S. application Ser. No. 13/996,989, filed Aug. 21, 2013. Application Ser. No. 13/996,989 is the national phase under 35 U.S.C. §371 of International Application No. PCT/DK2011/000154 filed on Dec. 22, 2011, which claims priority under 35 U.S.C. 119(e) to U.S. Provisional Application No. 61/426,378 filed on Dec. 22, 2010; U.S. Provisional Application No. 61/448,350 filed on Mar. 2, 2011 and U.S. Provisional Application No. 61/534,055 filed on Sep. 13, 2011, all of which are hereby expressly incorporated by reference into the present application.

FIELD OF THE INVENTION

This invention relates to novel derivatives of 3-O-acyl-ingenol and 3-O-carbamoyl-ingenol and derivatives thereof and their use as a medicament and in therapy. The invention also provides pharmaceutical compositions comprising said compounds and methods of treating diseases with said compounds.

BACKGROUND OF THE INVENTION

Ingenol-3-angelate (PEP005, ingenol mebutate) is a diterpene-ester of the ingenol family which is isolated from various *Euphorbia* species, particularly from *Euphorbia peplus*. The compound is presently subject for clinical development for the treatment of actinic keratosis and for non-melanoma skin cancer.

WO99/08994 describes isolation of compounds from *Euphorbia* plant and their use in cancer and other neoplastic diseases hereunder actinic keratosis or solar keratosis.

Ingenol-3-acylates, mainly of long-chain saturated and unsaturated aliphatic fatty acids, have been isolated from various *Euphorbia* species [H. Gotta, Z. Naturforschung, (1984), 39b, 683-94; K. Abo, Fitoterapia, (1988), 244-46, S. Zayed, 3. Cancer Res. Clin. Oncol. (2001), 127, 40-47]. Furthermore, a small number ingenol-3-acylates have been prepared by semi-synthesis (B. Sorg et. al., Z. Naturforsch., (1982), 37b, 748-56). Some of these ingenol derivatives have been described and tested to be strong irritants and strong tumor-promoting agents. [B. Sorg et. al., Z. Naturforsch., (1982), 37b, 748-56; B. Sorg et. al., Carcinogenesis, (1987), 8, 1-4].

Besides the aliphatic ingenol esters, aromatic esters of ingenol are known. Milliamine C, an ingenol-3-anthraniloate derivative has been described (Marston, A. Planta Medica, (1983), 47, 141-47). Also ingenol-3-benzoate has been described (Sorg, B.; Z Naturforschung, (1982), 37b, 748-56).

Heteroaromatic or heterocyclic 3-O-acyl ingenol derivatives have not previously been disclosed.

Ingenol-3-carbamates have not previously been disclosed. Differently substituted ingenol carbamates have been mentioned in U.S. Pat. Nos. 5,955,501, 5,891,906, 5,891,870 and WO9202484.

Angelic acid and angelic acid esters, as present in ingenol-3-angelate, are prone to isomerisation of the double bond to form the tiglate ester, particularly at basic pH [Beeby, P., Tetrahedron Lett. (1977), 38, 3379-3382, Hoskins, W. M., J. Chem. Soc. Perkin Trans. 1, (1977), 538-544, Bohlmann, F. et. al., Chem. Ber. (1970), 103, 561-563].

Furthermore, ingenol-3-acylates are known to be unstable as they rearrange to afford the ingenol-5-acylates and ingenol-20-acylates [Sorg, B. et. al, Z. Naturforsch., (1982), 37B, 748-756].

Ingenol-3-angelate is believed to have a dual mode of action: 1) Induction of cell death by direct cytoxicity or induction of apoptosis and 2) an immunostimulatory effect dominated by neutrophil recruitment and activation (Rosen, R. H., et al., *J Am Acad Derm* (2011), e-published November 2011; Ersvaer, E., et al., *Toxins*, (2010), 2, 174-194). Nanomolar concentrations of the agent cause activation and modulation of protein kinase C (PKC) classical and novel isoforms, with particular importance of PKCdelta. Through activation of PKCdelta the agent induces apoptosis in susceptible cells (Hampson, P., et al., *Blood*, (2005), 106, 1362-1368; Cozzi, S. J., et al., *Cancer Res*, (2006), 66, 10083-10091). Rapid cytotoxicity on cancer cells is observed at high micromolar concentrations (Ogbourne, S. M., et al., *Cancer Res* (2004), 64, 2833-2839). Through activation of various PKC isoforms the agent also induces pro-inflammatory effects, including release of pro-inflammatory mediators (Challacombe, J. M., et al., *J Immunol* (2006), 177, 8123-8132, activation of vascular endothelium (Hampson, P., et al., *Cancer Immunol Immunother*, (2008), 57, 1241-1251); chemoattraction of neutrophils through induction of interleukin 8 in keratinocytes and development of specific anti-cancer immune responses by CD8+ cells through adjuvant properties in animal models (Le, T. T., et al., *Vacccine*, (2009), 27, 3053-3062).

Compounds exerting dual mode of action by induction of cell death by direct cytoxicity or induction of apoptosis, and by an immunostimulatory effect involving neutrophil recruitment and activation, may be useful for treatment of conditions associated with hyperplasia or neoplasia. Compounds inducing cell death by primary and/or secondary necrosis and compounds exhibiting a pro-apoptotic effect may reduce unwanted cell growth and remove unwanted cells, and furthermore, stimulation of the innate immune response and adjuvant effects may augment the biological response against aberrant or transformed cells.

Compounds inducing cell death by primary and/or secondary necrosis may be useful for treatment of cosmetic conditions, as these compounds may kill or remove unwanted tissue or cells.

There is a need to find new ingenol derivatives which induce cell death by cytotoxicity or apoptosis and/or induce an immunostimulatory effect.

The present invention provides heterocyclic 3-O-acyl ingenol derivatives and 3-O-carbamoyl ingenol derivatives useful for treatment of conditions associated with the use of ingenol-3-angelate or useful for conditions which are affected by induction of cell death by cytoxicity or induction of apoptosis and/or by an immunostimulatory effect.

Compounds of the present invention stimulate neutrophil oxidative burst, which is part of the innate immune response.

Compounds of the present invention stimulate keratinocyte IL-8 release, thus inducing an immunostimulatory effect.

Some compounds of the present invention induce rapid necrosis.

Some compounds of the present invention exhibit activity in the B16 mouse melanoma model indicating that the compounds possess anti-tumor activity and are able to kill neoplastic and transformed cells.

SUMMARY OF THE INVENTION

Some compounds of the present invention exhibit favorable stability properties.

In an embodiment the invention provides a compound of the general formula I

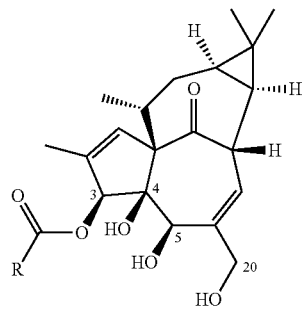

I wherein R is heteroaryl which may optionally be substituted by one or more substituents independently selected from R7;

or R is heterocycloalkyl or heterocycloalkenyl, wherein said heterocycloalkyl or heterocycloalkenyl are optionally substituted by one or more substituents independently selected from R8;

or R is X;

R7 represents halogen, cyano or hydroxyl;

or R7 represents ($C_1$-$C_4$)alkyl, ($C_2$-$C_4$)-alkenyl, ($C_3$-$C_7$)-cycloalkyl, heterocycloalkyl, aryl, heteroaryl arylalkyl, heterocycloalkylalkyl or ($C_3$-$C_7$)-cycloalkylalkyl, wherein said ($C_1$-$C_4$)alkyl, ($C_2$-$C_4$)-alkenyl, ($C_3$-$C_7$)-cycloalkyl, heterocycloalkyl, aryl, heteroaryl arylalkyl, heterocycloalkylalkyl or ($C_3$-$C_7$)-cycloalkylalkyl are optionally substituted by one or more substituents independently selected from R9;

or R7 represents —NRaCORb, —CONRaRb, —COORc, —OCORa, —ORa, —OCONRaRb, —NRaCOORb, —NRaCONRaRb, —NRaSO2NRaRb, —NRaSO2Rb, —SO2NRaRb, —SO2Ra, —S(O)Ra, —SRa or —NRaRb;

R9 represents halogen, cyano, hydroxy, ($C_1$-$C_4$)alkyl, halo($C_1$-$C_4$)alkyl, —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa or =O;

R8 represents halogen, cyano or hydroxyl;

or R8 represents ($C_1$-$C_4$)alkyl, ($C_2$-$C_4$)alkenyl, aryl, heteroaryl, ($C_3$-$C_7$)-cycloalkyl or heterocycloalkyl, wherein said $C_1$-$C_4$)alkyl, ($C_2$-$C_4$)alkenyl, aryl, heteroaryl, ($C_3$-$C_7$)-cycloalkyl or heterocycloalkyl are optionally substituted by one or more substituents independently selected from R10, or R8 represents —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O, =N—ORa, —O—N=CRaRb, NRaRb or —C(O)N(Ra)O—Rb;

R10 represents halogen, cyano, hydroxy, ($C_1$-$C_4$)-alkyl, ($C_1$-$C_4$)alkoxy, halo($C_1$-$C_4$)alkyl, halo($C_1$-$C_4$)alkoxy, hydroxy($C_1$-$C_4$)alkyl, cyano($C_1$-$C_4$)alkyl, aryl, heteroaryl, cycloalkyl, heterocycloalkyl, —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa or =O;

Ra and Rb represents hydrogen, ($C_1$-$C_4$)alkyl, halo($C_1$-$C_4$)alkyl, ($C_1$-$C_4$)alkoxy($C_1$-$C_4$)alkyl, hydroxy($C_1$-$C_4$)alkyl, cyano($C_1$-$C_4$)alkyl, aryl, heteroaryl, cycloalkyl or heterocycloalkyl;

Rc represents hydrogen, ($C_1$-$C_4$)alkyl, halo($C_1$-$C_4$)alkyl, ($C_1$-$C_4$)alkoxy($C_1$-$C_4$)alkyl, hydroxy($C_1$-$C_x$)alkyl, cyano ($C_1$-$C_x$)alkyl, aryl, heteroaryl, cycloalkyl or heterocycloalkyl;

X represents —NR11R12 wherein R11 and R12 independently represent hydrogen, or wherein R11 and R12 independently represents ($C_1$-$C_6$) alkyl, ($C_2$-$C_6$)alkenyl or ($C_2$-$C_6$)alkynyl, cycloalkyl, cycloalkenyl, aryl, heteroaryl, heterocycloalkyl, heterocycloalkenyl, cycloalkylalkyl, cycloalkenylalkyl, arylalkyl, heteroarylalkyl, heterocycloalkylalkyl, heterocycloalkenylalkyl, alkylcycloalkyl, alkylcycloalkenyl, alkylaryl, alkylheteroaryl or alkylheterocycloalkyl, wherein said ($C_1$-$C_6$) alkyl, ($C_2$-$C_6$)alkenyl or ($C_2$-$C_6$)alkynyl, cycloalkyl, cycloalkenyl, aryl, heteroaryl, heterocycloalkyl, heterocycloalkenyl, cycloalkylalkyl, cycloalkenylalkyl, arylalkyl, heteroarylalkyl, heterocycloalkylalkyl, heterocycloalkenylalkyl, alkylcycloalkyl, alkylcycloalkenyl, alkylaryl, alkylheteroaryl or alkylheterocycloalkyl are optionally substituted by one or more substituents independently selected from R13;

R13 represents halogen, cyano or hydroxyl, or R13 represents ($C_1$-$C_4$)alkyl, ($C_2$-$C_4$)alkenyl, aryl, ($C_3$-$C_7$)cycloalkyl, heteroaryl or heterocycloalkyl, wherein said ($C_1$-$C_4$)alkyl, ($C_2$-$C_4$)alkenyl, aryl, ($C_3$-$C_7$)cycloalkyl, heteroaryl or heterocycloalkyl are optionally substituted by one or more substituents selected from R14 or R13 represents —NRdCORe, —COORf, —OCORd, —CONRdRe, —OCONRdRe, —NRdCOORe, —NRdCONRdRe, —NRdSO2Re, —NRdSO2NRdRe, —SO2NRdRe, —SO2Rd, —S(O)Rd, —ORd, —SRd, =O, =N—ORd, —O—N=CRdRe, —NRdRe or —C(O)N(Rd)-ORe wherein Rd and Re independently represents hydrogen, ($C_1$-$C_4$)alkyl, halo($C_1$-$C_4$)alkyl, ($C_1$-$C_4$)alkoxy($C_1$-$C_4$) alkyl, hydroxy($C_1$-$C_4$)alkyl, cyano($C_1$-$C_4$)alkyl, aryl, heteroaryl, cycloalkyl or heterocycloalkyl;

Rf represents hydrogen, ($C_1$-$C_4$)alkyl, halo($C_1$-$C_4$)alkyl, ($C_1$-$C_4$)alkoxyl($C_1$-$C_4$)alkyl, hydroxy($C_1$-$C_4$)alkyl, cyano ($C_1$-$C_4$)alkyl, aryl, heteroaryl, cycloalkyl or heterocycloalkyl;

R14 represents halogen, hydroxyl, cyano, ($C_1$-$C_4$)alkyl, ($C_1$-$C_4$)alkoxy, halo($C_1$-$C_4$)alkyl, halo($C_1$-$C_4$)alkoxy, hydroxy($C_1$-$C_4$)alkyl, cyano($C_1$-$C_4$)alkyl, aryl, heteroaryl, cycloalkyl, heterocycloalkyl, —NRdCORe, —COORf, —OCORd, —CONRdRe, —OCONRdRe, —NRdCOORe, —NRdCONRdRe, —NRdSO2Re, —NRdSO2NRdRe, —SO2NRdRe, —SO2Rd, —S(O)Rd, —ORd, —SRd or =O;

and pharmaceutically acceptable salts, prodrugs, hydrates and solvates thereof.

In an embodiment the invention provides a compound of formula I, for use as a medicament in therapy.

In an embodiment the invention provides a use of a compound according to formula I, for the manufacture of a pharmaceutical compound.

In an embodiment the invention provides a pharmaceutical composition comprising a compound of formula I or a pharmaceutically acceptable stereoisomer, salt or in vivo hydrolysable ester thereof together with a pharmaceutically acceptable vehicle or excipient.

In an embodiment the invention provides a pharmaceutical composition suitable for topical administration comprising a compound of formula I or a pharmaceutically acceptable stereoisomer, salt or in vivo hydrolysable ester thereof together with a pharmaceutically acceptable vehicle or excipient.

In an embodiment the invention provides a compound of formula I for use in the treatment, prevention, amelioration or prophylaxis of physiological disorders or diseases associated with hyperplasia or neoplasia.

In an embodiment the invention provides use of a compound of formula I for the manufacture of a medicament for the treatment, amelioration or prophylaxis of physiological disorders or diseases associated with hyperplasia or neoplasia.

In an embodiment the invention provides a method of preventing, treating, amelioration or prophylaxis of physiological disorders or diseases associated with hyperplasia or neoplasia by administration to a subject in need thereof a compound of formula I above.

In an embodiment the invention provides a compound of formula I for use in the treatment or amelioration of cosmetic indications.

In an embodiment the invention provides use of compound according to formula I for the manufacture of a medicament for the treatment or amelioration of cosmetic indications.

In an embodiment the invention provides a method of treatment or amelioration of cosmetic indications by administration to a subject in need thereof a compound of formula I above.

In an embodiment the invention provides a pharmaceutical composition comprising a compound of formula I or a pharmaceutically acceptable stereoisomer, salt or in vivo hydrolysable ester thereof in combination with one or more other therapeutically active agents.

DETAILED DESCRIPTION OF THE INVENTION

An embodiment the invention provides a compound of the general formula I

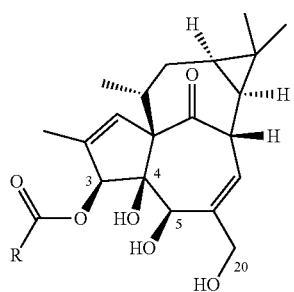

I wherein R is heteroaryl which may optionally be substituted by one or more substituents independently selected from R7;

or R is heterocycloalkyl or heterocycloalkenyl, each of which may optionally be substituted by one or more substituents independently selected from R8;

or R is X;

R7 represents halogen, cyano or hydroxyl;

or R7 represents $(C_1-C_4)$alkyl, $(C_2-C_4)$alkenyl, $(C_3-C_7)$cycloalkyl, heterocycloalkyl, aryl, heteroaryl, each of which is optionally substituted by one or more substituents independently selected from R9;

or R7 represents —NRaCORb, —CONRaRb, —COORc, —OCORa, —ORa, —OCONRaRb, —NRaCOORb, —NRaCONRaRb, —NRaSO2NRaRb, —NRaSO2Rb, —SO2NRaRb, —SO2Ra, —S(O)Ra, —Sra or —NRaRb;

R9 represents halogen, cyano, hydroxy, $(C_1-C_4)$alkyl, halo$(C_1-C_4)$alkyl, —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa or =O;

R8 represents halogen, cyano, hydroxyl;

or R8 represents $(C_1-C_4)$alkyl, $(C_2-C_4)$alkenyl, aryl, heteroaryl, $(C_3-C_7)$cycloalkyl or heterocycloalkyl, each of which is optionally substituted by one or more substituents independently selected from R10, or R8 represents —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O, =N—ORa, —O—N=CRaRb, NRaRb or —C(O)N(Ra)O—Rb;

R10 represents halogen, cyano, hydroxy, $(C_1-C_4)$alkyl, $(C_1-C_4)$alkoxy, halo$(C_1-C_4)$alkyl, halo$(C_1-C_4)$alkoxy, hydroxy$(C_1-C_4)$alkyl, cyano$(C_1-C_4)$alkyl, aryl, heteroaryl, cycloalkyl, heterocycloalkyl, —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa or =O;

Ra and Rb represents hydrogen, $(C_1-C_4)$alkyl, halo$(C_1-C_4)$alkyl, $(C_1-C_4)$alkoxy$(C_1-C_4)$alkyl, hydroxy$(C_1-C_4)$alkyl, cyano$(C_1-C_4)$alkyl, aryl, heteroaryl, cycloalkyl or heterocycloalkyl;

Rc represents hydrogen, $(C_1-C_4)$alkyl, halo$(C_1-C_4)$alkyl, $(C_1-C_4)$alkoxy$(C_1-C_4)$alkyl, hydroxy$(C_1-C_x)$alkyl, cyano$(C_1-C_x)$alkyl, aryl, heteroaryl, cycloalkyl or heterocycloalkyl;

X represents —NR11R12 wherein R11 and R12 independently represent hydrogen, or wherein R11 and R12 independently represents $(C_1-C_6)$alkyl, $(C_2-C_6)$alkenyl or $(C_2-C_6)$alkynyl, cycloalkyl, cycloalkenyl, aryl, heteroaryl, heterocycloalkyl, heterocycloalkenyl, cycloalkylalkyl, cycloalkenylalkyl, arylalkyl, heteroarylalkyl, heterocycloalkylalkyl, heterocycloalkenylalkyl, alkylcycloalkyl, alkylcycloalkenyl, alkylaryl, alkylheteroaryl or alkylheterocycloalkyl, which may optionally be substituted by one or more substituents independently selected from R13;

R13 represents halogen, cyano, hydroxyl, or R13 represents $(C_1-C_4)$alkyl, $(C_2-C_4)$alkenyl, aryl, $(C_3-C_7)$cycloalkyl, heteroaryl or heterocycloalkyl, each of which may be substituted by one or more substituents selected from R14, or R13 represents —NRdCORe, —COORf, —OCORd, —CONRdRe, —OCONRdRe, —NRdCOORe, —NRdCONRdRe, —NRdSO2Re, —NRdSO2NRdRe, —SO2NRdRe, —SO2Rd, —S(O)Rd, —ORd, —SRd, =O, =N—ORd, —O—N=CRdRe, —NRdRe or —C(O)N(Rd)-ORe wherein Rd and Re independently represents hydrogen, $(C_1-C_4)$alkyl, halo$(C_1-C_4)$alkyl, $(C_1-C_4)$alkoxy$(C_1-C_4)$alkyl, hydroxy$(C_1-C_4)$alkyl, cyano$(C_1-C_4)$alkyl, aryl, heteroaryl, cycloalkyl or heterocycloalkyl;

Rf represents hydrogen, $(C_1-C_4)$alkyl, halo$(C_1-C_4)$alkyl, $(C_1-C_4)$alkoxyl$(C_1-C_4)$alkyl, hydroxy$(C_1-C_4)$alkyl, cyano$(C_1-C_4)$alkyl, aryl, heteroaryl, cycloalkyl or heterocycloalkyl;

R14 represents halogen, hydroxyl, cyano, $(C_1-C_4)$alkyl, $(C_1-C_4)$alkoxy, halo$(C_1-C_4)$alkyl, halo$(C_1-C_4)$alkoxy, hydroxy$(C_1-C_4)$alkyl, cyano$(C_1-C_4)$alkyl, aryl, heteroaryl, cycloalkyl, heterocycloalkyl, —NRdCORe, —COORf, —OCORd, —CONRdRe, —OCONRdRe, —NRdCOORe, —NRdCONRdRe, —NRdSO2Re, —NRdSO2NRdRe, —SO2NRdRe, —SO2Rd, —S(O)Rd, —ORd, —SRd or =O;

and pharmaceutically acceptable salts, prodrugs, hydrates and solvates thereof.

Another embodiment the invention provides a compound of the general formula I above wherein R is heteroaryl which may optionally be substituted by one or more substituents independently selected from R7, or R is heterocycloalkyl or heterocycloalkenyl, each of which may optionally be substituted by one or more substituents independently selected from R8, R7 represents halogen, cyano, hydroxyl;

or R7 represents $(C_1-C_4)$alkyl, $(C_2-C_4)$-alkenyl, $(C_3-C_7)$-cycloalkyl, heterocycloalkyl, aryl, heteroaryl, each of which may optionally be substituted by one or more substituents independently selected from R9;

or R7 represents —NRaCORb, —CONRaRb, —COORc, —OCORa, —ORa, —OCONRaRb, —NRaCOORb, —NRaCONRaRb, —NRaSO2NRaRb, —NRaSO2Rb, —SO2NRaRb, —SO2Ra, —S(O)Ra, —SRa;

R9 represents halogen, cyano, hydroxy, $(C_1-C_4)$alkyl, halo$(C_1-C_4)$alkyl, —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O;

R8 represents halogen, cyano, hydroxyl;

or R8 represents $(C_1-C_4)$-alkyl, $(C_2-C_4)$alkenyl, aryl, heteroaryl, $(C_3-C_7)$-cycloalkyl, heterocycloalkyl, each of which is optionally substituted by one or more substituents independently selected from R10, or R8 represents —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O;

R10 represents halogen, cyano, hydroxy, $(C_1-C_4)$-alkyl, halo$(C_1-C_4)$alkyl, —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O;

Ra and Rb represents hydrogen, $(C_1-C_4)$alkyl, halo$(C_1-C_4)$alkyl, $(C_1-C_4)$alkoxy$(C_1-C_4)$alkyl, hydroxy$(C_1-C_4)$alkyl, cyano$(C_1-C_4)$alkyl;

Rc represents $(C_1-C_4)$alkyl, halo$(C_1-C_4)$alkyl, $(C_1-C_4)$alkoxy$(C_1-C_4)$alkyl, hydroxy$(C_1-C_4)$alkyl, cyano$(C_1-C_4)$alkyl;

and pharmaceutically acceptable salts, prodrugs, hydrates and solvates thereof.

An embodiment of the invention provides a compound of formula I wherein R is heteroaryl.

An embodiment of the invention provides a compound of formula I, wherein heteroaryl is isoxazolyl, pyridyl, quinolyl, isoquinolyl, indolyl, furyl, thiazolyl, imidazolyl, pyrazolyl, oxazolyl, thienyl, pyrimidinyl, 1,2,3-triazolyl, indazolyl, cinnolyl or 1,2-benzoxazolyl.

An embodiment of the invention provides a compound of formula I, wherein R is heteroaryl and wherein said heteroaryl is isoxazolyl, pyridyl, quinolyl, isoquinolyl, indolyl, furyl, thiazolyl, imidazolyl, pyrazolyl, oxazolyl, thienyl, pyrimidinyl, 1,2,3-triazolyl, indazolyl, cinnolyl, 1,2-benzoxazolyl, imidazothiazolyl, imidazopyridinyl, pyrrolyl, isothiazolyl, tetrahydroindazolyl or oxadiazolyl.

An embodiment of the invention provides a compound of formula I, wherein R is heteroaryl and wherein said heteroaryl is isoxazolyl, furyl, pyrazolyl, thienyl or pyrrolyl.

An embodiment of the invention provides a compound of formula I, wherein R is heteroaryl and wherein said heteroaryl is isoxazolyl.

An embodiment of the invention provides a compound of formula I, wherein R is heteroaryl and wherein said heteroaryl is furyl.

An embodiment of the invention provides a compound of formula I, wherein R is heteroaryl and wherein said heteroaryl is isoxazolyl, furyl, pyrazolyl, thienyl or pyrrolyl, and wherein R7 represents $(C_1-C_4)$alkyl.

An embodiment of the invention provides a compound of formula I, wherein R is heteroaryl and wherein said heteroaryl is isoxazolyl, furyl, pyrazolyl, thienyl or pyrrolyl, and wherein R7 represents $(C_1-C_2)$alkyl.

An embodiment of the invention provides a compound of formula I, wherein R is heteroaryl, and wherein heteroaryl is isoxazolyl or furyl and wherein R7 represents $(C_1-C_2)$alkyl.

An embodiment of the invention provides a compound of formula I, wherein R is heteroaryl and wherein said heteroaryl is isoxazolyl, furyl, pyrazolyl, thienyl or pyrrolyl, and wherein R7 represents phenyl.

An embodiment of the invention provides a compound of formula I, wherein R is heteroaryl and wherein said heteroaryl is isoxazolyl, furyl, pyrazolyl, thienyl or pyrrolyl, and wherein R7 represents phenyl or $(C_1-C_4)$alkyl and wherein R9 represents $(C_1-C_4)$alkyl, halogen or —ORa.

An embodiment of the invention provides a compound of formula I, wherein R is heteroaryl and wherein said heteroaryl is indolyl, indazolyl or tetrahydroindazolyl. An embodiment of the invention provides a compound of formula I, wherein R is heteroaryl and wherein said heteroaryl is indolyl, indazolyl or tetrahydroindazolyl, and wherein R7 represents $(C_1-C_4)$alkyl or —ORa.

An embodiment of the invention provides a compound of formula I, wherein R7 is independently selected one or more times from the group of $(C_1-C_4)$alkyl, aryl or halogen.

An embodiment of the invention provides a compound of formula I, wherein R7 is independently selected one or more times from the group of $(C_1-C_4)$alkyl, $(C_2-C_4)$alkenyl, aryl, arylalkyl, heterocycloalkylalkyl, $(C_3-C_7)$-cycloalkylalkyl, $(C_3-C_7)$-cycloalkyl —COORc, —ORa or halogen.

An embodiment of the invention provides a compound of formula I wherein R7 is selected from phenyl, methyl, ethyl, isopropyl, Cl or Br.

An embodiment of the invention provides a compound of formula wherein R7 is selected from phenyl, methyl, ethyl, isopropyl, t-butyl, piperidyl, tert-butyloxycarbonyl, benzyl, tetrahydropyranylmethyl, —OCH$_3$, cyclopropyl, allyl, cyclopropylmethyl, Cl, Br or I.

An embodiment of the invention provides a compound of formula I above, wherein R9 is halogen or —ORa.

An embodiment of the invention provides a compound of formula I above, wherein R9 is halogen, —ORa, $(C_1-C_4)$ alkyl or —SO2Ra.

An embodiment of the invention provides a compound of formula I, wherein R9 is Cl, F or —OCH₃.

An embodiment of the invention provides a compound of formula I above, wherein R9 is Cl, F, —OCH₃, methyl or methylsulfonyl.

An embodiment of the invention provides a compound of formula I, wherein R is heterocycloalkyl.

An embodiment of the invention provides a compound of formula I above, wherein R is heterocycloalkyl or heterocycloalkenyl.

An embodiment of the invention provides a compound of formula I, wherein heterocycloalkyl is pyrrolidinyl, piperidinyl, morpholinyl or 5-oxabicyclo[2.2.2]octane.

An embodiment of the invention provides a compound of formula I, wherein R8 is $(C_1\text{-}C_4)$alkyl.

An embodiment of the invention provides a compound of formula I above, wherein R is heterocycloalkyl or heterocycloalkenyl and wherein said heterocycloalkyl or heterocycloalkenyl is pyrrolidinyl, piperidinyl, morpholinyl, 5-oxabicyclo[2.2.2]octanyl, oxaspiro[4.5]dec-1-enyl, oxo-thiazolyl, dihydrothiazolyl, oxo-pyranyl, azepanyl, azabicyclo[3.2.2]nonanyl, benzoxazinyl, quinoxalinyl, isoindolinyl, dihydroquinolinyl, indolinyl or dihydroquinoxalinyl.

An embodiment of the invention provides a compound of formula I above, wherein R is heterocycloalkyl and wherein said heterocycloalkyl is indolinyl, benzoxazinyl or dihydroquinolinyl.

An embodiment of the invention provides a compound of formula I above, wherein R8 is methyl.

An embodiment of the invention provides a compound of formula I, wherein R8 is $(C_1\text{-}C_4)$alkyl, aryl or =O.

An embodiment of the invention provides a compound of formula I, wherein R is —NR11R12.

An embodiment of the invention provides a compound of formula I, wherein R11 and R12 independently represents hydrogen, $(C_1\text{-}C_6)$alkyl, aryl, cycloalkyl, arylalkyl, heteroaryl or cycloalkylalkyl.

An embodiment of the invention provides a compound of formula I above, wherein R11 and R12 independently represents hydrogen, $(C_1\text{-}C_6)$alkyl, aryl, cycloalkyl, arylalkyl, heteroaryl, cycloalkylalkyl, heteroarylalkyl, heterocycloalkyl, heterocycloalkylalkyl, $(C_2\text{-}C_6)$alkenyl or $(C_2\text{-}C_6)$alkynyl.

An embodiment of the invention provides a compound of formula I above, wherein R11 and R12 independently represents hydrogen, $(C_1\text{-}C_6)$alkyl, aryl or arylalkyl.

An embodiment of the invention provides a compound of formula I above, wherein R11 and R12 independently represents hydrogen, $(C_1\text{-}C_4)$alkyl, cycloalkyl, phenyl or benzyl.

An embodiment of the invention provides a compound of formula I above, wherein R11 and R12 independently represents hydrogen, $(C_1\text{-}C_4)$alkyl, phenyl or benzyl, wherein said $(C_1\text{-}C_4)$alkyl, phenyl or benzyl is optionally substituted by one or more substituents selected from R13, wherein R13 represents halogen, $(C_1\text{-}C_4)$alkyl or —ORa.

An embodiment of the invention provides a compound of formula I, wherein R11 and R12 independently represents hydrogen, methyl, ethyl, isopropyl, phenyl, benzyl, cyclohexyl, indanyl, tetralinyl, phenylethyl, cyclopropylmethyl or pyrazolyl.

An embodiment of the invention provides a compound of formula I above, wherein R11 and R12 independently represents hydrogen, methyl, ethyl, isopropyl, phenyl, benzyl, cyclohexyl, indanyl, tetralinyl, phenylethyl, cyclopropylmethyl, pyrazolyl, isoxazolylmethyl, cyclopentyl, cyclopropyl, pyridyl, piperidyl, tetrahydropyranylmethyl, tetrahydropyranyl, cyclobutyl, allyl, propynyl or thiazolyl.

An embodiment of the invention provides a compound of formula I, wherein R13 represents $(C_1\text{-}C_4)$alkyl, cyano or F.

An embodiment of the invention provides a compound of formula I above, wherein R13 represents $(C_1\text{-}C_4)$alkyl, cyano, halogen, =O, —ORa or —COORf.

An embodiment of the invention provides a compound of formula I above, wherein R13 represents methyl, cyano, F, =O, —OCH₃ or —COOC(CH₃)₃.

An embodiment of the invention provides a compound of formula I, wherein R11 or R12 independently represent hydrogen.

An embodiment of the invention provides a compound of formula I, said compound being:

Ingenol 3-(5-methyl-3-phenyl-isoxazole-4-carboxylate) or
Ingenol 3-(5-methyl-3-(2-chloro-6-fluoro-phenyl)-isoxazole-4-carboxylate) or
Ingenol 3-(1S-camphanate) or
Ingenol 3-(3-phenyltriazole-4-carboxylate or
Ingenol 3-(2-phenylpyrazole-3-carboxylate or
Ingenol 3-(1-methylindazole-3-carboxylate) or
Ingenol 3-(3-ethyl-5-methyl-isoxazole-4-carboxylate) or
Ingenol 3-(3-methyl-5-methyl-isoxazole-4-carboxylate) or
Ingenol 3-(1-methylindole-3-carboxylate) or
Ingenol 3-(3-phenylthiophene-2-carboxylate) or
Ingenol 3-(5-phenylisoxazole-3-carboxylate) or
Ingenol 3-(N-ethyl-carbamate) or
Ingenol 3-(N,N-dimethyl-carbamate) or
Ingenol 3-(morpholine-4-carboxylate) or
Ingenol 3-(pyrrolidine-1-carboxylate) or
Ingenol 3-(N-methyl-N-phenyl-carbamate) or
Ingenol 3-(N,N-diethyl-carbamate) or
Ingenol 3-(piperidine-1-carboxylate) or
Ingenol 3-(N-benzyl-N-methyl-carbamate) or
Ingenol 3-(N-cyclohexyl-N-methyl-carbamate) or
Ingenol 3-(N-cyclohexyl-carbamate) or
Ingenol 3-(N-phenyl-carbamate) or
Ingenol 3-(N-(indan-1-yl)-carbamate) or
Ingenol 3-(3,3-dimethyl-piperidine-1-carboxylate) or
Ingenol 3-(N-Methyl-N-tetralin-1-yl-carbamate) or
Ingenol 3-(N-(2-cyano-1-methyl-ethyl)-N-methyl-carbamate) or
Ingenol 3-(N-methyl-N—((S)-1-phenethyl)-carbamate) or
Ingenol 3-(N-methyl-N-(cyclopropylmethyl)-carbamate) or
Ingenol 3-(isoquinoline-1-carboxylate) or
Ingenol 3-(quinoline-4-carboxylate) or
Ingenol 3-(cinnoline-4-carboxylate) or
Ingenol 3-(3-phenylimidazole-4-carboxylate) or
Ingenol 3-(5-phenyloxazole-4-carboxylate) or
Ingenol 3-(1,2-benzoxazole-3-carboxylate) or
Ingenol 3-(3-isopropyl-5-methyl-isoxazole-4-carboxylate) or
Ingenol 3-(3-(2-methoxyphenyl)-5-methyl-isoxazole-4-carboxylate) or
Ingenol 3-(4-bromo-2-methyl-pyrazole-3-carboxylate) or
Ingenol 3-(4-bromo-2-ethyl-pyrazole-3-carboxylate) or
Ingenol 3-(4-chloro-2-methyl-pyrazole-3-carboxylate) or
Ingenol 3-(5-bromopyrimidine-4-carboxylate) or
Ingenol 3-(3-bromopyridine-2-carboxylate) or
Ingenol 3-(5-methylthiazole-4-carboxylate) or
Ingenol 3-(4-chloro-1-methyl-pyrazole-3-carboxylate) or
Ingenol 3-(2,4-dimethylthiazole-5-carboxylate) or
Ingenol 3-(2,5-dimethyloxazole-4-carboxylate) or
Ingenol 3-(2,4-dimethylfuran-3-carboxylate) or
Ingenol 3-(3,5-diethylisoxazole-4-carboxylate) or
Ingenol 3-(N-(3-fluoro-phenyl)-N-methyl-carbamate) or Ingenol 3-(N-(2,5-dimethylpyrazol-3-yl)-N-methyl-carbamate) or
Ingenol 3-(1H-indole-7-carboxylate) or
Ingenol 3-(2-tert-butyl-5-methyl-pyrazole-3-carboxylate) or
Ingenol 3-(5-tert-butyl-2-methyl-pyrazole-3-carboxylate) or
Ingenol 3-(6-methylimidazo[2,1-b]thiazole-5-carboxylate) or
Ingenol 3-(2-methylimidazo[1,2-a]pyridine-3-carboxylate) or
Ingenol 3-(2,4,5-trimethylfuran-3-carboxylate) or
Ingenol 3-(3-methylthiophene-2-carboxylate) or
Ingenol 3-(2-methyl-4-(1-piperidyl)pyrazole-3-carboxylate) or
Ingenol 3-(2-chloro-5-isopropyl-thiazole-4-carboxylate) or
Ingenol 3-(4-chloro-2,5-dimethyl-pyrazole-3-carboxylate) or
Ingenol 3-(1,2,4-trimethylpyrrole-3-carboxylate) or
Ingenol 3-(1,3,5-trimethylpyrrole-2-carboxylate) or
Ingenol 3-(1-ethyl-3,5-dimethylpyrrole-2-carboxylate) or
Ingenol 3-(1-tert-butyloxycarbonyl-3,3-dimethylpyrrolidine-2-carboxylate) or
Ingenol 3-((2S)-1-phenylpyrrolidine-2-carboxylate) or
Ingenol 3-(1-isopropyl-3,5-dimethyl-pyrazole-4-carboxylate) or
Ingenol 3-(5-ethyl-3-isopropyl-isoxazole-4-carboxylate) or
Ingenol 3-(2-methylindazole-3-carboxylate) or
Ingenol 3-(5-methyl-3-tert-butyl-isoxazole-4-carboxylate) or
Ingenol 3-(2-methyl-3-oxo-4-oxaspiro[4.5]dec-1-ene-1-carboxylate) or
Ingenol 3-(1-tert-butyl-3,5-dimethyl-pyrazole-4-carboxylate) or
Ingenol 3-(3,5-dimethylisothiazole-4-carboxylate) or
Ingenol 3-(5-iodo-3-methyl-isothiazole-4-carboxylate) or
Ingenol 3-(4-(4-methoxyphenyl)-2-methyl-pyrazole-3-carboxylate) or
Ingenol 3-(4-(2-methylphenyl)-2-methyl-pyrazole-3-carboxylate) or
Ingenol 3-(2-methyl-4-(4-methylsulfonylphenyl)pyrazole-3-carboxylate) or
Ingenol 3-(2-methyl-4-phenyl-pyrazole-3-carboxylate) or
Ingenol 3-(3,5-dimethyl-1-phenyl-pyrazole-4-carboxylate) or
Ingenol 3-(1,5-dimethyl-3-phenyl-pyrazole-4-carboxylate) or
Ingenol 3-(1-benzyl-3,5-dimethyl-pyrazole-4-carboxylate) or
Ingenol 3-(3,5-dimethyl-1-(tetrahydropyran-4-ylmethyl)pyrazole-4-carboxylate) or
Ingenol 3-(4-methyl-2-oxo-3H-thiazole-5-carboxylate) or
Ingenol 3-(2-methyl-4,5,6,7-tetrahydroindazole-3-carboxylate) or
Ingenol 3-(1,2-dimethylindole-3-carboxylate) or
Ingenol 3-(5-methoxy-1,2-dimethyl-indole-3-carboxylate) or
Ingenol 3-(1,3,5-trimethylpyrazole-4-carboxylate) or
Ingenol 3-(4-methyl-1,2,5-oxadiazole-3-carboxylate) or
Ingenol 3-(2-methoxy-4-methyl-thiazole-5-carboxylate) or
Ingenol 3-(4,5-dimethylisoxazole-3-carboxylate) or
Ingenol 3-(4-bromo-1-methyl-pyrazole-3-carboxylate) or
Ingenol 3-(1,3-dimethylindole-2-carboxylate) or
Ingenol 3-(5-methoxy-1,3-dimethyl-indole-2-carboxylate) or
Ingenol 3-(2,4-dimethyl-6-oxo-pyran-3-carboxylate) or
Ingenol 3-(1-methyl-3-phenyl-indole-2-carboxylate) or
Ingenol 3-(3-methyl-5-(trifluoromethyl)isoxazole-4-carboxylate) or
Ingenol 3-(1,3-dimethylpyrrole-2-carboxylate) or
Ingenol 3-(3,5-dimethyl-1-(2,2,2-trifluoroethyl)pyrazole-4-carboxylate) or
Ingenol 3-(1-cyclopropyl-2,5-dimethyl-pyrrole-3-carboxylate) or
Ingenol 3-(1,2,5-trimethylpyrrole-3-carboxylate) or
Ingenol 3-(2,4-dimethyl-1H-pyrrole-3-carboxylate) or
Ingenol 3-(1-methylpyrrole-2-carboxylate) or
Ingenol 3-(4-methyl-1H-pyrrole-2-carboxylate) or
Ingenol 3-(1,5-dimethylpyrrole-2-carboxylate) or
Ingenol 3-(3-methyl-1H-pyrrole-2-carboxylate) or
Ingenol 3-(1-cyclopropylpyrrole-2-carboxylate) or
Ingenol 3-(1-ethyl-2,4-dimethyl-pyrrole-3-carboxylate) or
Ingenol 3-(1-allyl-2,4-dimethyl-pyrrole-3-carboxylate) or
Ingenol 3-(1-(cyclopropylmethyl)-2,4-dimethyl-pyrrole-3-carboxylate) or
Ingenol 3-(1-(2-methoxyethyl)-2,4-dimethyl-pyrrole-3-carboxylate) or
Ingenol 3-(N-(3,5-dimethylisoxazol-4-yl)-N-methyl-carbamate) or
Ingenol 3-(N-(1,5-dimethylpyrazol-3-yl)-N-methyl-carbamate) or
Ingenol 3-(N-cyclopentyl-N-methyl-carbamate) or
Ingenol 3-(N-cyclopropyl-N-methyl-carbamate) or
Ingenol 3-(N-methyl-N-(2-pyridyl)-carbamate) or
Ingenol 3-(4-oxo-2,3-dihydroquinoline-1-carboxylate) or
Ingenol 3-(3,4-dihydro-2H-quinoline-1-carboxylate) or
Ingenol 3-(indoline-1-carboxylate) or
Ingenol 3-(azepane-1-carboxylate) or
Ingenol 3-(N-(4-chloro-phenyl)-N-methyl-carbamate) or
Ingenol 3-(N-(4-fluoro-phenyl)-N-methyl-carbamate) or
Ingenol 3-(N-methyl-N-(2-methoxy-phenyl)-carbamate) or
Ingenol 3-(N-methyl-N-(2-methyl-phenyl)-carbamate) or
Ingenol 3-(3-oxo-2,4-dyhidroquinoxaline-1-carboxylate) or
Ingenol 3-(N-ethyl-N-phenyl-carbamate) or
Ingenol 3-(2-trifluoromethyl-pyrrolidine-1-carboxylate) or
Ingenol 3-(3-azabicyclo[3.2.2]nonane-3-carboxylate) or
Ingenol 3-(2,3-dihydro-1,4-benzoxazine-4-carboxylate) or
Ingenol 3-(N-(2-fluoro-phenyl)-N-methyl-carbamate) or
Ingenol 3-(3-methyl-2,3-dihydro-1,4-benzoxazine-4-carboxylate) or
Ingenol 3-(2-trifluoromethyl-pyrrolidine-1-carboxylate) (ISOMER A) or
Ingenol 3-(2-trifluoromethyl-pyrrolidine-1-carboxylate) (ISOMER B) or
Ingenol 3-(N-methyl-N—(N-(tert-butyloxycarbonyl)-4-piperidyl)-carbamate) or
Ingenol 3-(N-methyl-N-(3-methyl-phenyl)-carbamate) or
Ingenol 3-(3,4-dihydro-2H-quinoxaline-1-carboxylate) or
Ingenol 3-(isoindoline-2-carboxylate) or
Ingenol 3-(N-methyl-N-(tetrahydropyran-4-yl)methyl)-carbamate) or
Ingenol 3-(N-methyl-N-(tetrahydropyran-4-yl)-carbamate) or
Ingenol 3-(N-methyl-N-(3-methoxy-phenyl)-carbamate) or
Ingenol 3-(N-cyclobutyl-N-methyl-carbamate) or
Ingenol 3-(N-allyl-N-methyl-carbamate) or
Ingenol 3-(N-methyl-N-prop-2-ynyl-carbamate) or
Ingenol 3-(N-methyl-N-(4-methylthiazol-2-yl)-carbamate) or
Ingenol 3-(N-(4-cyano-phenyl)-N-methyl-carbamate).

An embodiment of the invention provides a compound of formula I, said compound being Ingenol 3-(N-methyl-N-phenyl-carbamate).

An embodiment of the invention provides a compound of formula I, said compound being Ingenol 3-(N-(3-fluoro-phenyl)-N-methyl-carbamate).

An embodiment of the invention provides a compound of formula I, said compound being Ingenol 3-(3-ethyl-5-methyl-isoxazole-4-carboxylate)

An embodiment of the invention provides a compound of formula I, said compound being Ingenol 3-(2,4-dimethyl-furan-3-carboxylate).

An embodiment of the invention provides a compound of formula I, said compound being Ingenol 3-(3,5-diethylisoxazole-4-carboxylate).

An embodiment of the invention provides a compound of formula I, said compound being Ingenol 3-(2,4,5-trimethyl-furan-3-carboxylate).

An embodiment of the invention provides a compound of formula I, said compound being Ingenol 3-(2-methyl-4-phenyl-pyrazole-3-carboxylate).

An embodiment of the invention provides a compound of formula I, said compound being Ingenol 3-(3-methylthio-phene-2-carboxylate).

An embodiment of the invention provides a compound of formula I, said compound being Ingenol 3-(indoline-1-carboxylate).

An embodiment of the invention provides a compound of formula I, said compound being Ingenol 3-(5-methyl-3-phenyl-isoxazole-4-carboxylate).

An embodiment of the invention provides a compound of formula I, said compound being Ingenol 3-(pyrrolidine-1-carboxylate).

DEFINITIONS

In the present context, the term "$(C_a\text{-}C_b)$alkyl" wherein a and b are integers refers to a straight or branched chain alkyl radical having from a to b carbon atoms, e.g. 1-7 or 1-6, such as 1-4 or 1-3 carbon atoms. Thus when a is 1 and b is 7, for example, the term includes methyl, ethyl, n-propyl, isopropyl, n-butyl, isobutyl, sec-butyl, tert-butyl, pentyl, isopentyl, hexyl, isohexyl and heptyl.

The term "carbocyclic" refers to a mono-, bi- or tricyclic radical having up to 13 ring atoms, e.g. 3-13 or 3-10 ring atoms, all of which are carbon, and includes aryl, cycloalkyl and cycloalkenyl.

The term "cycloalkyl" refers to a mono-, bi- or tricyclic saturated cycloalkane radical, comprising 3-13 carbon atoms, such as 3-10, such as 3-8, such as 3-5 carbon atoms, and includes, for example, cyclopropyl, cyclobutyl, cyclopentyl, cyclohexyl, cycloheptyl, cyclooctyl, bicyclo[2.2.1]heptanyl and adamantyl.

The term "$(C_a\text{-}C_b)$alkenyl" wherein a and b are integers refers to a mono-, di- or triunsaturated straight or branched chain alkenyl radical having from a to b carbon atoms, e.g. 2-7 or 2-6 or 2-4 or 2-3 carbon atoms. Thus when a is 1 and b is 7, for example, the term includes ethenyl, allyl, propenyl; 1-, 2- or 3-butenyl; 1-, 2-, 3- or 4-pentenyl; 1-, 2-, 3-, 4- or 5-hexenyl.

The term "cycloalkenyl" refers to mono-, di- or triunsaturated non-aromatic cyclic hydrocarbons radicals, including polycyclic radicals, comprising 3-13 carbon atoms, such as 3-10, such as 3-8, such as 3-5 carbon atoms, and includes, for example, cyclopropenyl, cyclobutenyl, cyclopentenyl or cyclohexenyl.

The term "$(C_a\text{-}C_b)$alkynyl" wherein a and b are integers refers to a straight or branched chain hydrocarbon radical having from a to b carbon atoms, e.g. 2-7 or 2-6 or 2-4 or 2-3 carbon atoms, comprising 1-2 C—C triple bonds. Thus when a is 1 and b is 7, for example, the term includes ethynyl, propynyl, butynyl, pentynyl or hexynyl.

The term "heterocyclic" refers to a carbocyclic radical as defined above, comprising 1-4 heteroatoms, selected from O, N, or S, and includes heteroaryl, heterocycloalkyl and heterocycloalkenyl.

The term "heterocycloalkyl" refers to a cycloalkyl radical, including polycyclic radicals, optionally fused with carbocyclic rings, comprising 1-4 heteroatoms, selected from O, N, or S.

The term "heterocycloalkyl" furthermore refers to a cycloalkyl radical, including polycyclic radicals, optionally fused with carbocyclic rings, including aryl provided that the point of attachment is through the non-aromatic ring, the cycloalkyl radical comprising 1-4 heteroatoms, selected from O, N, or S. E.g. piperazinyl, tetrahydrofuranyl, pyrrolidinyl, dioxolanyl, morpholinyl, imidazolidinyl, piperidinyl, 5-oxabicyclo[2.2.2]octane, dihydroquinolinyl, indolinyl, dihydroquinoxalinyl, oxo-thiazolyl, oxo-pyranyl, azepanyl, azabicyclo[3.2.2]nonanyl, benzoxazinyl, quinoxalinyl, isoindolinyl, indolinyl or tetrahydropyranyl, in particular tetrahydrofuranyl, pyrrolidinyl, dioxolanyl, morpholinyl, imidazolidinyl, piperidinyl or 5-oxabicyclo[2.2.2]octane.

The term "heterocycloalkenyl" refers to a cycloalkenyl radical as defined above, including polycyclic radicals, optionally fused with carbocyclic rings, comprising 1-4 heteroatoms, selected from O, N, or S, e.g. dihydropyranyl, dihydrothiazolyl.

The term "aryl" refers to a radical of aromatic carbocyclic rings comprising 6-10 carbon atoms, in particular phenyl, and optionally fused carbocyclic rings with at least one aromatic ring, in particular 5- or 6-membered rings. Thus the term includes for example 1,2,3,4-tetrahydro-naphthalenyl, phenyl, naphthyl, indenyl or indanyl, in particular phenyl, naphthyl, indenyl or indanyl.

The term "heteroaryl" refers to radicals of heterocyclic aromatic rings, optionally fused with carbocyclic rings or heterocyclic rings, comprising 1-4 heteroatoms, selected from O, S and N, and 1-12 carbon atoms, such as 1-4 heteroatoms and 1-6 carbon atoms, in particular 5- or 6-membered rings with 1-4 heteroatoms, or optionally fused bicyclic rings with 1-4 heteroatoms, and wherein at least one ring is aromatic. Thus the term includes, for example, pyridyl, quinolyl, isoquinolyl, indolyl, tetrazolyl, furyl, thiazolyl, imidazolyl, imidazo[1,2-a]pyrimidinyl, pyrrolyl, pyrazolyl, oxazolyl, isoxazolyl, oxadiazolyl, 1,2,4-triazolyl, thienyl, pyrazinyl, pyrimidinyl, 1,2,3-triazolyl, isothiazolyl, imidazo[2,1-b]thiazolyl, benzimidazolyl, benzofuranyl, benzofuranyl, benzothiophenyl, benzothiazolyl, benzooxazolyl, indazolyl, cinnolyl, 1,2-benzoxazolyl, imidazothiazolyl, imidazopyridinyl, pyrrolyl, isothiazolyl, tetrahydroindazolyl, oxadiazolyl in particular pyridyl, quinolyl, isoquinolyl, indolyl, tetrazolyl, furyl, thiazolyl, imidazolyl, imidazo[1,2-a]pyrimidinyl, pyrrolyl, pyrazolyl, oxazolyl, isoxazolyl, oxadiazolyl, 1,2,4-triazolyl, thienyl, pyrazinyl, pyrimidinyl, 1,2,3-triazolyl, isothiazolyl, imidazo[2,1-b]thiazolyl, benzimidazolyl, benzofuranyl, benzofuranyl, benzothiophenyl, benzothiazolyl, benzooxazolyl, indazolyl, or in particular pyridyl, quinolyl, isoquinolyl, indolyl, tetrazolyl, furyl, thiazolyl, imidazolyl, imidazo[1,2-a]pyrimidinyl, pyrrolyl, pyrazolyl, oxazolyl, isoxazolyl, oxadiazolyl, 1,2,4-triazolyl, thienyl, pyrazinyl, pyrimidinyl, 1,2,3-triazolyl, isothiazolyl, imidazo[2,1-b]thiazolyl, benzimidazolyl, benzofuranyl, benzofuranyl, benzothiophenyl, benzothiazolyl, benzooxazolyl, indazolyl, cinnolyl, 1,2-benzoxazolyl.

The term "halogen" is intended to indicate a substituent from the 7th main group of the periodic table, preferably fluoro, chloro and bromo.

The term "alkoxy" is intended to indicate a radical of the formula —OR, wherein R is alkyl as indicated above, e.g. methoxy, ethoxy, n-propoxy, isopropoxy, butoxy, etc.

The term "haloalkoxy" is intended to indicate a radical of the formula —O—R—$X_{(1-3)}$, wherein R is alkyl as indicated above, and X is halogen as indicated above e.g. trifluoromethoxy.

The term hydroxyalkyl is intended to indicate a primary, secondary or tertiary radical of the formula —R—OH, wherein R is alkyl as indicated above, e.g. hydroxymethyl or hydroxyethyl.

The term cyanoalkyl is intended to indicate a primary, secondary or tertiary radical of the formula —R—CN, wherein R is alkyl as indicated above, e.g. cyanomethyl or cyanoethyl.

The term haloalkyl is intended to indicate a primary, secondary or tertiary radical of the formula —R—$X_{(1-3)}$, wherein R is alkyl as indicated above, and X is halogen as indicated above, e.g. trifluoromethyl, 2,2,2-trifluoroethyl or difluoromethyl.

When two or more of the above defined terms are used in combination, such as arylalkyl, heteroarylalkyl, cycloalkylalkyl and the like, it is to be understood that the first mentioned radical is a substituent on the latter mentioned radical, where the point of attachment to another part of the molecule, is on the latter radical.

The term "alkoxyalkyl" is intended to indicate an alkyl radical as defined above, which is substituted with an alkoxy radical as defined above, i.e. —R—O—R, wherein each R is alkyl, same or different, as indicated above, e.g. methoxymethyl, ethoxymethyl.

The term "cycloalkylalkyl" is intended to indicate a radical of the formula —R'-cycloalkyl, wherein R' is alkyl as defined above such as;

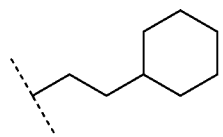

The term "cycloalkenylalkyl" is intended to indicate a radical of the formula —R'— cycloalkenyl, wherein R' is alkyl as defined above such as;

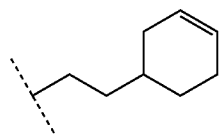

The term "arylalkyl" is intended to indicate a radical of the formula —R'—Ar, wherein R' is alkyl as defined above and Ar is aryl as defined above such as;

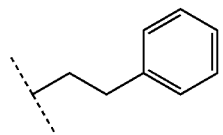

The term "heteroarylalkyl" is intended to indicate a radical of the formula —R'-Het, wherein R' is alkyl as defined above and Het is heteroaryl as defined above such as;

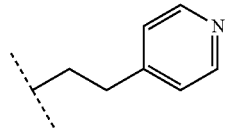

The term "heterocycloalkylalkyl" is intended to indicate a radical of the formula —R'— heterocycloalkyl, wherein R' is alkyl as defined above such as;

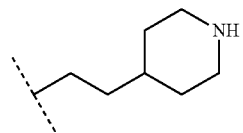

The term "heterocycloalkenylalkyl" is intended to indicate a radical of the formula —R'— heterocycloalkenyl, wherein R' is alkyl as defined above such as;

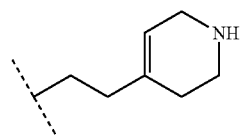

The term alkylcycloalkyl is intended to indicate a radical of the formula -cycloalkyl-R' wherein R' is alkyl as defined above such as;

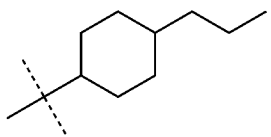

The term "alkylcycloalkenyl" is intended to indicate a radical of the formula -cycloalkenyl-R', wherein R' is alkyl as defined above such as;

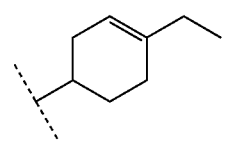

The term "alkylaryl" is intended to indicate a radical of the formula —Ar—R', wherein R' is alkyl as defined above and Ar is aryl as defined above such as;

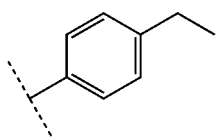

The term "alkylheteroaryl" is intended to indicate a radical of the formula -Het-R', wherein R' is alkyl as defined above and Het is heteroaryl as defined above such as;

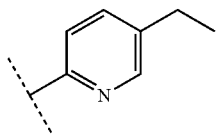

The term "alkylheterocycloalkyl" is intended to indicate a radical of the formula -heterocycloalkyl-R', wherein R' is alkyl as defined above such as;

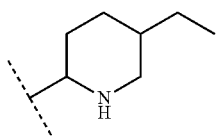

The term 'substituted' as applied to any moiety herein is intended to indicate substitution with compatible substituents.

The term "pharmaceutically acceptable salt" is intended to indicate salts prepared by reacting a compound of formula I comprising a basic moiety with a suitable inorganic or organic acid, such as hydrochloric, hydrobromic, hydroiodic, sulfuric, nitric, phosphoric, formic, acetic, 2,2-dichloroacetic, choline, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I comprising an acidic moiety may also be prepared by reaction with a suitable base such as sodium hydroxide, potassium hydroxide, magnesium hydroxide, calcium hydroxide, ammonia, or suitable non-toxic amines, such as lower alkylamines, for example triethylamine, hydroxy-lower alkylamines, for example 2-hydroxyethylamine, bis-(2-hydroxyethyl)-amine, cycloalkylamines, for example dicyclohexylamine, or benzylamines, for example N,N'-dibenzylethylenediamine, and dibenzylamine, or L-arginine or L-lysine.

The present invention further includes prodrugs of compounds of general formula I, such as esters, acetals, ketals, or other derivatives which undergo a biotransformation in vivo before exhibiting their pharmacological effects.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

The term "cancer" in the context of the present invention is intended to cover skin cancer such as non-melanoma skin cancer, malignant melanoma, Merkel cell carcinoma, squamous cell carcinoma, basal cell carcinoma. Basal cell carcinomas covers as well superficial basal cell carcinomas as nodular basal cell carcinoma. Squamous cell carcinoma covers squamous cell carcinoma in situ (Bowen's disease), invasive squamous cell carcinoma, cutaneous squamous cell carcinoma, mucosal squamous cell carcinoma, head and neck squamous cell carcinoma. Other cancer types includes haematological cancer such as myeloid cancers in particular such as acute myeloid leukemia and chronic myeloid leukemia; Cancer of the prostate and bladder including benign prostatic hyperplasia, prostatis intraepithelial carcinoma, carcinoma of the bladder, adenocarcinoma of the prostate and renal cell carcinoma. Other cancer include AIDS related cancer, acoustic neoma, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (bcc), bladder cancer, bone cancers, bowel cancer, brain stem glioma, brain and CNS cancers, breast cancer, CNS cancers, carcinoid cancers, cervical cancer, childhood brain cancers, childhood cancer, childhood soft tissue sarcoma, chondrosarcoma, choriocarcinoma, colorectal cancers, cutaneous T-Cell lymphoma, dermatof[iota]brosarcoma-protuberans, desmoplastic small round cell cancer, ductal carcinoma, endocrine cancers, endometrial cancer, ependymoma, esophageal cancer, Ewing's sarcoma, extra hepatic bile duct cancer, eye cancer, eye: melanoma, retinoblastoma, fallopian tube cancer, fanconi anaemia, fibrosarcoma, gall bladder cancer, gastric cancer, gastrointestinal cancers, gastrointestinal carcinoid cancer, genitourinary cancers, germ cell cancers, gestational trophoblastic disease, glioma, gynecological cancers, hematological malignancies including acute myeloid leukemia, head and neck cancer, hepatocellular cancer, hereditary breast cancer, histiocytosis, Hodgkin's disease, human papillomavirus, hydatidiform mole, hypercalcemia, hypopharynx cancer, intra-ocular melanoma, isle T-cell cancer, Kaposi's sarcoma, kidney cancer, Langerhan's cell histiocytosis, laryngeal cancer, leiomyosarcoma, li-fraumeni syndrome, lip cancer, liposarcoma, liver cancer, lung cancer, lymphedema, lymphoma, Hodgkin's lymphoma, non-Hodgkin's lymphoma, male breast cancer, malignant rhabdoid cancer of kidney, medulloblastoma, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-small cell lung cancer (nscic), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral neuroectodermal cancers, pituitary cancer, polycythemia vera, prostate cancer, rare cancers and associated disorders, retinoblastoma, rhabdomyosarcoma, rothmund Thomson syndrome, salivary gland cancer, sarcoma, schwannoma, sezary syndrome, small cell lung cancer (scic), small intestine cancer, soft tissue sarcoma, spinal cord cancers, stomach cancer, synovial sarcoma, testicular cancer, thymus cancer, thyroid cancer, transitional cell cancer (bladder), transitional cell cancer (renal-pelvis-/-ureter), trophoblastic cancer, urethral cancer, urinary system cancer, uroplakins, uterine sarcoma, uterus cancer, vaginal Cancer, vulva cancer, Waldenstrom's macroglobulinemia and Wilms' Cancer. The solid cancer which is treated using the methods of the present invention may be a primary lesion or may be the result of metastasis of a primary cancer. Furthermore, if the solid cancer is a metastasis of a primary cancer, the primary cancer may be either a primary solid cancer as described above or may be a dispersed primary cancer.

In an embodiment of the invention "cancer" is skin cancer.

In embodiments of the invention, skin cancer is non-melanoma skin cancer, malignant melanoma, Merkel cell carcinoma, squamous cell carcinoma, squamous cell carcinoma, basal cell carcinoma such as superficial basal cell carcinomas or nodular basal cell carcinoma.

The phrase "physiological disorders or diseases associated with hyperplasia or neoplasia" in the context of the present invention is intended to cover disorders or diseases such as cutaneous warts, including common warts (*Verruca vulgaris*), plantar warts (*Verruca plantaris*) and flat warts (*verruca plana*); Genital warts (*condyloma acuminatum*), Pyogenic granuloma, Haemangioma, Scleroderma; Cancers and precancerous lesions such as Actinic keratosis, Squamous cell carcinoma including squamous cell carcinoma in situ (Bowen's disease), invasive squamous cell carcinoma, cutaneous squamous cell carcinoma, mucosal squamous cell carcinoma, head and neck squamous cell carcinoma;

Basal cell carcinoma including Superficial basal cell carcinoma and Nodular basal cell carcinoma; Bladder cancer, Lentigo maligna, Cervical dysplasia, Vulva dysplasia and anal dysplasia, Primary melanoma in situ, Head and neck cancer, Cutaneous metastases of any cancer, Kaposi's sarcoma, Keratoacanthoma, Merkel cell tumor, Prostate cancer, Mycosis fungoides, Intraepithelial neoplasias including anal, cervical, ductal, oral, perianal, prostatic, penile, vaginal and vulvar intraepithelial neoplasia.

The term "cosmetic indications" in the context of the present invention is intended to cover indications such as: Photodamaged skin, Seborrheic keratosis, Scars, Keloids, Melasma, Poikiloderma of Civatte, Tattoo removal, Naevi andSkin tags.

The term "photodamaged skin" in the context of the present invention is intended to cover fine lines, wrinkles and UV-ageing. UV ageing is often manifested by an increase in the epidermal thickness or epidermal atrophy and most notably by solar elastosis, the accumulation of elastin containing material just below the dermal-epidermal junction. Collagen and elastic fibres become fragmented and disorganised. At a cosmetic level this can be observed as a reddening and/or thickening of the skin resulting a leathery appearance, skin fragility and irregular pigmentation, loss of tone and elasticity, as well as wrinkling, dryness, sunspots and deep furrow formation.

The term "viral infections" in the context of the present invention is intended to cover HPV infections leading to formation of warts on the body, such as the skin, genitals and mouth. HPV refers to human papilloma virus. Other viruses are selected from adeno-, papova-, herpes- (such as simplex) varicella-zoster, Epstein-Barr-, CMV-, Pox- (such as small pox-) vaccinia-, hepatitis A-, hepatitis B-, hepatitis C-, Rhino-, polio-, rubella-, arbo-, rabies-, influenza-A and B, measles-, mumps-viruses, and HIV, HTLV I and II. In an embodiment of the invention HPV infection refers to common warts or genital warts.

The term "bacterial infections" in the context of the present invention is intended to cover prokaryotic and eukaryotic bacterial infections and Gram positive and Gram negative and Gram variable bacteria and intracellular bacteria. Examples of bacteries includes *Treponema, Borrelia, Neisseria, Legionella, Bordetella, Escherichia, Salmonella, Shigella, Klebsiella, Yersinia, Vibrio, Hemophilus, Rickettsia, Chlamydia, Mycoplasma, Staphylococcus, Streptococcus, Bacillus, Clostridium, Corynebacterium, Proprionibacterium, Mycobacterium, Ureaplasma* and *Listeria*. In particular the species: *Treponema pallidum, Borrelia Burgdorferi, Neisseria gonorrhoea, Legionella pneumophila, Bordetella pertussis, Escherichia coli, Salmonella typhi, salmonella typhimurium, Shigella dysenteriae, Klebsiella pneumoniae, Yersinia pestis, Vibrio cholerae, Hemophilus influenza, Rickettsia rickettsii, Chlamydia trachomatis, Mycoplasma pneumonia, Staphylococcus aureus, Streptococcus pneumoniae, Streptococcus pyogenes, Bacillus anthracis, Clostridium botulinum, Clostridium tetani, clostridium perfringens, Corynebacterium diphteriae, Proprionibacterium acne, Mycobacterium tuberculosis, Mycobacterium leprae* and *Listeriare monocytogenes*. Lower eukaryotic organism includes yeast and fungus such as *Pneumocystis nerinii, Candida albicans, Aspergillus, Histoplasma capsulatum, Blastomyces dermatitidis, Cryptococcus neoformans, Trichophyton* and *Microsporum*. Complex eukaryotic organism includes worms, insects, aracnids, nematodes, aemobe, *Entamoeba histolytica, Giardia lamblia, Trichonomonas vaginalis, Trypanosoma brucei gembiense, Trypanosoma cruzi, Blantidium coli, Toxoplasma gondii, Cryptosporidium* or *Leishmania*.

In the context of the present invention the term "wound healing" means: reducing or minimizing scar tissue or improving cosmesis or functional outcome in a wound and scar reduction, wherein the wound is cutaneous, chronic or for example diabetes associated, and includes cuts and lacerations, surgical incisions, punctures, graces, scratches, compression wounds, abrasions, friction wounds, chronic wounds, ulcers, thermal effect wounds, chemical wounds, wounds resulting from pathogenic infections, skin graft/transplant donor and recipient sites, immune response conditions, oral wounds, stomach or intestinal wounds, damaged cartilage or bone, amputation sides and corneal lesions.

The compounds of the present invention are contemplated in the treatment of cancer, actinic keratosis, seborrheic keratosis, viral infections, bacterial infections, wound healing, and treatment of photodamaged skin.

In an embodiment of the invention the compounds of the invention are contemplated for use in the treatment of superficial basal cell carcinoma (BCC), nodular BCC, squamous cell carcinoma or squamous cell carcinoma in situ (SCCIS).

In an embodiment of the invention the compounds of the invention are contemplated for use in the treatment of actinic keratosis.

In an embodiment of the invention the compounds of the invention are contemplated for use in the treatment of Seborrheic keratosis.

In an embodiment of the invention the compounds of the invention are contemplated for use in the treatment of photodamaged skin.

In an embodiment of the invention the compounds of the invention are contemplated for use in the treatment of or lesions caused by HPV infection.

In an embodiment of the invention the lesions are common warts or genital warts.

In an embodiment of the invention the compounds of the invention are contemplated for use in the treatment of squamous cell carcinoma in situ or invasive squamous cell carcinoma.

In an embodiment of the invention the compounds of the invention are contemplated for use in the treatment of cutaneous squamous cell carcinoma, mucosal squamous cell carcinoma or head and neck squamous cell carcinoma.

In an embodiment of the invention the compounds of the invention are contemplated for use in the treatment of superficial basal cell carcinoma or nodular basal cell carcinoma.

In an embodiment of the invention the compounds of the invention are contemplated for use in the treatment of cutaneous warts or genital warts In an embodiment of the invention the compounds of the invention are contemplated for use in the treatment of common warts, plantar warts and flat warts.

In an embodiment of the invention the compounds of the invention are contemplated for use in the treatment of lentigo maligna.

In an embodiment of the invention the compounds of the invention are contemplated for use in the treatment of cervical intraepithelial neoplasia, anal intraepithelial neoplasia or vulva intraepithelial neoplasia.

In an embodiment of the invention the compounds of the invention are contemplated for use in the treatment of acute myeloid leukemia.

In an embodiment the invention provides a method of treatment of cancer, actinic keratosis, seborrheic keratosis, viral infections, bacterial infections, wound healing, and treatment of photodamaged skin by administration to a subject in need thereof a compound of formula I.

In an embodiment the invention provides a method of treatment actinic keratosis by administration to a subject in need thereof a compound of formula I above.

In an embodiment the invention provides a method of treatment Seborrheic keratosis by administration to a subject in need thereof a compound of formula I above.

In an embodiment the invention provides a method of treatment photodamaged skin by administration to a subject in need thereof a compound of formula I above.

In an embodiment the invention provides a method of treatment of lesions caused by HPV infection by administration to a subject in need thereof a compound of formula I above.

In an embodiment the invention provides a method of treatment of common warts or genital warts by administration to a subject in need thereof a compound of formula I above.

In an embodiment the invention provides a method of treatment of cutaneous squamous cell carcinoma, mucosal squamous cell carcinoma or head and neck squamous cell carcinoma by administration to a subject in need thereof a compound of formula I above.

In an embodiment the invention provides a method of treatment of common warts, plantar warts and flat warts by administration to a subject in need thereof a compound of formula I above.

In an embodiment the invention provides a method of treatment of lentigo maligna by administration to a subject in need thereof a compound of formula I above.

In an embodiment the invention provides a method of treatment of cervical intraepithelial neoplasia, anal intraepithelial neoplasia or vulva intraepithelial neoplasia by administration to a subject in need thereof a compound of formula I above.

In an embodiment the invention provides use a compound according to formula I above in the manufacture of a pharmaceutical composition for the treatment or amelioration of a disease, disorder or condition responsive to stimulation of neutrophil oxidative burst.

In an embodiment the invention provides use of a compound according to formula I above in the manufacture of a pharmaceutical composition for the treatment or amelioration of a disease, disorder or condition responsive to stimulation of keratinocyte IL-8 release.

In an embodiment the invention provides use of a compound according to formula I above in the manufacture of a pharmaceutical composition for the treatment or amelioration of a disease, disorder or condition responsive to induction of necrosis.

In an embodiment the invention provides a method of preventing, treating, amelioration or prophylaxis of physiological disorders or diseases responsive to stimulation of neutrophil oxidative burst by administration to a subject in need thereof a compound according to formula I above.

In an embodiment the invention provides a method of preventing, treating, amelioration or prophylaxis of physiological disorders or diseases responsive to stimulation of keratinocyte IL-8 release by administration to a subject in need thereof a compound according to formula I above.

In an embodiment the invention provides a method of preventing, treating, amelioration or prophylaxis of physiological disorders or diseases responsive to responsive to induction of necrosis by administration to a subject in need thereof a compound according to formula I above.

In an embodiment the invention provides a compound according to formula I above for use in the treatment or amelioration of a disease, disorder or condition responsive to stimulation of neutrophil oxidative burst.

In an embodiment the invention provides a compound according to formula I above for use in the treatment or amelioration of a disease, disorder or condition responsive to stimulation of keratinocyte IL-8 release.

In an embodiment the invention provides a compound according to formula I above for use in the treatment or amelioration of a disease, disorder or condition responsive to induction of necrosis.

In an embodiment the invention provides a method of treatment of acute myeloid leukemia by administration to a subject in need thereof a compound of formula I above.

In an embodiment the invention provides a compound of formula I, for use in the treatment, prevention, amelioration or prophylaxis of physiological disorders or diseases associated with actinic keratosis, seborrheic keratosis, cancer, photodamaged skin or lesions caused by HPV infection.

In an embodiment the invention provides the use of a compound of formula I, for the manufacture of a medicament for the treatment, amelioration or prophylaxis of physiological disorders or diseases associated with actinic keratosis, Seborrheic keratosis, cancer, photodamaged skin or lesions caused by HPV infection.

In an embodiment the invention provides a method of preventing, treating, amelioration or prophylaxis of physiological disorders or diseases associated with actinic keratosis, Seborrheic keratosis, cancer, photodamaged skin or lesions caused by HPV infection by administration to a subject in need thereof a compound of formula I.

Pharmaceutical Compositions

For use in therapy, compounds of the present invention are typically in the form of a pharmaceutical composition. The invention therefore relates to a pharmaceutical composition comprising a compound of formula I, together with a pharmaceutically acceptable excipient or vehicle. The excipient must be "acceptable" in the sense of being compatible with the other ingredients of the composition and not deleterious to the recipient thereof.

Pharmaceutical compositions of the invention may be in unit dosage form such as tablets, pills, capsules, powders, granules, elixirs, syrups, emulsions, ampoules, suppositories or parenteral solutions or suspensions; for oral, parenteral, opthalmic, transdermal, intra-articular, topical, pulmonal, nasal, buccal or rectal administration or in any other manner appropriate for the formulation of compounds of the invention and in accordance with accepted practices such as those disclosed in *Remington: The Science and Practice of Pharmacy*, 21$^{st}$ ed., 2000, Lippincott Williams & Wilkins.

For oral administration in the form of a tablet or capsule, a compound of formula I may suitably be combined with an oral, non-toxic, pharmaceutically acceptable carrier such as ethanol, glycerol, water or the like. Furthermore, suitable binders, lubricants, disintegrating agents, flavouring agents and colourants may be added to the mixture, as appropriate. Suitable binders include, e.g., lactose, glucose, starch, gelatin, acacia gum, tragacanth gum, sodium alginate, carboxymethylcellulose, polyethylene glycol, waxes or the like. Lubricants include, e.g., sodium oleate, sodium stearate, magnesium stearate, sodium benzoate, sodium acetate, sodium chloride or the like. Disintegrating agents include, e.g., starch, methyl cellulose, agar, bentonite, xanthan gum or the like. Additional excipients for capsules include macrogols or lipids.

For the preparation of solid compositions such as tablets, the active compound of formula I is mixed with one or more excipients, such as the ones described above, and other pharmaceutical diluents such as water to make a solid preformulation composition containing a homogenous mixture of a compound of formula I. The term "homogenous" is understood to mean that the compound of formula I is dispersed evenly throughout the composition so that the composition may readily be subdivided into equally effective unit dosage forms such as tablets or capsules.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.01 mg and 200 mg, preferably between 0.01 mg and 20 mg, such as 0.01-5 mg of a compound of formula I.

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.01 to 200 mg/kg body weight. The compound may be administered as a bolus (i.e. the entire daily dose is administered at once) or in divided doses two or more times a day.

If the treatment involves administration of another therapeutically active compound it is recommended to consult *Goodman & Gilman's The Pharmacological Basis of Therapeutics*, 9$^{th}$ Ed., J. G. Hardman and L. E. Limbird (Eds.), McGraw-Hill 1995, for useful dosages of said compounds. The administration of a compound of the present invention with one or more other active compounds may be either concomitantly or sequentially.

Liquid formulations for either oral or parenteral administration of the compound of the invention include, e.g., aqueous solutions, syrups, aqueous or oil suspensions and emulsion with edible oils such as cottonseed oil, sesame oil, coconut oil or peanut oil.

Suitable dispersing or suspending agents for aqueous suspensions include synthetic or natural gums such as tragacanth, alginate, acacia, dextran, sodium carboxymethylcellulose, gelatin, methylcellulose or polyvinylpyrolidone.

For parenteral administration, e.g. intramuscular, intraperitoneal, subcutaneous or intravenous injection or infusion, the pharmaceutical composition preferably comprises a compound of formula I dissolved or solubilised in an appropriate, pharmaceutically acceptable solvent. For parenteral administration, the composition of the invention may include a sterile aqueous or non-aqueous solvent, in particular water, isotonic saline, isotonic glucose solution, buffer solution or other solvent conventionally used for parenteral administration of therapeutically active substances. The composition may be sterilised by, for instance, filtration through a bacteria-retaining filter, addition of a sterilising agent to the composition, irradiation of the composition, or heating the composition. Alternatively, the compound of the invention may be provided as a sterile, solid preparation, e.g. a freeze-dried powder, which is dissolved in sterile solvent immediately prior to use. The composition intended for parenteral administration may additionally comprise conventional additives such as stabilisers, buffers or preservatives, e.g. antioxidants such as methyl hydroxybenzoate or the like.

Compositions for rectal administration may be in the form of a suppository incorporating the active ingredient and a carrier such as cocoa butter, or in the form of an enema. Compositions suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Compositions suitable for topical administration, including ophthalmic treatment, include liquid or semi-liquid preparations such as liniments, lotions, gels, applicants, oil-in-water or water-in-oil emulsions such as creams, ointments or pastes; or solutions or suspensions such as drops. Compositions for ophthalmic treatment may preferably additionally contain a cyclodextrin. Compositions suitable for administration to the nasal or buccal cavity or for inhalation include powder, self-propelling and spray formulations, such as aerosols and atomizers.

Human skin, in particular the outer layer, the stratum corneum, provides an effective barrier against penetration of microbial pathogens and toxic chemicals. While this property of skin is generally beneficial, it complicates the dermal administration of pharmaceuticals in that a large quantity, if not most, of the active ingredient applied on the skin of a patient suffering from a dermal disease may not penetrate into the viable layers of the skin where it exerts its activity.

Penetration of the skin is facilitated by addition of penetration enhancers which include isopropyl alcohol, sulphoxides, azones, pyrrolidines, alkanols, and glycols. In embodiments of the invention the penetrations enhancers includes DMSO, laurocapram, 2-pyrrolidone, decanol and propylene glycol. In an embodiment of the invention the penetration enhancer is isopropyl alcohol.

In embodiments of the invention the therapeutically active compound is dissolved in a suitable solvent. Suitable solvents are glycols, ketone, acetates and ethers. Ingenol compounds have been shown to have good stability in alcohols such as benzyl alcohol and isopropyl alcohol. In general, ingenol compounds have previously shown to have good stability at low pH. In embodiments of the present invention pH the pharmaceutical formulation is below 7. In embodiments of the present invention the pH of the pharmaceutical formulation is below 6. In embodiments of the present invention the pH of the pharmaceutical formulation is below 4.5. In embodiments of the present invention the pH of the pharmaceutical formulation is below 4.0. In embodiments of the present invention the pH of the pharmaceutical formulation is below 4.5 and no less than 2.5. In embodiments of the present invention the pH of the pharmaceutical formulation is below 4.0 and no less than 2.5. The preferred pH range can be obtained by including an appropriate buffer. In an embodiment of the invention the buffer is an acetate buffer. In embodiments of the invention a citrate buffer is used. In embodiments of the invention a mixed citrate-phosphate buffer is used.

In one embodiment, the composition is an ointment. According to the current FDA classification, an ointment is a semisolid dosage from which may contain water and volatile substances in an amount of up to 20% by weight and which contains more than 50% by weight of hydrocarbons, waxes or polyols in the vehicle. Thus, according to the invention, the ointment may be a water-in-oil composition in which case the nanosuspension may be added as such to the lipophilic components of the composition, such that the composition contains up to 10% by weight or, preferably, up to 5% by weight of the aqueous phase. Alternatively, the composition may be a non-aqueous ointment which contains less than about 2%, preferably less than 1%, of free water by weight of the composition.

The ointment carrier may suitably contain a paraffin selected from paraffins consisting of hydrocarbons with chain lengths from $C_{5-60}$ and mixtures thereof. A frequently used ointment carrier is petrolatum, or white soft paraffin, which is composed of hydrocarbons of different chain lengths, peaking at about $C_{40-44}$, or a mixture of petrolatum and liquid paraffin (consisting of hydrocarbons of different chain lengths peaking at $C_{28-40}$). While petrolatum provides occlusion of the treated skin surface, reducing transdermal loss of water and potentiating the therapeutic effect of the active ingredient in the composition, it tends to have a greasy and/or tacky feel which persists for quite some time after application, and it is not easily spreadable. It may therefore be preferred to employ paraffins consisting of hydrocarbons of a somewhat lower chain length, such as paraffins consisting of hydrocarbons with chain lengths peaking at $C_{14-16}/C_{18-22}/C_{20-22}/C_{20-26}$ or mixtures thereof. It has been found that such paraffins are more cosmetically acceptable in that they are less tacky and/or greasy on application and more easily spreadable. They are therefore expected to result in improved patient compliance. Suitable paraffins of this type are manufactured by Sonneborn and marketed under the trade name Sonnecone, e.g. Sonnecone CM, Sonnecone DM1, Sonnecone DM2 and Sonnecone HV. These paraffins are further disclosed and characterized in WO08/141078 which is incorporated herein by reference. (The hydrocarbon composition of the paraffins has been determined by gas chromatography.)

To impart a desired viscosity to the composition, it may suitably include a lipophilic viscosity-increasing ingredient such as a wax. The wax may be a mineral wax composed of a mixture of high molecular weight hydrocarbons, e.g. saturated $C_{35-70}$ alkanes, such as microcrystalline wax. Alternatively, the wax may be a vegetable or animal wax, e.g. esters of $C_{14-32}$ fatty acids and $C_{14-32}$ fatty alcohols, such as beeswax. The amount of viscosity-increasing ingredient may vary according to the viscosifying power of the ingredient, but may typically be in the range of about 1-20% by weight of the composition. When the viscosity-increasing ingredient is microcrystalline wax it is typically present in an amount in the range of about 5-15% by weight, e.g. about 10% by weight, of the composition.

To maintain good physical stability of the composition, in particular to avoid separation of the aqueous and lipid phases therein, it may be advantageous to include a water-in-oil emulsifier with an HLB value of 3-8. Examples of such emulsifiers are polyoxyethylene $C_{8-22}$ alkyl ethers, e.g. polyoxyethylene stearyl ether, polyoxyethylene cetyl ether, polyoxyethylene oleyl ether or polyoxyethylene lauryl ether. The amount of emulsifier is typically in the range of 2-10% w/w of the composition. In another embodiment, the composition is a cream which may comprise similar components to the ointment, but which is typically an oil-in-water-emulsion containing a substantial amount of water.

The composition may also comprise other components commonly used in dermal formulations, e.g. antioxidants (e.g. alpha-tocopherol), preservatives such as benzyl alcohol, sodium edetate, pigments, skin soothing agents, skin healing agents and skin conditioning agents such as urea, allantoin or bisabolol, cf. *CTFA Cosmetic Ingredients Handbook*, $2^{nd}$ Ed., 1992. In an embodiment of the invention the preservative is benzyl alcohol.

In an embodiment the composition is a gel. Suitable gelling agents include, water soluble cellulose derived polymers, such as hydroxyalkyl cellulose polymers. In embodiments of the invention the polymers are hydroxymethylcellulose, hydroxyethylcellulose, hydroxypropylcellulose and hydroxypropylmethylcellulose. Other gelling agents are celluloses such as carboxymethyl cellulose, methylhydroxyethyl cellulose and methyl cellulose, carbomer such as carbopol and carrageenans. In embodiments of the invention the gelling agent is cellulose derived. In embodiments of the invention the cellulose is a hydroxyalkylcellulose, such as hydroxyethylcellulose.

In an embodiment of the invention the composition comprises active compound, penetration enhancer, preservative, gelling agent and buffer at a pH of below 4 and not less than 2.5. For topical administration, the compound of formula I may typically be present in an amount of from 0.001 to 20% by weight of the composition, such as 0.01% to about 10%. In embodiments of the present invention the active compound is present in 0.05-1%. In an embodiment of the present invention the active compound is present in 0.01-0.5%. In an embodiment of the present invention the active compound is present in a concentration of around 0.1%. In an embodiment of the invention the composition comprises 0,005-0.1% active compound, 20-40% isopropyl alcohol, 0.5-10% benzyl alcohol, 0.5-5% hydroxyl ethyl cellulose and citrate buffer to 100%. Formulation of ingenol derivatives in a gel for topical application has been described in WO07/068963, which is incorporated by reference.

METHODS OF PREPARATION

The compounds of formula I may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all compounds falling into a given class may be compatible with some of the reaction conditions required in some of the methods described. Such restrictions to the substituents which are compatible with the reaction conditions will be readily apparent to one skilled in the art and alternative methods can be used. The compounds of the present invention or any intermediate may be purified if required using standard methods well known to a synthetic organist chemist, e.g. methods described in W. Armarego "Purification of Laboratory Chemicals", Butterworth-Heinemann, 6$^{th}$ ed. 2009. Starting materials are either known compounds, commercially available, or they may be prepared by routine synthetic methods well known to a person skilled in the art.

The compounds of the invention may for example be prepared according to the following non-limiting general methods and examples

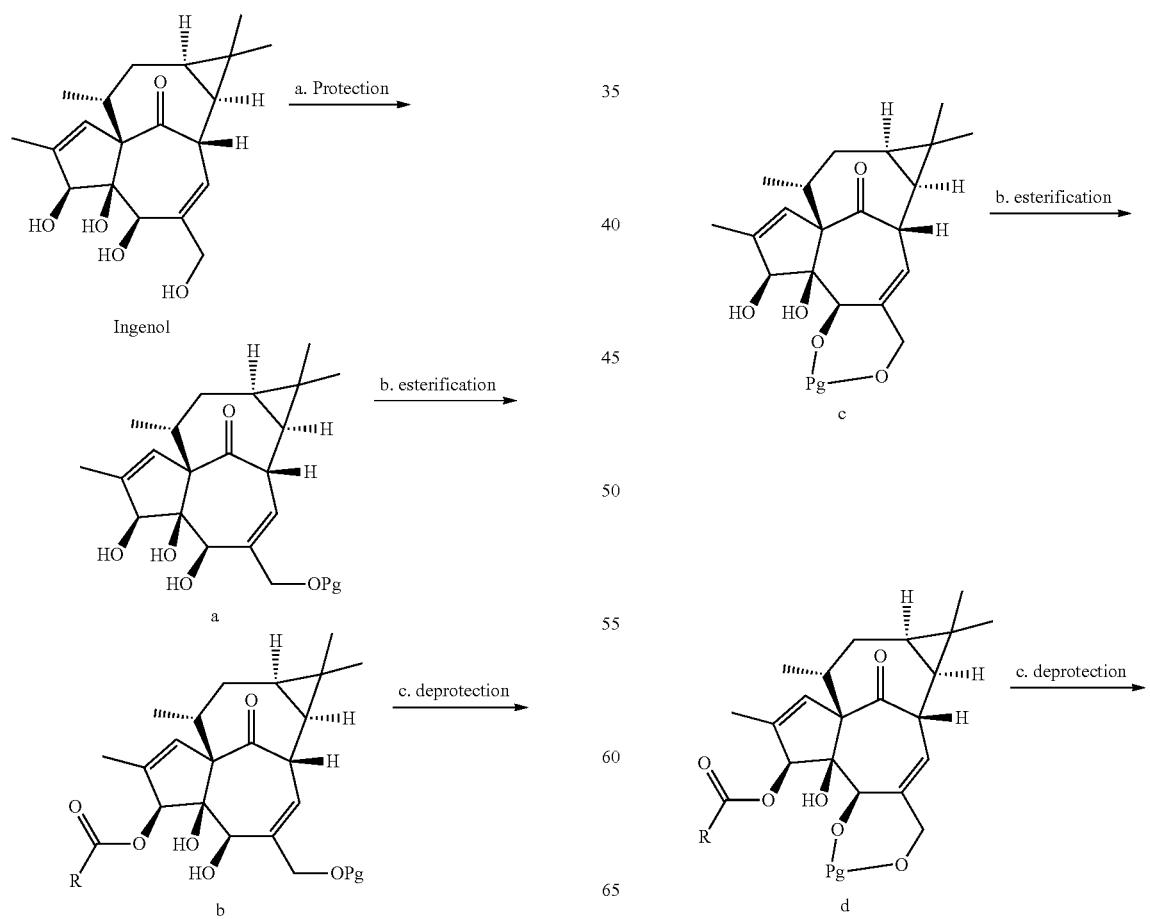

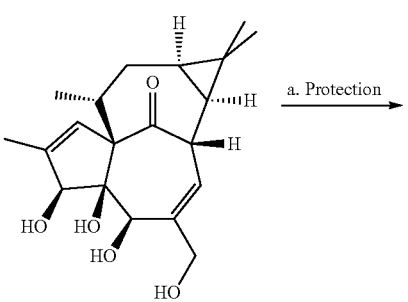

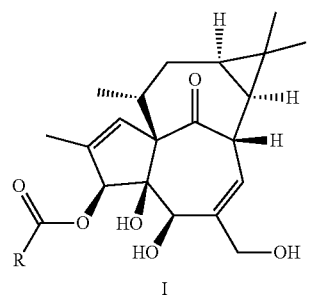

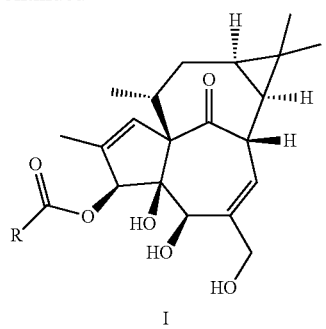

Scheme 3

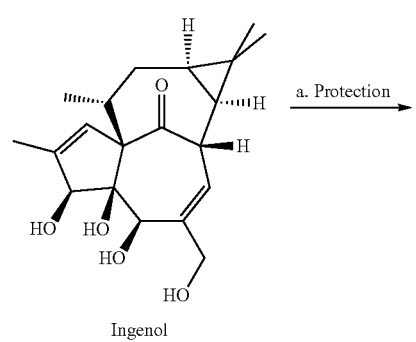

Scheme 4

The compounds of the general formula I can for example be synthesised according to Scheme 1, 2, 3 or 4 by reacting ingenol with a hydroxyl protecting agent or a dihydroxyl protecting agent to afford the protected ingenol derivatives a or c according to methods described in, but not limited to "Protective Groups in Organic Synthesis", 4th ed. P. G. M. Wuts; T. W. Greene, John Wiley, 2007 or in P. J. Kocienski, "Protecting Groups", 3rd ed. G. Thieme, 2003 and references cited therein.

For example compound a, wherein the protective group (Pg) is triphenylmethyl, can be synthesised by reacting ingenol with a triphenylmethyl reagent such as triphenylmethylpyridinium fluoroborate or triphenylmethyl chloride in a suitable solvent such as pyridine, N,N-dimethylformamide or dichloromethane in the presence or in the absence of base (e.g. Opferkuch et. al., Z. Naturforschung, (1981), 36B, 878). Compound a, wherein the protective group (Pg) is silyl, can for example be synthesised by reacting ingenol with a silyl chloride such as tert-butyldimethylsilyl chloride, tert-butyldiphenylsilyl chloride or triisopropylsilyl chloride in a suitable solvent such as N,N-dimethylformamide, pyridine, dichloromethane, tetrahydrofuran or acetonitrile in the presence of a suitable base such as imidazole, triethylamine, N,N-diisopropylethylamine or 4-(N,N-dimethylamino)pyridine (e.g. Sorg, B. et. al, Z. Naturforsch., (1982), 37B, 1640-47), or by reacting compound (II) with a silyl triflate such as tert-butyldimethylsilyl trifluoromethanesulfonate in a suitable solvent such as dichloromethane in the presence of a suitable base such as triethylamine.

Compound a wherein Pg is 2-tetrahydropyranyl, can for example be synthesised by reacting ingenol with dihydropyran in a suitable solvent such as dichloromethane or acetonitrile in the presence of a suitable acid such as p-toluenesulfonic acid. Compound c wherein the protective group (Pg) represents an acetal such as benzylidene acetal can for example be prepared by reacting ingenol with benzaldehyde or benzaldehyde dimethyl acetal in a suitable solvent such as dichloromethane or N,N-dimethylformamide in the presence of a suitable acid such as p-toluenesulfonic acid. Compound c wherein the protective group (Pg) represents a ketal such as isopropylidene ketal can for example be synthesised by reacting ingenol with a ketone such as acetone or a dimethoxy ketal such as 2,2-dimethoxy propane in a suitable solvent such as dichloromethane or N,N-dimethylformamide in the presence of a suitable acid such as p-toluenesulfonic acid (e.g B. Sorg, Z. Naturforsch. (1982), 37b, 748-756). Acetone and 2,2-dimethoxy propane can also act as solvents.

As depicted in scheme 1 and 2 the protected ingenol derivatives a or c may be esterified to give compounds of the general formula b or d according to methods for esterification of hydroxyl groups described in, but not limited to "Esterification" by J. Otera, Wiley-VCH, 2003 and references cited therein. Compound b or d can for example be synthesised by reacting compound a or c with an activated acid derivative such as an acid halide such as acid chloride. The esterification by reaction with acid chloride can take place in a suitable solvent such as dichloromethane or toluene without an activator, or it can take place in the presence of a base such as pyridine, triethylamine or 4-(N,N-dimethylamino)pyridine (e.g. B. Sorg, Z. Naturforsch. (1982), 37b, 748-756). Compound b or d can for example be synthesised by reacting compound a or c with activated acid derivative such as an acid anhydride. The esterification by reaction with an acid anhydride can take place without a catalyst (e.g. Opferkuch et. al., Z. Naturforschung, (1981), 36B, 878), or in the presence of an acidic catalyst using an acid such as perchloric acid or a Lewis acid such as scandium (III) triflate or bismuth (III) triflate, or in the presence of a base such as sodium hydrogencarbonate or triethylamine.

Compound b or d can for example be synthesised by reacting compound a or c with an activated acid derivative such as a mixed anhydride of an acid such as trichlorobenzoic acid. The esterification by reaction with a mixed anhydride can take place in a suitable solvent without a catalyst, or in the presence of an acidic catalyst using an acid such as perchloric acid or a Lewis acid such as scandium (III) triflate or bismuth (III) triflate, or in the presence of a base such as sodium hydrogencarbonate or triethylamine. Compound b or d can for example be synthesised by reacting compound a or c with an acid in the presence a coupling reagent such as a carbodiimide such as dicyclohexylcarbodiimide or N-(3-dimethylaminopropyl)-N'-ethylcarbodiimide with or without the presence of a base such as 4-(N,N-dimethylamino)pyridine and with or without catalysts such as 4-(N,N-dimethylamino)pyridine in a suitable solvent such as dichloromethane (e.g Appendino et. al., Eur. J. Org. Chem. (1999), 3413). Solid-supported coupling reagents can also be used in the esterification step [Nam, N.-H., Journal of Combinatorial Chemistry, (2003), 5, 479-545, or "Esterification" by J. Otera, Wiley-VCH, 2003].

Compounds of formula b, d or I of scheme 1 or 2 above, can for example be synthesised enzymatic esterification by reacting compound a, c or ingenol with an acyl donor such as an acid anhydride, an ester such as vinyl ester or a thioester in the presence of an enzyme such as a lipase or an esterase.

As depicted in scheme 3 and 4 the protected ingenol derivatives a or c may be carbamoylated to give compounds of the general formula b or d according to methods for carbamoylation of hydroxyl groups described in, but not limited to "Functions Containing a Carbonyl Group and at Least One Chalcogen (but not Halogen)" by H. Eckert in "Comprehensive Organic Functional Group Transformations II" Eds. A. R. Katritzky and R. J. K. Taylor, Vol 6, p. 440-444, Elsevier, 2005 and references cited therein. Compound b or d can for example be synthesised by reacting compound a or c with an activated carbamic acid derivative such as a carbamoyl halide such as a carbamoyl chloride. The carbamoylation by reaction with a carbamoyl chloride can take place in a suitable solvent such as acetonitrile, dichloromethane or toluene without an activator, or it can take place in the presence of a base such as pyridine, triethylamine, potassium carbonate or 4-(N,N-dimethylamino)pyridine.

Compound b or d can for example be synthesised by reacting compound a or c with an isocyanate to give N-mono-substituted carbamates. The carbamate formation by reaction with an isocyanate can take place in a suitable solvent such as dichloromethane or acetonitrile without a catalyst, or it can take place in the presence of a base such as triethylamine.

The compounds of formula I may be prepared by selective removal of the protective groups Pg from the compounds of the general structure b or d according to methods for deprotection of hydroxyl or dihydroxyl protective groups described, in but not limited to "Protective Groups in Organic Synthesis", 4th ed. P. G. M. Wuts; T. W. Greene, John Wiley, 2007 or in P. J. Kocienski, "Protecting Groups", 3rd ed. G. Thieme, 2003 and references cited therein.

Compounds of general formula I can for example be prepared from compounds of general formula d wherein Pg represents an acetal such as benzylidene acetal or a ketal such as an isopropyliden ketal by cleavage of the protecting group in the presence of a suitable acid such as aqueous hydrogen chloride, acetic acid, trifluoroacetic acid or p-toluenesulfonic acid in a suitable solvent such as methanol or aqueous tetrahydrofuran. Compounds of general formula I can for example be prepared from compounds of general formula b wherein Pg represents an alkoxyalkyl such as 2-tetrahydropyranyl by cleaving the acetal moiety, for example by acid catalysed cleavage in the presence of a suitable acid such as p-toluenesulfonic acid in a suitable solvent such as methanol.

Compounds of general formula I can for example be prepared from compounds of general formula b wherein Pg represents silyl such as tert-butyldimethylsilyl by reacting compound b with a suitable acid such as hydrogen chloride in a suitable solvent such as methanol or by reacting with a fluoride source such as tetra n-butylammonium fluoride or tetrafluorosilane in a suitable solvent such as tetrahydrofuran or acetonitrile. Compounds of general formula I can for example be prepared from compounds of general formula b wherein Pg represents triphenylmethyl by reacting compound b with a suitable acid such as formic acid or trifluoroacetic acid in a suitable solvent such as ether, methanol or dichloromethane.

EXAMPLES

General

All the starting materials used are commercially available, unless otherwise described. For 1H nuclear magnetic resonance (NMR) spectra, chemical shift values (δ) (in ppm) are quoted; tetramethylsilane (δ=0.00) is as standard. The value of a defined singlet (s), doublet (d), triplet (t), quartet (q)) or a range (m) is given. Carbamates may show duplicate signals, due to the existence of syn/anti rotamers. All organic solvents used were anhydrous, unless otherwise specified. Flash chromatography was performed on silica gel. Appropriate mixtures of ethyl acetate and heptane were used as eluents unless otherwise noted. Compounds were detected on TLC plates by development with aqueous potassium permanganate solution.

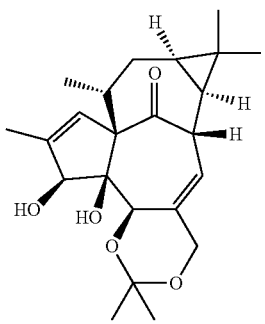

Ingenol-5,20-acetonide

Ingenol (1.00 g, 2.30 mmol) was dissolved in a solution of p-toluenesulphonic acid monohydrate in acetone (0.47 mg/mL, 22.5 mL). The solution was stirred at room temperature for 25 min. To this solution was added a saturated aqueous solution of NaHCO$_3$ (0.2 mL). The obtained mixture was concentrated in vacuo. The residue was taken up in brine and extracted with ethyl acetate. The combined organic phases were dried over sodium sulfate and concentrated in vacuo. The residue was purified by flash chromatography (heptane/ethyl acetate 19:1→heptane/ethyl acetate 0:1), giving the title compound as a white solid (616 mg, 69%). (See also: Opferkuch, H. J. et. al., Z. Naturforsch., (1981), 86b, 878-887.)

$^1$H NMR (300 MHz, CDCl$_3$) δ 5.91 (q, J=1.5 Hz, 1H), 5.79 (m, 1H), 4.25 (d, J=4.5 Hz, 1H), 4.20-4.07 (m, 3H), 3.93 (s, 1H), 3.51 (s, 1H), 2.57-2.41 (m, 2H), 2.25 (ddd, J=15.7, 8.4, 2.9 Hz, 1H), 1.85 (d, J=1.5 Hz, 3H), 1.77 (dt, J=15.8, 5.9 Hz, 1H), 1.41 (s, 3H), 1.35 (s, 3H), 1.13 (s, 3H), 1.05 (s, 3H), 1.00-0.87 (m, 4H), 0.70 (td, J=8.4, 6.4 Hz, 1H).

General Procedures for the Preparation of Compounds of General Formula II

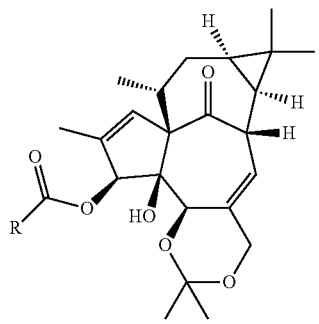

Procedure a

A mixture of carboxylic acid (0.100 mmol), dicyclohexylcarbodiimide (0.100 mmol), 4-(N,N-dimethylamino)-pyridine (0.0025 mmol) and ingenol-5,20-acetonide (0.050 mmol) were stirred at room temperature in dichloromethane for 20-24 h. The mixture was mixed with ethyl acetate, filtered and washed with saturated aqueous sodium chloride. The organic phase was dried with sodium sulphate, concentrated in vacuo and purified by flash chromatography (heptane→heptane/ethyl acetate 7:3), giving the title compound as a white solid.

Procedure b

A mixture of acyl chloride (0.0625 mmol), diisopropylethylamine (0.075 mmol), 4-(N,N-dimethylamino)-pyridine (0.070 mmol) and ingenol-5,20-acetonide (0.050 mmol) were stirred at 55° C. in tetrahydrofuran for 6-20 h. The mixture was mixed with ethyl acetate, filtered and washed with saturated aqueous sodium chloride. The organic phase was dried with sodium sulphate, concentrated in vacuo and purified by flash chromatography (heptane→heptane/ethyl acetate 7:3), giving the title compound as a white solid.

Procedure c

A mixture of carboxylic acid (0.100 mmol), dicyclohexylcarbodiimide (0.100 mmol), 4-(N,N-dimethylamino)-pyridine (0.025 mmol) and ingenol-5,20-acetonide (0.050 mmol) were stirred in a microwave oven at 150° C. in acetonitrile for 5 min. The mixture was mixed with ethyl acetate, filtered and washed with saturated aqueous sodium chloride. The organic phase was dried with sodium sulphate, concentrated in vacuo and purified by flash chromatography (heptane→heptane/ethyl acetate 7:3), giving the title compound as a white solid.

Procedure d

A mixture of acyl chloride (0.125 mmol), diisopropylethylamine (0.250 mmol), 4-(N,N-dimethylamino)-pyridine (0.025 mmol) and ingenol-5,20-acetonide (0.050 mmol) were stirred in a microwave oven at 150° C. in acetonitrile for 10-30 min. The mixture was mixed with ethyl acetate, filtered and washed with saturated aqueous sodium chloride. The organic phase was dried with sodium sulphate, concen- General Procedure for the Preparation of
Compounds of General Formula I

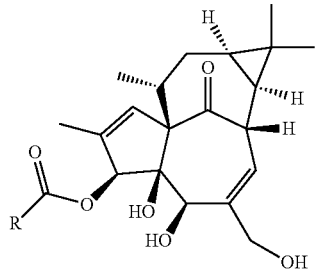

I

Procedure e

Ingenol-5,20-acetonide-3-acylate or ingenol-5,20-acetonide-3-carbamate (0.10 mmol) was dissolved in tetrahydrofuran (0.47 mL) under argon. An aqueous solution of HCl (4 M, 4.7 µL) was added. The solution was stirred at room temperature for 20-27 h. Tetrahydrofuran may be replaced with methanol and the reaction time at room temperature shortened to 0.5 h. The solution was concentrated in vacuo. The residue was purified by flash chromatography (heptane/ethyl acetate 5:1→heptane/ethyl acetate 3:7), giving the title compound. For more polar compounds a dichloromethane/methanol 98:2→dichloromethane/methanol 95:5 gradient was used.

General Procedure for the Preparation of
Carbamoyl Chlorides

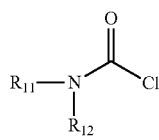

Procedure f

To a solution of a secondary amine (1.2 mmol) in dichloromethane (2 ml) at 0° C. was added potassium hydrogen carbonate (3.0 mmol) or a tertiary amine, such as triethylamine or pyridine, followed by triphosgene (1.0 mmol). The mixture was stirred at 0° C. for 2 h, filtered and washed with dichloromethane. The combined filtrates were concentrated in vacuo giving the title compound.

General Procedures for the Preparation of
Ingenol-5,20-Acetonide-3-Carbamate Compounds
of General Formula III

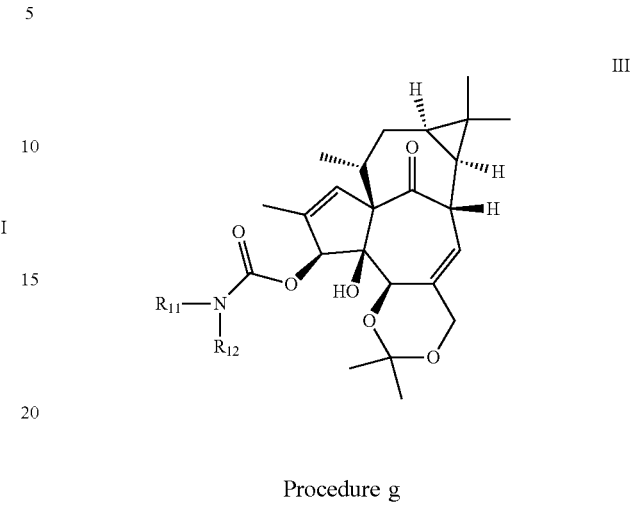

Procedure g

A mixture of a carbamoyl chloride (0.390 mmol), potassium carbonate (0.616 mmol), and ingenol-5,20-acetonide (0.077 mmol) was stirred at 80° C. in acetonitrile for 16-24 h. The mixture was filtered and washed with dichloromethane. The combined filtrates were concentrated in vacuo and purified by flash chromatography (heptane→heptane/ethyl acetate 7:3), giving the title compound.

Procedure h

A mixture of a carbamoyl chloride (0.390 mmol), potassium carbonate (0.616 mmol), and ingenol-5,20-acetonide (0.077 mmol) was stirred in a microwave oven at 160° C. in acetonitrile for 10 min. The mixture was filtered and washed with dichloromethane. The combined filtrates were concentrated in vacuo and purified by flash chromatography (heptane→heptane/ethyl acetate 7:3), giving the title compound.

Procedure i

A mixture of an isocyanate (0.231 mmol), potassium carbonate (0.385 mmol), and ingenol-5,20-acetonide (0.077 mmol) was stirred at 80° C. in acetonitrile for 16-24 h. The mixture was filtered and washed with dichloromethane. The combined filtrates were concentrated in vacuo and purified by flash chromatography (heptane→heptane/ethyl acetate 7:3), giving the title compound.

Procedure j

To a solution of ingenol-5,20-acetonide (0.10 mmol) in tetrahydrofuran at 0° C. under argon atmosphere was dropwise added 1 M lithiumbis(trimethylsilyl)amide in THF (0.10 mmol). After stirring for 10 min a carbamoyl chloride (0.20 mmol), dissolved in 0.2 ml THF, was dropwise added and the reaction mixture was slowly returned to room temperature overnight. The mixture was added 2 drops of water followed by dichloromethane (1 ml), filtrated and concentrated in vacuo. The crude product was purified by flash chromatography (heptane→heptane/ethyl acetate 7:3), giving the title compound.

General procedure for preparation of 4-aryl substituted 1-methylpyrazole-5-carboxylic acids Procedure k

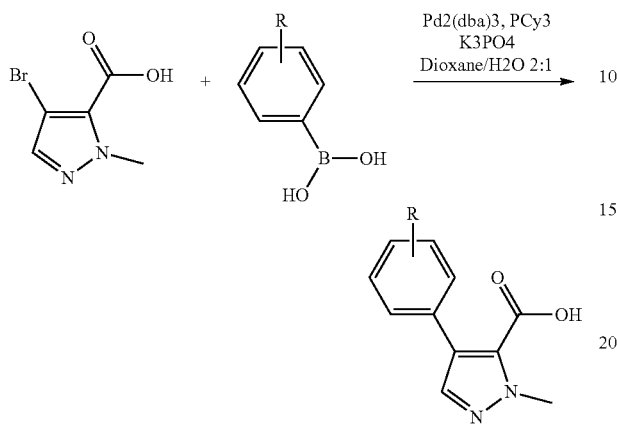

The method described by G. C. Fu et al *Angew. Chem.* 2006, 118, 1304-1306 was employed.

A heterogeneous mixture of 1-methyl-4-bromopyrazole-5-carboxylic acid (1 mmol), Tris(dibenzylideneacetone)dipalladium(0) (0.1 mmol), tricyclohexyl phosphine (0.2 mmol), potassium phosphate (3 mmol) and the appropriate phenylboronic acid (1.5 mmol), water (2 mL) and dioxane (4 mL) were stirred in an argon atmosphere in a microwave oven at 180° C. for 20 min. The mixture was cooled to room temperature and partly evaporated, added 5N aq NaOH (1 mL), washed 3 times with diethyl ether. The aqueous solution was acidified with 4N HCl, the precipitate was isolated by filtration and dried to provide the crude 4-aryl substituted 1-methylpyrazole-5-carboxylic acid which was used without further purification.

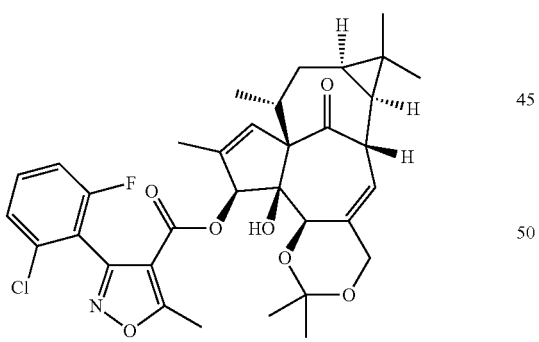

Preparation 601

Ingenol-5,20-acetonide-3-(5-methyl-3-(2-chloro-6-fluoro-phenyl)-isoxazole-4-carboxylate (Compound 601)

Compound 601 was prepared according to Procedure d.
Starting material: 5-Methyl-3-(2-chloro-6-fluoro-phenyl)-isoxazole-4-carbonyl chloride.
$^1$H NMR (300 MHz, CDCl$_3$) δ 7.41-7.33 (m, 1H), 7.27-7.24 (m, 1H), 7.08-7.02 (m, 1H), 5.85-5.84 (d, 1H), 5.76-5.74 (m, 1H), 5.57 (s, 1H), 4.23-4.06 (m, 3H), 3.94 (s, 1H), 3.18 (s, 1H), 2.82 (s, 3H), 2.21-2.12 (m, 1H), 1.96-1.90 (m, 1H), 1.69-1.62 (m, 1H), 1.61 (d, 3H), 1.47 (s, 3H), 1.39 (s, 3H), 1.03 (s, 3H), 1.03 (s, 3H), 0.90-0.78 (m, 1H), 0.73 (d, 3H), 0.66-0.58 (m, 1H).

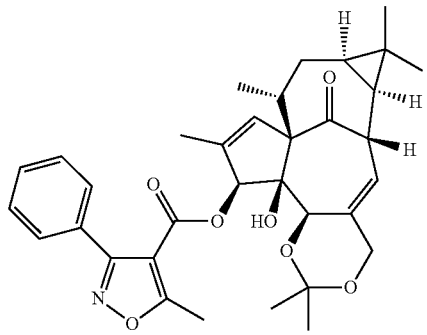 [SMILES: CC1=C[C@]23C(=O)[C@@H](C=C4COC(C)(C)O[C@H]4[C@]2(O)[C@H]1OC(=O)c1c(-c2ccccc2)noc1C)[C@H]1[C@@H](C[C@H]3C)C1(C)C]

Preparation 602

Ingenol-5,20-acetonide-3-(5-methyl-3-phenyl-isoxazole-4-carboxylate) (Compound 602)

Compound 602 was prepared according to Procedure d.
Starting material: 5-Methyl-3-phenyl-isoxazole-4-carbonyl chloride.
$^1$H NMR (300 MHz, CDCl$_3$) δ 7.57-7.53 (m, 2H), 7.47-7.37 (m, 3H), 5.95 (d, 1H), 5.76 (m, 1H), 5.68 (s, 1H), 4.23-4.04 (m, 3H), 3.97 (s, 1H), 3.12 (s, 1H), 2.77 (s, 3H), 2.11-2.01 (m, 1H), 1.95-1.87 (m, 1H), 1.72 (d, 3H), 1.59-1.49 (m, 1H), 1.45 (s, 3H), 1.40 (s, 3H), 1.04 (s, 3H), 1.03 (s, 3H), 0.90-0.80 (m, 1H), 0.71 (d, 3H), 0.65-0.57 (m, 1H).

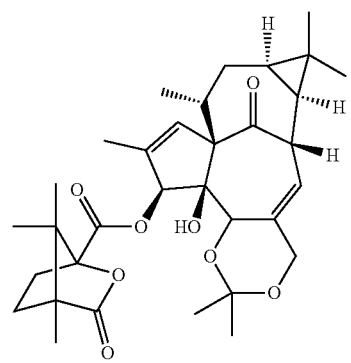

Preparation 603

Ingenol-5,20-acetonide-3-(1S-camphanate) (Compound 603)

Compound 603 was prepared according to Procedure d.
Starting material: (1S)-Camphanic chloride.
$^1$H NMR (300 MHz, CDCl$_3$) δ 6.10-6.09 (m, 1H), 5.80-5.79 (m, 1H), 5.66 (s, 1H), 4.25-4.11 (m, 3H), 4.02 (s, 1H), 3.17 (s, 1H), 2.61-2.56 (m, 1H), 2.48-2.39 (m, 1H), 2.29-2.20 (m, 1H), 2.09-2.02 (m, 1H), 1.94-1.88 (m, 1H), 1.79-1.65 (m, 5H), 1.45 (s, 3H), 1.42 (s, 3H), 1.12 (s, 3H), 1.10 (s, 3H), 1.09 (s, 3H), 1.05 (s, 3H), 0.99-0.86 (m, 7H), 0.73-0.65 (m, 1H).

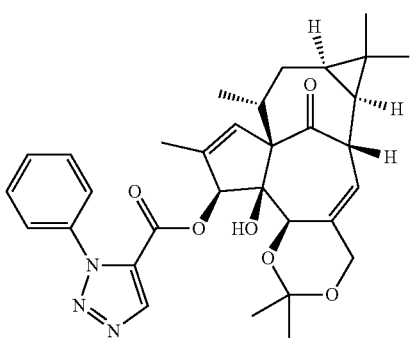 [SMILES: CC1=C[C@]23C(=O)[C@@H](C=C4COC(C)(C)O[C@H]4[C@]2(O)[C@H]1OC(=O)c1cnnn1-c1ccccc1)[C@H]1[C@@H](C[C@H]3C)C1(C)C]

Preparation 604

Ingenol-5,20-acetonide-3-(3-phenyltriazole-4-carboxylate) (Compound 604)

Compound 604 was prepared according to Procedure c. Starting material: 3-phenyltriazole-4-carboxylic acid.

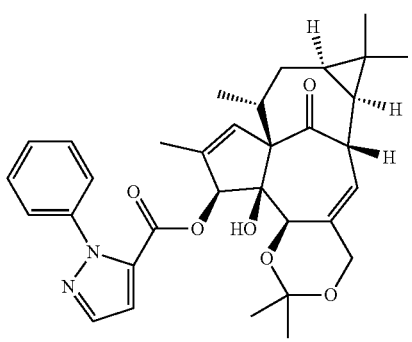 [SMILES: CC1=C[C@]23C(=O)[C@@H](C=C4COC(C)(C)O[C@H]4[C@]2(O)[C@H]1OC(=O)c1ccnn1-c1ccccc1)[C@H]1[C@@H](C[C@H]3C)C1(C)C]

Preparation 605

Ingenol-5,20-acetonide-3-(2-phenylpyrazole-3-carboxylate) (Compound 605)

Compound 605 was prepared according to Procedure h, where "carbamoyl chloride" was replaced with 2-phenylpyrazole-3-carbonyl chloride.

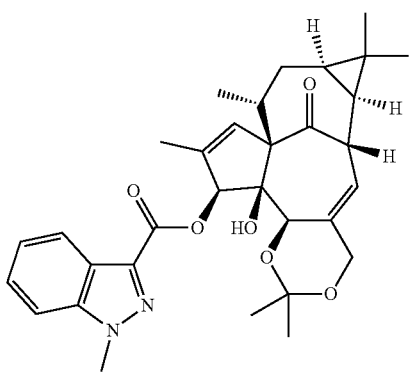 [SMILES: CC1=C[C@]23C(=O)[C@@H](C=C4COC(C)(C)O[C@H]4[C@]2(O)[C@H]1OC(=O)c1nn(C)c2ccccc12)[C@H]1[C@@H](C[C@H]3C)C1(C)C]

Preparation 606

Ingenol-5,20-acetonide-3-(1-methylindazole-3-carboxylate) (Compound 606)

Compound 606 was prepared according to Procedure h, where "carbamoyl chloride" was replaced with 1-methylindazole-3-carbonyl chloride.

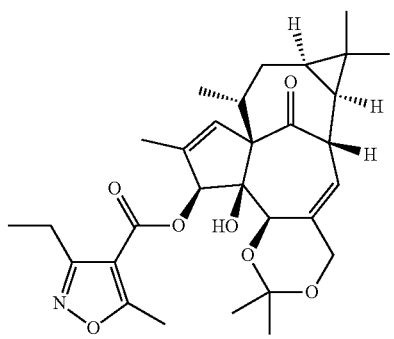 [SMILES: CCc1noc(C)c1C(=O)O[C@H]1C(C)=C[C@]23C(=O)[C@@H](C=C4COC(C)(C)O[C@H]4[C@]12O)[C@H]1[C@@H](C[C@H]3C)C1(C)C]

Preparation 607

Ingenol-5,20-acetonide-3-(3-ethyl-5-methyl-isoxazole-4-carboxylate) (Compound 607)

Compound 607 was prepared according to Procedure c. Starting material: 3-Ethyl-5-methyl-isoxazole-4-carboxylic acid.

$^1$H NMR (300 MHz, CDCl$_3$) 6.12 (m, 1H), 5.82-5.80 (m, 1H), 5.72 (s, 1H), 4.28-4.11 (m, 3H), 4.05 (s, 1H), 3.26 (s, 1H), 2.89 (q, 2H), 2.65 (s, 3H), 2.63-2.59 (m, 1H), 2.30-2.24 (m, 1H), 1.81 (d, 3H), 1.79-1.71 (m, 1H), 1.48 (s, 3H), 1.45 (s, 3H), 1.28 (t, 3H), 1.08 (s, 3H), 1.05 (s, 3H), 1.01 (d, 3H), 0.94-0.86 (m, 1H), 0.74-0.66 (m, 1H).

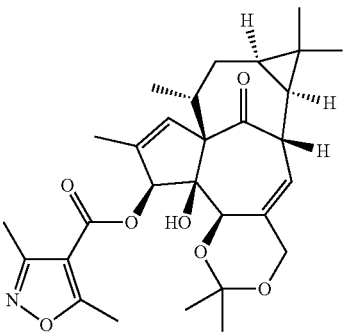

Preparation 608

Ingenol-5,20-acetonide-3-(3,5-dimethyl-isoxazole-4-carboxylate) (Compound 608)

Compound 608 was prepared according to Procedure c. Starting material: 3,5-Dimethyl-isoxazole-4-carboxylic acid.

$^1$H NMR (300 MHz, CDCl$_3$) 6.12 (s, 1H), 5.81-5.80 (m, 1H), 5.70 (s, 1H), 4.27-4.11 (m, 3H), 4.05 (s, 1H), 3.27 (s, 1H), 2.65 (s, 3H), 2.63-2.59 (m, 1H), 2.43 (s, 3H), 2.33-2.23

(m, 1H), 1.82-1.70 (m, 4H), 1.49 (s, 3H), 1.45 (s, 3H), 1.09 (s, 3H), 1.05 (s, 3H), 1.01 (d, 3H), 0.94-0.87 (m, 1H), 0.74-0.65 (m, 1H).

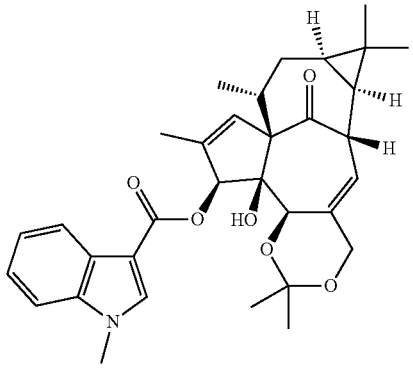 [SMILES: CC1=C[C@]23C(=O)[C@@H](C=C4COC(C)(C)O[C@H]4[C@]2(O)[C@H]1OC(=O)c1cn(C)c2ccccc12)[C@H]1[C@@H](C[C@H]3C)C1(C)C]

Preparation 609

Ingenol-5,20-acetonide-3-(1-methylindole-3-carboxylate) (Compound 609)

Compound 609 was prepared according to Procedure c.
Starting material: 1-methylindole-3-carboxylic acid.

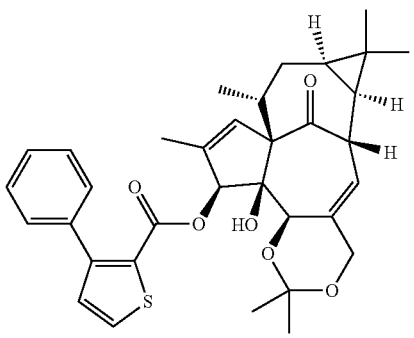 [SMILES: CC1=C[C@]23C(=O)[C@@H](C=C4COC(C)(C)O[C@H]4[C@]2(O)[C@H]1OC(=O)c1sccc1-c1ccccc1)[C@H]1[C@@H](C[C@H]3C)C1(C)C]

Preparation 610

Ingenol-5,20-acetonide-3-(3-phenylthiophene-2-carboxylate) (Compound 610)

Compound 610 was prepared according to Procedure c.
Starting material: 3-Phenylthiophene-2-carboxylic acid.

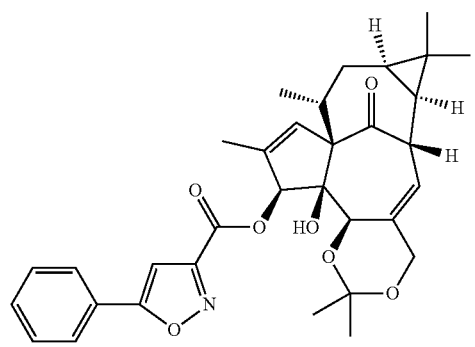 [SMILES: CC1=C[C@]23C(=O)[C@@H](C=C4COC(C)(C)O[C@H]4[C@]2(O)[C@H]1OC(=O)c1cc(-c2ccccc2)on1)[C@H]1[C@@H](C[C@H]3C)C1(C)C]

Preparation 611

Ingenol-520-acetonide-3-(5-phenylisoxazole-3-carboxylate) (Compound 611)

Compound 611 was prepared according to Procedure d.
Starting material: 5-Phenylisoxazole-3-carbonyl chloride.
$^1$H NMR (300 MHz, CDCl$_3$) 7.83-7.78 (m, 2H), 7.52-7.47 (m, 3H), 6.90 (s, 1H), 6-16-6.15 (m, 1H), 5.81 (m, 2H), 4.28-4.08 (m, 4H), 3.29 (s, 1H), 2.73-2.68 (m, 1H), 2.30-2.21 (m, 1H), 1.85 (d, 3H), 1.82-1.75 (m, 1H), 1.50 (s, 3H), 1.47 (s, 3H), 1.08 (s, 3H), 1.05 (d, 3H), 1.04 (s, 3H), 0.95-0.88 (m, 1H), 0.74-0.67 (m, 1H).

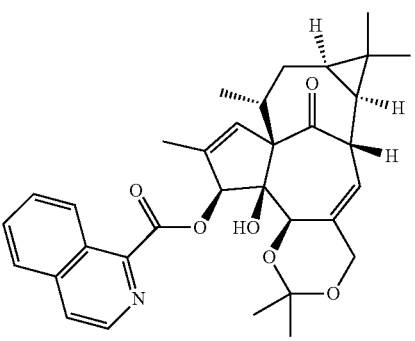 [SMILES: CC1=C[C@]23C(=O)[C@@H](C=C4COC(C)(C)O[C@H]4[C@]2(O)[C@H]1OC(=O)c1nccc2ccccc12)[C@H]1[C@@H](C[C@H]3C)C1(C)C]

Preparation 612

Ingenol-5,20-acetonide-3-(isoquinoline-1-carboxylate) (Compound 612)

Compound 612 was prepared according to Procedure c.
Starting material: Isoquinoline-1-carboxylic acid.
$^1$H NMR (300 MHz, CDCl$_3$) δ 8.76-8.73 (m, 1H), 8.58 (d, 1H), 7.90 (d, 1H), 7.81 (d, 1H), 7.77-7.72 (m, 1H), 7.70-7.64 (m, 1H), 6.15 (m, 1H), 6.00 (s, 1H), 5.82-5.80 (m, 1H), 4.47 (s, 1H), 4.29-4.22 (m, 3H), 4.10 (s, 1H), 2.74-2.69 (m, 1H), 2.45-2.35 (m, 1H), 1.90 (d, 3H), 1.87-1.80 (m, 1H), 1.49 (s, 3H), 1.47 (s, 3H), 1.15 (s, 3H), 1.07 (s, 3H), 0.98-0.88 (m, 4H), 0.77-0.69 (m, 1H).

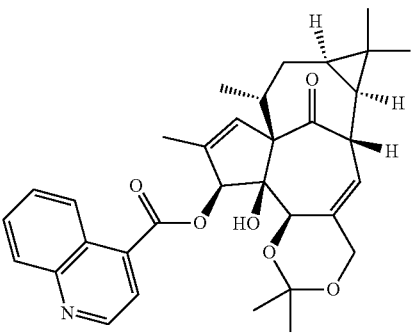 [SMILES: CC1=C[C@]23C(=O)[C@@H](C=C4COC(C)(C)O[C@H]4[C@]2(O)[C@H]1OC(=O)c1ccnc2ccccc12)[C@H]1[C@@H](C[C@H]3C)C1(C)C]

Preparation 613

Ingenol-5,20-acetonide-3-(quinoline-4-carboxylate) (Compound 613)

Compound 613 was prepared according to Procedure c.
Starting material: Quinoline-4-carboxylic acid.

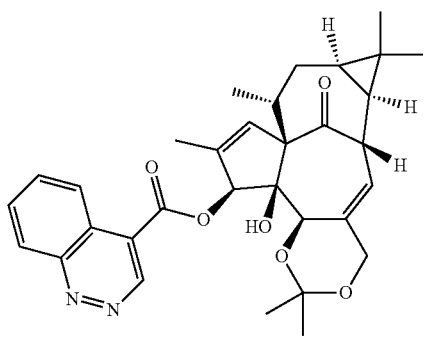 [SMILES: CC1=C[C@]23C(=O)[C@@H](C=C4COC(C)(C)O[C@H]4[C@]2(O)[C@H]1OC(=O)c1cnnc2ccccc12)[C@H]1[C@@H](C[C@H]3C)C1(C)C]

Preparation 614

Ingenol-5,20-acetonide-3-(cinnoline-4-carboxylate) (Compound 614)

Compound 614 was prepared according to Procedure c.
Starting material: Cinnoline-4-carboxylic acid.
$^1$H NMR (300 MHz, CDCl$_3$) δ 9.71 (s, 1H), 8.94-8.91 (m, 1H), 8.67-8.64 (m, 1H), 7.96-7.86 (m, 2H), 6.21-6.20 (m, 1H), 5.93 (s, 1H), 5.85-5.84 (m, 1H), 4.32-4.13 (m, 4H), 3.36 (s, 1H), 2.74-2.69 (m, 1H), 2.38-2.28 (m, 1H), 1.87 (d, 3H), 1.86-1.79 (m, 1H), 1.53 (s, 3H), 1.52 (s, 3H), 1.09 (s, 3H), 1.05 (s, 3H), 1.04 (d, 3H), 0.96-0.89 (m, 1H), 0.77-0.69 (m, 1H).

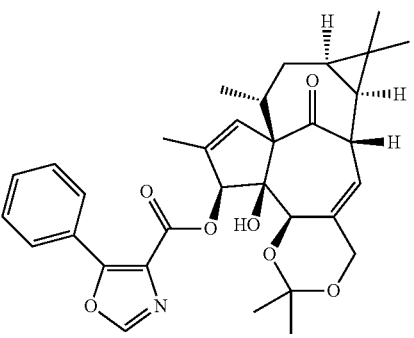

Preparation 616

Ingenol-5,20-acetonide-3-(5-phenyloxazole-4-carboxylate) (Compound 616)

Compound 616 was prepared according to Procedure c.
Starting material: 5-Phenyloxazole-4-carboxylic acid.
$^1$H NMR (300 MHz, CDCl$_3$) δ 7.95-7.91 (m, 3H), 7.48-7.42 (m, 3H), 6.07-6.06 (m, 1H), 5.78-5.75 (m, 2H), 4.24-4.08 (m, 3H), 4.03-4.02 (m, 1H), 3.39 (s, 1H), 2.37-2.29 (m, 1H), 2.20-2.11 (m, 1H), 1.83 (d, 3H), 1.68-1.58 (m, 1H), 1.47 (s, 3H), 1.43 (s, 3H), 1.05 (s, 3H), 1.03 (s, 3H), 0.91-0.84 (m, 1H) 0.84 (d, 3H), 0.68-0.60 (m, 1H).

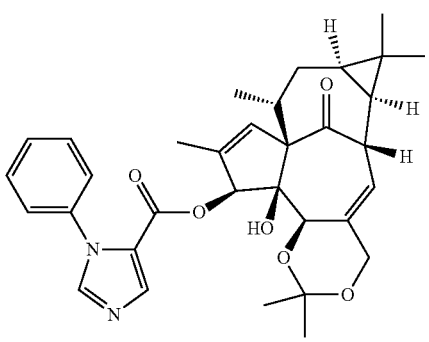 [SMILES: CC1=C[C@]23C(=O)[C@@H](C=C4COC(C)(C)O[C@H]4[C@]2(O)[C@H]1OC(=O)c1cncn1-c1ccccc1)[C@H]1[C@@H](C[C@H]3C)C1(C)C]

Preparation 615

Ingenol-5,20-acetonide-3-(3-phenylimidazole-4-carboxylate) (Compound 615)

Compound 615 was prepared according to Procedure c.
Starting material: 3-Phenylimidazole-4-carboxylic acid.
$^1$H NMR (300 MHz, CDCl$_3$) δ 7.89 (d, 1H), 7.67 (d, 1H), 7.48-7.45 (m, 3H), 7.35-7.32 (m, 2H), 6.00-5.99 (m, 1H), 5.77-5.76 (m, 1H), 5.62 (s, 1H), 4.22-4.07 (m, 3H), 3.97 (bs, 1H), 3.17 (s, 1H), 2.34-2.29 (m, 1H), 2.25-2.16 (m, 1H), 1.76-1.67 (m, 4H), 1.40 (s, 3H), 1.37 (s, 3H), 1.07 (s, 3H), 1.04 (s, 3H), 0.92-0.84 (m, 4H), 0.71-0.63 (m, 1H).

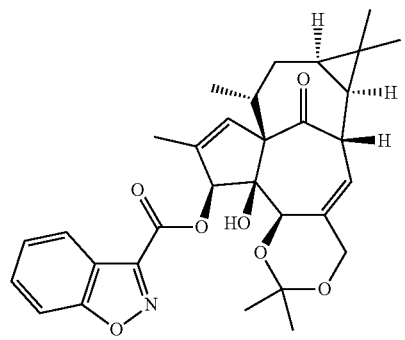 [SMILES: CC1=C[C@]23C(=O)[C@@H](C=C4COC(C)(C)O[C@H]4[C@]2(O)[C@H]1OC(=O)c1noc2ccccc12)[C@H]1[C@@H](C[C@H]3C)C1(C)C]

Preparation 617

Ingenol-5,20-acetonide-3-(1,2-benzoxazole-3-carboxylate) (Compound 617)

Compound 617 was prepared according to Procedure c.
Starting material: 1,2-Benzoxazole-3-carboxylic acid.
$^1$H NMR (300 MHz, CDCl$_3$) δ 8.14-8.11 (m, 1H), 7.70-7.60 (m, 2H), 7.46-7.39 (m, 1H), 6.21-6.19 (m, 1H), 5.89 (s, 1H), 5.83-5.81 (m, 1H), 4.30-4.11 (m, 4H), 3.34 (s, 1H), 2.77-2.72 (m, 1H), 2.30-2.21 (m, 1H), 1.89 (d, 3H), 1.81-1.72 (m, 1H), 1.52 (s, 3H), 1.49 (s, 3H), 1.07 (s, 3H), 1.05 (d, 3H), 1.04 (s, 3H), 0.95-0.88 (m, 1H), 0.74-0.66 (m, 1H).

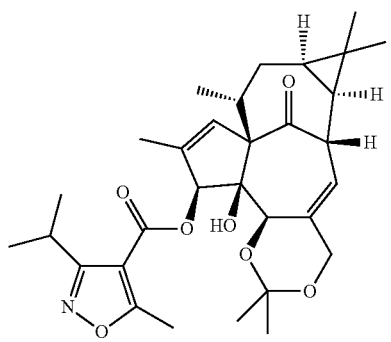 [SMILES: CC1=C[C@]23C(=O)[C@@H](C=C4COC(C)(C)O[C@H]4[C@]2(O)[C@H]1OC(=O)c1c(C(C)C)noc1C)[C@H]1[C@@H](C[C@H]3C)C1(C)C]

Preparation 618

Ingenol-5,20-acetonide-3-(3-isopropyl-5-methyl-isoxazole-4-carboxylate) (Compound 618)

Compound 618 was prepared according to Procedure c.

Starting material: 3-Isopropyl-5-methyl-isoxazole-4-carboxylic acid.

$^1$H NMR (300 MHz, CDCl$_3$) δ 6.12-6.11 (m, 1H), 5.82-5.79 (m, 1H), 5.73 (s, 1H), 4.28-4.10 (m, 3H), 4.06-4.05 (m, 1H), 3.46 (septet, 1H), 3.26 (s, 1H), 2.65 (s, 3H), 2.63-2.57 (m, 1H), 2.33-2.24 (m, 1H), 1.81 (d, 3H), 1.79-1.70 (m, 1H), 1.48 (s, 3H), 1.46 (s, 3H), 1.33 (d, 3H), 1.31 (d, 3H), 1.08 (s, 3H), 1.05 (s, 3H), 1.00 (d, 3H), 0.94-0.87 (m, 1H), 0.74-0.66 (m, 1H).

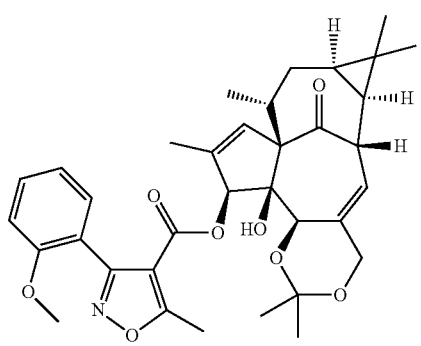 [SMILES: COc1ccccc1-c1noc(C)c1C(=O)O[C@H]1C(C)=C[C@]23C(=O)[C@@H](C=C4COC(C)(C)O[C@H]4[C@]12O)[C@H]1[C@@H](C[C@H]3C)C1(C)C]

Preparation 619

Ingenol-5,20-acetonide-3-(3-(2-methoxyphenyl)-5-methyl-isoxazole-4-carboxylate) (Compound 619)

Compound 619 was prepared according to Procedure c.

Starting material: 3-(2-Methoxyphenyl)-5-methyl-isoxazole-4-carboxylic acid.

$^1$H NMR (300 MHz, CDCl$_3$) δ 7.44-7.35 (m, 2H), 7.04-6.99 (m, 1H), 6.96-6.92 (d, 1H), 5.93-5.91 (m, 1H), 5.75-5.72 (m, 1H), 5.67 (s, 1H), 4.20-4.13 (m, 2H), 4.06-4.00 (m, 1H), 3.92 (s, 1H), 3.76 (s, 3H), 2.98 (s, 1H), 2.74 (s, 3H), 2.03-1.95 (m, 1H), 1.87-1.78 (m, 1H), 1.69 (d, 3H), 1.58-1.50 (m, 1H), 1.42 (s, 3H), 1.38 (s, 3H), 1.04 (s, 3H), 1.03 (s, 3H), 0.88-0.80 (m, 1H), 0.76 (d, 3H), 0.66-0.58 (m, 1H).

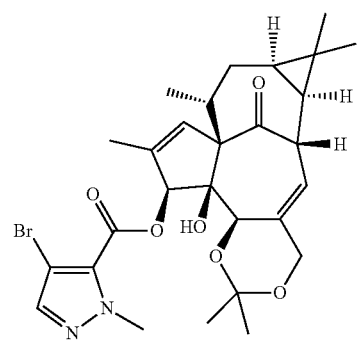 [SMILES: CC1=C[C@]23C(=O)[C@@H](C=C4COC(C)(C)O[C@H]4[C@]2(O)[C@H]1OC(=O)c1c(Br)cnn1C)[C@H]1[C@@H](C[C@H]3C)C1(C)C]

Preparation 620

Ingenol-5,20-acetonide-3-(4-bromo-2-methyl-pyrazole-3-carboxylate) (Compound 620)

Compound 620 was prepared according to Procedure c.
Starting material: 4-Bromo-2-methyl-pyrazole-3-carboxylic acid.

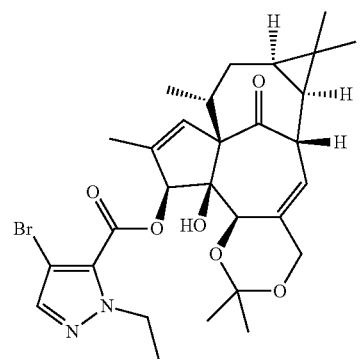 [SMILES: CCn1ncc(Br)c1C(=O)O[C@H]1C(C)=C[C@]23C(=O)[C@@H](C=C4COC(C)(C)O[C@H]4[C@]12O)[C@H]1[C@@H](C[C@H]3C)C1(C)C]

Preparation 621

Ingenol-5,20-acetonide-3-(4-bromo-2-ethyl-pyrazole-3-carboxylate) (Compound 621)

Compound 621 was prepared according to Procedure c.
Starting material: 4-Bromo-2-ethyl-pyrazole-3-carboxylic acid.

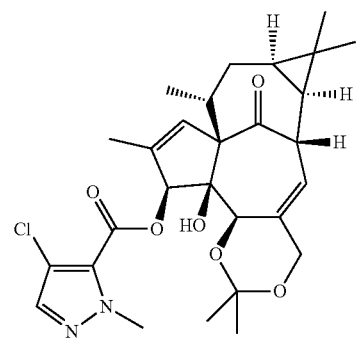 [SMILES: CC1=C[C@]23C(=O)[C@@H](C=C4COC(C)(C)O[C@H]4[C@]2(O)[C@H]1OC(=O)c1c(Cl)cnn1C)[C@H]1[C@@H](C[C@H]3C)C1(C)C]

Preparation 622

Ingenol-5,20-acetonide-3-(4-chloro-2-methyl-pyrazole-3-carboxylate) (Compound 622)

Compound 622 was prepared according to Procedure c.
Starting material: 4-Chloro-2-methyl-pyrazole-3-carboxylic acid.

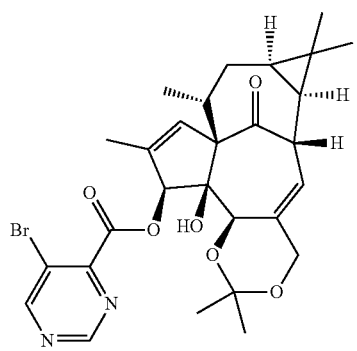 [SMILES: CC1=C[C@]23C(=O)[C@@H](C=C4COC(C)(C)O[C@H]4[C@]2(O)[C@H]1OC(=O)c1ncncc1Br)[C@H]1[C@@H](C[C@H]3C)C1(C)C]

Preparation 623

Ingenol-5,20-acetonide-3-(5-bromopyrimidine-4-carboxylate) (Compound 623)

Compound 623 was prepared according to Procedure d, but extending the reaction time to 40 min.
Starting material: 5-Bromopyrimidine-4-carbonyl chloride, prepared from 5-bromopyrimidine-4-carboxylic acid by reaction with 1.25 eq. oxalyl chloride in dichloromethane and a drop of dimethylformamide at room temperature for 30 min followed by evaporation of volatiles in vacuum.

$^1$H NMR (300 MHz, CDCl$_3$) δ 9.20 (s, 1H), 9.00 (s, 1H), 6.16-6.14 (m, 1H), 5.85 (s, 1H), 5.83-5.80 (m, 1H), 4.27-4.14 (m, 3H), 4.07-4.06 (m, 1H), 3.44 (s, 1H), 2.66-2.59 (m, 1H), 2.31-2.22 (m, 1H), 1.88 (d, 3H), 1.79-1.70 (m, 1H), 1.49 (s, 3H), 1.46 (s, 3H), 1.09 (s, 3H), 1.05 (s, 3H), 0.96 (d, 3H), 0.95-0.88 (m, 1H), 0.73-0.65 (m, 1H).

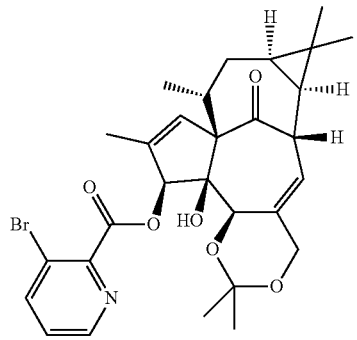 [SMILES: CC1=C[C@]23C(=O)[C@@H](C=C4COC(C)(C)O[C@H]4[C@]2(O)[C@H]1OC(=O)c1ncccc1Br)[C@H]1[C@@H](C[C@H]3C)C1(C)C]

Preparation 624

Ingenol-5,20-acetonide-3-(3-bromopyridine-2-carboxylate) (Compound 624)

Compound 624 was prepared according to Procedure d, but extending the reaction time to 40 min.

Starting material: 3-Bromopyridine-2-carbonyl chloride, prepared from 3-bromopyridine-2-carboxylic acid by reaction with 1.25 eq. oxalyl chloride in dichloromethane and a drop of dimethylformamide at room temperature for 30 min followed by evaporation of volatiles in vacuum.

$^1$H NMR (300 MHz, CDCl$_3$) δ 8.60 (dd, 1H), 7.99 (dd, 1H), 7.30 (dd, 1H), 6.13-6.12 (m, 1H), 5.89 (s, 1H), 5.80-5.77 (m, 1H), 4.20-4.15 (m, 3H), 4.05 (s, 1H), 3.85 (s, 1H), 2.70-2.60 (m, 1H), 2.32-2.23 (m, 1H), 1.89 (d, 3H), 1.80-1.71 (m, 1H), 1.47 (s, 3H), 1.44 (s, 3H), 1.10 (s, 3H), 1.05 (s, 3H), 0.96 (d, 3H), 0.95-0.89 (m, 1H), 0.73-0.85 (m, 1H).

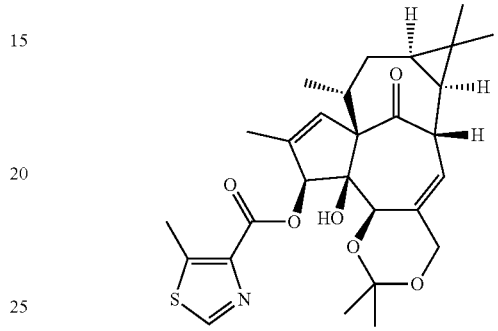

Preparation 625

Ingenol-5,20-acetonide-3-(5-methylthiazole-4-carboxylate) (Compound 625)

Compound 625 was prepared according to Procedure c.
Starting material: 5-Methylthiazole-4-carboxylic acid.

$^1$H NMR (300 MHz, CDCl$_3$) δ 8.85 (s, 1H), 6.13-6.11 (m, 1H), 5.79-5.77 (m, 2H), 4.25-4.13 (m, 3H), 4.06-4.05 (m, 1H), 3.50 (s, 1H), 2.78 (s, 3H), 2.72-2.67 (m, 1H), 2.31-2.22 (m, 1H), 1.85 (d, 3H), 1.81-1.72 (m, 1H), 1.48 (s, 3H), 1.45 (s, 3H), 1.08 (s, 3H), 1.05 (s, 3H), 1.02 (d, 3H), 0.95-0.88 (m, 1H), 0.74-0.66 (m, 1H).

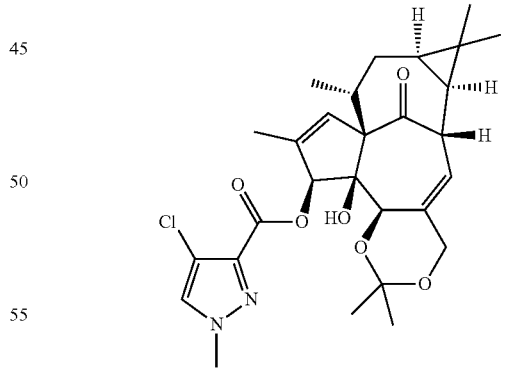

Preparation 626

Ingenol-5,20-acetonide-3-(4-chloro-1-methyl-pyrazole-3-carboxylate) (Compound 626)

Compound 626 was prepared according to Procedure c.
Starting material: 4-Chloro-1-methyl-pyrazole-3-carboxylic acid.

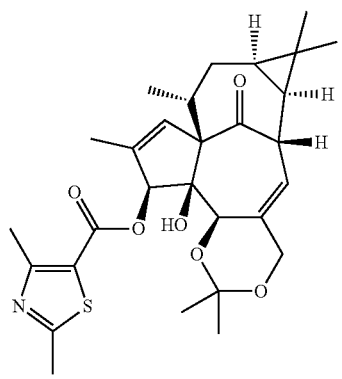

Preparation 627

Ingenol-5,20-acetonide-3-(2,4-dimethylthiazole-5-carboxylate) (Compound 627)

Compound 627 was prepared according to Procedure c.
Starting material: 2,4-Dimethylthiazole-5-carboxylic acid.
$^1$H NMR (300 MHz, CDCl$_3$) δ 6.10-6.09 (m, 1H), 5.80-5.79 (m, 1H), 5.68 (s, 1H), 4.26-4.12 (m, 3H), 4.04-4.03 (m, 1H), 3.22 (s, 1H), 2.70 (s, 3H), 2.68 (s, 3H), 2.68-2.63 (m, 1H), 2.32-2.22 (m, 1H), 1.82-1.73 (m, 4H), 1.48 (s, 3H), 1.44 (s, 3H), 1.08 (s, 3H), 1.05 (s, 3H), 1.02 (d, 3H), 0.94-0.88 (m, 1H), 0.74-0.66 (m, 1H).

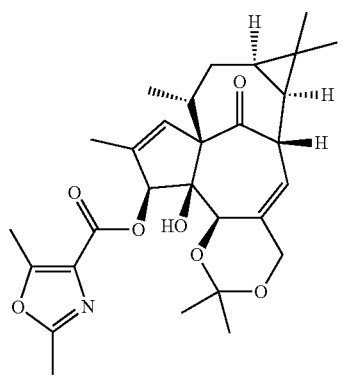

Preparation 628

Ingenol-5,20-acetonide-3-(2,5-dimethyloxazole-4-carboxylate) (Compound 628)

Compound 628 was prepared according to Procedure c.
Starting material: 2,5-Dimethyloxazole-4-carboxylic acid.
$^1$H NMR (300 MHz, CDCl$_3$) δ 6.10-6.09 (m, 1H), 5.80-5.78 (m, 1H), 5.73 (s, 1H), 4.27-4.12 (m, 3H), 4.04 (bs, 1H), 3.37 (s, 1H), 2.67-2.62 (m, 1H), 2.55 (s, 3H), 2.43 (s, 3H), 2.31-2.22 (m, 1H), 1.82 (d, 3H), 1.79-1.71 (m, 1H), 1.47 (s, 3H), 1.41 (s, 3H), 1.08 (s, 3H), 1.04 (s, 3H), 1.01 (d, 3H), 0.94-0.87 (m, 1H), 0.73-0.65 (m, 1H).

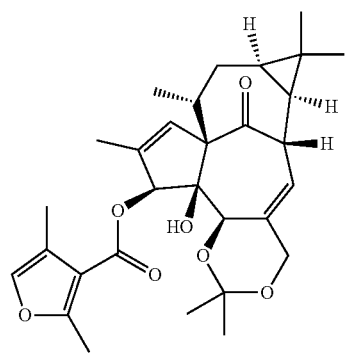 [SMILES: CC1=C[C@]23C(=O)[C@@H](C=C4COC(C)(C)O[C@H]4[C@]2(O)[C@H]1OC(=O)c1c(C)coc1C)[C@H]1[C@@H](C[C@H]3C)C1(C)C]

Preparation 629

Ingenol-5,20-acetonide-3-(2,4-dimethylfuran-3-carboxylate) (Compound 629)

Compound 629 was prepared according to Procedure d.
Starting material: 2,4-Dimethylfuran-3-carbonyl chloride.
$^1$H NMR (300 MHz, CDCl$_3$) δ 7.05 (q, 1H), 6.09-6.08 (m, 1H), 6.80-6.78 (m, 1H), 5.73 (s, 1H), 4.26-4.12 (m, 3H), 4.05 (s, 1H), 3.34 (s, 1H), 2.69-2.62 (m, 1H), 2.54 (s, 3H), 2.33-2.24 (m, 1H), 2.13 (d, 3H), 1.81 (d, 3H), 1.78-1.69 (m, 1H), 1.48 (s, 3H), 1.44 (s, 3H), 1.08 (s, 3H), 1.05 (s, 3H), 1.00 (d, 3H), 0.91-0.86 (m, 1H), 0.74-0.65 (m, 1H).

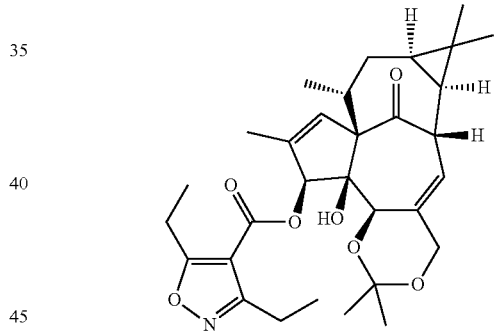

Preparation 630

Ingenol-5,20-acetonide-3-(3,5-diethylisoxazole-4-carboxylate) (Compound 630)

Compound 630 was prepared according to Procedure d.
Starting material: 3,5-Diethylisoxazole-4-carbonyl chloride, prepared from 3,5-diethylisoxazole-4-carboxylic acid by reaction with 1.25 eq. oxalyl chloride in dichloromethane and a drop of dimethylformamide at room temperature for 30 min followed by evaporation of volatiles in vacuum.
$^1$H NMR (300 MHz, CDCl$_3$) δ 6.13-6.11 (m, 1H), 5.82-5.80 (m, 1H), 5.73 (s, 1H), 4.28-4.11 (m, 3H), 4.05 (m, 1H), 3.26 (s, 1H), 3.09 (q, 2H), 2.89 (q, 2H), 2.62-2.57 (m, 1H), 2.34-2.24 (m, 1H), 1.81 (d, 3H), 1.79-1.70 (m, 1H), 1.48 (s, 3H), 1.45 (s, 3H), 1.30 (t, 3H), 1.29 (t, 3H), 1.08 (s, 3H), 1.05 (s, 3H), 1.01 (d, 3H), 0.93-0.87 (m, 1H), 0.74-0.66 (m, 1H).

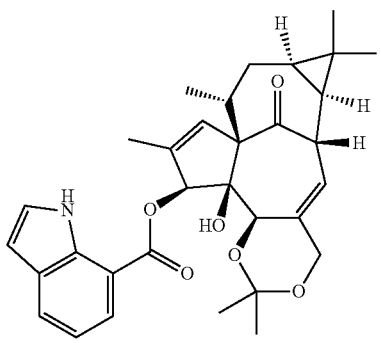 [SMILES: CC1=C[C@]23C(=O)[C@@H](C=C4COC(C)(C)O[C@H]4[C@]2(O)[C@H]1OC(=O)c1cccc2cc[nH]c12)[C@H]1[C@@H](C[C@H]3C)C1(C)C]

Preparation 631

Ingenol-5,20-acetonide-3-(1H-indole-7-carboxylate) (Compound 631)

Compound 631 was prepared according to Procedure c.
Starting material: 1H-Indole-7-carboxylic acid.

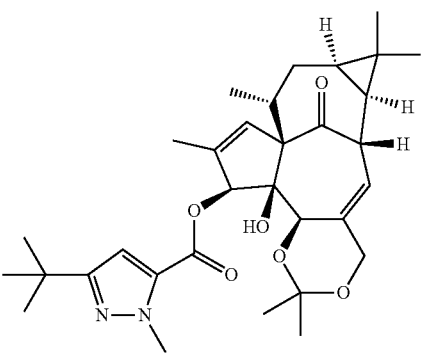

Preparation 633

Ingenol-5,20-acetonide-3-(5-tert-butyl-2-methyl-pyrazole-3-carboxylate) (Compound 633)

Compound 633 was prepared according to Procedure c, but replacing acetonitrile with N,N-dimethylformamide.
Starting material: 5-tert-Butyl-2-methyl-pyrazole-3-carboxylic acid.

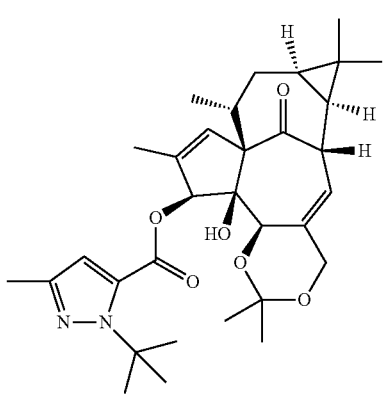

Preparation 632

Ingenol-5,20-acetonide-3-(2-tert-butyl-5-methyl-pyrazole-3-carboxylate) (Compound 632)

Compound 632 was prepared according to Procedure c, but replacing acetonitrile with N,N-dimethylformamide.
Starting material: 2-tert-Butyl-5-methyl-pyrazole-3-carboxylic acid.
$^1$H NMR (300 MHz, CDCl$_3$) δ 6.61 (s, 1H), 6.08-6.06 (m, 1H), 5.82-5.79 (m, 1H), 5.70 (s, 1H), 4.28-4.10 (m, 3H), 4.05-4.04 (m, 1H), 3.19 (s, 1H), 2.67-2.61 (m, 1H), 2.31-2.22 (m, 4H), 1.83-1.74 (m, 4H), 1.70 (s, 9H), 1.47 (s, 3H), 1.46 (s, 3H), 1.10 (s, 3H), 1.05 (s, 3H), 1.01 (d, 3H), 0.95-0.90 (m, 1H), 0.74-0.67 (m, 1H).

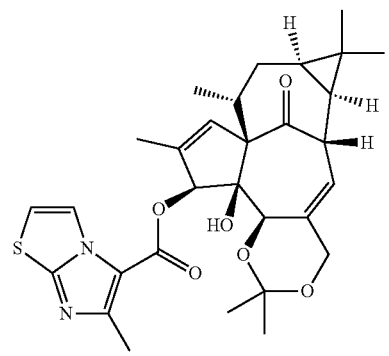 [SMILES: CC1=C[C@]23C(=O)[C@@H](C=C4COC(C)(C)O[C@H]4[C@]2(O)[C@H]1OC(=O)c1c(C)nc2sccn12)[C@H]1[C@@H](C[C@H]3C)C1(C)C]

Preparation 634

Ingenol-5,20-acetonide-3-(6-methylimidazo[2,1-b]thiazole-5-carboxylate) (Compound 634)

Compound 634 was prepared according to Procedure c, but replacing acetonitrile with N,N-dimethylformamide.
Starting material: 6-Methylimidazo[2,1-b]thiazole-5-carboxylic acid.

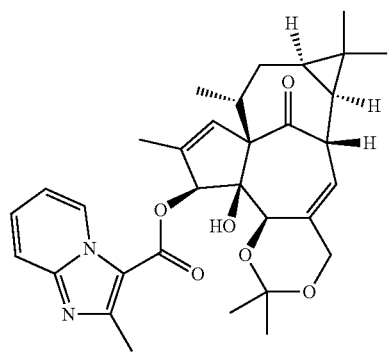 [SMILES: CC1=C[C@]23C(=O)[C@@H](C=C4COC(C)(C)O[C@H]4[C@]2(O)[C@H]1OC(=O)c1c(C)nc2ccccn12)[C@H]1[C@@H](C[C@H]3C)C1(C)C]

Preparation 635

Ingenol-5,20-acetonide-3-(2-methylimidazo[1,2-a]pyridine-3-carboxylate) (Compound 635)

Compound 635 was prepared according to Procedure c, but replacing acetonitrile with N,N-dimethylformamide.

Starting material: 2-Methylimidazo[1,2-a]pyridine-3-carboxylic acid.

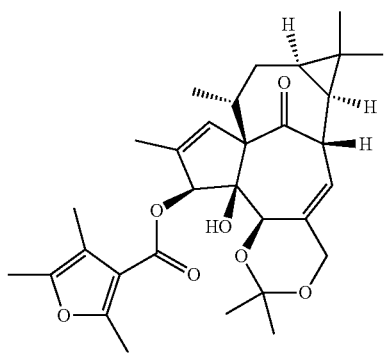

Preparation 636

Ingenol-5,20-acetonide-3-(2,4,5-trimethylfuran-3-carboxylate) (Compound 636)

Compound 636 was prepared according to Procedure c.
Starting material: 2,4,5-Trimethylfuran-3-carboxylic acid.

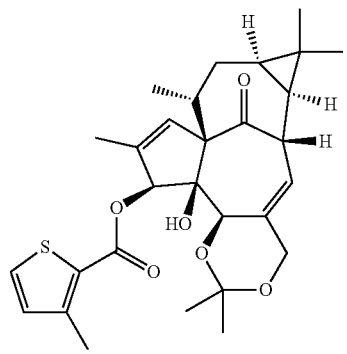 [SMILES: CC1=C[C@]23C(=O)[C@@H](C=C4COC(C)(C)O[C@H]4[C@]2(O)[C@H]1OC(=O)c1sccc1C)[C@H]1[C@@H](C[C@H]3C)C1(C)C]

Preparation 637

Ingenol-5,20-acetonide-3-(3-methylthiophene-2-carboxylate) (Compound 637)

Compound 637 was prepared according to Procedure c.
Starting material: 3-Methylthiophene-2-carboxylic acid.

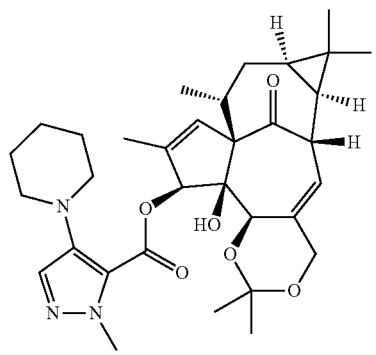 [SMILES: CC1=C[C@]23C(=O)[C@@H](C=C4COC(C)(C)O[C@H]4[C@]2(O)[C@H]1OC(=O)c1c(N2CCCCC2)cnn1C)[C@H]1[C@@H](C[C@H]3C)C1(C)C]

Preparation 638

Ingenol-5,20-acetonide-3-(2-methyl-4-(1-piperidyl)pyrazole-3-carboxylate) (Compound 638)

Compound 638 was prepared according to Procedure d.
Starting material: 2-Methyl-4-(1-piperidyl)pyrazole-3-carbonyl chloride, prepared from 2-methyl-4-(1-piperidyl)pyrazole-3-carboxylic acid by reaction with 1.25 eq. oxalyl chloride in dichloromethane and a drop of dimethylformamide at room temperature for 30 min followed by evaporation of volatiles in vacuum.

$^1$H NMR (300 MHz, CDCl$_3$) δ 7.27 (s, 1H), 6.15-6.13 (m, 1H), 5.80-5.76 (m, 2H), 4.26-4.4.10 (m, 6H), 4.05-4.04 (m, 1H), 3.58 (s, 1H), 2.99-2.83 (m, 4H), 2.77-2.72 (m, 1H), 2.31-2.21 (m, 1H), 1.84 (d, 3H), 1.76-1.51 (m, 7H), 1.49 (s, 3H), 1.44 (s, 3H), 1.07 (s, 3H), 1.04 (s, 3H), 1.01 (d, 3H), 0.93-0.86 (m, 1H), 0.72-0.64 (m, 1H).

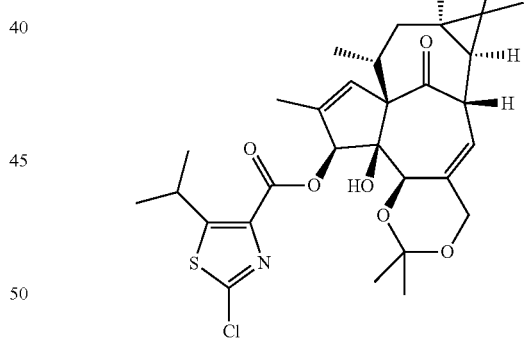

Preparation 639

Ingenol-5,20-acetonide-3-(2-chloro-5-isopropyl-thiazole-4-carboxylate) (Compound 639)

Compound 639 was prepared according to Procedure c.
Starting material: 2-chloro-5-isopropyl-thiazole-4-carboxylic acid.

$^1$H NMR (300 MHz, CDCl$_3$) δ 6.13-6.12 (m, 1H), 5.80-5.77 (m, 2H), 4.25-4.03 (m, 5H), 3.46 (s, 1H), 2.70-2.65 (m, 1H), 2.33-2.23 (m, 1H), 1.83 (d, 3H), 1.81-1.74 (m, 1H), 1.47 (s, 3H), 1.43 (s, 3H), 1.32 (d, 6H), 1.09 (s, 3H), 1.05 (s, 3H), 1.02 (d, 3H), 0.95-0.88 (m, 1H), 0.74-0.66 (m, 1H).

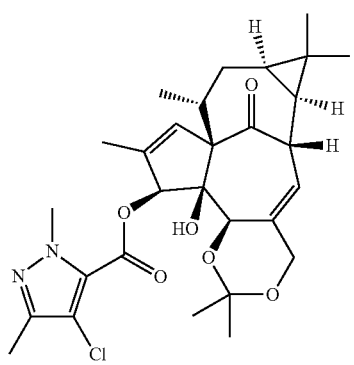

Preparation 640

Ingenol-5,20-acetonide-3-(4-chloro-2,5-dimethyl-pyrazole-3-carboxylate) (Compound 640)

Compound 640 was prepared according to Procedure c.
Starting material: 4-Chloro-2,5-dimethyl-pyrazole-3-carboxylic acid.

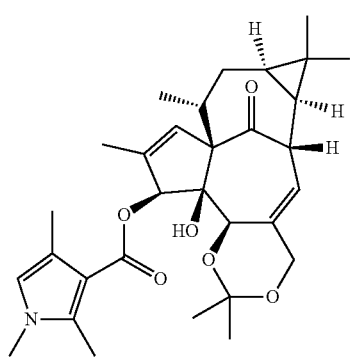

Preparation 641

Ingenol-5,20-acetonide-3-(1,2,4-trimethylpyrrole-3-carboxylate) (Compound 641)

Compound 641 was prepared according to Procedure c.
Starting material: 1,2,4-Trimethylpyrrole-3-carboxylic acid.
$^1$H NMR (300 MHz, CDCl$_3$) δ 6.28 (m, 1H), 6.06-6.04 (m, 1H), 5.78-5.75 (m, 2H), 4.21-4.15 (m, 3H), 4.05-4.04 (m, 1H), 3.52 (s, 1H), 3.46 (s, 3H), 2.73-2.68 (m, 1H), 2.48 (s, 3H), 2.33-2.23 (m, 1H), 2.20 (s, 3H), 1.81 (d, 3H), 1.78-1.68 (m, 1H), 1.48 (s, 3H), 1.43 (s, 3H), 1.07 (s, 3H), 1.04 (s, 3H), 0.99 (d, 3H), 0.93-0.86 (m, 1H), 0.72-0.64 (m, 1H).

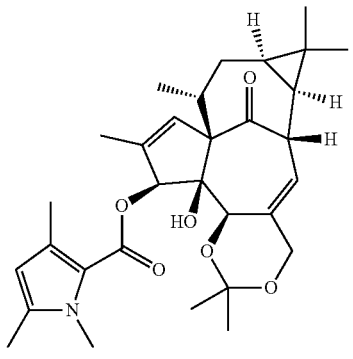

Preparation 642

Ingenol-5,20-acetonide-3-(1,3,5-trimethylpyrrole-2-carboxylate) (Compound 642)

Compound 642 was prepared according to Procedure c.
Starting material: 1,3,5-Trimethylpyrrole-2-carboxylic acid.

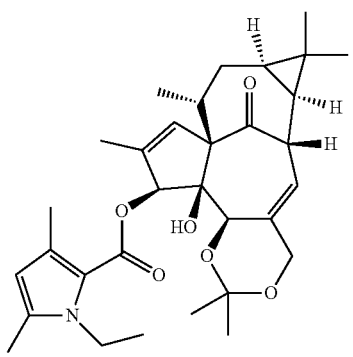

Preparation 643

Ingenol-5,20-acetonide-3-(1-ethyl-3,5-dimethylpyrrole-2-carboxylate) (Compound 643)

Compound 643 was prepared according to Procedure c.
Starting material: 1-Ethyl-3,5-dimethylpyrrole-2-carboxylic acid.

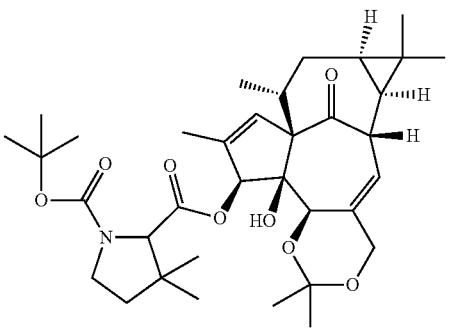 [SMILES: CC1=C[C@]23C(=O)[C@@H](C=C4COC(C)(C)O[C@H]4[C@]2(O)[C@H]1OC(=O)C1N(C(=O)OC(C)(C)C)CCC1(C)C)[C@H]1[C@@H](C[C@H]3C)C1(C)C]

Preparation 644

Ingenol-5,20-acetonide-3-(1-tert-butyloxycarbonyl-3,3-dimethylpyrrolidine-2-carboxylate) (Compound 644)

Compound 644 was prepared according to Procedure c.
Starting material: 1-tert-Butyloxycarbonyl-3,3-dimethylpyrrolidine-2-carboxylic acid.

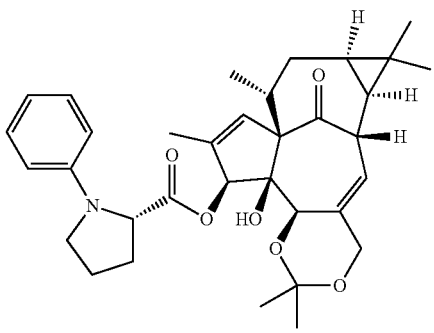 [SMILES: CC1=C[C@]23C(=O)[C@@H](C=C4COC(C)(C)O[C@H]4[C@]2(O)[C@H]1OC(=O)[C@@H]1CCCN1c1ccccc1)[C@H]1[C@@H](C[C@H]3C)C1(C)C]

Preparation 645

Ingenol-5,20-acetonide-3-((2S)-1-phenylpyrrolidine-2-carboxylate) (Compound 645)

Compound 645 was prepared according to Procedure a, but replacing dichloromethane with acetonitrile and reacting at 90° C. for 18 h.
Starting material: (2S)-1-phenylpyrrolidine-2-carboxylic acid.

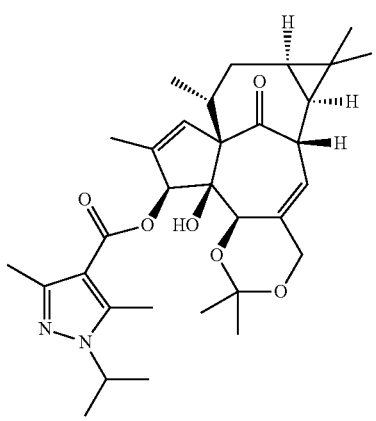

Preparation 646

Ingenol-5,20-acetonide-3-(1-isopropyl-3,5-dimethyl-pyrazole-4-carboxylate) (Compound 646)

Compound 646 was prepared according to Procedure d, but with reaction temperature 160° C.
Starting material: 1-Isopropyl-3,5-dimethyl-pyrazole-4-carbonyl chloride, prepared from 1-isopropyl-3,5-dimethyl-pyrazole-4-carboxylic acid by reaction with 1.25 eq. oxalyl chloride in dichloromethane and a drop of dimethylformamide at room temperature for 30 min followed by evaporation of volatiles in vacuum.

$^1$H NMR (300 MHz, CDCl$_3$) δ 6.09-6.06 (m, 1H), 5.80-5.77 (m, 1H), 5.73 (s, 1H), 4.42 (septet, 1H), 4.25-4.12 (m, 3H), 4.05 (s, 1H), 3.39 (s, 1H), 2.70-2.65 (m, 1H), 2.52 (s, 3H), 2.41 (s, 3H), 2.33-2.24 (m, 1H), 1.82 (d, 3H), 1.78-1.69 (m, 1H), 1.48-1.44 (m, 12H), 1.07 (s, 3H), 1.05 (s, 3H), 1.00 (d, 3H), 0.93-0.86 (m, 1H), 0.73-0.65 (m, 1H).

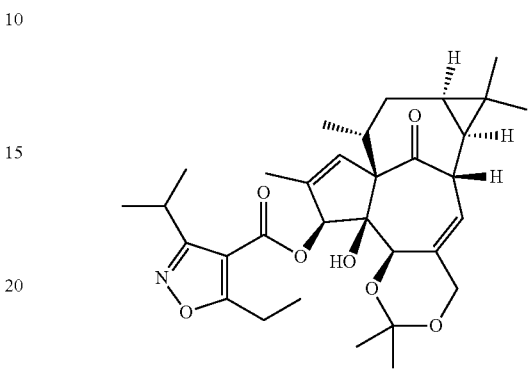

Preparation 647

Ingenol-5,20-acetonide-3-(5-ethyl-3-isopropyl-isoxazole-4-carboxylate) (Compound 647)

Compound 647 was prepared according to Procedure a, but replacing dichloromethane with acetonitrile and reacting at 90° C. for 18 h.
Starting material: 5-Ethyl-3-isopropyl-isoxazole-4-carboxylic acid.

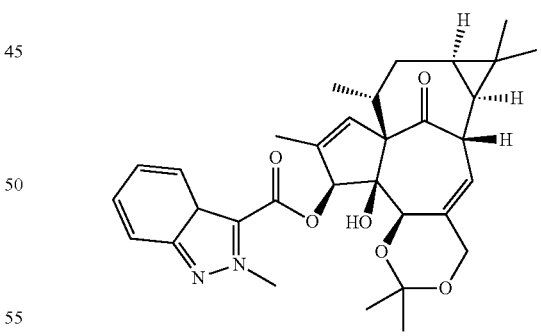

Preparation 648

Ingenol-5,20-acetonide-3-(2-methylindazole-3-carboxylate) (Compound 648)

Compound 648 was prepared according to Procedure a, but replacing dichloromethane with acetonitrile and reacting at 90° C. for 18 h.

Starting material: 2-methylindazole-3-carboxylic acid.

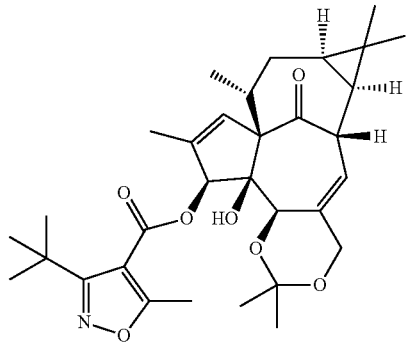

Preparation 649

Ingenol-5,20-acetonide-3-(5-methyl-3-tert-butyl-isoxazole-4-carboxylate) (Compound 648)

Compound 649 was prepared according to Procedure c.
Starting material: 5-Methyl-3-tert-butyl-isoxazole-4-carboxylic acid.

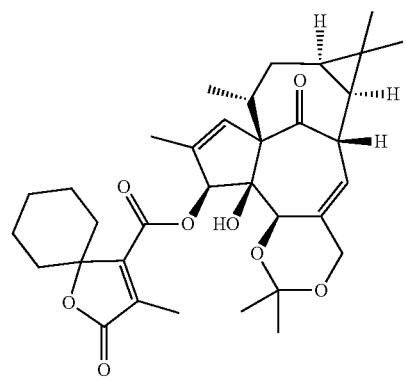

Preparation 650

Ingenol-5,20-acetonide-3-(2-methyl-3-oxo-4-oxaspiro[4.5]dec-1-ene-1-carboxylate) (Compound 650)

Compound 650 was prepared according to Procedure c, but keeping the reaction temperature at 140° C. for 1 h.
Starting material: 2-Methyl-3-oxo-4-oxaspiro[4.5]dec-1-ene-1-carboxylic acid.

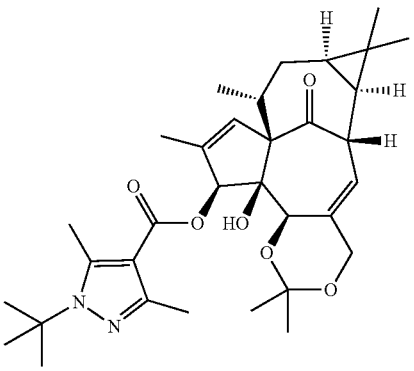

Preparation 651

Ingenol-5,20-acetonide-3-(1-tert-butyl-3,5-dimethyl-pyrazole-4-carboxylate) (Compound 651)

Compound 651 was prepared according to Procedure c.
Starting material: 1-tert-Butyl-3,5-dimethyl-pyrazole-4-carboxylic acid.

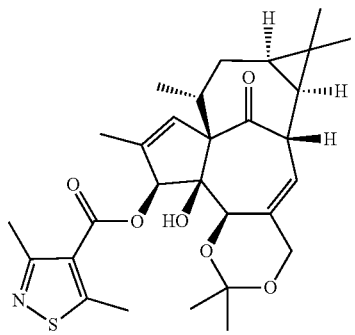

Preparation 652

Ingenol-5,20-acetonide-3-(3,5-dimethylisothiazole-4-carboxylate) (Compound 652)

Compound 652 was prepared according to Procedure c.
Starting material: 3,5-Dimethylisothiazole-4-carboxylic acid.

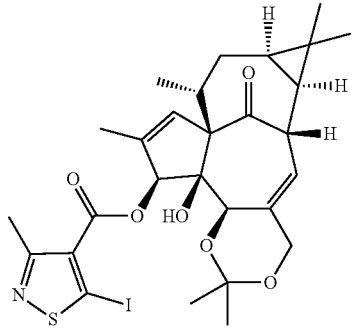

Preparation 653

Ingenol-5,20-acetonide-3-(5-iodo-3-methyl-isothiazole-4-carboxylate) (Compound 653)

Compound 653 was prepared according to Procedure c.
Starting material: 5-Iodo-3-methyl-isothiazole-4-carboxylic acid.

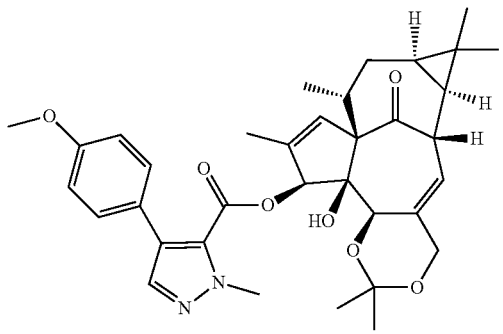

Preparation 654

Ingenol-5,20-acetonide-3-(4-(4-methoxyphenyl)-2-methyl-pyrazole-3-carboxylate) (Compound 654)

Compound 654 was prepared according to Procedure d.
Starting material: 4-(4-Methoxyphenyl)-2-methyl-pyrazole-3-carbonyl chloride, prepared from 4-(4-methoxyphenyl)-2-methyl-pyrazole-3-carboxylic acid by reaction with 1.25 eq. oxalyl chloride in dichloromethane and a drop of dimethylformamide at room temperature for 30 min followed by evaporation of volatiles in vacuum. 4-(4-Methoxyphenyl)-2-methyl-pyrazole-3-carboxylic acid was prepared according to Procedure k with (4-methoxyphenyl)boronic acid as starting material.

$^1$H NMR (300 MHz, CDCl$_3$) δ 7.43 (s, 1H), 7.28-7.23 (m, 2H), 6.88-6.82 (m, 2H), 5.95-5.94 (m, 1H), 5.76-5.71 (m, 1H), 5.71 (s, 1H), 4.22 (s, 3H), 4.20-4.00 (m, 3H), 3.96 (t, 1H), 3.81 (s, 3H), 3.07 (s, 1H), 2.04-1.94 (m, 1H), 1.75-1.70 (m, 4H), 1.52-1.45 (m, 4H), 1.41 (s, 3H), 1.02 (s, 6H), 0.90-0.78 (m, 1H), 0.68 (d, 3H), 0.63-0.55 (m, 1H).

Preparation 655

Ingenol-5,20-acetonide-3-(4-(2-methylphenyl)-2-methyl-pyrazole-3-carboxylate) (Compound 655)

Compound 655 was prepared according to Procedure d, but with reaction temperature 100° C.

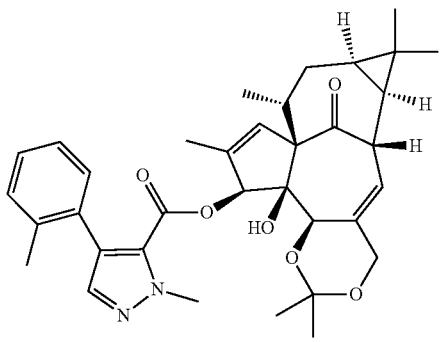

Starting material: 4-(2-Methylphenyl)-2-methyl-pyrazole-3-carbonyl chloride, prepared from 4-(2-methylphenyl)-2-methyl-pyrazole-3-carboxylic acid by reaction with 1.25 eq. oxalyl chloride in dichloromethane and a drop of dimethylformamide at room temperature for 30 min followed by evaporation of volatiles in vacuum. 4-(2-Methylphenyl)-2-methyl-pyrazole-3-carboxylic acid was prepared according to Procedure k with (2-methylphenyl)boronic acid as starting material.

$^1$H NMR (300 MHz, CDCl$_3$) δ 7.37 (s, 1H), 7.22-7.09 (m, 4H), 5.83-5.82 (m, 1H), 5.74-5.72 (m, 1H), 5.60 (s, 1H), 4.25 (s, 3H), 4.21-3.99 (m, 3H), 3.91 (s, 1H), 2.99 (s, 1H), 2.14 (s, 3H), 2.04-1.95 (m, 1H), 1.72-1.67 (m, 1H), 1.58-1.53 (d, 4H), 1.47 (s, 3H), 1.39 (s, 3H), 1.03 (s, 6H), 0.84-0.77 (m, 1H), 0.69 (d, 3H), 0.64-0.56 (m, 1H).

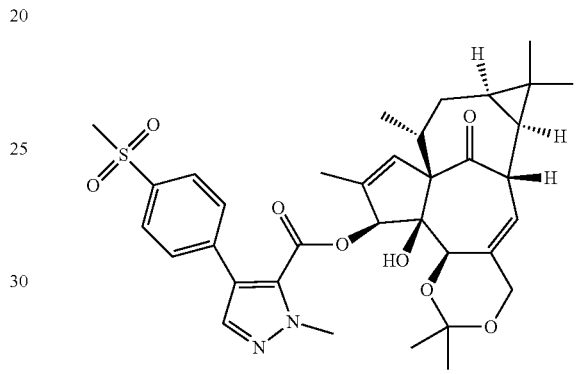

Preparation 656

Ingenol-5,20-acetonide-3-(2-methyl-4-(4-methylsulfonylphenyl)pyrazole-3-carboxylate) (Compound 656)

Compound 656 was prepared according to Procedure d, but with reaction temperature 100° C.

Starting material: 4-(4-methylsulfonylphenyl)-2-methyl-pyrazole-3-carbonyl chloride, prepared from 4-(4-methylsulfonylphenyl)-2-methyl-pyrazole-3-carboxylic acid by reaction with 1.25 eq. oxalyl chloride in dichloromethane and a drop of dimethylformamide at room temperature for 30 min followed by evaporation of volatiles in vacuum. 4-(4-Methylsulfonylphenyl)-2-methyl-pyrazole-3-carboxylic acid was prepared according to Procedure k with (4-methylsulfonylphenyl)boronic acid as starting material.

$^1$H NMR (300 MHz, CDCl$_3$) δ 7.97-7.89 (m, 2H), 7.63-7.54 (m, 2H), 7.51 (s, 1H), 5.98-5.96 (m, 1H), 5.78-5.75 (m, 1H), 5.68 (s, 1H), 4.25 (s, 3H), 4.20-3.98 (m, 4H), 3.18 (s, 1H), 3.06 (s, 3H), 2.12-2.03 (m, 1H), 1.92-1.87 (m, 1H), 1.69 (d, 3H), 1.59-1.50 (m, 1H), 1.48 (s, 3H), 1.43 (s, 3H), 1.03 (s, 3H), 1.02 (s, 3H), 0.86-0.79 (m, 1H), 0.68 (d, 3H), 0.65-0.57 (m, 1H).

1H), 3.41 (s, 1H), 2.73-2.68 (m, 1H), 2.53 (s, 3H), 2.50 (s, 3H), 2.36-2.26 (m, 1H), 1.84 (d, 3H), 1.80-1.71 (m, 1H), 1.50 (s, 3H), 1.46 (s, 3H), 1.08 (s, 3H), 1.05 (s, 3H), 1.01 (d, 3H), 0.94-0.87 (m, 1H), 0.74-0.68 (m, 1H).

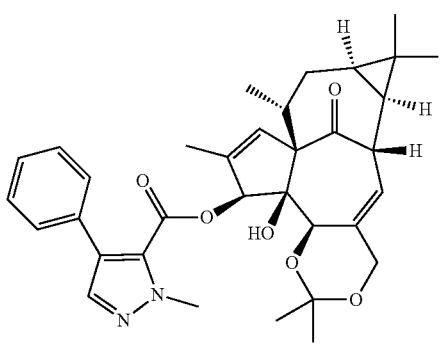

Preparation 657

Ingenol-5,20-acetonide-3-(2-methyl-4-phenyl-pyrazole-3-carboxylate) (Compound 657)

Compound 657 was prepared according to Procedure d, but with reaction temperature 100° C.

Starting material: 2-methyl-4-phenyl-pyrazole-3-carbonyl chloride, prepared from 2-methyl-4-phenyl-pyrazole-3-carboxylic acid by reaction with 1.25 eq. oxalyl chloride in dichloromethane and a drop of dimethylformamide at room temperature for 30 min followed by evaporation of volatiles in vacuum. 2-Methyl-4-phenyl-pyrazole-3-carboxylic acid was prepared according to Procedure k with phenylboronic acid as starting material.

$^1$H NMR (300 MHz, CDCl$_3$) δ 7.46 (s, 1H), 7.34-7.28 (m, 5H), 5.91 (m, 1H), 5.75-5.73 (m, 1H), 5.69 (s, 1H), 4.23-3.94 (m, 7H), 3.08 (s, 1H), 2.03-1.93 (m, 1H), 1.80-1.73 (m, 1H), 1.67 (d, 3H), 1.52-1.44 (m, 4H), 1.41 (s, 3H), 1.02 (s, 3H), 1.02 (s, 3H), 0.84-0.78 (m, 1H), 0.65 (d, 3H), 0.62-0.54 (m, 1H).

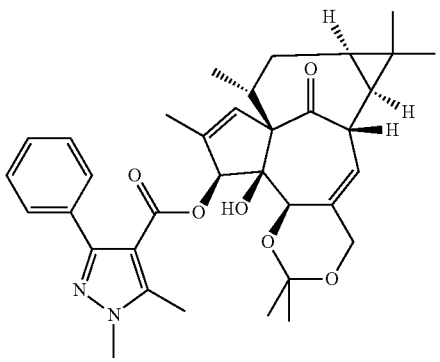

Preparation 659

Ingenol-5,20-acetonide-3-(1,5-dimethyl-3-phenyl-pyrazole-4-carboxylate) (Compound 659)

Compound 659 was prepared according to Procedure d.
Starting material: 1,5-Dimethyl-3-phenyl-pyrazole-4-carboxylic acid.

$^1$H NMR (300 MHz, CDCl$_3$) δ 7.51-7.46 (m, 2H), 7.38-7.31 (m, 3H), 5.90-5.89 (m, 1H), 5.74-5.71 (m, 2H), 4.16-3.94 (m, 4H), 3.84 (s, 3H), 3.12 (s, 1H), 2.60 (s, 3H), 2.03-1.93 (m, 1H), 1.85-1.80 (m, 1H), 1.71 (d, 3H), 1.52-1.46 (m, 4H), 1.39 (s, 3H), 1.02 (s, 3H), 1.02 (s, 3H), 0.85-0.79 (m, 1H), 0.67 (d, 3H), 0.63-0.55 (m, 1H).

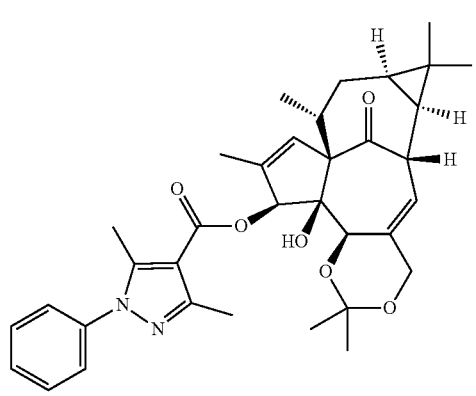

Preparation 658

Ingenol-5,20-acetonide-3-(3,5-dimethyl-1-phenyl-pyrazole-4-carboxylate) (Compound 658)

Compound 658 was prepared according to Procedure d, but with reaction temperature 140° C.
Starting material: 3,5-Dimethyl-1-phenyl-pyrazole-4-carboxylic acid.

$^1$H NMR (300 MHz, CDCl$_3$) δ 7.52-7.37 (m, 5H), 6.11-6.10 (m, 1H), 5.81-5.78 (m, 2H), 4.27-4.12 (m, 3H), 4.07 (s,

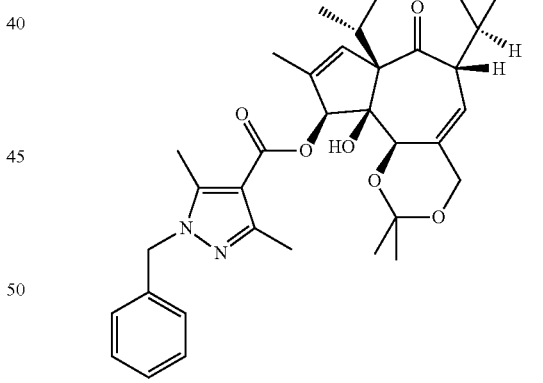

Preparation 660

Ingenol-5,20-acetonide-3-(1-benzyl-3,5-dimethyl-pyrazole-4-carboxylate) (Compound 660)

Compound 660 was prepared according to Procedure d.
Starting material: 1-Benzyl-3,5-dimethyl-pyrazole-4-carboxylic acid.

$^1$H NMR (300 MHz, CDCl$_3$) δ 7.36-7.25 (m, 3H), 7.14-7.11 (m, 2H), 6.09-6.07 (m, 1H), 5.80-5.77 (m, 1H), 5.73 (s, 1H), 5.24 (s, 2H), 4.26-4.11 (m, 3H), 4.05 (s, 1H), 3.38 (s, 1H), 2.69-2.64 (m, 1H), 2.47 (s, 3H), 2.44 (s, 3H), 2.33-2.23

(m, 1H), 1.81 (d, 3H), 1.78-1.70 (m, 1H), 1.47 (s, 3H), 1.43 (s, 3H), 1.07 (s, 3H), 1.05 (s, 3H), 0.99 (d, 3H), 0.94-0.86 (m, 1H), 0.73-0.65 (m, 1H).

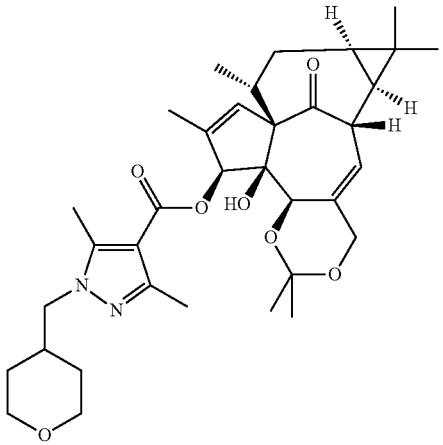 [SMILES: CC1=C[C@]23C(=O)[C@@H](C=C4COC(C)(C)O[C@H]4[C@]2(O)[C@H]1OC(=O)c1c(C)nn(CC2CCOCC2)c1C)[C@H]1[C@@H](C[C@H]3C)C1(C)C]

Preparation 661

Ingenol-5,20-acetonide-3-(3,5-dimethyl-1-(tetrahydropyran-4-ylmethyl)pyrazole-4-carboxylate) (Compound 661)

Compound 661 was prepared by heating a mixture of ingenol-5,20-acetonide-3-(3,5-dimethyl-1H-pyrazole-4-carboxylate) (15 mg), 4-iodomethyl-tetrahydro-2H-pyran (80 mg) and potassium carbonate (40 mg) in N,N-dimethylformamide (0.5 ml) at 120° C. in a microwave oven for 20 min. Addition of water and extraction with dichloromethane, followed by evaporation of solvent, gave a crude product which was purified by chromatography as described in Procedure c to give the title compound. Ingenol-5,20-acetonide-3-(3,5-dimethyl-1H-pyrazole-4-carboxylate) was prepared by Procedure c with 3,5-dimethyl-1H-pyrazole-4-carboxylic acid as starting material.

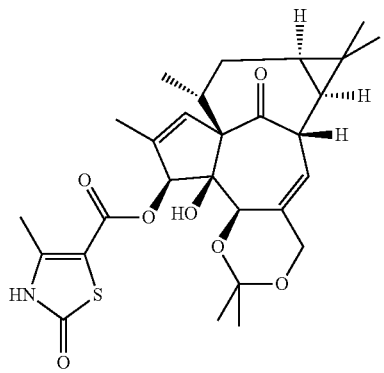

Preparation 662

Ingenol-5,20-acetonide-3-(4-methyl-2-oxo-3H-thiazole-5-carboxylate) (Compound 662)

Compound 662 was prepared according to Procedure d.
Starting material: 4-Methyl-2-oxo-3H-thiazole-5-carbonyl chloride, prepared from 4-methyl-2-oxo-3H-thiazole-5-carboxylic acid by reaction with 1.25 eq. oxalyl chloride in dichloromethane and a drop of dimethylformamide at room temperature for 30 min followed by evaporation of volatiles in vacuum.

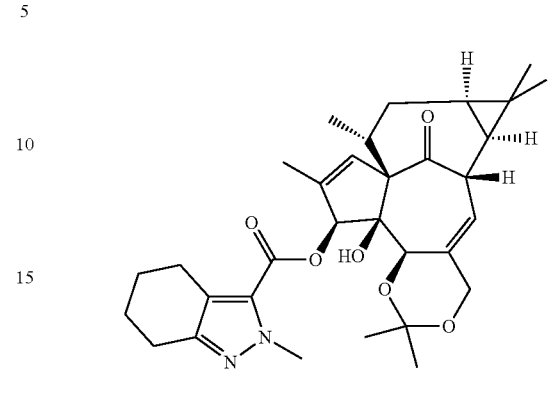

Preparation 663

Ingenol-5,20-acetonide-3-(2-methyl-4,5,6,7-tetrahydroindazole-3-carboxylate) (Compound 663)

Compound 663 was prepared according to Procedure d.
Starting material: 2-Methyl-4,5,6,7-tetrahydroindazole-3-carbonyl chloride, prepared from 2-methyl-4,5,6,7-tetrahydroindazole-3-carboxylic acid by reaction with 1.25 eq. oxalyl chloride in dichloromethane and a drop of dimethylformamide at room temperature for 30 min followed by evaporation of volatiles in vacuum.
$^1$H NMR (300 MHz, CDCl$_3$) δ 6.12-6.11 (m, 1H), 5.81-5.79 (m, 1H), 5.72 (s, 1H), 4.28-4.06 (m, 7H), 3.30 (s, 1H), 2.72-2.61 (m, 5H), 2.32-2.23 (m, 1H), 1.82-1.66 (m, 8H), 1.49 (s, 3H), 1.45 (s, 3H), 1.08 (s, 3H), 1.05 (s, 3H), 1.01 (d, 3H), 0.93-0.87 (m, 1H), 0.73-0.65 (m, 1H).

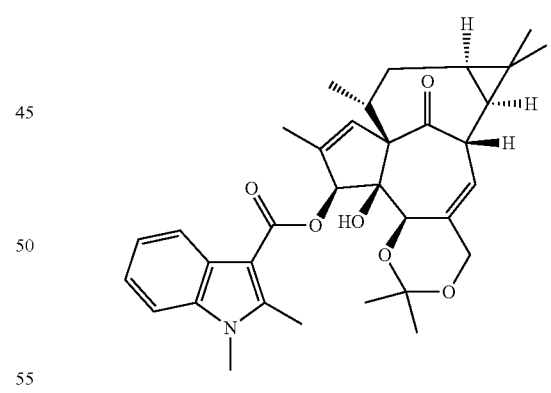

Preparation 664

Ingenol-5,20-acetonide-3-(1,2-dimethylindole-3-carboxylate) (Compound 664)

Compound 664 was prepared according to Procedure d.
Starting material: 1,2-dimethylindole-3-carbonyl chloride, prepared from 1,2-dimethylindole-3-carboxylic acid by reaction with 1.25 eq. oxalyl chloride in dichloromethane and a drop of dimethylformamide at room temperature for 30 min followed by evaporation of volatiles in vacuum.

$^1$H NMR (300 MHz, CDCl$_3$) δ 8.12-8.09 (m, 1H), 7.32-7.18 (m, 3H), 6.14 (m, 1H), 5.84 (s, 1H), 5.79-5.77 (m, 1H), 4.26-4.10 (m, 4H), 3.70 (s, 3H), 3.55 (s, 1H), 2.84-2.77 (m, 4H), 2.33-2.24 (m, 1H), 1.88 (d, 3H), 1.74-1.63 (m, 1H), 1.51 (s, 3H), 1.46 (s, 3H), 1.06-1.03 (m, 9H), 0.93-87 (m, 1H), 0.72-0.64 (m, 1H).

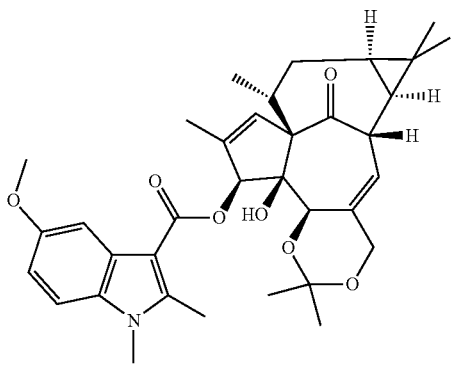 [SMILES: COc1ccc2c(c1)c(C(=O)O[C@H]1C(C)=C[C@]34C(=O)[C@@H](C=C5COC(C)(C)O[C@H]5[C@]13O)[C@H]1[C@@H](C[C@H]4C)C1(C)C)c(C)n2C]

Preparation 665

Ingenol-5,20-acetonide-3-(5-methoxy-1,2-dimethyl-indole-3-carboxylate) (Compound 665)

Compound 665 was prepared according to Procedure d, but extending reaction time to 75 min.

Starting material: 5-Methoxy-1,2-dimethyl-indole-3-carbonyl chloride, prepared from 5-methoxy-1,2-dimethyl-indole-3-carboxylic acid by reaction with 1.25 eq. oxalyl chloride in dichloromethane and a drop of dimethylformamide at room temperature for 30 min followed by evaporation of volatiles in vacuum.

$^1$H NMR (300 MHz, CDCl$_3$) δ 7.64 (d, 1H), 7.18 (d, 1H), 6.87 (dd, 1H), 6.14-6.12 (m, 1H), 5.84 (s, 1H), 5.80-5.77 (m, 1H), 4.26-4.07 (m, 4H), 3.84 (s, 3H), 3.67 (s, 3H), 3.63 (s, 1H), 2.81-2.75 (m, 4H), 2.32-2.22 (m, 1H), 1.89 (d, 3H), 1.74-1.65 (m, 1H), 1.51 (s, 3H), 1.46 (s, 3H), 1.06 (s, 3H), 1.03 (s, 3H), 1.02 (d, 3H), 0.97-0.87 (m, 1H), 0.71-0.63 (m, 1H).

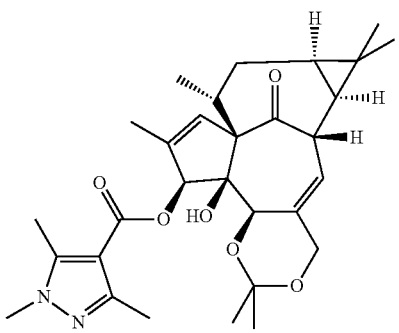

Preparation 666

Ingenol-5,20-acetonide-3-(1,3,5-trimethylpyrazole-4-carboxylate) (Compound 666)

Compound 666 was prepared according to Procedure d.
Starting material: 1,3,5-Trimethylpyrazole-4-carbonyl chloride, prepared from 1,3,5-trimethylpyrazole-4-carboxylic acid by reaction with 1.25 eq. oxalyl chloride in dichloromethane and a drop of dimethylformamide at room temperature for 30 min followed by evaporation of volatiles in vacuum.

$^1$H NMR (300 MHz, CDCl$_3$) δ 6.09-6.08 (m, 1H), 5.80-5.77 (m, 1H), 5.73 (s, 1H), 4.26-4.05 (m, 4H), 3.73 (s, 3H), 3.39 (s, 1H), 2.69-2.64 (m, 1H), 2.49 (s, 3H), 2.39 (s, 3H), 2.33-2.23 (m, 1H), 1.82 (d, 3H), 1.77-1.68 (m, 1H), 1.48 (s, 3H), 1.44 (s, 3H), 1.07 (s, 3H), 1.05 (s, 3H), 1.00 (d, 3H), 0.93-0.86 (m, 1H), 0.73-0.65 (m, 1H).

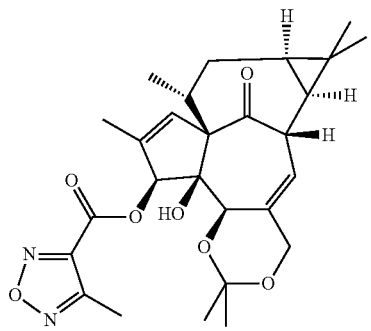 [SMILES: CC1=C[C@]23C(=O)[C@@H](C=C4COC(C)(C)O[C@H]4[C@]2(O)[C@H]1OC(=O)c1nonc1C)[C@H]1[C@@H](C[C@H]3C)C1(C)C]

Preparation 667

Ingenol-5,20-acetonide-3-(4-methyl-1,2,5-oxadiazole-3-carboxylate) (Compound 667)

Compound 667 was prepared according to Procedure d.
Starting material: 4-Methyl-1,2,5-oxadiazole-3-carbonyl chloride, prepared from 4-methyl-1,2,5-oxadiazole-3-carboxylic acid by reaction with 1.25 eq. oxalyl chloride in dichloromethane and a drop of dimethylformamide at room temperature for 30 min followed by evaporation of volatiles in vacuum.

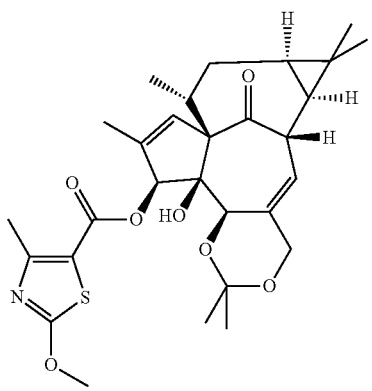

Preparation 668

Ingenol-5,20-acetonide-3-(2-methoxy-4-methyl-thiazole-5-carboxylate) (Compound 668)

Compound 668 was prepared according to Procedure d.
Starting material: 2-Methoxy-4-methyl-thiazole-5-carbonyl chloride, prepared from 2-methoxy-4-methyl-thiazole- 5-carboxylic acid by reaction with 1.25 eq. oxalyl chloride in dichloromethane and a drop of dimethylformamide at room temperature for 30 min followed by evaporation of volatiles in vacuum.

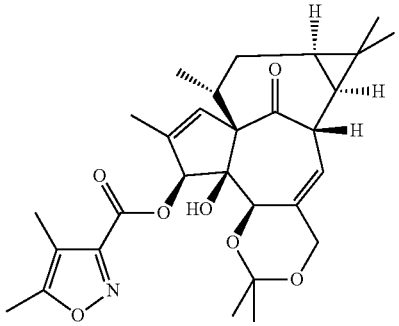

Preparation 669

Ingenol-5,20-acetonide-3-(4,5-dimethylisoxazole-3-carboxylate) (Compound 669)

Compound 669 was prepared according to Procedure d.

Starting material: 4,5-Dimethylisoxazole-3-carbonyl chloride, prepared from 2-methoxy-4-methyl-thiazole-5-carboxylic acid by reaction with 1.25 eq. oxalyl chloride in dichloromethane and a drop of dimethylformamide at room temperature for 30 min followed by evaporation of volatiles in vacuum.

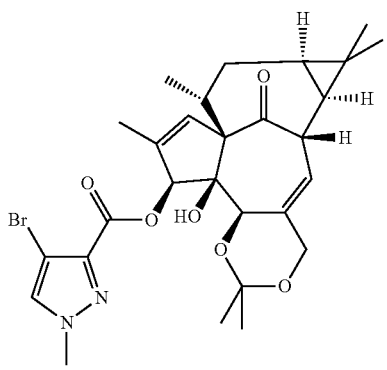 [SMILES: CC1=C[C@]23C(=O)[C@@H](C=C4COC(C)(C)O[C@H]4[C@]2(O)[C@H]1OC(=O)c1nn(C)cc1Br)[C@H]1[C@@H](C[C@H]3C)C1(C)C]

Preparation 670

Ingenol-5,20-acetonide-3-(4-bromo-1-methyl-pyrazole-3-carboxylate) (Compound 670)

Compound 670 was prepared according to Procedure d.

Starting material: 4-Bromo-1-methyl-pyrazole-3-carbonyl chloride, prepared from 4-bromo-1-methyl-pyrazole-3-carboxylic acid by reaction with 1.25 eq. oxalyl chloride in dichloromethane and a drop of dimethylformamide at room temperature for 30 min followed by evaporation of volatiles in vacuum.

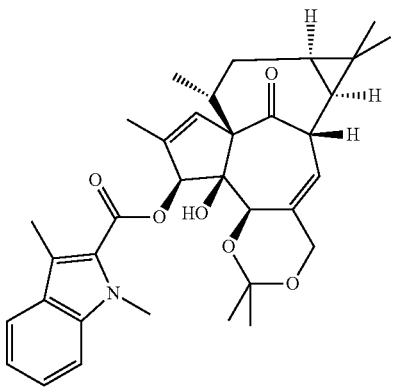 [SMILES: CC1=C[C@]23C(=O)[C@@H](C=C4COC(C)(C)O[C@H]4[C@]2(O)[C@H]1OC(=O)c1c(C)c2ccccc2n1C)[C@H]1[C@@H](C[C@H]3C)C1(C)C]

Preparation 671

Ingenol-5,20-acetonide-3-(1,3-dimethylindole-2-carboxylate) (Compound 671)

Compound 671 was prepared according to Procedure d.

Starting material: 1,3-Dimethylindole-2-carbonyl chloride, prepared from 1,3-dimethylindole-2-carboxylic acid by reaction with 1.25 eq. oxalyl chloride in dichloromethane and a drop of dimethylformamide at room temperature for 30 min followed by evaporation of volatiles in vacuum.

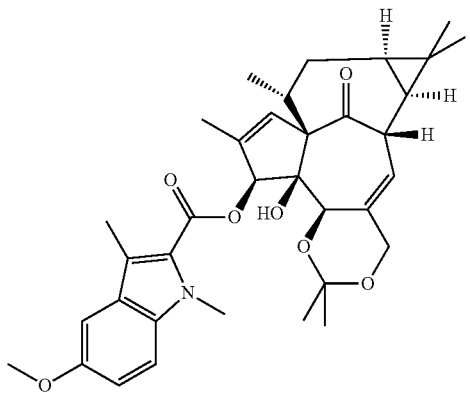

Preparation 672

Ingenol-5,20-acetonide-3-(5-methoxy-1,3-dimethyl-indole-2-carboxylate) (Compound 672)

Compound 672 was prepared according to Procedure d.

Starting material: 5-Methoxy-1,3-dimethyl-indole-2-carbonyl chloride, prepared from 5-methoxy-1,3-dimethyl-indole-2-carboxylic acid by reaction with 1.25 eq. oxalyl chloride in dichloromethane and a drop of dimethylformamide at room temperature for 30 min followed by evaporation of volatiles in vacuum.

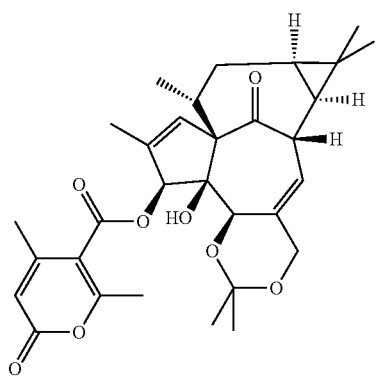 [SMILES: CC1=C[C@]23C(=O)[C@@H](C=C4COC(C)(C)O[C@H]4[C@]2(O)[C@H]1OC(=O)c1c(C)cc(=O)oc1C)[C@H]1[C@@H](C[C@H]3C)C1(C)C]

Preparation 673

Ingenol-5,20-acetonide-3-(2,4-dimethyl-6-oxo-pyran-3-carboxylate) (Compound 673)

Compound 673 was prepared according to Procedure c.
Starting material: 2,4-Dimethyl-6-oxo-pyran-3-carboxylic acid.

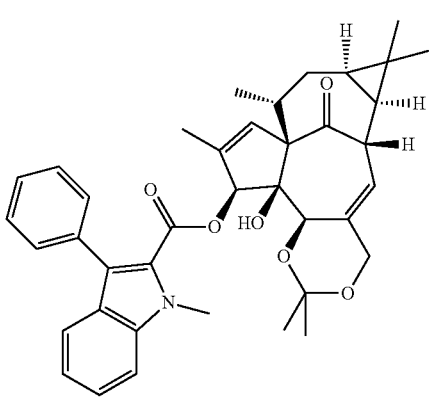 [SMILES: CC1=C[C@]23C(=O)[C@@H](C=C4COC(C)(C)O[C@H]4[C@]2(O)[C@H]1OC(=O)c1c(-c2ccccc2)c2ccccc2n1C)[C@H]1[C@@H](C[C@H]3C)C1(C)C]

Preparation 674

Ingenol-5,20-acetonide-3-(1-methyl-3-phenyl-indole-2-carboxylate) (Compound 674)

Compound 674 was prepared according to Procedure d.
Starting material: 1-Methyl-3-phenyl-indole-2-carbonyl chloride, prepared from 1-methyl-3-phenyl-indole-2-carboxylic acid by reaction with 1.25 eq. oxalyl chloride in dichloromethane and a drop of dimethylformamide at room temperature for 30 min followed by evaporation of volatiles in vacuum.

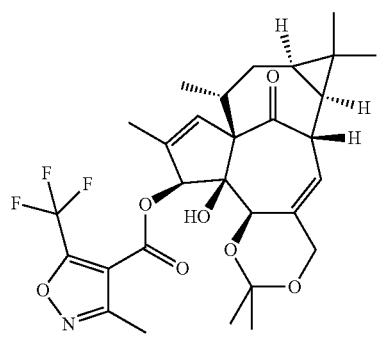 [SMILES: CC1=C[C@]23C(=O)[C@@H](C=C4COC(C)(C)O[C@H]4[C@]2(O)[C@H]1OC(=O)c1c(C)noc1C(F)(F)F)[C@H]1[C@@H](C[C@H]3C)C1(C)C]

Preparation 675

Ingenol-5,20-acetonide-3-(3-methyl-5-(trifluoromethyl)isoxazole-4-carboxylate) (Compound 675)

Compound 675 was prepared according to Procedure c.
Starting material: 3-Methyl-5-(trifluoromethyl)isoxazole-4-carboxylic acid.

Preparation 676

Ingenol-5,20-acetonide-3-(1,3-dimethylpyrrole-2-carboxylate) (Compound 676)

Compound 676 was prepared according to Procedure c, but changing the reaction conditions to 60 min at 140° C.
Starting material: 1,3-Dimethylpyrrole-2-carboxylic acid.

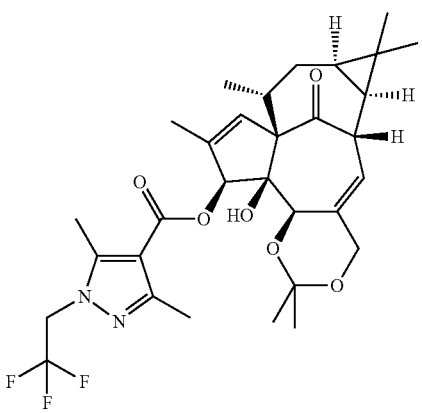 [SMILES: CC1=C[C@]23C(=O)[C@@H](C=C4COC(C)(C)O[C@H]4[C@]2(O)[C@H]1OC(=O)c1c(C)nn(CC(F)(F)F)c1C)[C@H]1[C@@H](C[C@H]3C)C1(C)C]

Preparation 677

Ingenol-5,20-acetonide-3-(3,5-dimethyl-1-(2,2,2-trifluoroethyl)pyrazole-4-carboxylate) (Compound 677)

Compound 677 was prepared according to Procedure d.

Starting material: 3,5-Dimethyl-1-(2,2,2-trifluoroethyl)pyrazole-4-carbonyl chloride, prepared from 2,2,2-trifluoroethyl)pyrazole-4-carboxylic acid by reaction with 1.25 eq. oxalyl chloride in dichloromethane and a drop of dimethylformamide at room temperature for 30 min followed by evaporation of volatiles in vacuum.

$^1$H NMR (300 MHz, CDCl$_3$) δ 6.11-6.09 (m, 1H), 5.80-5.79 (m, 1H), 5.73 (s, 1H), 4.61 (q, 2H), 4.27-4.05 (m, 4H), 3.35 (s, 1H), 2.68-2.61 (m, 1H), 2.56 (s, 3H), 2.41 (s, 3H), 2.35-2.24 (m, 1H), 1.82 (d, 3H), 1.79-1.70 (m, 1H), 1.48 (s, 3H), 1.45 (s, 3H), 1.08 (s, 3H), 1.05 (s, 3H), 1.01 (d, 3H), 0.93-0.86 (m, 1H), 0.73-0.65 (m, 1H).

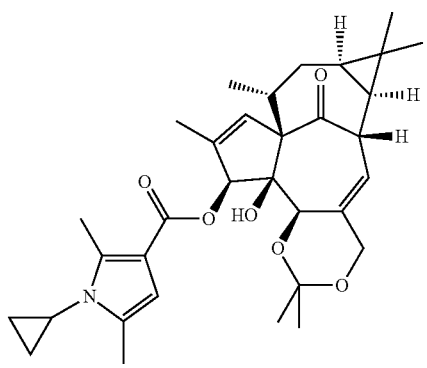 [SMILES: CC1=C[C@]23C(=O)[C@@H](C=C4COC(C)(C)O[C@H]4[C@]2(O)[C@H]1OC(=O)c1cc(C)n(C2CC2)c1C)[C@H]1[C@@H](C[C@H]3C)C1(C)C]

Preparation 678

Ingenol-5,20-acetonide-3-(1-cyclopropyl-2,5-dimethyl-pyrrole-3-carboxylate) (Compound 678)

Compound 678 was prepared according to Procedure d, but extending the reaction time to 60 min.

Starting material: 1-Cyclopropyl-2,5-dimethyl-pyrrole-3-carbonyl chloride, prepared from 1-cyclopropyl-2,5-dimethyl-pyrrole-3-carboxylic acid by reaction with 1.25 eq. oxalyl chloride in dichloromethane and a drop of dimethylformamide at room temperature for 30 min followed by evaporation of volatiles in vacuum.

$^1$H NMR (300 MHz, CDCl$_3$) δ 6.16 (m, 1H), 6.04-6.02 (m, 1H), 5.77-5.74 (m, 1H), 5.73 (s, 1H), 4.18-4.13 (m, 3H), 4.03 (s, 1H), 3.36 (s, 1H), 2.94-2.86 (m, 1H), 2.71-2.66 (m, 1H), 2.59 (s, 3H), 2.32-2.23 (m, 4H), 1.80-1.71 (m, 4H), 1.46 (s, 3H), 1.42 (s, 3H), 1.13-1.07 (m, 5H), 1.04 (s, 3H), 1.02 (d, 3H), 0.94-0.88 (m, 3H), 0.73-0.65 (m, 1H).

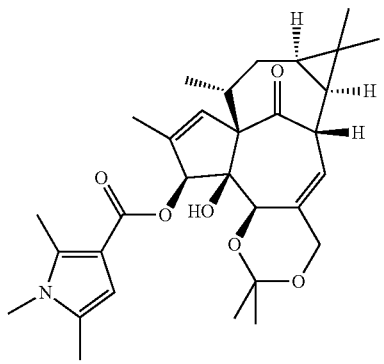

Preparation 679

Ingenol-5,20-acetonide-3-(1,2,5-trimethylpyrrole-3-carboxylate) (Compound 679)

Compound 679 was prepared according to Procedure d, but extending the reaction time to 100 min.

Starting material: 1,2,5-Trimethylpyrrole-3-carbonyl chloride, prepared from 1,2,5-trimethylpyrrole-3-carboxylic acid by reaction with 1.25 eq. oxalyl chloride in dichloromethane and a drop of dimethylformamide at room temperature for 30 min followed by evaporation of volatiles in vacuum.

$^1$H NMR (300 MHz, CDCl$_3$) δ 6.22-6.21 (m, 1H), 6.04-6.02 (m, 1H), 5.77-5.73 (m, 2H), 4.19-4.14 (m, 3H), 4.03 (s, 1H), 3.40 (s, 3H), 3.38 (s, 1H), 2.72-2.66 (m, 1H), 2.51 (s, 3H), 2.32-2.23 (m, 1H), 2.19 (d, 3H), 1.80 (d, 3H), 1.78-1.71 (m, 1H), 1.47 (s, 3H), 1.42 (s, 3H), 1.07 (s, 3H), 1.04 (s, 3H), 1.02 (d, 3H), 0.94-0.88 (m, 1H), 0.73-0.65 (m, 1H).

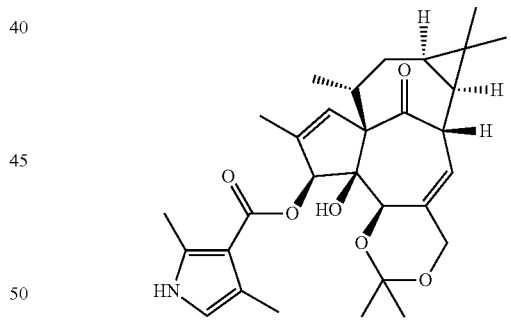

Preparation 680

Ingenol-5,20-acetonide-3-(2,4-dimethyl-1H-pyrrole-3-carboxylate) (Compound 680)

Compound 680 was prepared according to Procedure d.

Starting material: 2,4-Dimethyl-1H-pyrrole-3-carbonyl chloride, prepared from 2,4-dimethyl-1H-pyrrole-3-carboxylic acid by reaction with 1.25 eq. oxalyl chloride in dichloromethane and a drop of dimethylformamide at room temperature for 30 min followed by evaporation of volatiles in vacuum.

$^1$H NMR (300 MHz, CDCl$_3$) δ 10.40 bs, 1H), 6.11-6.10 (m, 1H), 5.96-5.95 (m, 1H), 5.86-5.83 (m, 1H), 5.75 (s, 1H), 4.30-4.10 (m, 4H), 3.72 (bs, 1H), 2.66-2.61 (m, 1H), 2.41 (s, 3H), 2.33-2.23 (m, 4H), 1.87-1.76 (m, 4H), 1.47 (s, 3H), 1.46 (s, 3H), 1.12 (s, 3H), 1.07 (s, 3H), 0.97 (d, 3H), 0.95-0.89 (m, 1H), 0.77-0.69 (m, 1H).

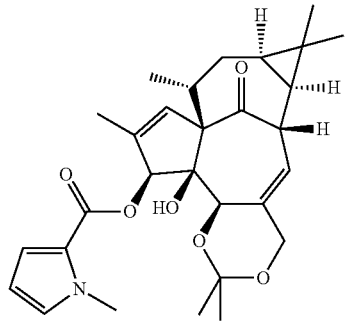 [SMILES: CC1=C[C@]23C(=O)[C@@H](C=C4COC(C)(C)O[C@H]4[C@]2(O)[C@H]1OC(=O)c1cccn1C)[C@H]1[C@@H](C[C@H]3C)C1(C)C]

Preparation 681

Ingenol-5,20-acetonide-3-(1-methylpyrrole-2-carboxylate) (Compound 681)

Compound 681 was prepared according to Procedure d.
Starting material: 1-Methylpyrrole-2-carbonyl chloride, prepared from 1-methylpyrrole-2-carboxylic acid by reaction with 1.25 eq. oxalyl chloride in dichloromethane and a drop of dimethylformamide at room temperature for 30 min followed by evaporation of volatiles in vacuum.

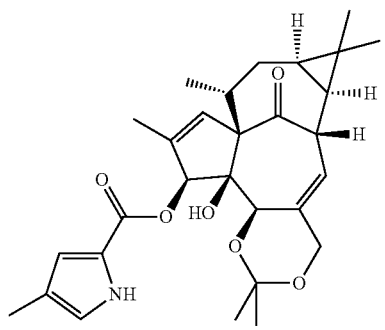

Preparation 682

Ingenol-5,20-acetonide-3-(4-methyl-1H-pyrrole-2-carboxylate) (Compound 682)

Compound 682 was prepared according to Procedure d, but extending the reaction time to 75 min.
Starting material: 4-Methyl-1H-pyrrole-2-carbonyl chloride, prepared from 4-methyl-1H-pyrrole-2-carboxylic acid by reaction with 1.25 eq. oxalyl chloride in dichloromethane and a drop of dimethylformamide at room temperature for 30 min followed by evaporation of volatiles in vacuum.

$^1$H NMR (300 MHz, CDCl$_3$) δ 8.97 (bs, 1H), 6.76-6.72 (m, 2H), 6.08-6.07 (m, 1H), 5.79-5.76 (m, 1H), 5.70 (s, 1H), 4.25-4.12 (m, 3H), 4.04-4.03 (m, 1H), 3.29 (s, 1H), 2.67-2.62 (m, 1H), 2.31-2.21 (m, 1H), 2.12 (s, 3H), 1.82-1.73 (m, 4H), 1.47 (s, 3H), 1.43 (s, 3H), 1.08 (s, 3H), 1.04 (s, 3H), 1.03 (d, 3H), 0.95-0.88 (m, 1H), 0.74-0.66 (m, 1H).

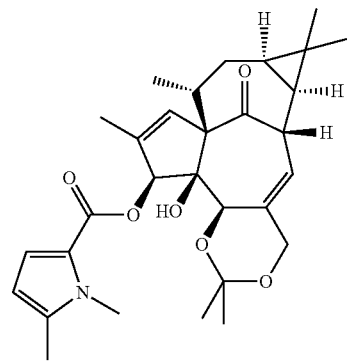 [SMILES: CC1=C[C@]23C(=O)[C@@H](C=C4COC(C)(C)O[C@H]4[C@]2(O)[C@H]1OC(=O)c1ccc(C)n1C)[C@H]1[C@@H](C[C@H]3C)C1(C)C]

Preparation 683

Ingenol-5,20-acetonide-3-(1,5-dimethylpyrrole-2-carboxylate) (Compound 683)

Compound 683 was prepared according to Procedure c, but extending the reaction time to 40 min.
Starting material: 1,5-Dimethylpyrrole-2-carboxylic acid.

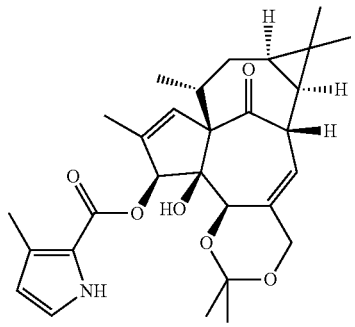

Preparation 684

Ingenol-5,20-acetonide-3-(3-methyl-1H-pyrrole-2-carboxylate) (Compound 684)

Compound 684 was prepared according to Procedure c, but extending the reaction time to 40 min.
Starting material: 3-Methyl-1H-pyrrole-2-carboxylic acid.

$^1$H NMR (300 MHz, CDCl$_3$) δ 8.93 (bs, 1H), 6.86 (t, 1H), 6.12-6.08 (m, 2H), 5.80-5.77 (m, 1H), 5.71 (s, 1H), 4.26-4.13 (m, 3H), 4.05-4.04 (m, 1H), 3.38 (s, 1H), 2.69-2.64 (m, 1H), 2.35-2.23 (m, 4H), 1.82 (d, 3H), 1.79-1.70 (m, 1H), 1.48 (s, 3H), 1.44 (s, 3H), 1.07 (s, 3H), 1.04 (s, 3H), 1.02 (d, 3H), 0.94-0.88 (m, 1H), 0.73-0.65 (m, 1H).

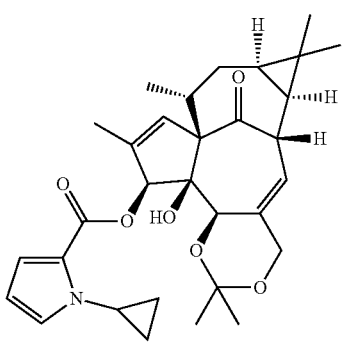 [SMILES: CC1=C[C@]23C(=O)[C@@H](C=C4COC(C)(C)O[C@H]4[C@]2(O)[C@H]1OC(=O)c1cccn1C1CC1)[C@H]1[C@@H](C[C@H]3C)C1(C)C]

Preparation 685

Ingenol-5,20-acetonide-3-(1-cyclopropylpyrrole-2-carboxylate) (Compound 685)

Compound 685 was prepared according to Procedure d.
Starting material: 1-Cyclopropylpyrrole-2-carbonyl chloride, prepared from 1-cyclopropylpyrrole-2-carboxylic acid by reaction with 1.25 eq. oxalyl chloride in dichloromethane and a drop of dimethylformamide at room temperature for 30 min followed by evaporation of volatiles in vacuum.

$^1$H NMR (300 MHz, CDCl$_3$) δ 6.92 (dd, 1H), 6.88 (t, 1H), 6.09-6.06 (m, 2H), 5.79-5.75 (m, 2H), 4.24-4.13 (m, 3H), 4.05-4.04 (m, 1H), 3.79-3.71 (m, 1H), 3.32 (s, 1H), 2.70-2.65 (m, 1H), 2.32-2.23 (m, 1H), 1.84-1.73 (m, 4H), 1.47 (s, 3H), 1.44 (s, 3H), 1.09 (s, 3H), 1.05-0.88 (m, 11H), 0.74-0.66 (m, 1H).

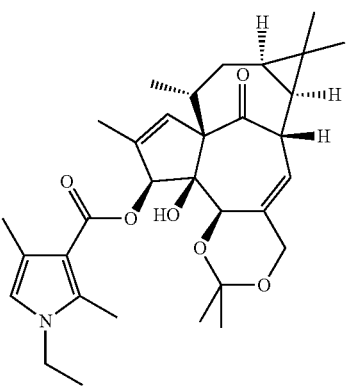

Preparation 686

Ingenol-5,20-acetonide-3-(1-ethyl-2,4-dimethyl-pyrrole-3-carboxylate) (Compound 686)

Compound 686 was prepared according to Procedure d.
Starting material: 1-Ethyl-2,4-dimethyl-pyrrole-3-carbonyl chloride, prepared from 1-ethyl-2,4-dimethyl-pyrrole-3-carboxylic acid by reaction with 1.25 eq. oxalyl chloride in dichloromethane and a drop of dimethylformamide at room temperature for 30 min followed by evaporation of volatiles in vacuum.

$^1$H NMR (300 MHz, CDCl$_3$) δ 6.33-6.32 (m, 1H), 6.06-6.04 (m, 1H), 5.77-5.75 (m, 2H), 4.21-4.17 (m, 3H), 4.04 (s, 1H), 3.81 (t, 2H), 3.54 (s, 1H), 2.74-2.69 (m, 1H), 2.50 (s, 3H), 2.34-2.24 (m, 1H), 2.21 (s, 3H), 1.82 (d, 3H), 1.76-1.67 (m, 1H), 1.47 (s, 3H), 1.42 (s, 3H), 1.33 (t, 3H), 1.07 (s, 3H), 1.04 (s, 3H), 0.99 (d, 3H), 0.93-0.86 (m, 1H), 0.72-0.64 (m, 1H).

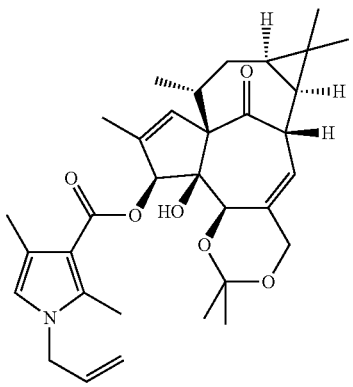

Preparation 687

Ingenol-5,20-acetonide-3-(1-allyl-2,4-dimethyl-pyrrole-3-carboxylate) (Compound 687)

Compound 687 was prepared according to Procedure d.
Starting material: 1-Allyl-2,4-dimethyl-pyrrole-3-carbonyl chloride, prepared from 1-allyl-2,4-dimethyl-pyrrole-3-carboxylic acid by reaction with 1.25 eq. oxalyl chloride in dichloromethane and a drop of dimethylformamide at room temperature for 30 min followed by evaporation of volatiles in vacuum.

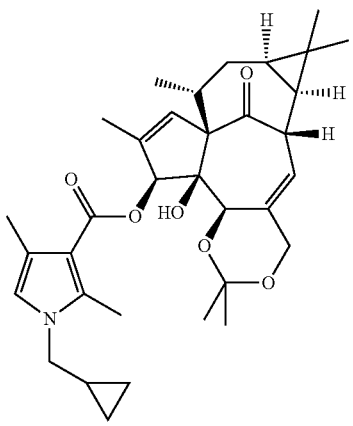

Preparation 688

Ingenol-5,20-acetonide-3-(1-(cyclopropylmethyl)-2,4-dimethyl-pyrrole-3-carboxylate) (Compound 688)

Compound 688 was prepared according to Procedure d.
Starting material: 1-(Cyclopropylmethyl)-2,4-dimethyl-pyrrole-3-carbonyl chloride, prepared from 1-(cyclopropylmethyl)-2,4-dimethyl-pyrrole-3-carboxylic acid by reaction with 1.25 eq. oxalyl chloride in dichloromethane and a drop of dimethylformamide at room temperature for 30 min followed by evaporation of volatiles in vacuum.

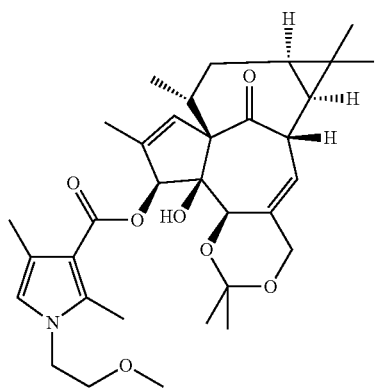

Preparation 689

Ingenol-5,20-acetonide-3-(1-(2-methoxyethyl)-2,4-dimethyl-pyrrole-3-carboxylate) (Compound 689)

Compound 689 was prepared according to Procedure d.

Starting material: 1-(2-Methoxyethyl)-2,4-dimethyl-pyrrole-3-carbonyl chloride, prepared from 1-(2-methoxyethyl)-2,4-dimethyl-pyrrole-3-carboxylic acid by reaction with 1.25 eq. oxalyl chloride in dichloromethane and a drop of dimethylformamide at room temperature for 30 min followed by evaporation of volatiles in vacuum.

$^1$H NMR (300 MHz, CDCl$_3$) δ 6.36 (m, 1H), 6.06-6.04 (m, 1H), 5.77-5.75 (m, 2H), 4.21-4.14 (m, 3H), 4.04 (s, 1H), 3.94 (t, 2H), 3.58 (t, 2H), 3.53 (s, 1H), 3.33 (s, 3H), 2.73-2.68 (m, 1H), 2.51 (s, 3H), 2.33-2.23 (m, 1H), 2.20 (d, 3H), 1.81 (d, 3H), 1.76-1.67 (m, 1H), 1.47 (s, 3H), 1.42 (s, 3H), 1.07 (s, 3H), 1.04 (s, 3H), 0.99 (d, 3H), 0.93-0.86 (m, 1H), 0.72-0.64 (m, 1H).

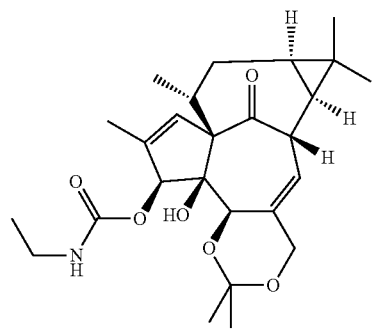 [SMILES: CCNC(=O)O[C@H]1C(C)=C[C@]23C(=O)[C@@H](C=C4COC(C)(C)O[C@H]4[C@]12O)[C@H]1[C@@H](C[C@H]3C)C1(C)C]

Preparation 801

Ingenol-5,20-acetonide-3-(N-ethyl-carbamate) (Compound 801)

Compound 801 was prepared according to Procedure i.
Starting material: Ethyl isocyanate.

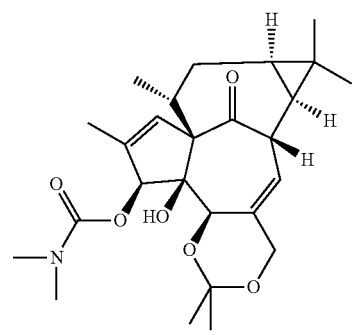

Preparation 802

Ingenol-5,20-acetonide-3-(N,N-dimethyl-carbamate) (Compound 802)

Compound 802 was prepared according to Procedure g.
Starting material: N,N-Dimethylcarbamoyl chloride.

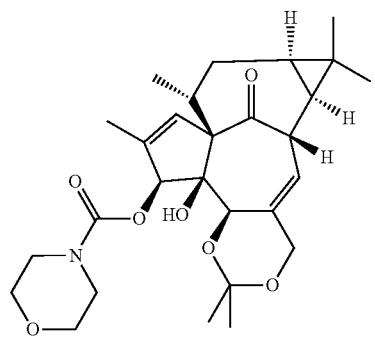 [SMILES: CC1=C[C@]23C(=O)[C@@H](C=C4COC(C)(C)O[C@H]4[C@]2(O)[C@H]1OC(=O)N1CCOCC1)[C@H]1[C@@H](C[C@H]3C)C1(C)C]

Preparation 803

Ingenol-5,20-acetonide-3-(morpholine-4-carboxylate) (Compound 803)

Compound 803 was prepared according to Procedure g.
Starting material: Morpholine-4-carbonyl chloride.
$^1$H NMR (300 MHz, CDCl$_3$) δ 6.04-6.03 (m, 1H), 5.77-5.76 (m, 1H), 5.45 (s, 1H), 4.23-4.12 (m, 3H), 3.97 (s, 1H), 3.70-3.63 (m, 4H), 3.50-3.47 (m, 5H), 2.52-2.47 (m, 1H), 2.34-2.25 (m, 1H), 1.78 (d, 3H), 1.77-1.70 (m, 1H), 1.46 (s, 3H), 1.39 (s, 3H), 1.10 (s, 3H), 1.05 (s, 3H), 0.97 (d, 3H), 0.94-0.85 (m, 1H), 0.73-0.65 (m, 1H).

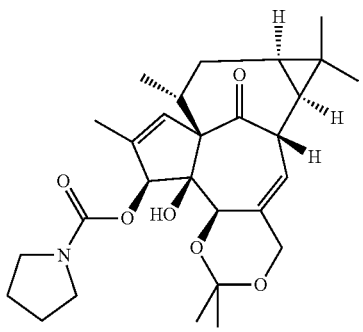 [SMILES: CC1=C[C@]23C(=O)[C@@H](C=C4COC(C)(C)O[C@H]4[C@]2(O)[C@H]1OC(=O)N1CCCC1)[C@H]1[C@@H](C[C@H]3C)C1(C)C]

Preparation 804

Ingenol-5,20-acetonide-3-(pyrrolidine-1-carboxylate) (Compound 804)

Compound 804 was prepared according to Procedure g.

Starting material: Pyrrolidine-1-carbonyl chloride.

$^1$H NMR (300 MHz, CDCl$_3$) δ 6.01 (m, 1H), 5.76-5.74 (m, 1H), 5.44 (s, 1H), 4.16-4.11 (m, 3H), 3.96 (s, 1H), 3.65 (s, 1H), 3.44-3.33 (m, 4H), 2.61-2.55 (m, 1H), 2.33-2.44 (m, 1H), 1.90-1.85 (m, 4H), 1.79 (d, 3H), 1.78-1.70 (m, 1H), 1.45 (s, 3H), 1.38 (s, 3H), 1.10 (s, 3H), 1.05 (s, 3H), 0.98 (d, 3H), 0.94-0.85 (m, 1H), 0.72-0.65 (m, 1H).

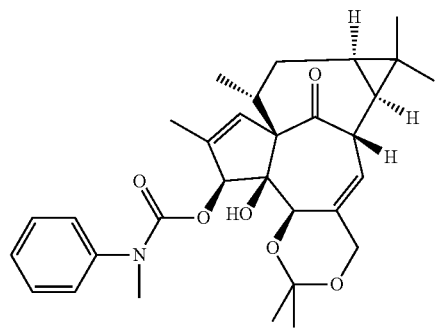 [SMILES: CC1=C[C@]23C(=O)[C@@H](C=C4COC(C)(C)O[C@H]4[C@]2(O)[C@H]1OC(=O)N(C)c1ccccc1)[C@H]1[C@@H](C[C@H]3C)C1(C)C]

Preparation 805

Ingenol-5,20-acetonide-3-(N-methyl-N-phenyl-carbamate) (Compound 805)

Compound 805 was prepared according to Procedure g.

Starting material: N-Methyl-N-phenyl-carbamoyl chloride.

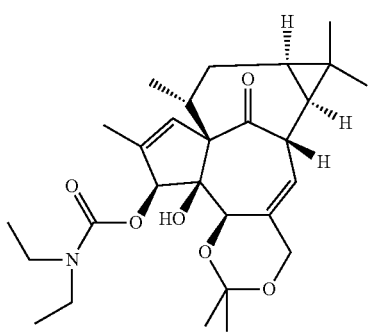 [SMILES: CCN(CC)C(=O)O[C@H]1C(C)=C[C@]23C(=O)[C@@H](C=C4COC(C)(C)O[C@H]4[C@]12O)[C@H]1[C@@H](C[C@H]3C)C1(C)C]

Preparation 806

Ingenol-5,20-acetonide-3-(N,N-diethyl-carbamate) (Compound 806)

Compound 806 was prepared according to Procedure g.

Starting material: N,N-Diethyl-carbamoyl chloride.

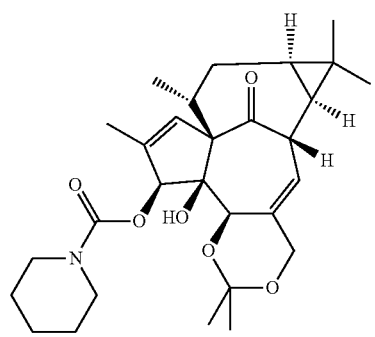 [SMILES: CC1=C[C@]23C(=O)[C@@H](C=C4COC(C)(C)O[C@H]4[C@]2(O)[C@H]1OC(=O)N1CCCCC1)[C@H]1[C@@H](C[C@H]3C)C1(C)C]

Preparation 807

Ingenol-5,20-acetonide-3-(piperidine-1-carboxylate) (Compound 807)

Compound 807 was prepared according to Procedure g.

Starting material: Piperidine-1-carbonyl chloride.

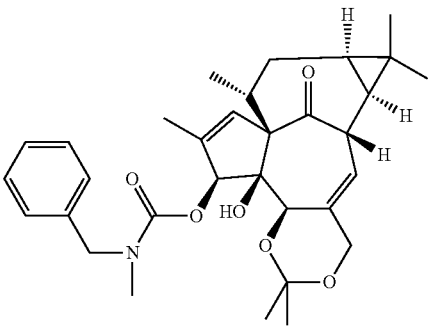 [SMILES: CC1=C[C@]23C(=O)[C@@H](C=C4COC(C)(C)O[C@H]4[C@]2(O)[C@H]1OC(=O)N(C)Cc1ccccc1)[C@H]1[C@@H](C[C@H]3C)C1(C)C]

Preparation 808

Ingenol-5,20-acetonide-3-(N-benzyl-N-methyl-carbamate) (Compound 808)

Compound 808 was prepared according to Procedure g.

Starting material: N-Benzyl-N-methyl-carbamoyl chloride, prepared from N-benzyl-N-methyl-amine according to Procedure f.

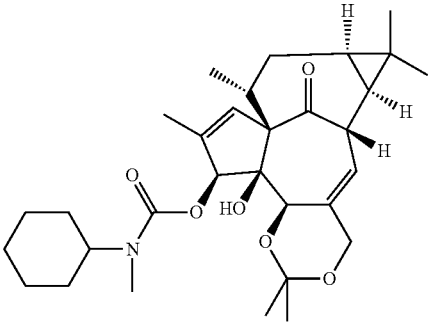 [SMILES: CC1=C[C@]23C(=O)[C@@H](C=C4COC(C)(C)O[C@H]4[C@]2(O)[C@H]1OC(=O)N(C)C1CCCCC1)[C@H]1[C@@H](C[C@H]3C)C1(C)C]

Preparation 809

Ingenol-5,20-acetonide-3-(N-cyclohexyl-N-methyl-carbamate) (Compound 809)

Compound 809 was prepared according to Procedure g.

Starting material: N-Cyclohexyl-N-methyl-carbamoyl chloride, prepared from N-cyclohexyl-N-methyl-amine according to Procedure f.

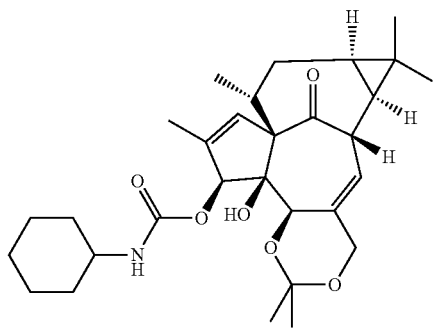 [SMILES: CC1=C[C@]23C(=O)[C@@H](C=C4COC(C)(C)O[C@H]4[C@]2(O)[C@H]1OC(=O)NC1CCCCC1)[C@H]1[C@@H](C[C@H]3C)C1(C)C]

Preparation 810

Ingenol-5,20-acetonide-3-(N-cyclohexyl-carbamate) (Compound 810)

Compound 810 was prepared according to Procedure i.
Starting material: Cyclohexyl isocyanate.

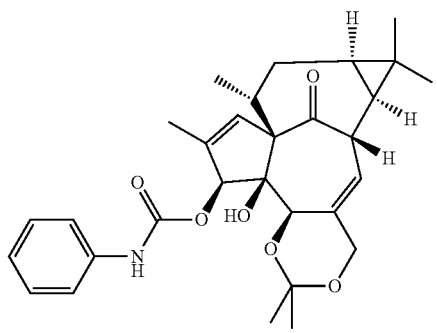 [SMILES: CC1=C[C@]23C(=O)[C@@H](C=C4COC(C)(C)O[C@H]4[C@]2(O)[C@H]1OC(=O)Nc1ccccc1)[C@H]1[C@@H](C[C@H]3C)C1(C)C]

Preparation 811

Ingenol-5,20-acetonide-3-(N-phenyl-carbamate) (Compound 811)

Compound 811 was prepared according to Procedure i.
Starting material: Phenyl isocyanate.

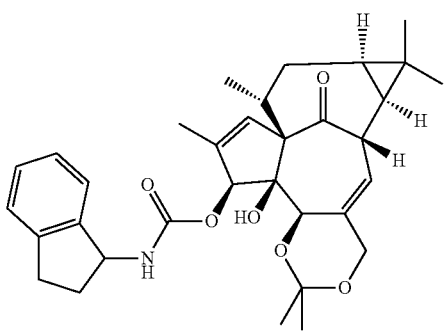 [SMILES: CC1=C[C@]23C(=O)[C@@H](C=C4COC(C)(C)O[C@H]4[C@]2(O)[C@H]1OC(=O)NC1CCc2ccccc21)[C@H]1[C@@H](C[C@H]3C)C1(C)C]

Preparation 812

Ingenol-5,20-acetonide-3-(N-(indan-1-yl)-carbamate) (Compound 812)

Compound 812 was prepared according to Procedure i.
Starting material: Isocyanato-1-indane.

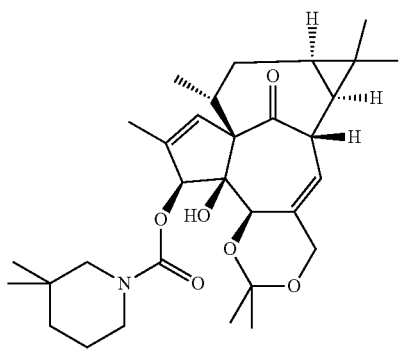

Preparation 813

Ingenol-5,20-acetonide-3-(3,3-dimethyl-piperidine-1-carboxylate) (Compound 813)

Compound 813 was prepared according to Procedure i.
Starting material: 3,3-Dimethyl-piperidine-1-carbonyl chloride, prepared from 3,3-dimethyl-piperidine according to Procedure f.

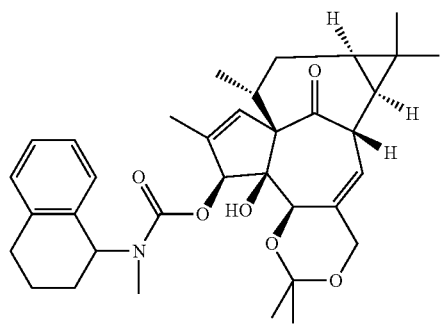 [SMILES: CC1=C[C@]23C(=O)[C@@H](C=C4COC(C)(C)O[C@H]4[C@]2(O)[C@H]1OC(=O)N(C)C1CCCc2ccccc21)[C@H]1[C@@H](C[C@H]3C)C1(C)C]

Preparation 814

Ingenol-5,20-acetonide-3-(N-Methyl-N-tetralin-1-yl-carbamate) (Compound 814)

Compound 814 was prepared according to Procedure i.

Starting material: N-Methyl-N-tetralin-1-yl-carbamoyl chloride, prepared from N-methyl-N-(tetralin-1-yl)-amine according to Procedure f.

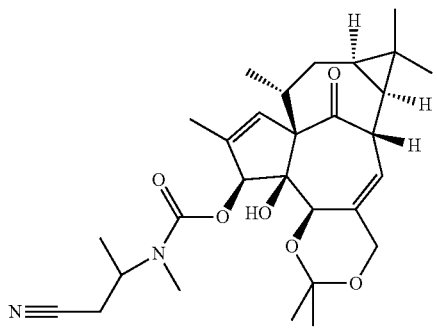 [SMILES: CC1=C[C@]23C(=O)[C@@H](C=C4COC(C)(C)O[C@H]4[C@]2(O)[C@H]1OC(=O)N(C)C(C)CC#N)[C@H]1[C@@H](C[C@H]3C)C1(C)C]

Preparation 815

Ingenol-5,20-acetonide-3-(N-(2-cyano-1-methyl-ethyl)-N-methyl-carbamate) (Compound 815)

Compound 815 was prepared according to Procedure h.

Starting material: N-(2-cyano-1-methyl-ethyl)-N-methyl-carbamoyl chloride, prepared from N-(2-cyano-1-methyl-ethyl)-N-methyl-amine according to Procedure f.

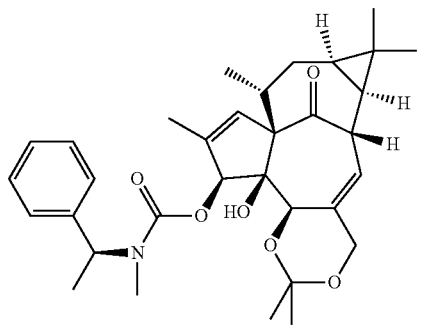 [SMILES: CC1=C[C@]23C(=O)[C@@H](C=C4COC(C)(C)O[C@H]4[C@]2(O)[C@H]1OC(=O)N(C)[C@@H](C)c1ccccc1)[C@H]1[C@@H](C[C@H]3C)C1(C)C]

Preparation 816

Ingenol-5,20-acetonide-3-(N-methyl-N—((S)-1-phenethyl)-carbamate) (Compound 816)

Compound 816 was prepared according to Procedure h.

Starting material: N-Methyl-N—((S)-1-phenethyl)-carbamoyl chloride, prepared from N-methyl-N—((S)-1-phenylethyl)-amine according to Procedure f.

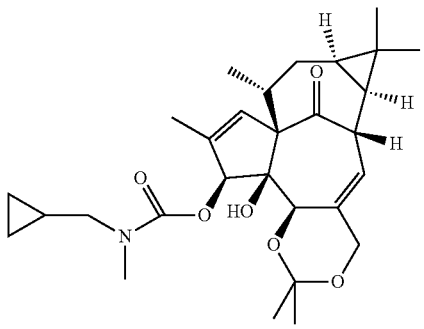 [SMILES: CC1=C[C@]23C(=O)[C@@H](C=C4COC(C)(C)O[C@H]4[C@]2(O)[C@H]1OC(=O)N(C)CC1CC1)[C@H]1[C@@H](C[C@H]3C)C1(C)C]

Preparation 817

Ingenol-5,20-acetonide-3-(N-methyl-N-(cyclopropylmethyl)-carbamate) (Compound 817)

Compound 817 was prepared according to Procedure h.

Starting material: N-(Cyclopropylmethyl)-N-methyl-carbamoyl chloride, prepared from N-(cyclopropylmethyl)-N-methyl-amine according to Procedure f.

$^1$H NMR (300 MHz, CDCl$_3$) δ 6.03-6.02 (m, 1H), 5.76-5.74 (m, 1H), 5.45 (s, 1H), 4.17-4.12 (m, 3H), 3.97 (s, 1H), 3.59 (m, 1H), 3.30-3.13 (m, 2H), 2.99 (s, 3H), 2.56 (bs, 1H), 2.34-2.25 (m, 1H), 1.79-1.70 (m, 4H), 1.45 (s, 3H), 1.39 (s, 3H), 1.29 (m, 1H), 1.10 (s, 3H), 1.05 (s, 3H), 0.98 (d, 3H), 0.94-0.86 (m, 1H), 0.72-0.65 (m, 1H), 0.53-0.48 (m, 2H), 0.24-0.16 (m, 2H).

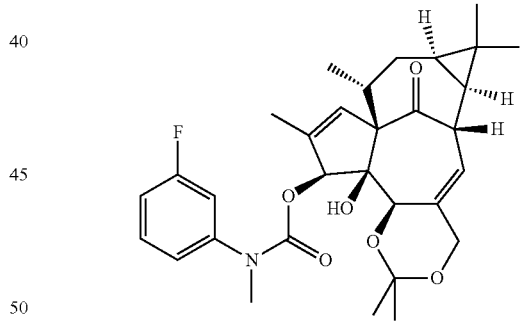

Preparation 818

Ingenol-5,20-acetonide-3-(N-(3-fluoro-phenyl)-N-methyl-carbamate) (Compound 818)

Compound 818 was prepared according to Procedure j.

Starting material: N-(3-Fluorophenyl)-N-methyl-carbamoyl chloride, prepared from 3-fluoro-N-methyl-aniline according to Procedure f with pyridine as the tertiary amine.

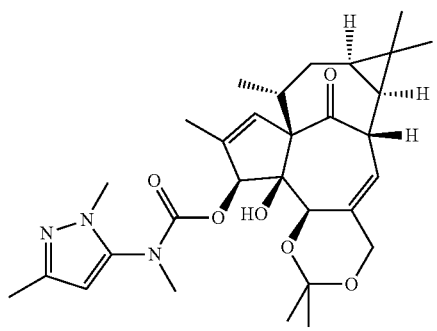

Preparation 819

Ingenol-5,20-acetonide-3-(N-(2,5-dimethylpyrazol-3-yl)-N-methyl-carbamate) (Compound 819)

Compound 819 was prepared according to Procedure h.
Starting material: N-(2,5-Dimethylpyrazol-3-yl)-N-methyl-carbamoyl chloride, prepared from N,1,3-trimethyl-1H-pyrazol-5-amine according to Procedure f.

$^1$H NMR (300 MHz, CDCl3) δ 5.96 (bs, 1H), 5.86 (s, 1H), 5.76-5.74 (m, 1H), 4.21-4.05 (m, 3H), 3.95 (s, 1H), 3.61 (s, 3H), 3.20 (s, 3H), 3.11 (bs, 1H), 2.21 (s, 3H), 1.84-1.74 (m, 4H), 1.57 (s, 3H), 1.45 (s, 3H), 1.38 (s, 3H), 1.07 (s, 3H), 1.04 (s, 3H), 0.90-0.83 (m, 1H), 0.75 (bd, 3H), 0.68-0.60 (m, 1H).

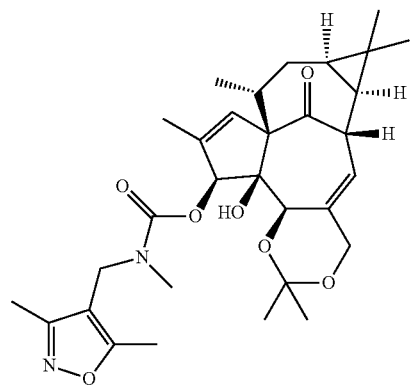

Preparation 820

Ingenol-5,20-acetonide-3-(N-(3,5-dimethylisoxazol-4-yl)-N-methyl-carbamate) (Compound 820)

Compound 820 was prepared according to Procedure h.
Starting material: N-[(3,5-Dimethylisoxazol-4-yl)methyl]-N-methyl-carbamoyl chloride, prepared from 1-(3,5-dimethylisoxazol-4-yl)-N-methyl-methanamine according to Procedure f.

$^1$H NMR (300 MHz, CDCl3) δ 6.05 (s, 1H), 5.78-5.76 (m, 1H), 5.46 (s, 1H), 4.24-4.11 (m, 4H), 3.98 (s, 1H), 3.52 (s, 1H), 2.78 (s, 3H), 2.50 (bs, 1H), 2.37 (s, 3H), 2.30-2.21 (m, 4H), 1.78 (d, 3H), 1.77-1.68 (m, 1H), 1.46 (s, 3H), 1.41 (s, 3H), 1.09 (s, 3H), 1.05 (s, 3H), 0.96 (d, 3H), 0.94-0.89 (m, 1H), 0.72-0.64 (m, 1H).

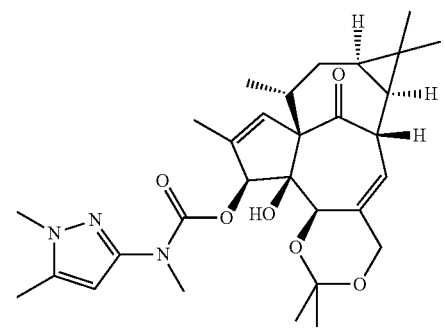

Preparation 821

Ingenol-5,20-acetonide-3-(N-(1,5-dimethylpyrazol-3-yl)-N-methyl-carbamate) (Compound 821)

Compound 821 was prepared according to Procedure h.
Starting material: N-(1,5-Dimethylpyrazol-3-yl)-N-methyl-carbamoyl chloride, prepared from N,1,5-trimethyl-pyrazol-3-amine according to Procedure f.

$^1$H NMR (300 MHz, CDCl3) δ 5.96 (bs, 1H), 5.86 (s, 1H), 5.76-5.74 (m, 1H), 5.42 (s, 1H), 4.21-4.05 (m, 3H), 3.95 (s, 1H), 3.61 (s, 3H), 3.20 (s, 3H), 3.11 (bs, 1H), 2.21 (s, 3H), 2.12-2.02 (m, 1H), 1.82-1.64 (m, 5H), 1.45 (s, 3H), 1.38 (s, 3H), 1.07 (s, 3H), 1.04 (s, 3H), 0.90-0.85 (m, 1H), 0.75 (bs, 3H), 0.68-0.60 (m, 1H).

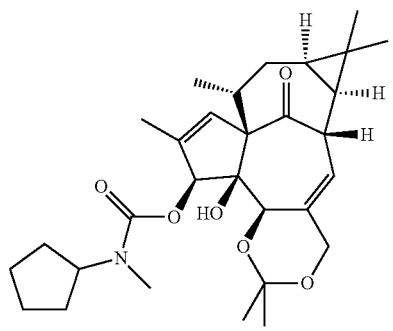 [SMILES: CC1=C[C@]23C(=O)[C@@H](C=C4COC(C)(C)O[C@H]4[C@]2(O)[C@H]1OC(=O)N(C)C1CCCC1)[C@H]1[C@@H](C[C@H]3C)C1(C)C]

Preparation 822

Ingenol-5,20-acetonide-3-(N-cyclopentyl-N-methyl-carbamate) (Compound 822)

Compound 822 was prepared according to Procedure h.
Starting material: N-Cyclopentyl-N-methyl-carbamoyl chloride, prepared from N-methylcyclopentanamine according to Procedure f.

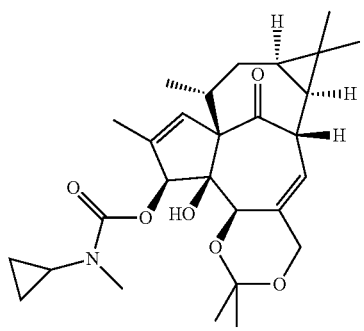 [SMILES: CC1=C[C@]23C(=O)[C@@H](C=C4COC(C)(C)O[C@H]4[C@]2(O)[C@H]1OC(=O)N(C)C1CC1)[C@H]1[C@@H](C[C@H]3C)C1(C)C]

Preparation 823

Ingenol-5,20-acetonide-3-(N-cyclopropyl-N-methyl-carbamate) (Compound 823)

Compound 823 was prepared according to Procedure h.

Starting material: N-Cyclopropyl-N-methyl-carbamoyl chloride, prepared from N-methylcyclopropanamine according to Procedure f.

$^1$H NMR (300 MHz, CDCl3) δ 6.04-6.01 (m, 1H), 5.77-5.74 (m, 1H), 5.47 (s, 1H), 4.17-4.12 (m, 3H), 3.98 (s, 1H), 3.52 (s, 1H), 3.27 (bs, 1H), 2.91 (s, 3H), 2.65-2.57 (m, 2H), 2.34-2.25 (m, 1H), 1.80-1.70 (m, 4H), 1.45 (s, 3H), 1.39 (s, 1H), 1.16-1.08 (m, 5H), 1.05 (s, 3H), 0.98 (d, 3H), 0.94-0.87 (m, 1H), 0.74-0.65 (m, 4H).

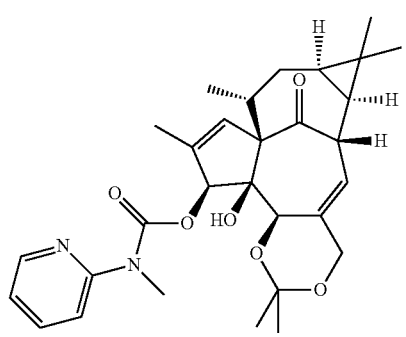 [SMILES: CC1=C[C@]23C(=O)[C@@H](C=C4COC(C)(C)O[C@H]4[C@]2(O)[C@H]1OC(=O)N(C)c1ccccn1)[C@H]1[C@@H](C[C@H]3C)C1(C)C]

Preparation 824

Ingenol-5,20-acetonide-3-(N-methyl-N-(2-pyridyl)-carbamate) (Compound 824)

Compound 824 was prepared according to Procedure j.

Starting material: N-Methyl-N-(2-pyridyl)carbamoyl chloride, prepared from N-methylpyridin-2-amine according to Procedure f.

$^1$H NMR (300 MHz, CDCl3) 68.38-8.36 (m, 1H), 7.73-7.67 (m, 1H), 7.43 (d, 1H), 7.09-7.05 (m, 1H), 6.00-5.98 (m, 1H), 5.76-5.74 (m, 1H), 5.71 (s, 1H), 5.04 (bs, 1H), 4.27-4.11 (m, 3H), 3.95 (s, 1H), 3.44 (s, 3H), 2.30-2.20 (m, 2H), 1.81 (d, 3H), 1.70-1.60 (m, 1H), 1.46 (s, 3H), 1.39 (s, 3H), 1.15 (s, 3H), 1.06 (s, 3H), 0.96-0.88 (m, 1H), 0.79 (d, 3H), 0.69-0.63 (m, 1H).

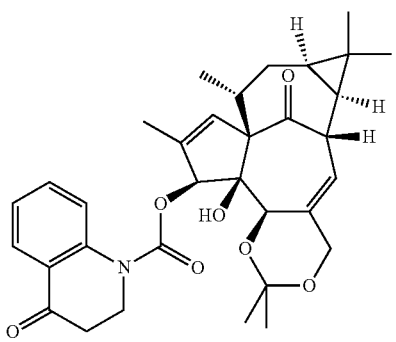 [SMILES: CC1=C[C@]23C(=O)[C@@H](C=C4COC(C)(C)O[C@H]4[C@]2(O)[C@H]1OC(=O)N1CCC(=O)c2ccccc21)[C@H]1[C@@H](C[C@H]3C)C1(C)C]

Preparation 825

Ingenol-5,20-acetonide-3-(4-oxo-2,3-dihydroquinoline-1-carboxylate) (Compound 825)

Compound 825 was prepared according to Procedure j.

Starting material: 4-Oxo-2,3-dihydroquinoline-1-carbonyl chloride, prepared from 2,3-dihydro-1H-quinolin-4-one according to Procedure f.

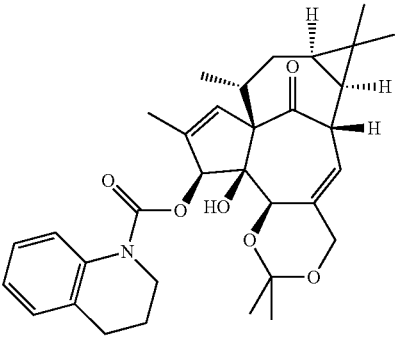 [SMILES: CC1=C[C@]23C(=O)[C@@H](C=C4COC(C)(C)O[C@H]4[C@]2(O)[C@H]1OC(=O)N1CCCc2ccccc21)[C@H]1[C@@H](C[C@H]3C)C1(C)C]

Preparation 826

Ingenol-5,20-acetonide-3-(3,4-dihydro-2H-quinoline-1-carboxylate) (Compound 826)

Compound 826 was prepared according to Procedure j.

Starting material: 3,4-Dihydro-2H-quinoline-1-carbonyl chloride, prepared from 1,2,3,4-tetrahydroquinoline according to Procedure f.

$^1$H NMR (300 MHz, CDCl3) δ 7.68 (d, 1H), 7.16-6.98 (m, 3H), 6.03 (d, 1H), 5.77-5.75 (m, 1H), 5.58 (s, 1H), 4.23-4.11 (m, 3H), 4.00 (s, 1H), 3.82-3.72 (m, 2H), 3.39 (s, 1H), 2.79 (t, 2H), 2.46-2.41 (m, 1H), 2.29-2.20 (m, 1H), 2.01-1.92 (m, 2H), 1.81 (d, 3H), 1.71-1.63 (m, 1H), 1.46 (s, 3H), 1.41 (s, 3H), 1.08 (s, 3H), 1.04 (s, 3H), 0.92-0.83 (m, 4H), 0.71-0.63 (m, 1H).

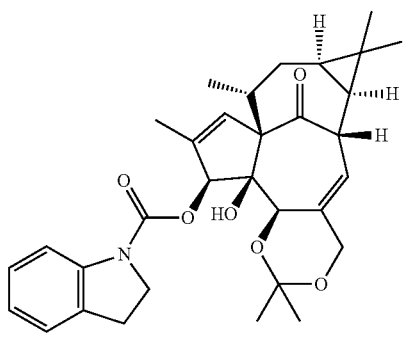 [SMILES: CC1=C[C@]23C(=O)[C@@H](C=C4COC(C)(C)O[C@H]4[C@]2(O)[C@H]1OC(=O)N1CCc2ccccc21)[C@H]1[C@@H](C[C@H]3C)C1(C)C]

Preparation 827

Ingenol-5,20-acetonide-3-(indoline-1-carboxylate) (Compound 827)

Compound 827 was prepared according to Procedure j.

Starting material: Indoline-1-carbonyl chloride, prepared from indoline according to Procedure f.

$^1$H NMR (300 MHz, CDCl3) δ 7.87 (bs, 1H), 7.22-7.09 (m, 2H), 6.99-6.92 (m, 1H), 6.09 (bs, 1H), 5.79-5.77 (m, 1H), 5.57 (s, 1H), 4.25-4.12 (m, 3H), 4.08-4.02 (m, 3H), 3.50 (bs, 1H), 3.18-3.10 (m, 2H), 2.64 bs, 1H), 2.34-2.24 (m, 1H), 1.84 (s, 3H), 1.79-1.70 (m, 1H), 1.49 (s, 3H), 1.43 (s, 3H), 1.08 (s, 3H), 1.05 (s, 3H), 1.01 (d, 3H), 0.94-0.86 (m, 1H), 0.73-0.65 (m, 1H).

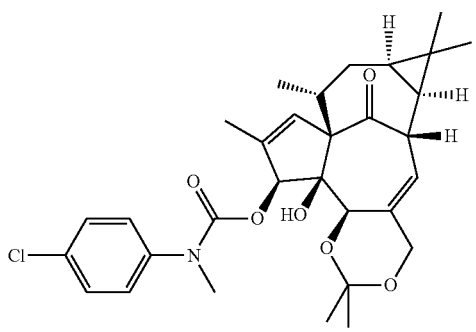

Preparation 829

Ingenol-5,20-acetonide-3-(N-(4-chloro-phenyl)-N-methyl-carbamate) (Compound 829)

Compound 829 was prepared according to Procedure j.

Starting material: N-(4-Chlorophenyl)-N-methyl-carbamoyl chloride, prepared from 4-chloro-N-methyl-aniline according to Procedure f.

$^1$H NMR (300 MHz, CDCl3) δ 7.31 (d, 2H), 7.20 (d, 2H), 5.94 (s, 1H), 5.76-5.73 (m, 1H), 5.45 (s, 1H), 4.21-4.07 (m, 3H), 3.95 (s, 1H), 3.29 (s, 3H), 3.22 (s, 1H), 3.14 (d, 1H), 2.17-2.07 (m, 1H), 1.75 (d, 3H), 1.63-1.57 (m, 1H), 1.45 (s, 3H), 1.39 (s, 3H), 1.08 (s, 3H), 1.04 (s, 3H), 0.90-0.83 (m, 1H), 0.76 (d, 3H), 0.69-0.61 (m, 1H).

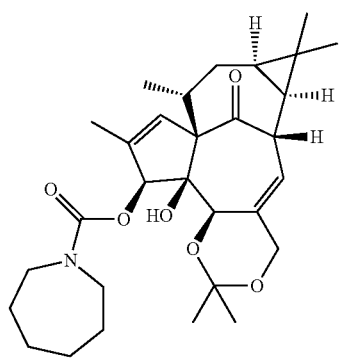 [SMILES: CC1=C[C@]23C(=O)[C@@H](C=C4COC(C)(C)O[C@H]4[C@]2(O)[C@H]1OC(=O)N1CCCCCC1)[C@H]1[C@@H](C[C@H]3C)C1(C)C]

Preparation 828

Ingenol-5,20-acetonide-3-(azepane-1-carboxylate) (Compound 828)

Compound 828 was prepared according to Procedure j.

Starting material: Azepane-1-carbonyl chloride, prepared from azepane according to Procedure f.

$^1$H NMR (300 MHz, CDCl3) δ 6.03-6.01 (m, 1H), 5.76-5.74 (m, 1H), 5.47 (s, 1H), 4.17-4.12 (m, 3H), 3.97 (s, 1H), 3.62 (s, 1H), 3.49-3.27 (m, 4H), 2.60-2.55 (m, 1H), 2.35-2.26 (m, 1H), 1.79-1.55 (m, 12H), 1.46 (s, 3H), 1.39 (s, 3H), 1.10 (s, 3H), 1.05 (s, 3H), 0.98 (d, 3H), 0.94-0.88 (m, 1H), 0.72-0.64 (m, 1H).

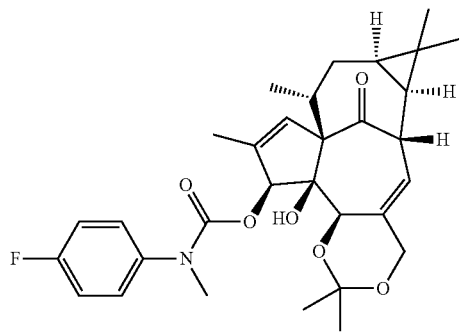 [SMILES: CC1=C[C@]23C(=O)[C@@H](C=C4COC(C)(C)O[C@H]4[C@]2(O)[C@H]1OC(=O)N(C)c1ccc(F)cc1)[C@H]1[C@@H](C[C@H]3C)C1(C)C]

Preparation 830

Ingenol-5,20-acetonide-3-(N-(4-fluoro-phenyl)-N-methyl-carbamate) (Compound 830)

Compound 830 was prepared according to Procedure j.

Starting material: N-(4-Fluorophenyl)-N-methyl-carbamoyl chloride, prepared from 4-fluoro-N-methyl-aniline according to Procedure f.

$^1$H NMR (300 MHz, CDCl3) δ 7.24-7.19 (m, 2H), 7.06-6.98 (m, 2H), 5.92 (bs, 1H), 5.76-5.73 (m, 1H), 5.45 (s, 1H), 4.17-4.06 (m, 3H), 3.95 (s, 1H), 3.28 (s, 3H), 3.23 (bs, 1H), 3.13 (d, 1H), 2.12-2.08 (m, 1H), 1.74 (d, 3H), 1.63-1.57 (m, 1H), 1.45 (s, 3H), 1.38 (s, 3H), 1.08 (s, 3H), 1.04 (s, 3H), 0.92-0.83 (m, 1H), 0.73 (d, 3H), 0.69-0.61 (m, 1H).

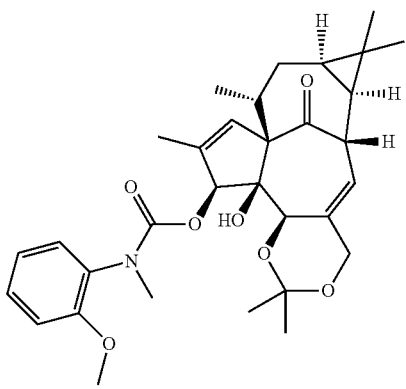 [SMILES: COc1ccccc1N(C)C(=O)O[C@H]1C(C)=C[C@]23C(=O)[C@@H](C=C4COC(C)(C)O[C@H]4[C@]12O)[C@H]1[C@@H](C[C@H]3C)C1(C)C]

Preparation 831

Ingenol-5,20-acetonide-3-(N-methyl-N-(2-methoxyphenyl)-carbamate) (Compound 831)

Compound 831 was prepared according to Procedure j.

Starting material: N-(2-Methoxyphenyl)-N-methyl-carbamoyl chloride, prepared from 2-methoxy-N-methyl-aniline according to Procedure f.

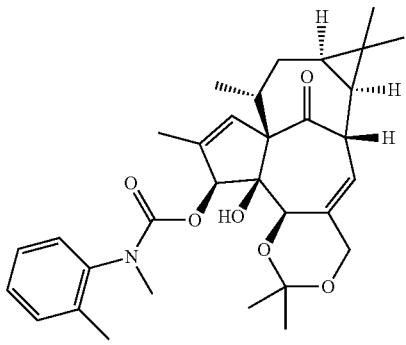 [SMILES: CC1=C[C@]23C(=O)[C@@H](C=C4COC(C)(C)O[C@H]4[C@]2(O)[C@H]1OC(=O)N(C)c1ccccc1C)[C@H]1[C@@H](C[C@H]3C)C1(C)C]

Preparation 832

Ingenol-5,20-acetonide-3-(N-methyl-N-(2-methylphenyl)-carbamate) (Compound 832)

Compound 832 was prepared according to Procedure j.

Starting material: N-(2-Methylphenyl)-N-methyl-carbamoyl chloride, prepared from 2-methyl-N-methyl-aniline according to Procedure f.

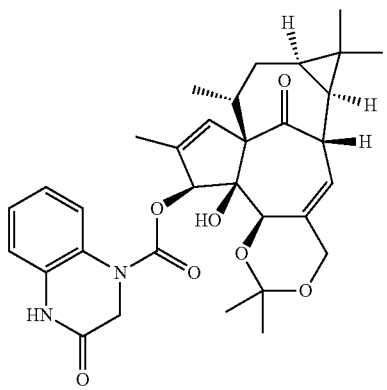 [SMILES: CC1=C[C@]23C(=O)[C@@H](C=C4COC(C)(C)O[C@H]4[C@]2(O)[C@H]1OC(=O)N1CC(=O)Nc2ccccc21)[C@H]1[C@@H](C[C@H]3C)C1(C)C]

Preparation 833

Ingenol-5,20-acetonide-3-(3-oxo-2,4-dihydroquinoxaline-1-carboxylate) (Compound 833)

Compound 833 was prepared according to Procedure j.
Starting material: 3-Oxo-2,4-dihydroquinoxaline-1-carbonyl chloride, prepared from 3,4-dihydro-1H-quinoxalin-2-one according to Procedure f.

$^1$H NMR (300 MHz, CDCl3) δ 8.82 (s, 1H), 7.72 (d, 1H), 7.15-7.01 (m, 2H), 6.90 (dd, 1H), 6.07-6.06 (m, 1H), 5.80-5.78 (m, 1H), 5.58 (s, 1H), 4.47 (d, 1H), 4.44 (d, 1H), 4.25-4.09 (m, 3H), 4.00 (s, 1H), 3.39 (s, 1H), 2.39 (bs, 1H), 2.29-2.20 (m, 1H), 1.81 (d, 3H), 1.72-1.63 (m, 1H), 1.45 (s, 3H), 1.42 (s, 3H), 1.08 (s, 3H), 1.04 (s, 3H), 0.92-0.84 (m, 4H), 0.71-0.63 (m, 1H).

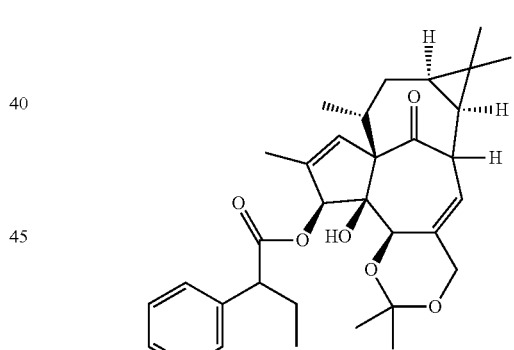

Preparation 834

Ingenol-5,20-acetonide-3-(N-ethyl-N-phenyl-carbamate) (Compound 834)

Compound 834 was prepared according to Procedure j.
Starting material: N-Ethyl-N-phenyl-carbamoyl chloride, prepared from N-ethyl-aniline according to Procedure f.

$^1$H NMR (300 MHz, CDCl3) δ 7.38-7.32 (m, 2H), 7.28-7.18 (m, 3H), 5.89 (s, 1H), 5.73-5.70 (m, 1H), 5.46 (s, 1H), 4.17-4.14 (m, 2H), 4.04 (bd, 1H), 3.94-3.93 (m, 1H), 3.79-3.64 (m, 2H), 3.16 (bs, 1H), 2.04-1.78 (m, 2H), 1.75 (d, 3H), 1.54-1.49 (m, 1H), 1.45 (s, 3H), 1.37 (s, 3H), 1.17 (t, 3H), 1.06 (s, 3H), 1.03 (s, 3H), 0.90-0.81 (m, 1H), 0.70-0.56 (m, 4H).

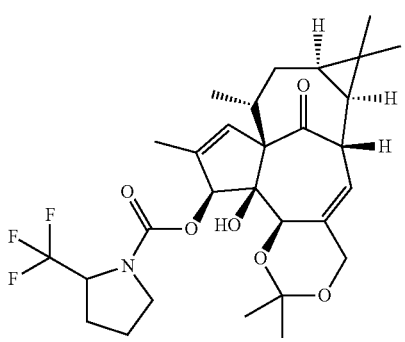 [SMILES: CC1=C[C@]23C(=O)[C@@H](C=C4COC(C)(C)O[C@H]4[C@]2(O)[C@H]1OC(=O)N1CCCC1C(F)(F)F)[C@H]1[C@@H](C[C@H]3C)C1(C)C]

Preparation 835

Ingenol-5,20-acetonide-3-(2-trifluoromethyl-pyrrolidine-1-carboxylate) (Compound 835)

Compound 835 was prepared according to Procedure j.
Starting material: 2-(Trifluoromethyl)pyrrolidine-1-carbonyl chloride, prepared from 2-(trifluoromethyl)pyrrolidine according to Procedure f.

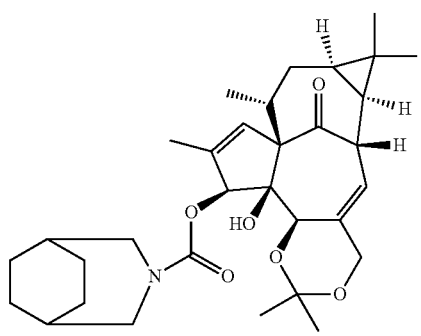 [SMILES: CC1=C[C@]23C(=O)[C@@H](C=C4COC(C)(C)O[C@H]4[C@]2(O)[C@H]1OC(=O)N1CC2CCC(CC2)C1)[C@H]1[C@@H](C[C@H]3C)C1(C)C]

Preparation 836

Ingenol-5,20-acetonide-3-(3-azabicyclo[3.2.2]nonane-3-carboxylate) (Compound 836)

Compound 836 was prepared according to Procedure j.
Starting material: 3-Azabicyclo[3.2.2]nonane-3-carbonyl chloride, prepared from 3-azabicyclo[3.2.2]nonane according to Procedure f.

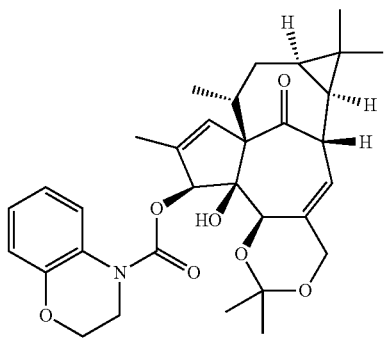 [SMILES: CC1=C[C@]23C(=O)[C@@H](C=C4COC(C)(C)O[C@H]4[C@]2(O)[C@H]1OC(=O)N1CCOc2ccccc21)[C@H]1[C@@H](C[C@H]3C)C1(C)C]

Preparation 837

Ingenol-5,20-acetonide-3-(2,3-dihydro-1,4-benzoxazine-4-carboxylate) (Compound 837)

Compound 837 was prepared according to Procedure j.
Starting material: 2,3-Dihydro-1,4-benzoxazine-4-carbonyl chloride, prepared from 2,3-dihydro-1,4-benzoxazine according to Procedure f.

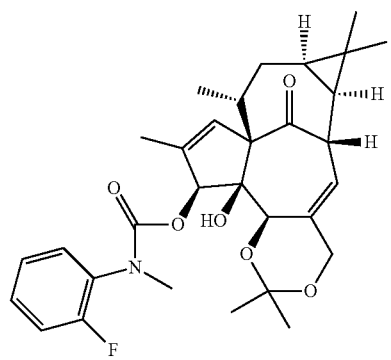 [SMILES: CC1=C[C@]23C(=O)[C@@H](C=C4COC(C)(C)O[C@H]4[C@]2(O)[C@H]1OC(=O)N(C)c1ccccc1F)[C@H]1[C@@H](C[C@H]3C)C1(C)C]

Preparation 838

Ingenol-5,20-acetonide-3-(N-(2-fluoro-phenyl)-N-methyl-carbamate) (Compound 838)

Compound 838 was prepared according to Procedure j.
Starting material: N-(2-Fluoro-phenyl)-N-methyl-carbamoyl chloride, prepared from 2-fluoro-N-methyl-aniline according to Procedure f.

$^1$H NMR (300 MHz, CDCl3) δ 7.29-7.21 (m, 2H), 7.14-7.06 (m, 2H), 5.87 (bs, 1H), 5.73-5.72 (m, 1H), 5.46 (s, 1H), 4.16-4.14 (m, 2H), 4.09-4.02 (m, 1H), 3.93 (s, 1H), 3.27 (s, 3H), 3.21 (s, 1H), 2.09-2.00 (m, 1H), 1.73 (bs, 4H), 1.52-1.45 (m, 4H), 1.38 (s, 3H), 1.07 (s, 3H), 1.03 (s, 3H), 0.88-0.82 (m, 1H), 0.65-0.55 (m, 4H).

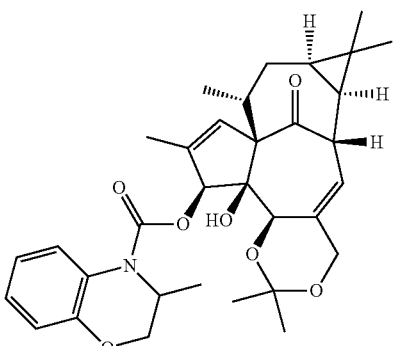

Preparation 839

Ingenol-5,20-acetonide-3-(3-methyl-2,3-dihydro-1,4-benzoxazine-4-carboxylate) (Compound 839)

Compound 839 (a mixture of diastereomers) was prepared according to Procedure j.

Starting material: 3-Methyl-2,3-dihydro-1,4-benzoxazine-4-carbonyl chloride, prepared from 3-methyl-3,4-dihydro-2H-1,4-benzoxazine according to Procedure f.

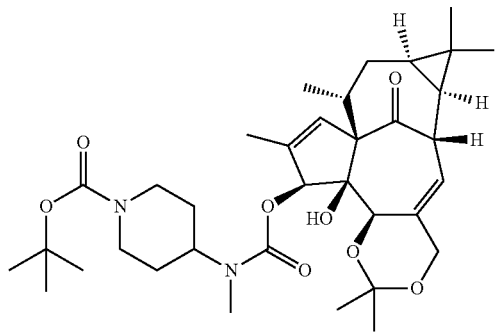 [SMILES: CC1=C[C@]23C(=O)[C@@H](C=C4COC(C)(C)O[C@H]4[C@]2(O)[C@H]1OC(=O)N(C)C1CCN(C(=O)OC(C)(C)C)CC1)[C@H]1[C@@H](C[C@H]3C)C1(C)C]

Preparation 842

Ingenol-5,20-acetonide-3-(N-methyl-N—(N-(tert-butyloxycarbonyl)-4-piperidyl)-carbamate) (Compound 842)

Compound 842 was prepared according to Procedure j.

Starting material: tert-Butyl 4-(chlorocarbonyl(methyl)amino)piperidine-1-carboxylate, prepared from tert-butyl 4-methylaminopiperidine-1-carboxylate according to Procedure f.

$^1$H NMR (300 MHz, CDCl3) δ 6.03-6.01 (m, 1H), 5.77-5.74 (m, 1H), 5.47 (s, 1H), 4.27-4.10 (m, 5H), 3.98 (s, 1H), 3.49-3.38 (m, 2H), 3.28 (bs, 1H), 2.78 (bs, 4H), 2.58-2.52 (m, 1H), 2.32-2.24 (m, 1H), 1.79-1.55 (m, 8H), 1.46 (s, 9H), 1.45 (s, 3H), 1.39 (s, 3H), 1.09 (s, 3H), 1.05 (s, 3H), 0.98 (d, 3H), 0.94-0.87 (m, 1H), 0.73-0.65 (m, 1H).

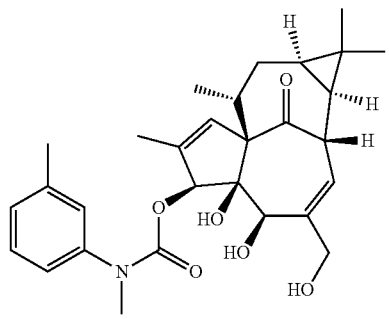 [SMILES: CC1=C[C@]23C(=O)[C@@H](C=C(CO)[C@@H](O)[C@]2(O)[C@H]1OC(=O)N(C)c1cccc(C)c1)[C@H]1[C@@H](C[C@H]3C)C1(C)C]

Preparation 843

Ingenol-5,20-acetonide-3-(N-methyl-N-(3-methyl-phenyl)-carbamate) (Compound 843)

Compound 843 was prepared according to Procedure j.

Starting material: N-Methyl-N-(3-methyl-phenyl)-carbamoyl chloride, prepared from N,3-dimethylaniline according to Procedure f.

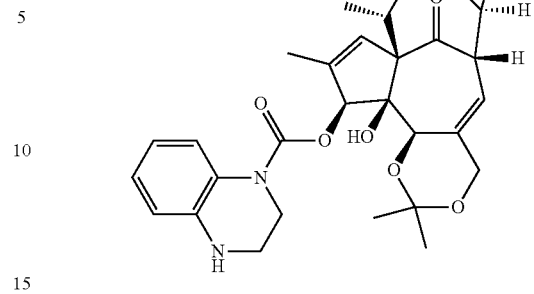

Preparation 844

Ingenol-5,20-acetonide-3-(3,4-dihydro-2H-quinoxaline-1-carboxylate) (Compound 844)

Compound 844 was prepared according to Procedure j.

Starting material: 3,4-Dihydro-2H-quinoxaline-1-carbonyl chloride, prepared from 1,2,3,4-tetrahydroquinoxaline according to Procedure f.

$^1$H NMR (300 MHz, CDCl3) δ 7.86 (bd, 1H), 7.67 (bs, 1H), 7.22-7.10 (m, 2H), 6.07-6.06 (m, 1H), 5.81-5.79 (m, 1H), 5.57 (s, 1H), 4.27-3.94 (m, 9H), 3.34 (s, 1H), 2.39 (bs, 1H), 2.30-2.21 (m, 1H), 1.82 (d, 3H), 1.73-1.64 (m, 1H), 1.47 (s, 3H), 1.43 (s, 3H), 1.09 (s, 3H), 1.05 (s, 3H), 0.92-0.84 (m, 4H), 0.71-0.63 (m, 1H).

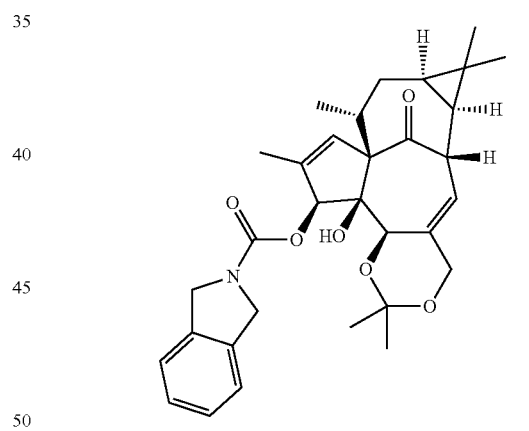

Preparation 845

Ingenol-5,20-acetonide-3-(isoindoline-2-carboxylate) (Compound 845)

Compound 845 was prepared according to Procedure j.

Starting material: Isoindoline-2-carbonyl chloride, prepared from isoindoline according to Procedure f.

$^1$H NMR (300 MHz, CDCl3) δ 7.32-7.25 (m, 4H), 6.07-6.06 (m, 1H), 5.78-5.76 (m, 1H), 5.51 (s, 1H), 4.79-4.72 (m, 4H), 4.20-4.13 (m, 3H), 4.00 (s, 1H), 3.59 (s, 1H), 2.66-2.61 (m, 1H), 2.35-2.25 (m, 1H), 1.82 (d, 3H), 1.81-1.72 (m, 1H), 1.48 (s, 3H), 1.41 (s, 3H), 1.09 (s, 3H), 1.04 (s, 3H), 1.01 (d, 3H), 0.94-0.86 (m, 1H), 0.73-0.65 (m, 1H).

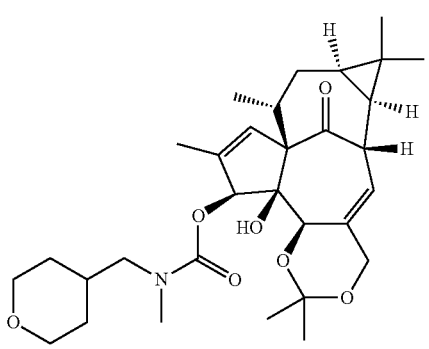 [SMILES: CC1=C[C@]23C(=O)[C@@H](C=C4COC(C)(C)O[C@H]4[C@]2(O)[C@H]1OC(=O)N(C)CC1CCOCC1)[C@H]1[C@@H](C[C@H]3C)C1(C)C]

Preparation 846

Ingenol-5,20-acetonide-3-(N-methyl-N-(tetrahydropyran-4-ylmethyl)-carbamate) (Compound 846)

Compound 846 was prepared according to Procedure j.

Starting material: N-Methyl-N-(tetrahydropyran-4-ylmethyl)-carbamoyl chloride, prepared from N-methyl-1-tetrahydropyran-4-yl-methanamine according to Procedure f.

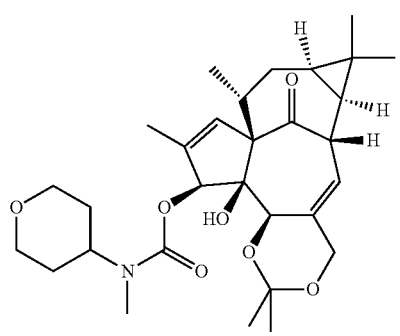 [SMILES: CC1=C[C@]23C(=O)[C@@H](C=C4COC(C)(C)O[C@H]4[C@]2(O)[C@H]1OC(=O)N(C)C1CCOCC1)[C@H]1[C@@H](C[C@H]3C)C1(C)C]

Preparation 847

Ingenol-5,20-acetonide-3-(N-methyl-N-(tetrahydropyran-4-yl)-carbamate) (Compound 847)

Compound 847 was prepared according to Procedure j.

Starting material: N-Methyl-N-(tetrahydropyran-4-yl)-carbamoyl chloride, prepared from N-methyltetrahydropyran-4-amine according to Procedure f.

$^1$H NMR (300 MHz, CDCl3) δ 6.04-6.03 (m, 1H), 5.77-5.75 (m, 1H), 5.48 (s, 1H), 4.22-3.98 (m, 7H), 3.45 (bs, 3H), 2.82 (s, 3H), 2.58-2.52 (m, 1H), 2.33-2.24 (m, 1H), 1.85-1.58 (m, 8H), 1.45 (s, 3H), 1.39 (s, 3H), 1.09 (s, 3H), 1.05 (s, 3H), 0.99 (d, 3H), 0.94-0.86 (m, 1H), 0.73-0.65 (m, 1H).

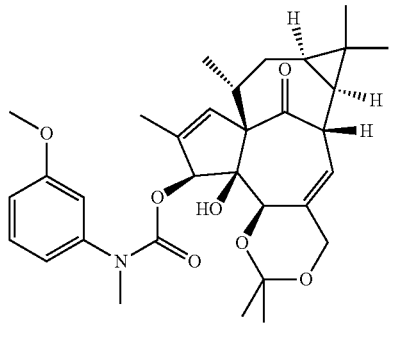 [SMILES: COc1cccc(N(C)C(=O)O[C@H]2C(C)=C[C@]34C(=O)[C@@H](C=C5COC(C)(C)O[C@H]5[C@]23O)[C@H]2[C@@H](C[C@H]4C)C2(C)C)c1]

Preparation 848

Ingenol-5,20-acetonide-3-(N-methyl-N-(3-methoxyphenyl)-carbamate) (Compound 848)

Compound 848 was prepared according to Procedure j.

Starting material: N-Methyl-N-(3-methoxy-phenyl)-carbamoyl chloride, prepared from N-methyl-3-methoxy-aniline according to Procedure f.

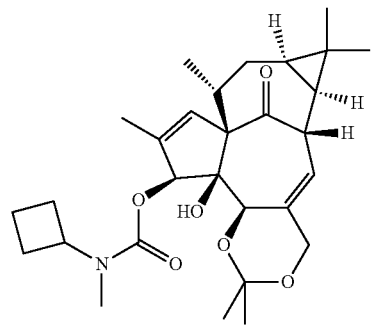 [SMILES: CC1=C[C@]23C(=O)[C@@H](C=C4COC(C)(C)O[C@H]4[C@]2(O)[C@H]1OC(=O)N(C)C1CCC1)[C@H]1[C@@H](C[C@H]3C)C1(C)C]

Preparation 849

Ingenol-5,20-acetonide-3-(N-cyclobutyl-N-methyl-carbamate) (Compound 849)

Compound 849 was prepared according to Procedure h.

Starting material: N-Cyclobutyl-N-methyl-carbamoyl chloride, prepared from N-methylcyclobutanamine according to Procedure f.

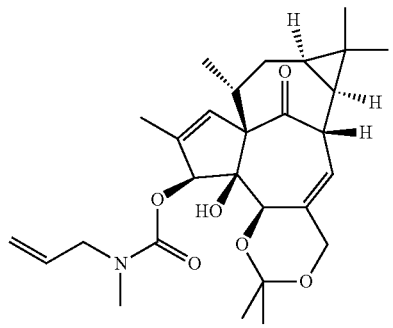 [SMILES: C=CCN(C)C(=O)O[C@H]1C(C)=C[C@]23C(=O)[C@@H](C=C4COC(C)(C)O[C@H]4[C@]12O)[C@H]1[C@@H](C[C@H]3C)C1(C)C]

Preparation 850

Ingenol-5,20-acetonide-3-(N-allyl-N-methyl-carbamate) (Compound 850)

Compound 850 was prepared according to Procedure h.

Starting material: N-Allyl-N-methyl-carbamoyl chloride, prepared from N-methylprop-2-en-1-amine according to Procedure f.

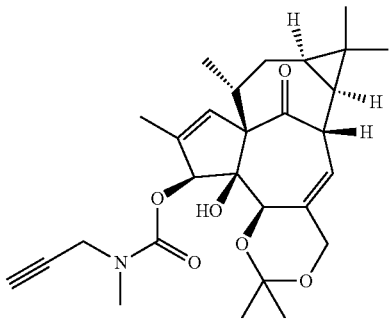 [SMILES: C#CCN(C)C(=O)O[C@H]1C(C)=C[C@]23C(=O)[C@@H](C=C4COC(C)(C)O[C@H]4[C@]12O)[C@H]1[C@@H](C[C@H]3C)C1(C)C]

Preparation 851

Ingenol-5,20-acetonide-3-(N-methyl-N-prop-2-ynyl-carbamate) (Compound 851)

Compound 851 was prepared according to Procedure h.

Starting material: N-Methyl-N-prop-2-ynyl-carbamoyl chloride, prepared from N-methylprop-2-yn-1-amine according to Procedure f.

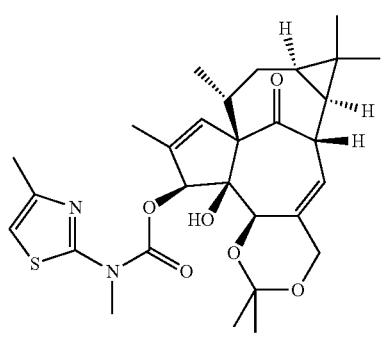 [SMILES: CC1=C[C@]23C(=O)[C@@H](C=C4COC(C)(C)O[C@H]4[C@]2(O)[C@H]1OC(=O)N(C)c1nc(C)cs1)[C@H]1[C@@H](C[C@H]3C)C1(C)C]

Preparation 852

Ingenol-5,20-acetonide-3-(N-methyl-N-(4-methyl-thiazol-2-yl)-carbamate) (Compound 852)

Compound 852 was prepared according to Procedure j.

Starting material: N-Methyl-N-(4-methylthiazol-2-yl)carbamoyl chloride, prepared from N,4-dimethylthiazol-2-amine according to Procedure f.

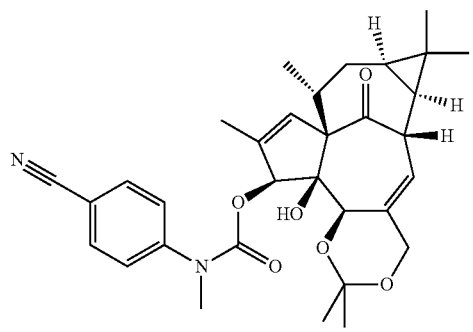 [SMILES: CC1=C[C@]23C(=O)[C@@H](C=C4COC(C)(C)O[C@H]4[C@]2(O)[C@H]1OC(=O)N(C)c1ccc(C#N)cc1)[C@H]1[C@@H](C[C@H]3C)C1(C)C]

Preparation 853

Ingenol-5,20-acetonide-3-(N-(4-cyano-phenyl)-N-methyl-carbamate) (Compound 853)

Compound 853 was prepared according to Procedure j.

Starting material: N-(4-Cyano-phenyl)-N-methyl-carbamoyl chloride, prepared from N-methyl-4-cyano-aniline according to Procedure f.

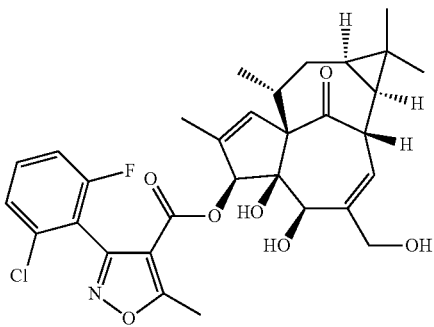 [SMILES: CC1=C[C@]23C(=O)[C@@H](C=C(CO)[C@@H](O)[C@]2(O)[C@H]1OC(=O)c1c(-c2c(F)cccc2Cl)noc1C)[C@H]1[C@@H](C[C@H]3C)C1(C)C]

Example 501

Ingenol 3-(5-methyl-3-(2-chloro-6-fluoro-phenyl)-isoxazole-4-carboxylate) (Compound 501)

Compound 501 was prepared according to Procedure e.

Starting material: Compound 601.

$^1$H NMR (300 MHz, CDCl$_3$) δ 7.42-7.34 (m, 1H), 7.28-7.25 (m, 1H), 7.09-7.03 (m, 1H), 6.02 (d, 1H), 5.85-5.84 (m, 1H), 5.56 (s, 1H), 4.46 (d, 1H), 4.18-4.07 (m, 3H), 3.99-3.97 (m, 1H), 3.51 (s, 1H), 2.83 (s, 3H), 2.21-2.13 (m, 1H), 1.88-1.82 (m, 1H), 1.69-1.60 (m, 1H), 1.64 (d, 3H), 1.59 (s, 1H), 1.03 (s, 3H), 1.03 (s, 3H), 0.90-0.82 (m, 1H), 0.73 (d, 3H), 0.67-0.59 (m, 1H).

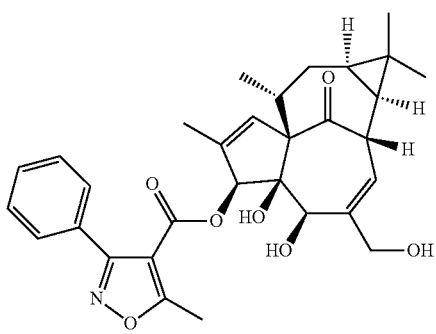 [SMILES: CC1=C[C@]23C(=O)[C@@H](C=C(CO)[C@@H](O)[C@]2(O)[C@H]1OC(=O)c1c(-c2ccccc2)noc1C)[C@H]1[C@@H](C[C@H]3C)C1(C)C]

Example 502

Ingenol 3-(5-methyl-3-phenyl-isoxazole-4-carboxylate) (Compound 502)

Compound 502 was prepared according to Procedure e. Starting material: Compound 602.

$^1$H NMR (300 MHz, CDCl$_3$) δ 7.56-7.53 (m, 2H), 7.48-7.38 (m, 3H), 6.00 (d, 1H), 5.94-5.93 (m, 1H), 5.66 (s, 1H), 4.31 (d, 1H), 4.16-4.01 (m, 3H), 3.98 (d, 1H), 3.36 (s, 1H), 2.77 (s, 3H), 2.29-2.25 (m, 1H), 2.05-1.96 (m, 1H), 1.80-1.74 (m, 1H), 1.74 (d, 3H), 1.27 (s, 1H), 1.03 (s, 3H), 1.02 (s, 3H), 0.90-0.82 (m, 1H), 0.71 (d, 3H), 0.65-0.57 (m, 1H).

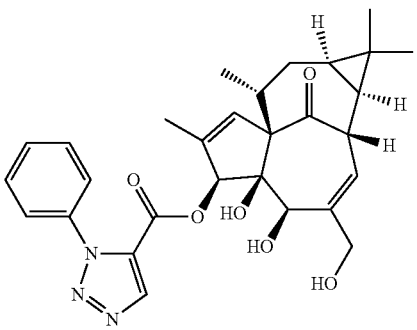

Example 504

Ingenol 3-(3-phenyltriazole-4-carboxylate) (Compound 504)

Compound 504 was prepared according to Procedure e. Starting material: Compound 604.

$^1$H NMR (300 MHz, CDCl$_3$) 8.28 (s, 1H), 7.55-7.49 (m, 5H), 6.05 (m, 1H), 6.02-6.01 (m, 1H), 5.70 (s, 1H), 4.69 (d, 1H), 4.15-4.10 (m, 3H), 4.01 (m, 1H), 3.55 (s, 1H), 2.40-2.37 (m, 1H), 2.24-2.15 (m, 2H), 1.75 (d, 3H), 1.74-1.64 (m, 1H), 1.04 (s, 3H), 1.04 (s, 3H), 0.92-0.85 (m, 4H), 0.71-0.63 (m, 1H).

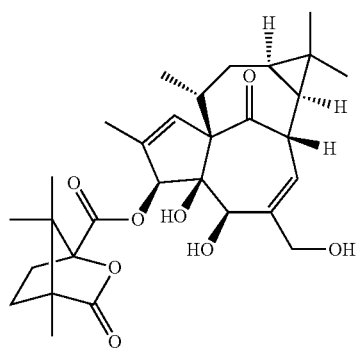

Example 503

Ingenol 3-(1S-camphanate) (Compound 503)

Compound 503 was prepared according to Procedure e. Starting material: Compound 603.

$^1$H NMR (300 MHz, CDCl$_3$) δ 6.09-6-05 (m, 2H), 5.69 (s, 1H), 4.28 (d, 1H), 4.21-4.12 (m, 3H), 4.03 (d, 1H), 3.62 (s, 1H), 2.55-2.42 (m, 2H), 2.31-2.21 (m, 2H), 2.12-2.03 (m, 1H), 1.99-1.89 (m, 1H), 1.80 (d, 3H), 1.77-1.65 (m, 2H), 1.13 (s, 3H), 1.09 (s, 6H), 1.05 (s, 3H), 0.98-0.86 (m, 7H), 0.74-0.66 (m, 1H).

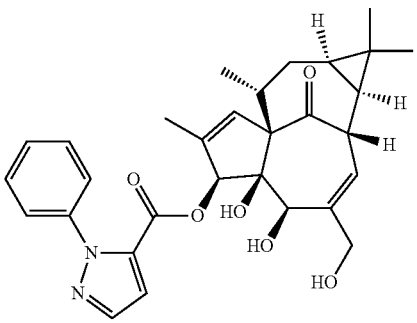 [SMILES: CC1=C[C@]23C(=O)[C@@H](C=C(CO)[C@@H](O)[C@]2(O)[C@H]1OC(=O)c1ccnn1-c1ccccc1)[C@H]1[C@@H](C[C@H]3C)C1(C)C]

Example 505

Ingenol 3-(2-phenylpyrazole-3-carboxylate) (Compound 505)

Compound 505 was prepared according to Procedure e. Starting material: Compound 605.

$^1$H NMR (300 MHz, DMSO-d$_6$) 7.82 (d, 1H), 7.49-7.45 (m, 5H), 7.03 (d, 1H), 5.86-5.83 (m, 2H), 5.81 (s, 1H), 5.35 (d, 1H), 5.14 (s, 1H), 4.62 (t, 1H), 4.14-4.10 (m, 1H), 3.91-3.86 (m, 2H), 3.58 (d, 1H), 2.28-2.10 (m, 2H), 1.70 (d, 3H), 1.69-1.58 (m, 1H), 1.02 (s, 3H), 1.01 (s, 3H), 0.80-0.70 (m, 4H), 0.62-0.54 (m, 1H).

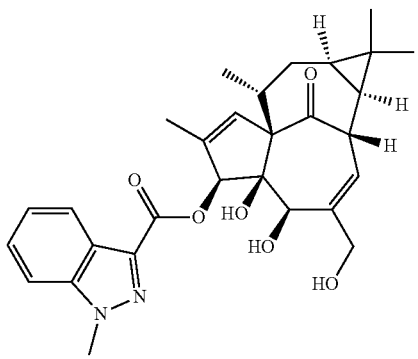 [SMILES: CC1=C[C@]23C(=O)[C@@H](C=C(CO)[C@@H](O)[C@]2(O)[C@H]1OC(=O)c1nn(C)c2ccccc12)[C@H]1[C@@H](C[C@H]3C)C1(C)C]

Example 506

Ingenol 3-(1-methylindazole-3-carboxylate) (Compound 506)

Compound 506 was prepared according to Procedure e.
Starting material: Compound 606.

$^1$H NMR (300 MHz, DMSO-d$_6$) 8.15-8.12 (m, 1H), 7.80-7.77 (m, 1H), 7.52-7.45 (m, $^1$H), 7.34-7.29 (m, 1H), 6.00 (m, 1H), 5.99 (s, 1H), 5.90-5.89 (m, 1H), 5.51 (d, 1H), 5.26 (s, 1H), 4.68 (t, 1H), 4.22-4.27 (m, 1H), 4.17 (s, 3H), 3.99-3.89 (m, 2H), 3.72 (d, 1H), 2.77-2.70 (m, 1H), 2.39-2.30 (m, 1H), 1.79 (d, 3H), 1.72-1.64 (m, 1H), 1.04 (s, 6H), 0.95 (d, 3H), 0.85-0.77 (m, 1H), 0.67-0.59 (m, 1H).

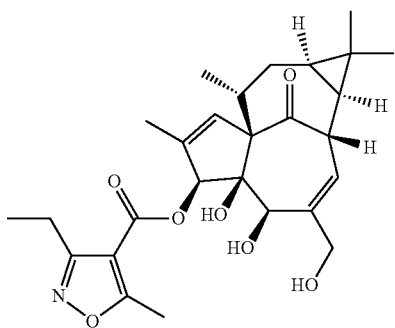 [SMILES: CCc1noc(C)c1C(=O)O[C@H]1C(C)=C[C@]23C(=O)[C@@H](C=C(CO)[C@@H](O)[C@]12O)[C@H]1[C@@H](C[C@H]3C)C1(C)C]

Example 507

Ingenol 3-(3-ethyl-5-methyl-isoxazole-4-carboxylate) (Compound 507)

Compound 507 was prepared according to Procedure e. Compound 507 was obtained as an amorphous compound.
Starting material: Compound 607.

$^1$H NMR (300 MHz, CDCl$_3$) 6.13-6.12 (m, 1H), 6.09-6.07 (m, 1H), 5.69 (s, 1H), 4.65 (bs, 1H), 4.24-4.15 (m, 3H), 4.11 (s, 1H), 3.68 (s, 1H), 2.88 (q, 2H), 2.66 (s, 3H), 2.59-2.54 (m, 1H), 2.34-2.15 (m, 2H), 1.83 (d, 3H), 1.79-1.71 (m, 1H), 1.29 (t, 3H), 1.07 (s, 3H), 1.05 (s, 3H), 1.01 (d, 3H), 0.96-0.90 (m, 1H), 0.74-0.66 (m, 1H).

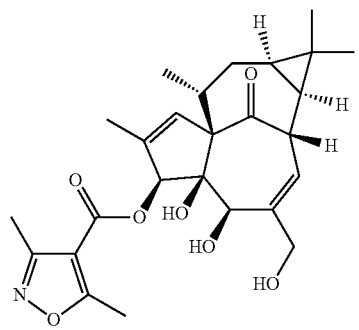

Example 508

Ingenol 3-(3-methyl-5-methyl-isoxazole-4-carboxylate) (Compound 508)

Compound 508 was prepared according to Procedure e.
Starting material: Compound 608.

$^1$H NMR (300 MHz, CDCl$_3$) 6.12 (m, 1H), 6.08-6.07 (m, 1H), 5.69 (s, 1H), 4.74 (m, 1H), 4.23-4.16 (m, 3H), 4.11 (s, 1H), 3.71 (s, 1H), 2.66 (s, 3H), 2.59-2.54 (m, 1H), 2.43 (s, 3H), 2.36-2.26 (m, 2H), 1.84-1.71 (m, 4H), 1.07 (s, 3H), 1.06 (s, 3H), 1.01 (d, 3H), 0.95-0.89 (m, 1H), 0.74-0.66 (m, 1H).

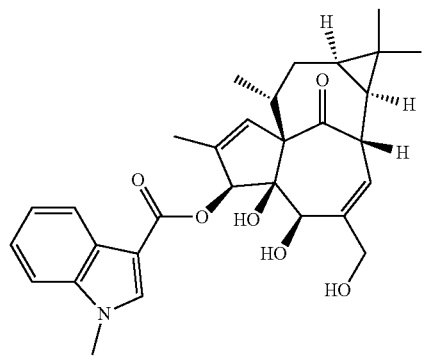 [SMILES: CC1=C[C@]23C(=O)[C@@H](C=C(CO)[C@@H](O)[C@]2(O)[C@H]1OC(=O)c1cn(C)c2ccccc12)[C@H]1[C@@H](C[C@H]3C)C1(C)C]

Example 509

Ingenol 3-(1-methylindole-3-carboxylate) (Compound 509)

Compound 509 was prepared according to Procedure e.
Starting material: Compound 609.

$^1$H NMR (300 MHz, CDCl$_3$) 8.13-8.10 (m, 1H), 7.81 (s, 1H), 7.39-7.28 (m, 3H), 6.10 (m, 1H), 6.06 (d, 1H), 5.69 (s, 1H), 4.43 (bs, 1H), 4.17-4.12 (m, 4H), 3.86 (s, 3H), 3.69 (s, 1H), 2.68-2.63 (m, 1H), 2.41 (bs, 1H), 2.29-2.20 (m, 1H), 1.87 (d, 3H), 1.80-1.71 (m, 1H), 1.05-1.03 (m, 9H), 0.99-0.93 (m, 1H), 0.73-0.65 (m, 1H).

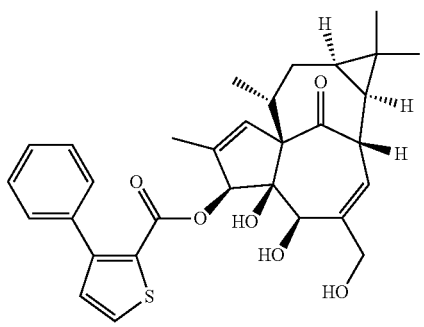 [SMILES: CC1=C[C@]23C(=O)[C@@H](C=C(CO)[C@@H](O)[C@]2(O)[C@H]1OC(=O)c1sccc1-c1ccccc1)[C@H]1[C@@H](C[C@H]3C)C1(C)C]

Example 510

Ingenol 3-(3-phenylthiophene-2-carboxylate) (Compound 510)

Compound 510 was prepared according to Procedure e.
Starting material: Compound 610.
$^1$H NMR (300 MHz, CDCl$_3$) 7.57 (d, 1H), 7.45-7.35 (m, 5H), 7.09 (d, 1H), 5.96-5.97 (m, 1H), 5.91 (d, 1H), 5.64 (s, 1H), 4.30 (d, 1H), 4.04-3.94 (m, 4H), 3.31 (s, 1H), 2.59 (bs, 1H), 2.10-2.04 (m, 2H), 1.77 (d, 3H), 1.64-1.55 (m, 1H), 1.01 (s, 3H), 0.97 (s, 3H), 0.90-0.82 (m, 4H), 0.66-0.58 (m, 1H).

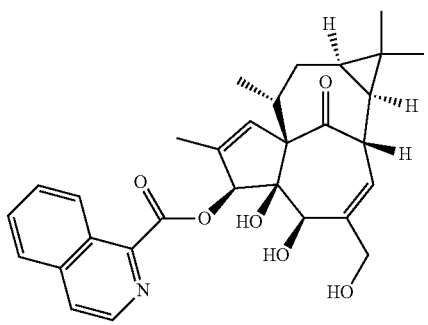

Example 512

Ingenol 3-(isoquinoline-1-carboxylate) (Compound 512)

Compound 512 was prepared according to Procedure e.
The title compound was purified by flash chromatography (dichloromethane/methanol 98:2→dichloromethane/methanol 95:5).
Starting material: Compound 612.
$^1$H NMR (300 MHz, CDCl$_3$) δ 8.73 (d, 1H), 8.55 (d, 1H), 7.93-7.85 (m, 2H), 7.81-7.71 (m, 2H), 6.16-6.15 (m, 1H), 6.09-6.07 (m, 1H), 6.04 (s, 1H), 5.67 (s, 1H), 5.30 (s, 1H), 4.29-4.18 (m, 3H), 3.60 (d, 1H), 2.68-2.63 (m, 1H), 2.45-2.36 (m, 2H), 1.94 (d, 3H), 1.90-1.82 (m, 1H), 1.17 (s, 3H), 1.09 (s, 3H), 1.02-0.95 (m, 4H), 0.78-0.70 (m, 1H).

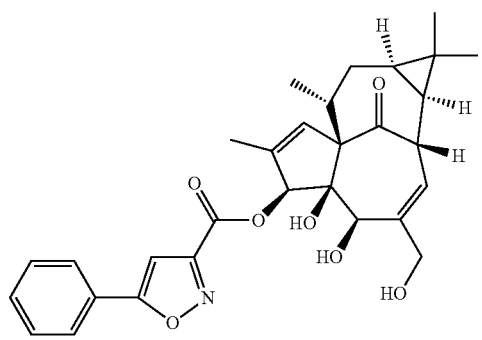 [SMILES: CC1=C[C@]23C(=O)[C@@H](C=C(CO)[C@@H](O)[C@]2(O)[C@H]1OC(=O)c1cc(-c2ccccc2)on1)[C@H]1[C@@H](C[C@H]3C)C1(C)C]

Example 511

Ingenol 3-(5-phenylisoxazole-3-carboxylate) (Compound 511)

Compound 511 was prepared according to Procedure e.
Starting material: Compound 611.
$^1$H NMR (300 MHz, CDCl$_3$) 7.82-7.77 (m, 2H), 7.51-7.47 (m, 3H), 6.92 (s, 1H), 6.15-6.14 (m, 1H), 6.07 (d, 1H), 5.89 (s, 1H), 4.47 (d, 1H), 4.20-4.09 (m, 4H), 3.86 (s, 1H), 2.68-2.60 (m, 2H), 2.29-2.23 (m, 1H), 1.87-1.76 (m, 4H), 1.06 (s, 3H), 1.05-1.02 (m, 6H), 1.00-0.89 (m, 1H), 0.74-0.67 (m, 1H).

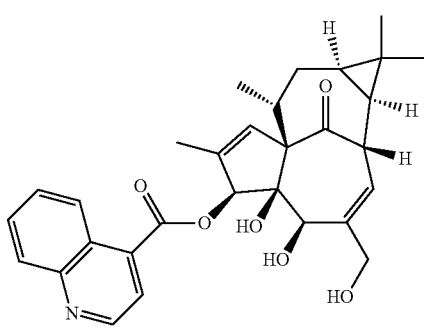 [SMILES: CC1=C[C@]23C(=O)[C@@H](C=C(CO)[C@@H](O)[C@]2(O)[C@H]1OC(=O)c1ccnc2ccccc12)[C@H]1[C@@H](C[C@H]3C)C1(C)C]

Example 513

Ingenol 3-(quinoline-4-carboxylate) (Compound 513)

Compound 513 was prepared according to Procedure e.
The title compound was purified by flash chromatography (dichloromethane/methanol 98:2→dichloromethane/methanol 95:5).
Starting material: Compound 613.
$^1$H NMR (300 MHz, CDCl$_3$) δ 9.04 (d, 1H), 8.84-8.80 (m, 1H), 8.20-8.17 (m, 1H), 7.88 (d, 1H), 7.79-7.75 (m, 1H), 7.68-7.62 (m, 1H), 6.17 (m, 1H), 6.10 (d, 1H), 5.94 (s, 1H), 4.76 (d, 1H), 4.29-4.19 (m, 4H), 3.84 (s, 1H), 2.67-2.61 (m, 1H), 2.40-2.31 (m, 2H), 1.88 (d, 3H), 1.85-1.76 (m, 1H), 1.08 (s, 3H), 1.06 (s, 3H), 1.01 (d, 3H), 0.98-0.92 (m, 1H), 0.76-0.68 (m, 1H).

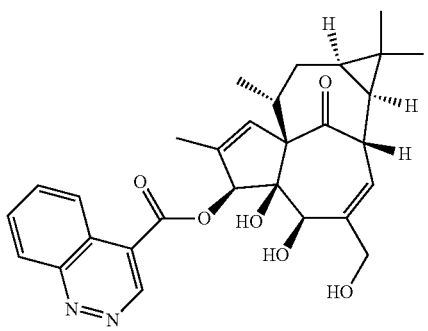 [SMILES: CC1=C[C@]23C(=O)[C@@H](C=C(CO)[C@@H](O)[C@]2(O)[C@H]1OC(=O)c1cnnc2ccccc12)[C@H]1[C@@H](C[C@H]3C)C1(C)C]

Example 514

Ingenol 3-(cinnoline-4-carboxylate) (Compound 514)

Compound 514 was prepared according to Procedure e. The title compound was purified by flash chromatography (dichloromethane/methanol 98:2→dichloromethane/methanol 95:5).

Starting material: Compound 614.

$^1$H NMR (300 MHz, DMSO-d$_5$) δ 9.65 (s, 1H), 8.89-8.86 (m, 1H), 8.65-8.61 (m, 1H), 8.10-8.00 (m, 2H), 6.14 (s, 1H), 6.04 (d, 1H), 5.93-5.92 (m, 1H), 5.78 (s, 1H), 5.59 (d, 1H), 4.69 (t, 1H), 4.28-4.23 (m, 1H), 4.04-3.92 (m, 2H), 3.73 (d, 1H), 2.64-2.57 (m, 1H), 2.45-2.37 (m, 1H), 1.83 (d, 3H), 1.80-1.71 (m, 1H), 1.08 (s, 3H), 1.05 (s, 3H), 0.93 (d, 3H), 0.85-0.79 (m, 1H), 0.69-0.61 (m, 1H).

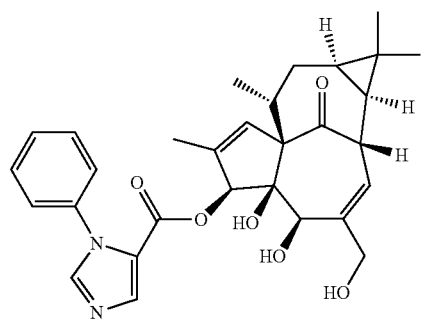 [SMILES: CC1=C[C@]23C(=O)[C@@H](C=C(CO)[C@@H](O)[C@]2(O)[C@H]1OC(=O)c1cncn1-c1ccccc1)[C@H]1[C@@H](C[C@H]3C)C1(C)C]

Example 515

Ingenol 3-(3-phenylimidazole-4-carboxylate) (Compound 515)

Compound 515 was prepared according to Procedure e. The title compound was purified by flash chromatography (dichloromethane/methanol 98:2-4 dichloromethane/methanol 95:5).

Starting material: Compound 615.

$^1$H NMR (300 MHz, CDCl$_3$) δ 7.89 (d, 1H), 7.68 (d, 1H), 7.49-7.44 (m, 3H), 7.37-7.32 (m, 2H), 6.00-5.98 (m, 2H), 5.61 (s, 1H), 5.30 (s, 1H), 4.53 (d, 1H), 4.14-4.10 (m, 3H), 3.98 (bs, 1H), 3.53 (s, 1H), 2.65 (bs, 1H), 2.30-2.15 (m, 2H), 1.73-1.65 (m, 4H), 1.04 (s, 6H), 0.93-0.85 (m, 4H), 0.71-0.63 (m, 1H).

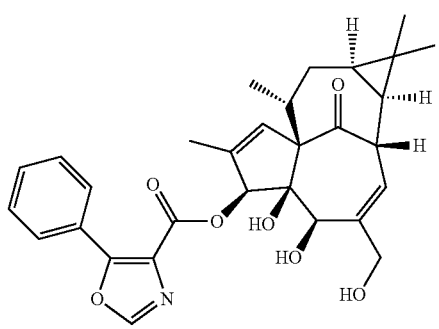 [SMILES: CC1=C[C@]23C(=O)[C@@H](C=C(CO)[C@@H](O)[C@]2(O)[C@H]1OC(=O)c1ncoc1-c1ccccc1)[C@H]1[C@@H](C[C@H]3C)C1(C)C]

Example 516

Ingenol 3-(5-phenyloxazole-4-carboxylate) (Compound 516)

Compound 516 was prepared according to Procedure e.

Starting material: Compound 616.

$^1$H NMR (300 MHz, DMSO-d$_6$) δ 8.56 (s, 1H), 7.92-7.88 (m, 2H), 7.53-7.48 (m, 3H), 5.92 (s, 1H), 5.90 (d, 1H), 5.86-5.85 (m, 1H), 5.42 (d, 1H), 5.00 (s, 1H), 4.63 (t, 1H), 4.14-4.08 (m, 1H), 3.98-3.85 (m, 2H), 3.64 (d, 1H), 2.25-2.10 (m, 2H), 1.75 (d, 3H), 1.51-1.44 (m, 1H), 1.01 (s, 3H), 0.99 (s, 3H), 0.77-0.70 (m, 4H), 0.58-0.50 (m, 1H).

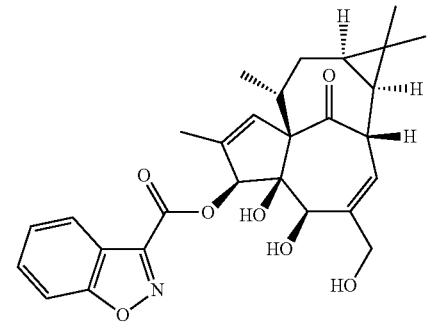 [SMILES: CC1=C[C@]23C(=O)[C@@H](C=C(CO)[C@@H](O)[C@]2(O)[C@H]1OC(=O)c1noc2ccccc12)[C@H]1[C@@H](C[C@H]3C)C1(C)C]

Example 517

Ingenol 3-(1,2-benzoxazole-3-carboxylate) (Compound 517)

Compound 517 was prepared according to Procedure e.

Starting material: Compound 617.

$^1$H NMR (300 MHz, CDCl$_3$) 8.17-8.14 (m, 1H), 7.70-7.61 (m, 2H), 7.47-7.42 (m, 1H), 6.19-6.18 (m, 1H), 6.09-6.08 (m, 1H), 5.97 (s, 1H), 4.47 (d, 1H), 4.26-4.16 (m, 3H), 4.12 (bs, 1H), 3.80 (s, 1H), 2.73-2.65 (m, 1H), 2.32-2.23 (m, 2H), 1.90 (d, 3H), 1.86-1.74 (m, 1H), 1.06-1.03 (m, 9H), 0.97-0.90 (m, 1H), 0.75-0.67 (m, 1H).

111

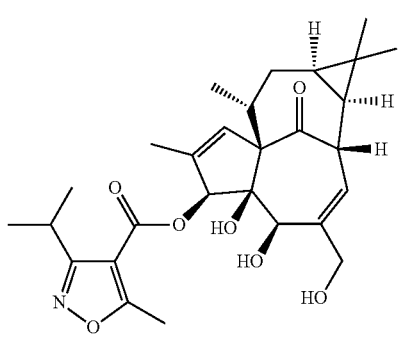 [SMILES: CC1=C[C@]23C(=O)[C@@H](C=C(CO)[C@@H](O)[C@]2(O)[C@H]1OC(=O)c1c(C(C)C)noc1C)[C@H]1[C@@H](C[C@H]3C)C1(C)C]

Example 518

Ingenol 3-(3-isopropyl-5-methyl-isoxazole-4-carboxylate) (Compound 518)

Compound 518 was prepared according to Procedure e. Starting material: Compound 618.

¹H NMR (300 MHz, CDCl₃) 6.13-6.12 (m, 1H), 6.08-6.07 (d, 1H), 5.69 (s, 1H), 4.67 (d, 1H), 4.23-4.18 (m, 3H), 4.11 (bs, 1H), 3.69 (s, 1H), 3.44 (septet, 1H), 2.65 (s, 3H), 2.60-2.51 (m, 1H), 2.35-2.22 (m, 2H), 1.83 (d, 3H), 1.79-1.70 (m, 1H), 1.33 (d, 3H), 1.32 (d, 3H), 1.07 (s, 3H), 1.06 (s, 3H), 1.00 (d, 3H), 0.96-0.86 (m, 1H), 0.74-0.66 (m, 1H).

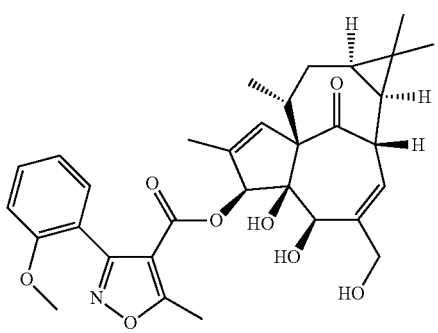 [SMILES: COc1ccccc1-c1noc(C)c1C(=O)O[C@H]1C(C)=C[C@]23C(=O)[C@@H](C=C(CO)[C@@H](O)[C@]12O)[C@H]1[C@@H](C[C@H]3C)C1(C)C]

Example 519

Ingenol 3-(3-(2-methoxyphenyl)-5-methyl-isoxazole-4-carboxylate) (Compound 519)

Compound 519 was prepared according to Procedure e. Starting material: Compound 619.

¹H NMR (300 MHz, CDCl₃) 7.46-7.36 (m, 2H), 7.04 (dt, 1H), 6.95 (d, 1H), 6.01 (d, 1H), 5.91-5.90 (m, 1H), 5.69 (s, 1H), 4.14-4.06 (m, 2H), 3.98 (dd, 1H), 3.91 (d, 1H), 3.82 (d, 1H), 3.77 (s, 3H), 3.26 (s, 1H), 2.75 (s, 3H), 2.26-2.21 (m, 1H), 1.99-1.89 (m, 1H), 1.72 (d, 3H), 1.65-1.61 (m, 1H), 1.55-1.46 (m, 1H), 1.04 (s, 3H), 1.04 (s, 3H), 0.90-0.83 (m, 1H), 0.74 (d, 3H), 0.65-0.57 (m, 1H).

112

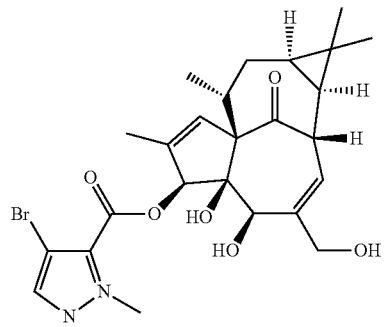

Example 520

Ingenol 3-(4-bromo-2-methyl-pyrazole-3-carboxylate) (Compound 520)

Compound 520 was prepared according to Procedure e. Starting material: Compound 620.

¹H NMR (300 MHz, CDCl₃) 7.52 (s, 1H), 6.15-6.14 (m, 1H), 6.08 (d, 1H), 5.84 (s, 1H), 5.30 (s, 1H), 4.21-4.05 (m, 7H), 3.85 (s, 1H), 2.77-2.73 (m, 1H), 2.30-2.17 (m, 2H), 1.87 (d, 3H), 1.80-1.72 (m, 1H), 1.08 (s, 3H), 1.06 (s, 3H), 1.00 (d, 3H), 0.97-0.90 (m, 1H), 0.75-0.67 (m, 1H).

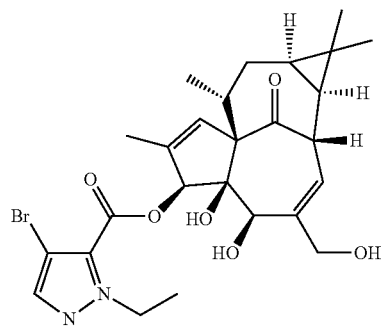

Example 521

Ingenol 3-(4-bromo-2-ethyl-pyrazole-3-carboxylate) (Compound 521)

Compound 521 was prepared according to Procedure e. Starting material: Compound 621.

¹H NMR (300 MHz, CDCl₃) 7.54 (s, 1H), 6.15-6.13 (m, 1H), 6.09-6.07 (m, 1H), 5.86 (s, 1H), 4.68-4.55 (m, 2H), 4.24-4.13 (m, 4H), 4.07 (d, 1H), 3.87 (s, 1H), 2.77-2.70 (m, 1H), 2.32-2.20 (m, 2H), 1.87 (d, 3H), 1.80-1.71 (m, 1H), 1.44 (t, 3H), 1.09 (s, 3H), 1.06 (s, 3H), 0.98 (d, 3H), 0.97-0.90 (m, 1H), 0.75-0.67 (m, 1H).

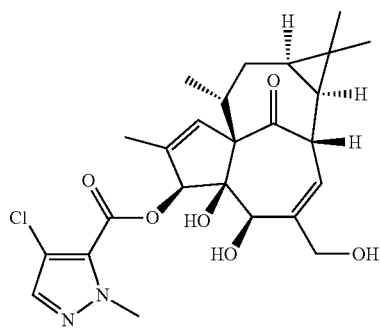 [SMILES: CC1=C[C@]23C(=O)[C@@H](C=C(CO)[C@@H](O)[C@]2(O)[C@H]1OC(=O)c1c(Cl)cnn1C)[C@H]1[C@@H](C[C@H]3C)C1(C)C]

Example 522

Ingenol 3-(4-chloro-2-methyl-pyrazole-3-carboxylate) (Compound 522)

Compound 522 was prepared according to Procedure e. Starting material: Compound 622.

$^1$H NMR (300 MHz, CDCl$_3$) 7.48 (s, 1H), 6.14-6.13 (m, 1H), 6.09-6.06 (m, 1H), 5.84 (s, 1H), 4.23-4.11 (m, 7H), 4.07-4.05 (d, 1H), 3.83 (s, 1H), 2.73-2.64 (m, 1H), 2.31-2.20 (m, 2H), 1.87 (d, 3H), 1.81-1.72 (m, 1H), 1.08 (s, 3H), 1.06 (s, 3H), 1.00 (d, 3H), 0.97-0.87 (m, 1H), 0.75-0.67 (m, 1H).

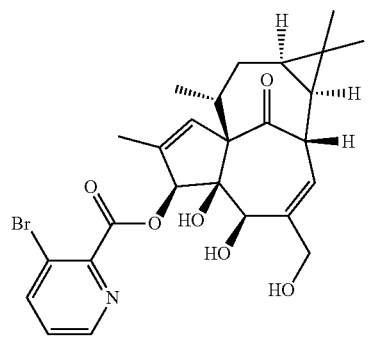

Example 524

Ingenol 3-(3-bromopyridine-2-carboxylate) (Compound 524)

Compound 524 was prepared according to Procedure e. Starting material: Compound 624.

$^1$H NMR (300 MHz, CDCl$_3$) 8.58 (dd, 1H), 8.03 (dd, 1H), 7.34 (dd, 1H), 6.11-6.13 (m, 1H), 6.07-6.05 (m, 1H), 5.98 (s, 1H), 4.74 (d, 1H), 4.21-4.15 (m, 3H), 4.00 (d, 1H), 3.69 (d, 1H), 2.56-2.48 (m, 2H), 2.34-2.24 (m, 1H), 1.91 (d, 3H), 1.83-1.74 (m, 1H), 1.12 (s, 3H), 1.05 (s, 3H), 0.98-0.92 (m, 4H), 0.75-0.67 (m, 1H).

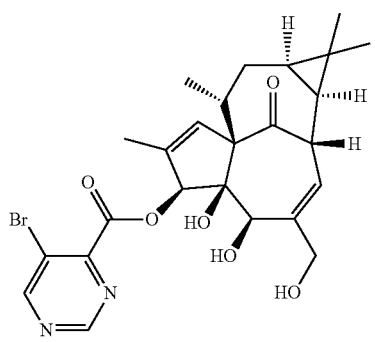 [SMILES: CC1=C[C@]23C(=O)[C@@H](C=C(CO)[C@@H](O)[C@]2(O)[C@H]1OC(=O)c1ncncc1Br)[C@H]1[C@@H](C[C@H]3C)C1(C)C]

Example 523

Ingenol 3-(5-bromopyrimidine-4-carboxylate) (Compound 523)

Compound 523 was prepared according to Procedure e. Starting material: Compound 623.

$^1$H NMR (300 MHz, CDCl$_3$) 9.21 (s, 1H), 9.02 (s, 1H), 6.16-6.14 (m, 1H), 6.09-6.07 (m, 1H), 5.96 (s, 1H), 4.22-4.12 (m, 4H), 4.06-4.04 (m, 2H), 2.57-2.52 (m, 1H), 2.33-2.24 (m, 2H), 1.90 (d, 3H), 1.88-1.79 (m, 1H), 1.10 (s, 3H), 1.06 (s, 3H), 0.98-0.90 (m, 4H), 0.75-0.67 (m, 1H).

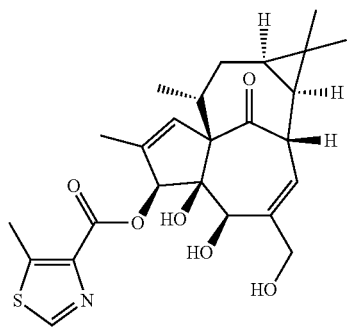

Example 525

Ingenol 3-(5-methylthiazole-4-carboxylate) (Compound 525)

Compound 525 was prepared according to Procedure e. Starting material: Compound 625.

$^1$H NMR (300 MHz, CDCl$_3$) 8.59 (s, 1H), 6.10-6.05 (m, 2H), 5.70 (s, 1H), 4.21-4.14 (m, 4H), 4.04 (s, 2H), 2.81 (s, 3H), 2.66-2.59 (m, 2H), 2.32-2.23 (m, 1H), 1.86 (d, 3H), 1.83-1.74 (m, 1H), 1.09 (s, 3H), 1.06 (s, 3H), 1.00 (d, 3H), 0.98-0.91 (m, 1H), 0.75-0.67 (m, 1H).

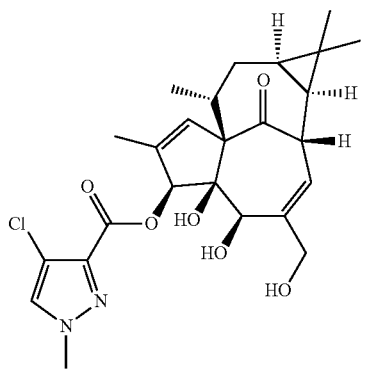 [SMILES: CC1=C[C@]23C(=O)[C@@H](C=C(CO)[C@@H](O)[C@]2(O)[C@H]1OC(=O)c1nn(C)cc1Cl)[C@H]1[C@@H](C[C@H]3C)C1(C)C]

Example 526

Ingenol 3-(4-chloro-1-methyl-pyrazole-3-carboxylate) (Compound 526)

Compound 526 was prepared according to Procedure e.
Starting material: Compound 626.

$^1$H NMR (300 MHz, CDCl$_3$) 7.47 (s, 1H), 6.10-6.05 (m, 2H), 5.82 (s, 1H), 4.18-4.12 (m, 3H), 4.04 (d, 1H), 3.96 (s, 3H), 3.87 (s, 1H), 3.79 (d, 1H), 2.70-2.63 (m, 1H), 2.34-2.21 (m, 2H), 1.87 (d, 3H), 1.82-1.73 (m, 1H), 1.09 (s, 3H), 1.05 (s, 3H), 1.00 (d, 3H), 0.98-0.92 (m, 1H), 0.74-0.67 (m, 1H).

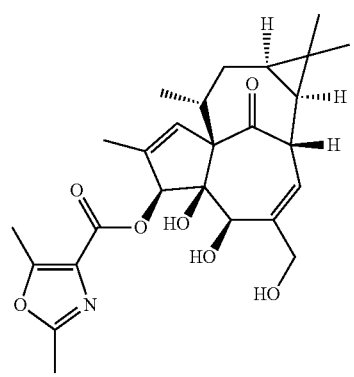

Example 528

Ingenol 3-(2,5-dimethyloxazole-4-carboxylate) (Compound 528)

Compound 528 was prepared according to Procedure e.
Starting material: Compound 628.

$^1$H NMR (300 MHz, CDCl$_3$) 6.03-6.00 (m, 2H), 5.74 (s, 1H), 4.51-4.47 (m, 2H), 4.25-4.10 (m, 3H), 4.02 (bs, 1H), 3.55 (s, 1H), 2.59 (s, 3H), 2.57-2.54 (m, 1H), 2.44 (s, 3H), 2.31-2.22 (m, 1H), 1.81 (d, 3H), 1.79-1.71 (m, 1H), 1.07 (s, 3H), 1.05 (s, 3H), 0.98 (d, 3H), 0.95-0.88 (m, 1H), 0.73-0.65 (m, 1H).

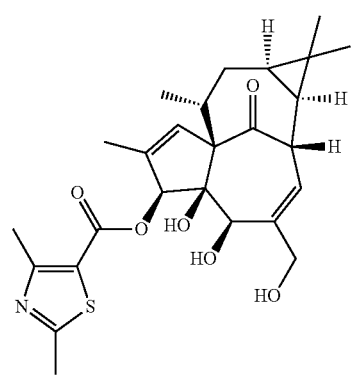

Example 527

Ingenol 3-(2,4-dimethylthiazole-5-carboxylate) (Compound 527)

Compound 527 was prepared according to Procedure e.
Starting material: Compound 627.

$^1$H NMR (300 MHz, CDCl$_3$) 6.10-6-08 (m, 1H), 6.07-6.05 (m, 1H), 5.69 (s, 1H), 4.61 (d, 1H), 4.21-4.15 (m, 3H), 4.08 (s, 1H), 3.62 (d, 1H), 2.70 (s, 3H), 2.69 (s, 3H), 2.62-2.54 (m, 2H), 2.32-2.25 (m, 1H), 1.82 (d, 3H), 1.80-1.73 (m, 1H), 1.07 (s, 3H), 1.05 (s, 3H), 1.01 (d, 3H), 0.97-0.90 (m, 1H), 0.74-0.66 (m, 1H).

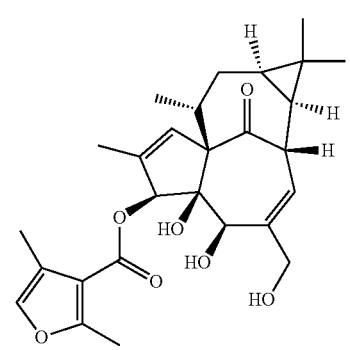 [SMILES: CC1=C[C@]23C(=O)[C@@H](C=C(CO)[C@@H](O)[C@]2(O)[C@H]1OC(=O)c1c(C)coc1C)[C@H]1[C@@H](C[C@H]3C)C1(C)C]

Example 529

Ingenol 3-(2,4-dimethylfuran-3-carboxylate) (Compound 529)

Compound 529 was prepared according to Procedure e.
Compound 529 was obtained as an amorphous compound.
Starting material: Compound 629.

$^1$H NMR (300 MHz, CDCl$_3$) 7.06 (q, 1H), 6.09-6.06 (m, 2H), 5.62 (m, 1H), 4.50 (d, 1H), 4.19-4.13 (m, 3H), 4.12-4.09 (m, 1H), 3.66 (s, 1H), 2.61-2.55 (m, 1H), 2.54 (s, 3H), 2.39 (t, 1H), 2.32-2.23 (m, 1H), 2.12 (d, 3H), 1.83 (d, 3H), 1.79-1.70 (m, 1H), 1.07 (s, 3H), 1.05 (s, 3H), 0.99 (d, 3H), 0.98-0.90 (m, 1H), 0.73-0.65 (m, 1H).

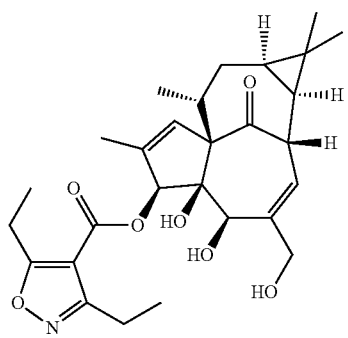 [SMILES: CCc1noc(CC)c1C(=O)O[C@H]1C(C)=C[C@]23C(=O)[C@@H](C=C(CO)[C@@H](O)[C@]12O)[C@H]1[C@@H](C[C@H]3C)C1(C)C]

Example 530

Ingenol 3-(3,5-diethylisoxazole-4-carboxylate) (Compound 530)

Compound 530 was prepared according to Procedure e.

Starting material: Compound 630.

$^1$H NMR (300 MHz, CDCl$_3$) 6.14-6.12 (m, 1H), 6.08-6.07 (m, 1H), 5.70 (s, 1H), 4.68 (d, 1H), 4.23-4.18 (m, 3H), 4.12-4.11 (m, 1H), 3.69 (s, 1H), 3.09 (dq, 2H), 2.89 (dq, 2H), 2.59-2.52 (m, 1H), 2.35-2.25 (m, 2H), 1.83 (d, 3H), 1.79-1.70 (m, 1H), 1.31 (t, 3H), 1.29 (t, 3H), 1.07 (s, 3H), 1.05 (s, 3H), 1.01 (d, 3H), 0.96-0.89 (m, 1H), 0.74-0.65 (m, 1H); 0.5 mol of ethyl acetate is observed: 4.12 (q, 0.5×2H), 2.04 (s, 0.5×3H), 1.26 (t, 0.5×3H).

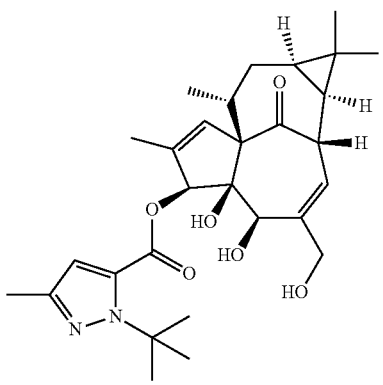

Example 532

Ingenol 3-(2-tert-butyl-5-methyl-pyrazole-3-carboxylate) (Compound 532)

Compound 532 was prepared according to Procedure e.

Starting material: Compound 632.

$^1$H NMR (300 MHz, CDCl$_3$) 6.65 (s, 1H), 6.09-6.06 (m, 2H), 5.69 (s, 1H), 4.40 (d, 1H), 4.20-4.13 (m, 3H), 4.08 (d, 1H), 3.54 (s, 1H), 2.60-2.55 (m, 1H), 2.33-2.24 (m, 5H), 1.82 (d, 3H), 1.80-1.75 (m, 1H), 1.70 (s, 9H), 1.08 (s, 3H), 1.06 (s, 3H), 1.01 (d, 3H), 0.98-0.91 (m, 1H), 0.75-0.67 (m, 1H).

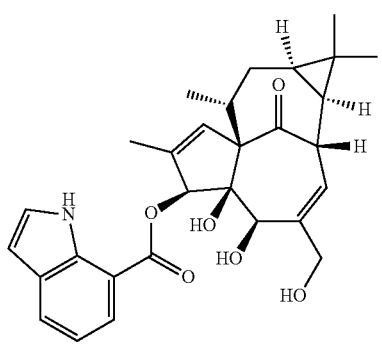 [SMILES: CC1=C[C@]23C(=O)[C@@H](C=C(CO)[C@@H](O)[C@]2(O)[C@H]1OC(=O)c1cccc2cc[nH]c12)[C@H]1[C@@H](C[C@H]3C)C1(C)C]

Example 531

Ingenol 3-(1H-indole-7-carboxylate) (Compound 531)

Compound 531 was prepared according to Procedure e.

Starting material: Compound 631.

$^1$H NMR (300 MHz, CDCl$_3$) 10.13 (bs, 1H), 7.90-7.85 (m, 2H), 7.31-7.29 (m, 1H), 7.18 (t, 1H), 6.62-6.60 (m, 1H), 6.13-6.12 (m, 1H), 6.08 (d, 1H), 5.84 (s, 1H), 4.69 (d, 1H), 4.27-4.16 (m, 4H), 3.85 (s, 1H), 2.71-2.66 (m, 1H), 2.43 (bs, 1H), 2.37-2.28 (m, 1H), 1.88 (d, 3H), 1.85-1.76 (m, 1H), 1.08 (s, 3H), 1.06 (s, 3H), 1.04 (d, 3H), 0.98-0.92 (m, 1H), 0.76-0.68 (m, 1H).

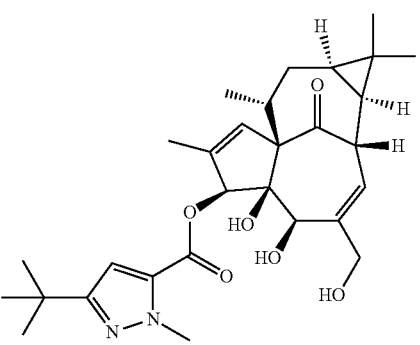 [SMILES: CC1=C[C@]23C(=O)[C@@H](C=C(CO)[C@@H](O)[C@]2(O)[C@H]1OC(=O)c1cc(C(C)(C)C)nn1C)[C@H]1[C@@H](C[C@H]3C)C1(C)C]

Example 533

Ingenol 3-(5-tert-butyl-2-methyl-pyrazole-3-carboxylate) (Compound 533)

Compound 533 was prepared according to Procedure e.

Starting material: Compound 633.

$^1$H NMR (300 MHz, CDCl$_3$) 6.63 (s, 1H), 6.12-6.10 (m, 1H), 6.08-6.06 (d, 1H), 5.71 (s, 1H), 4.57 (d, 1H), 4.20-4.15 (m, 3H), 4.13 (s, 3H), 4.10 (d, 1H), 3.62 (s, 1H), 2.61-2.55 (m, 1H), 2.40 (t, 1H), 2.32-2.23 (m, 1H), 1.83 (d, 3H), 1.82-1.73 (m, 1H), 1.31 (s, 9H), 1.07 (s, 3H), 1.05 (s, 3H), 1.03 (d, 3H), 0.97-0.91 (m, 1H), 0.75-0.67 (m, 1H).

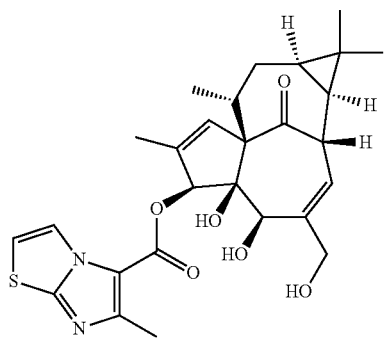 [SMILES: CC1=C[C@]23C(=O)[C@@H](C=C(CO)[C@@H](O)[C@]2(O)[C@H]1OC(=O)c1c(C)nc2sccn12)[C@H]1[C@@H](C[C@H]3C)C1(C)C]

Example 534

Ingenol
3-(6-methylimidazo[2,1-b]thiazole-5-carboxylate)
(Compound 534)

Compound 534 was prepared according to Procedure e.
Starting material: Compound 634.

¹H NMR (300 MHz, CDCl$_3$) 8.09 (d, 1H), 6.93 (d, 1H), 6.15-6.13 (m, 1H), 6.08 (d, 1H), 5.73 (s, 1H), 4.24-4.17 (m, 4H), 4.14-4.13 (m, 1H), 3.80 (bs, 1H), 2.63-2.59 (m, 5H), 2.33-2.25 (m, 1H), 1.86 (d, 3H), 1.80-1.71 (m, 1H), 1.06 (s, 3H), 1.05 (s, 3H), 1.02 (d, 3H), 0.97-0.90 (m, 1H), 0.74-0.66 (m, 1H).

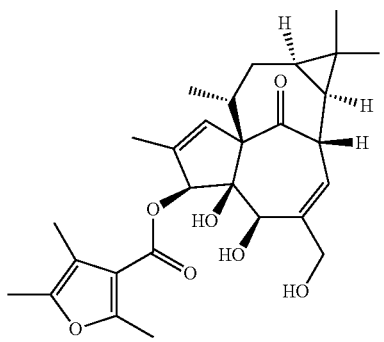

Example 536

Ingenol 3-(2,4,5-trimethylfuran-3-carboxylate)
(Compound 536)

Compound 536 was prepared according to Procedure e.
Starting material: Compound 636.

¹H NMR (300 MHz, CDCl$_3$) 6.07-6.04 (m, 2H), 5.63 (s, 1H), 4.65 (d, 1H), 4.20-4.14 (m, 3H), 4.09 (d, 1H), 3.71 (s, 1H), 2.80 (t, 1H), 2.62-2.56 (m, 1H), 2.50 (s, 3H), 2.32-2.23 (m, 1H), 2.17 (s, 3H), 2.04 (s, 3H), 1.82 (d, 3H), 1.78-1.69 (m, 1H), 1.06 (s, 3H), 1.05 (s, 3H), 0.98 (d, 3H), 0.94-0.90 (m, 1H), 0.72-0.65 (m, 1H).

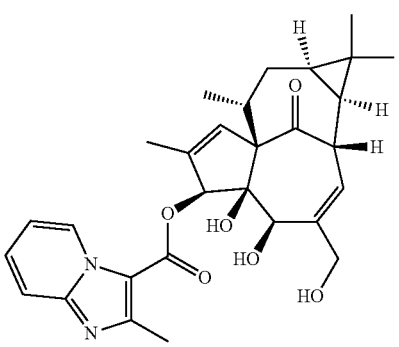 [SMILES: CC1=C[C@]23C(=O)[C@@H](C=C(CO)[C@@H](O)[C@]2(O)[C@H]1OC(=O)c1c(C)nc2ccccn12)[C@H]1[C@@H](C[C@H]3C)C1(C)C]

Example 535

Ingenol
3-(2-methylimidazo[1,2-a]pyridine-3-carboxylate)
(Compound 535)

Compound 535 was prepared according to Procedure e.
Starting material: Compound 635.

¹H NMR (300 MHz, CDCl$_3$) 9.37 (d, 1H), 8.09 (s, 1H), 7.74 (d, 1H), 7.49-7.43 (m, 1H), 7.06-7.01 (m, 1H), 6.19-6.08 (m, 2H), 5.80 (s, 1H), 4.33-4.17 (m, 4H), 3.43 (bs, 2H), 2.72-2.63 (m, 4H), 2.33-2.24 (m, 1H), 1.88 (d, 3H), 1.80-1.71 (m, 1H), 1.06 (s, 3H), 1.05 (s, 3H), 1.03 (d, 3H), 0.97-0.85 (m, 1H), 0.75-0.67 (m, 1H).

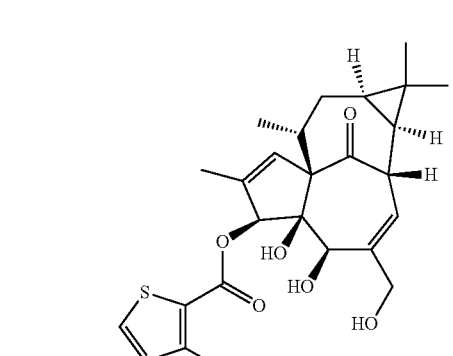

Example 537

Ingenol 3-(3-methylthiophene-2-carboxylate)
(Compound 537)

Compound 537 was prepared according to Procedure e.
Starting material: Compound 637.

¹H NMR (300 MHz, CDCl$_3$) 7.42 (d, 1H), 6.94 (d, 1H), 6.09-6.07 (m, 1H), 6.06-6.04 (m, 1H), 5.71 (s, 1H), 4.49 (bs, 1H), 4.22-4.12 (m, 3H), 4.09-4.08 (m, 1H), 3.63 (s, 1H), 2.70-2.60 (m, 2H), 2.57 (s, 3H), 2.32-2.22 (m, 1H), 1.84 (d, 3H), 1.81-1.72 (m, 1H), 1.05 (s, 3H), 1.04 (s, 3H), 1.02 (d, 3H), 0.96-0.90 (m, 1H), 0.73-0.66 (m, 1H).

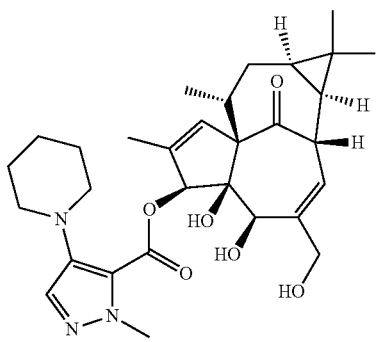 [SMILES: CC1=C[C@]23C(=O)[C@@H](C=C(CO)[C@@H](O)[C@]2(O)[C@H]1OC(=O)c1c(N2CCCCC2)cnn1C)[C@H]1[C@@H](C[C@H]3C)C1(C)C]

Example 538

Ingenol 3-(2-methyl-4-(1-piperidyl)pyrazole-3-carboxylate) (Compound 538)

Compound 538 was prepared according to Procedure e.
Starting material: Compound 638.
$^1$H NMR (300 MHz, CDCl$_3$) 7.36 (s, 1H), 6.10-6.07 (m, 2H), 5.69 (s, 1H), 4.23-4.13 (m, 3H), 4.10 (s, 3H), 4.01 (s, 1H), 2.97-2.82 (m, 4H), 2.68-2.62 (m, 1H), 2.31-2.22 (m, 1H), 1.87 (d, 3H), 1.84-1.59 (m, 8H), 1.55-1.49 (m, 2H), 1.10 (s, 3H), 1.05 (s, 3H), 0.99 (d, 3H), 0.98-0.94 (m, 1H), 0.74-0.66 (m, 1H).

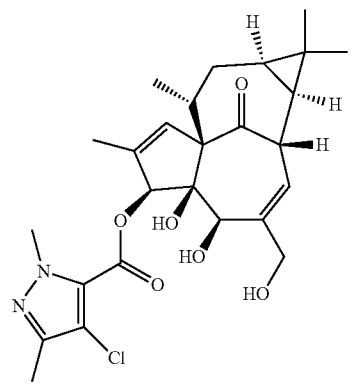

Example 540

Ingenol 3-(4-chloro-2,5-dimethyl-pyrazole-3-carboxylate) (Compound 540)

Compound 540 was prepared according to Procedure e.
Starting material: Compound 640.
$^1$H NMR (300 MHz, CDCl$_3$) 6.14-6.12 (m, 1H), 6.08-6.06 (m, 1H), 5.83 (s, 1H), 4.21-4.04 (m, 8H), 3.85 (s, 1H), 2.73-2.68 (m, 1H), 2.42 (bs, 1H), 2.30-2.21 (m, 4H), 1.86 (d, 3H), 1.81-1.72 (m, 1H), 1.08 (s, 3H), 1.06 (s, 3H), 1.00 (d, 3H), 0.97-0.90 (m, 1H), 0.75-0.67 (m, 1H).

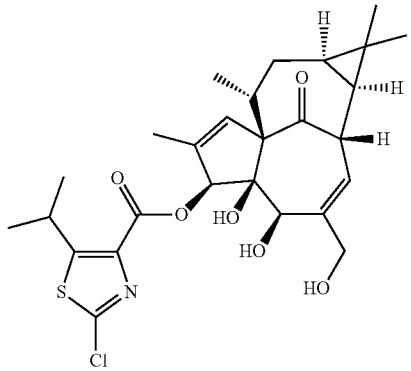 [SMILES: CC1=C[C@]23C(=O)[C@@H](C=C(CO)[C@@H](O)[C@]2(O)[C@H]1OC(=O)c1nc(Cl)sc1C(C)C)[C@H]1[C@@H](C[C@H]3C)C1(C)C]

Example 539

Ingenol 3-(2-chloro-5-isopropyl-thiazole-4-carboxylate) (Compound 539)

Compound 539 was prepared according to Procedure e.
Starting material: Compound 639.
$^1$H NMR (300 MHz, CDCl$_3$) 6.09-6.05 (m, 2H), 5.77 (s, 1H), 4.19-4.08 (m, 5H), 4.04-3.98 (m, 2H), 2.64-2.55 (m, 2H), 2.33-2.24 (m, 1H), 1.85 (d, 3H), 1.83-1.71 (m, 1H), 1.34 (d, 3H), 1.32 (d, 3H), 1.10 (s, 3H), 1.06 (s, 3H), 1.01 (d, 3H), 0.97-0.91 (m, 1H), 0.75-0.67 (m, 1H).

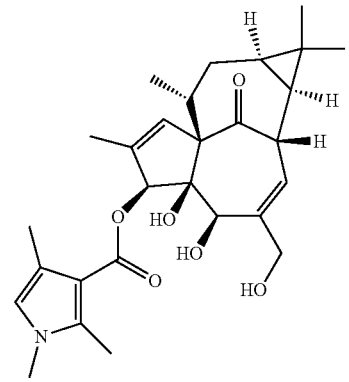 [SMILES: CC1=C[C@]23C(=O)[C@@H](C=C(CO)[C@@H](O)[C@]2(O)[C@H]1OC(=O)c1c(C)cn(C)c1C)[C@H]1[C@@H](C[C@H]3C)C1(C)C]

Example 541

Ingenol 3-(1,2,4-trimethylpyrrole-3-carboxylate) (Compound 541)

Compound 541 was prepared according to Procedure e.
Starting material: Compound 641.
$^1$H NMR (300 MHz, CDCl$_3$) 6.29 (m, 1H), 6.06-6.03 (m, 2H), 5.55 (s, 1H), 4.51 (d, 1H), 4.16-4.08 (m, 4H), 3.68 (s, 1H), 3.47 (s, 3H), 2.63-2.52 (m, 2H), 2.47 (s, 3H), 2.29-2.20 (m, 1H), 2.18 (s, 3H), 1.83 (d, 3H), 1.77-1.68 (m, 1H), 1.07 (s, 3H), 1.04 (s, 3H), 0.98 (d, 3H), 0.99-0.93 (m, 1H), 0.72-0.64 (m, 1H).

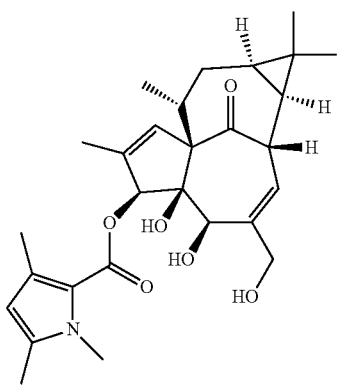 [SMILES: CC1=C[C@]23C(=O)[C@@H](C=C(CO)[C@@H](O)[C@]2(O)[C@H]1OC(=O)c1c(C)cc(C)n1C)[C@H]1[C@@H](C[C@H]3C)C1(C)C]

Example 542

Ingenol 3-(1,3,5-trimethylpyrrole-2-carboxylate) (Compound 542)

Compound 542 was prepared according to Procedure e.
Starting material: Compound 642.
$^1$H NMR (300 MHz, CDCl$_3$) 6.06-6.05 (m, 2H), 5.81 (s, 1H), 5.59 (s, 1H), 4.44 (d, 1H), 4.17-4.08 (m, 4H), 3.77 (s, 3H), 3.70 (s, 1H), 2.63-2.57 (m, 1H), 2.44 (t, 1H), 2.29-2.24 (m, 4H), 2.21 (s, 3H), 1.83 (d, 3H), 1.78-1.69 (m, 1H), 1.07 (s, 3H), 1.05 (s, 3H), 0.98 (d, 3H), 0.95-0.90 (m, 1H), 0.72-0.65 (m, 1H).

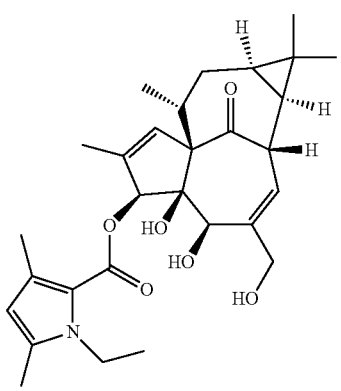 [SMILES: CCn1c(C)cc(C)c1C(=O)O[C@H]1C(C)=C[C@]23C(=O)[C@@H](C=C(CO)[C@@H](O)[C@]12O)[C@H]1[C@@H](C[C@H]3C)C1(C)C]

Example 543

Ingenol 3-(1-ethyl-3,5-dimethylpyrrole-2-carboxylate) (Compound 543)

Compound 543 was prepared according to Procedure e.
Starting material: Compound 643.
$^1$H NMR (300 MHz, CDCl$_3$) 6.07-6.05 (m, 2H), 5.81 (s, 1H), 5.58 (s, 1H), 4.43 (d, 1H), 4.32-4.24 (m, 2H), 4.17-4.09 (m, 4H), 3.67 (s, 1H), 2.62-2.57 (m, 1H), 2.36-2.34 (m, 1H), 2.30-2.20 (m, 7H), 1.84 (d, 3H), 1.78-1.69 (m, 1H), 1.27 (t, 3H), 1.07 (s, 3H), 1.05 (s, 3H), 0.98 (d, 3H), 0.95-0.90 (m, 1H), 0.72-0.65 (m, 1H).

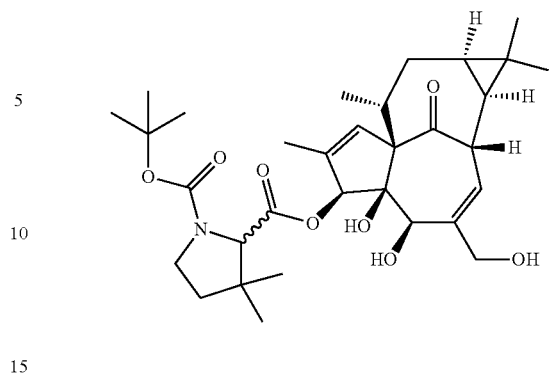

Example 544

Ingenol 3-(1-tert-butyloxycarbonyl-3,3-dimethylpyrrolidine-2-carboxylate) (Compound 544)

Compound 544 was prepared according to Procedure e.
Starting material: Compound 644.
$^1$H NMR (300 MHz, CDCl$_3$) showed a mixture of compounds.

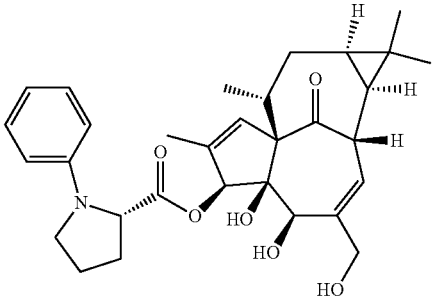 [SMILES: CC1=C[C@]23C(=O)[C@@H](C=C(CO)[C@@H](O)[C@]2(O)[C@H]1OC(=O)[C@@H]1CCCN1c1ccccc1)[C@H]1[C@@H](C[C@H]3C)C1(C)C]

Example 545

Ingenol 3-((2S)-1-phenylpyrrolidine-2-carboxylate) (Compound 545)

Compound 545 was prepared according to Procedure e with the following changes: Tetrahydrofuran was replaced with methanol and the reaction time at room temperature was 0.5 h.
Starting material: Compound 645.
$^1$H NMR (300 MHz, CDCl$_3$) 7.27-7.21 (m, 2H), 6.72 (t, 1H), 6.54 (d, 2H), 6.01-5.99 (m, 1H), 5.96 (d, 1H), 5.68 (s, 1H), 4.43 (dd, 1H), 4.13-4.03 (m, 2H), 3.88-3.83 (m, 2H), 3.49-3.37 (m, 3H), 2.70 (s, 1H), 2.46-2.39 (m, 1H), 2.28-2.20 (m, 2H), 2.13-1.96 (m, 3H), 1.75 (d, 3H), 1.68-1.57 (m, 1H), 1.49-1.40 (m, 1H), 1.03 (s, 3H), 0.96 (s, 3H), 0.89-0.81 (m, 4H), 0.62-0.54 (m, 1H).

125

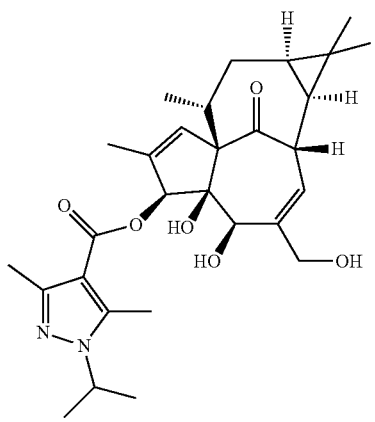

Example 546

Ingenol 3-(1-isopropyl-3,5-dimethyl-pyrazole-4-carboxylate) (Compound 546)

Compound 546 was prepared according to Procedure e.
Starting material: Compound 646.
¹H NMR (300 MHz, CDCl₃) 6.07-6.04 (m, 2H), 5.61 (s, 1H), 4.63 (d, 1H), 4.43 (septet, 1H), 4.19-4.10 (m, 4H), 3.70 (s, 1H), 2.70 (t, 1H), 2.62-2.58 (m, 1H), 2.52 (s, 3H), 2.40 (s, 3H), 2.31-2.22 (m, 1H), 1.83 (d, 3H), 1.79-1.70 (m, 1H), 1.46 (d, 6H), 1.07 (s, 3H), 1.04 (s, 3H), 0.99 (d, 3H), 0.97-0.90 (d, 1H), 0.73-0.65 (m, 1H).

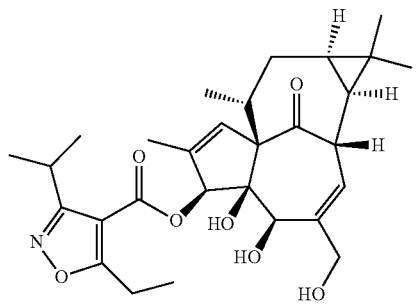 [SMILES: CCc1onc(C(C)C)c1C(=O)O[C@H]1C(C)=C[C@]23C(=O)[C@@H](C=C(CO)[C@@H](O)[C@]12O)[C@H]1[C@@H](C[C@H]3C)C1(C)C]

Example 547

Ingenol 3-(5-ethyl-3-isopropyl-isoxazole-4-carboxylate) (Compound 547)

Compound 547 was prepared according to Procedure e with the following changes: Tetrahydrofuran was replaced with methanol and the reaction time at room temperature was 0.5 h.
Starting material: Compound 647.
¹H NMR (300 MHz, CDCl₃) 6.13-6.12 (m, 1H), 6.08-6.06 (d, 1H), 5.71 (s, 1H), 4.75 (d, 1H), 4.23-4.17 (m, 3H), 4.13-4.10 (m, 1H), 3.70 (s, 1H), 3.45 (septet, 1H), 3.12-3.04 (m, 2H), 2.58-2.46 (m, 2H), 2.35-2.26 (m, 1H), 1.83 (d, 3H), 1.79-1.70 (m, 1H), 1.33 (d, 3H), 1.32 (d, 3H), 1.30 (t, 3H), 1.07 (s, 3H), 1.06 (s, 3H), 1.00 (d, 3H), 0.96-0.89 (m, 1H), 0.74-0.66 (m, 1H).

126

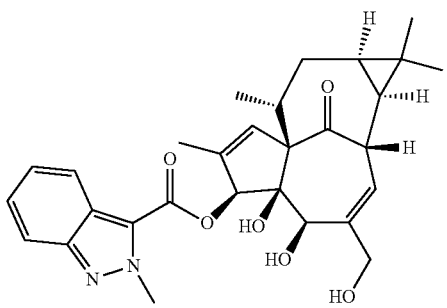 [SMILES: CC1=C[C@]23C(=O)[C@@H](C=C(CO)[C@@H](O)[C@]2(O)[C@H]1OC(=O)c1c2ccccc2nn1C)[C@H]1[C@@H](C[C@H]3C)C1(C)C]

Example 548

Ingenol 3-(2-methylindazole-3-carboxylate) (Compound 548)

Compound 548 was prepared according to Procedure e with the following changes: Tetrahydrofuran was replaced with methanol and the reaction time at room temperature was 0.5 h.
Starting material: Compound 648.
¹H NMR (300 MHz, CDCl₃) 7.97-7.94 (m, 1H), 7.81-7.78 (m, 1H), 7.39-7.34 (m, 1H), 7.31-7.26 (m, 1H), 6.22-6.21 (m, 1H), 6.10-6.08 (m, 1H), 5.86 (s, 1H), 4.75 (d, 1H), 4.54 (s, 3H), 4.26-4.18 (m, 4H), 3.80 (s, 1H), 2.74-2.69 (m, 1H), 2.32-2.22 (m, 2H), 1.91 (d, 3H), 1.75-1.67 (m, 1H), 1.07 (d, 3H), 1.05 (s, 3H), 1.04 (s, 3H), 0.97-0.90 (m, 1H), 0.73-0.65 (m, 1H).

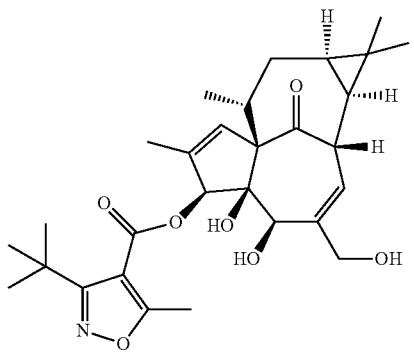 [SMILES: CC1=C[C@]23C(=O)[C@@H](C=C(CO)[C@@H](O)[C@]2(O)[C@H]1OC(=O)c1c(C(C)(C)C)noc1C)[C@H]1[C@@H](C[C@H]3C)C1(C)C]

Example 549

Ingenol 3-(5-methyl-3-tert-butyl-isoxazole-4-carboxylate) (Compound 549)

Compound 549 was prepared according to Procedure e.
Starting material: Compound 649.
¹H NMR (300 MHz, CDCl₃) 6.13-6.11 (m, 1H), 6.09-6.07 (m, 1H), 5.68 (s, 1H), 4.66 (bs, 1H), 4.22-4.15 (m, 3H), 4.12 (s, 1H), 3.67 (s, 1H), 2.62 (s, 3H), 2.60-2.53 (m, 1H), 2.33-2.23 (m, 2H), 1.83 (d, 3H), 1.78-1.69 (m, 1H), 1.44 (s, 9H), 1.07 (s, 3H), 1.06 (s, 3H), 0.98 (d, 3H), 0.96-0.89 (m, 1H), 0.74-0.66 (m, 1H).

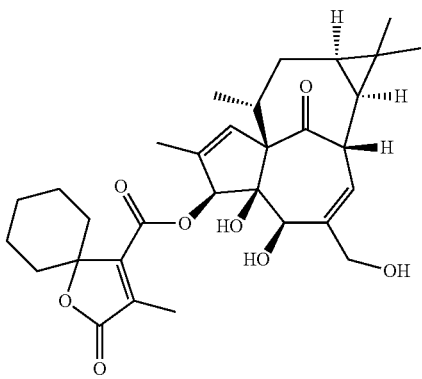 [SMILES: CC1=C[C@]23C(=O)[C@@H](C=C(CO)[C@@H](O)[C@]2(O)[C@H]1OC(=O)C1=C(C)C(=O)OC12CCCCC2)[C@H]1[C@@H](C[C@H]3C)C1(C)C]

Example 550

Ingenol 3-(2-methyl-3-oxo-4-oxaspiro[4.5]dec-1-ene-1-carboxylate) (Compound 550)

Compound 550 was prepared according to Procedure e with the following changes: Tetrahydrofuran was replaced with methanol and the reaction time at room temperature was 0.5 h.

Starting material: Compound 650.

$^1$H NMR (300 MHz, CDCl$_3$) 6.15-6.13 (m, 1H), 6.09-6.07 (m, 1H), 5.76 (s, 1H), 5.00 (d, 1H), 4.26-4.11 (m, 4H), 3.72 (s, 1H), 2.60-2.55 (m, 1H), 2.45-2.42 (m, 1H), 2.31-2.13 (m, 5H), 1.95-1.90 (m, 1H), 1.82 (d, 3H), 1.78-1.67 (m, 7H), 1.58-1.50 (m, 2H), 1.08 (s, 3H), 1.06 (s, 3H), 1.01 (d, 3H), 0.95-0.89 (m, 1H), 0.75-0.67 (m, 1H).

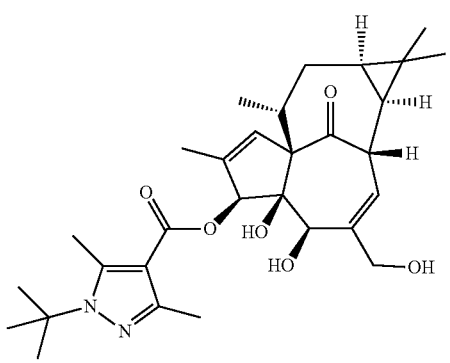 [SMILES: CC1=C[C@]23C(=O)[C@@H](C=C(CO)[C@@H](O)[C@]2(O)[C@H]1OC(=O)c1c(C)nn(C(C)(C)C)c1C)[C@H]1[C@@H](C[C@H]3C)C1(C)C]

Example 551

Ingenol 3-(1-tert-butyl-3,5-dimethyl-pyrazole-4-carboxylate) (Compound 551)

Compound 551 was prepared according to Procedure e.
Starting material: Compound 651.

$^1$H NMR (300 MHz, CDCl$_3$) 6.08-6.05 (m, 2H), 5.58 (s, 1H), 4.47 (bs, 1H), 4.17-4.10 (m, 4H), 3.65 (s, 1H), 2.71 (s, 3H), 2.62-2.57 (m, 1H), 2.36-2.21 (m, 5H), 1.83 (d, 3H), 1.79-1.70 (m, 1H), 1.65 (s, 9H), 1.07 (s, 3H), 1.05 (s, 3H), 0.99 (d, 3H), 0.96-0.91 (m, 1H), 0.73-0.65 (m, 1H).

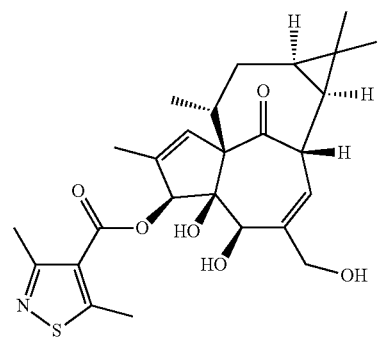

Example 552

Ingenol 3-(3,5-dimethylisothiazole-4-carboxylate) (Compound 552)

Compound 552 was prepared according to Procedure e.
Starting material: Compound 652.

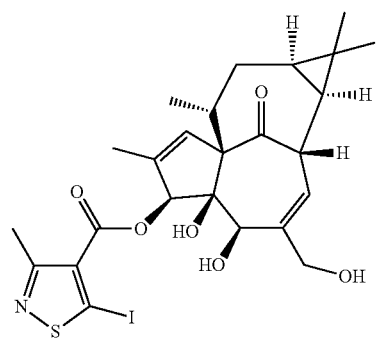

Example 553

Ingenol 3-(5-iodo-3-methyl-isothiazole-4-carboxylate) (Compound 553)

Compound 553 was prepared according to Procedure e.
Starting material: Compound 653.

$^1$H NMR (300 MHz, CDCl$_3$) 6.16-6.14 (m, 1H), 6.08 (d, 1H), 5.81 (s, 1H), 4.57 (d, 1H), 4.25-4.12 (m, 4H), 3.75 (s, 1H), 2.74 (s, 3H), 2.73-2.68 (m, 1H), 2.32-2.23 (m, 2H), 1.90 (d, 3H), 1.78-1.69 (m, 1H), 1.07 (s, 3H), 1.06 (s, 3H), 1.00 (d, 3H), 0.96-0.90 (m, 1H), 0.74-0.66 (m, 1H).

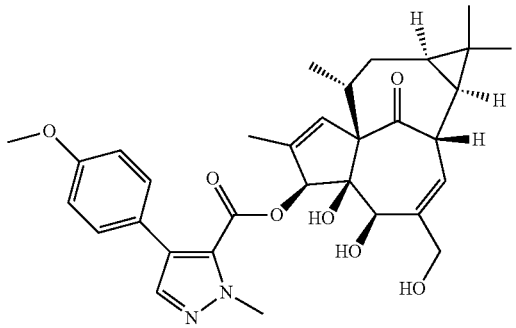

Example 554

Ingenol 3-(4-(4-methoxyphenyl)-2-methyl-pyrazole-3-carboxylate) (Compound 554)

Compound 554 was prepared according to Procedure e. Starting material: Compound 654.

$^1$H NMR (300 MHz, CDCl$_3$) 7.43 (s, 1H), 7.28-7.23 (m, 2H), 6.90-6.83 (m, 2H), 6.02-6.00 (m, 1H), 5.95-5.93 (m, 1H), 5.73 (s, 1H), 4.22 (s, 3H), 4.16-4.08 (m, 4H), 4.02-3.95 (m, 2H), 3.81 (s, 3H), 3.23 (s, 1H), 1.96-1.87 (m, 1H), 1.75 (d, 3H), 1.58-1.55 (m, 1H), 1.50-1.41 (m, 1H), 1.02 (s, 3H), 1.01 (s, 3H), 0.90-0.83 (m, 1H), 0.69 (d, 3H), 0.63-0.55 (m, 1H).

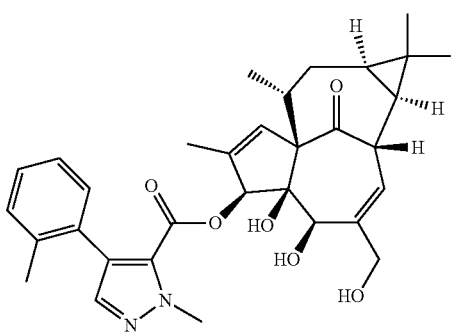 [SMILES: CC1=C[C@]23C(=O)[C@@H](C=C(CO)[C@@H](O)[C@]2(O)[C@H]1OC(=O)c1c(-c2ccccc2C)cnn1C)[C@H]1[C@@H](C[C@H]3C)C1(C)C]

Example 555

Ingenol 3-(4-(2-methylphenyl)-2-methyl-pyrazole-3-carboxylate) (Compound 555)

Compound 555 was prepared according to Procedure e. Starting material: Compound 655.

$^1$H NMR (300 MHz, CDCl$_3$) 7.37 (s, 1H), 7.24-7.11 (m, 4H), 6.00-5.98 (m, 1H), 5.87-5.85 (m, 1H), 5.62 (s, 1H), 4.25 (s, 3H), 4.16-4.06 (m, 2H), 3.97-3.88 (m, 3H), 3.00 (s, 1H), 2.36 (bs, 1H), 2.15 (s, 3H), 1.94-1.84 (m, 1H), 1.66 (d, 3H), 1.61-1.48 (m, 2H), 1.04 (s, 3H), 1.02 (s, 3H), 0.90-0.83 (m, 1H), 0.72 (d, 3H), 0.65-0.57 (m, 1H).

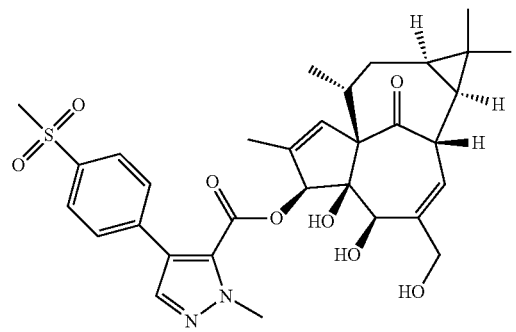

Example 556

Ingenol 3-(2-methyl-4-(4-methylsulfonylphenyl)pyrazole-3-carboxylate) (Compound 556)

Compound 556 was prepared according to Procedure e. Starting material: Compound 656.

$^1$H NMR (300 MHz, CDCl$_3$) 7.91 (d, 2H), 7.58 (d, 2H), 7.51 (s, 1H), 6.02-6.01 (d, 1H), 5.96-5.95 (m, 1H), 5.72 (s, 1H), 4.25 (s, 3H), 4.16-4.03 (m, 5H), 3.62 (bs, 1H), 3.07 (s, 3H), 2.14-2.05 (m, 1H), 1.85-1.80 (m, 1H), 1.71 (d, 3H), 1.58-1.49 (m, 1H), 1.33-1.29 (m, 1H), 1.02 (s, 3H), 1.01 (s, 3H), 0.90-0.80 (m, 1H), 0.68 (d, 3H), 0.65-0.57 (m, 1H).

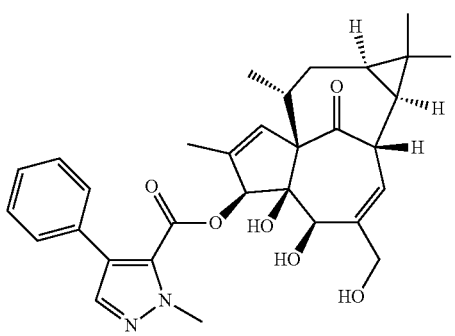 [SMILES: CC1=C[C@]23C(=O)[C@@H](C=C(CO)[C@@H](O)[C@]2(O)[C@H]1OC(=O)c1c(-c2ccccc2)cnn1C)[C@H]1[C@@H](C[C@H]3C)C1(C)C]

Example 557

Ingenol 3-(2-methyl-4-phenyl-pyrazole-3-carboxylate) (Compound 557)

Compound 557 was prepared according to Procedure e. Starting material: Compound 657.

$^1$H NMR (300 MHz, CDCl$_3$) 7.47 (s, 1H), 7.37-7.31 (m, 5H), 6.01 (d, 1H), 5.92-5.91 (m, 1H), 5.71 (s, 1H), 4.24 (s, 3H), 4.16-4.11 (m, 2H), 4.01-3.95 (m, 3H), 3.17 (s, 1H), 2.09-2.03 (m, 1H), 1.93-1.84 (m, 1H), 1.72 (d, 3H), 1.64-1.59 (m, 1H), 1.49-1.41 (m, 1H), 1.03 (s, 3H), 1.02 (s, 3H), 0.88-0.81 (m, 1H), 0.67 (d, 3H), 0.63-0.55 (m, 1H).

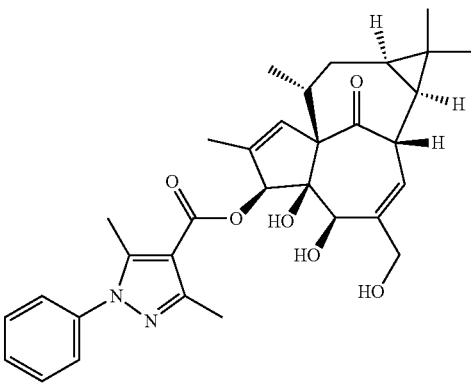 [SMILES: CC1=C[C@]23C(=O)[C@@H](C=C(CO)[C@@H](O)[C@]2(O)[C@H]1OC(=O)c1c(C)nn(-c2ccccc2)c1C)[C@H]1[C@@H](C[C@H]3C)C1(C)C]

Example 558

Ingenol 3-(3,5-dimethyl-1-phenyl-pyrazole-4-carboxylate) (Compound 558)

Compound 558 was prepared according to Procedure e. Starting material: Compound 658.

$^1$H NMR (300 MHz, CDCl$_3$) 7.53-7.37 (m, 5H), 6.10-6.09 (m, 1H), 6.07-6.05 (m, 1H), 5.67 (s, 1H), 4.70 (d, 1H), 4.22-4.11 (m, 4H), 3.75 (s, 1H), 2.72-2.61 (m, 2H), 2.52 (s, 3H), 2.49 (s, 3H), 2.35-2.25 (m, 1H), 1.86 (d, 3H), 1.80-1.71 (m, 1H), 1.08 (s, 3H), 1.05 (s, 3H), 1.00 (d, 3H), 0.98-0.90 (m, 1H), 0.74-0.66 (m, 1H).

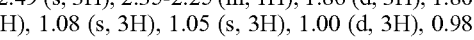

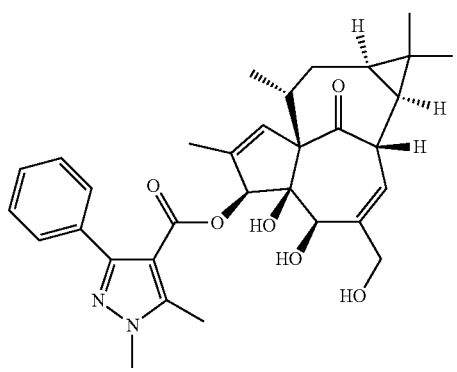 [SMILES: CC1=C[C@]23C(=O)[C@@H](C=C(CO)[C@@H](O)[C@]2(O)[C@H]1OC(=O)c1c(-c2ccccc2)nn(C)c1C)[C@H]1[C@@H](C[C@H]3C)C1(C)C]

Example 559

Ingenol 3-(1,5-dimethyl-3-phenyl-pyrazole-4-carboxylate) (Compound 559)

Compound 559 was prepared according to Procedure e. Starting material: Compound 659.

$^1$H NMR (300 MHz, CDCl$_3$) 7.49-7.45 (m, 2H), 7.38-7.33 (m, 3H), 5.98 (d, 1H), 5.89-5.87 (m, 1H), 5.64 (s, 1H), 4.11-4.08 (m, 2H), 3.99-3.94 (m, 3H), 3.85 (s, 3H), 3.21 (s, 1H), 2.60 (s, 3H), 2.46 (bs, 1H), 1.95-1.85 (m, 1H), 1.73 (d, 3H), 1.71-1.64 (m, 1H), 1.50-1.42 (m, 1H), 1.02 (s, 3H), 1.01 (s, 3H), 0.90-0.84 (m, 1H), 0.68 (d, 3H), 0.63-0.55 (m, 1H).

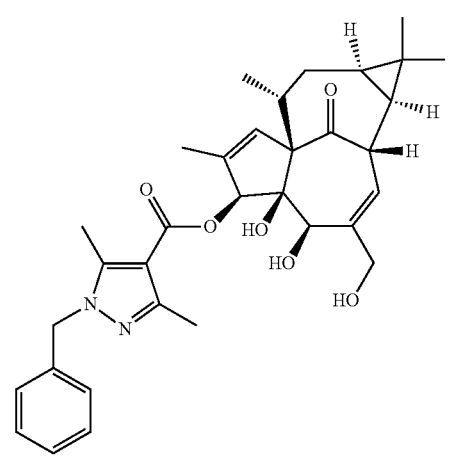 [SMILES: CC1=C[C@]23C(=O)[C@@H](C=C(CO)[C@@H](O)[C@]2(O)[C@H]1OC(=O)c1c(C)nn(Cc2ccccc2)c1C)[C@H]1[C@@H](C[C@H]3C)C1(C)C]

Example 560

Ingenol 3-(1-benzyl-3,5-dimethyl-pyrazole-4-carboxylate) (Compound 560)

Compound 560 was prepared according to Procedure e. Starting material: Compound 660.

$^1$H NMR (300 MHz, CDCl$_3$) 7.37-7.28 (m, 3H), 7.16-7.13 (m, 2H), 6.08-6.05 (m, 2H), 5.61 (s, 1H), 5.25 (s, 2H), 4.52 (bs, 1H), 4.18-4.10 (m, 4H), 3.67 (s, 1H), 2.61-2.56 (m, 1H), 2.45 (s, 3H), 2.44-2.41 (s, 4H), 2.31-2.22 (m, 1H), 1.82 (d, 3H), 1.79-1.70 (m, 1H), 1.07 (s, 3H), 1.05 (s, 3H), 0.98 (d, 3H), 0.94-0.86 (m, 1H), 0.73-0.65 (m, 1H).

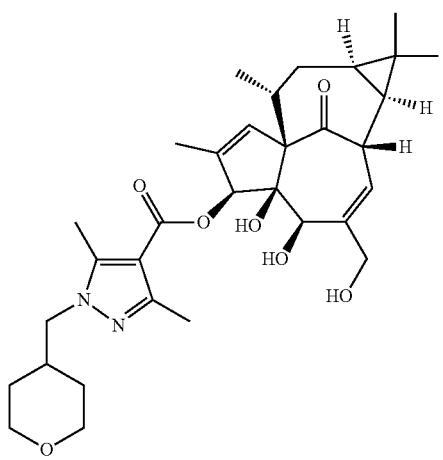 [SMILES: CC1=C[C@]23C(=O)[C@@H](C=C(CO)[C@@H](O)[C@]2(O)[C@H]1OC(=O)c1c(C)nn(CC2CCOCC2)c1C)[C@H]1[C@@H](C[C@H]3C)C1(C)C]

Example 561

Ingenol 3-(3,5-dimethyl-1-(tetrahydropyran-4-ylmethyl)pyrazole-4-carboxylate) (Compound 561)

Compound 561 was prepared according to Procedure e. Starting material: Compound 661.

$^1$H NMR (300 MHz, CDCl$_3$) 6.08-6.05 (m, 2H), 5.60 (s, 1H), 4.53 (bs, 1H), 4.17-4-11 (m, 4H), 4.00-3.95 (m, 2H), 3.87 (d, 2H), 3.67 (s, 1H), 3.40-3.32 (m, 2H), 2.62-2.57 (m, 1H), 2.51 (s, 3H), 2.39 (s, 3H), 2.32-2.13 (m, 2H), 1.84 (d, 3H), 1.79-1.70 (m, 1H), 1.55-1.35 (m, 5H), 1.07 (s, 3H), 1.05 (s, 3H), 0.99 (d, 3H), 0.95-0.85 (m, 1H), 0.73-0.66 (m, 1H).

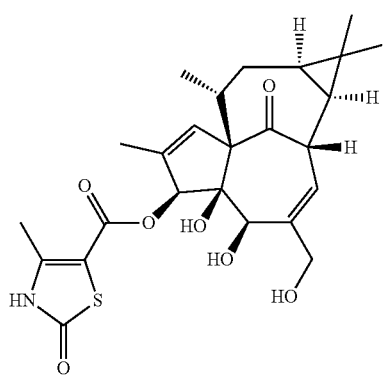

Example 562

Ingenol 3-(4-methyl-2-oxo-3H-thiazole-5-carboxylate) (Compound 562)

Compound 562 was prepared according to Procedure e. Starting material: Compound 662.

$^1$H NMR (300 MHz, DMSO-d$_6$) 11.91 (bs, 1H), 5.93 (m, 1H), 5.88-5.86 (m, 1H), 5.73 (s, 1H), 5.41 (d, 1H), 5.12 (s, 1H), 4.64 (t, 1H), 4.18 (m, 1H), 3.98-3.85 (m, 2H), 3.63-3.58 (m, 1H), 2.56-2.51 (m, 1H), 2.38 (s, 3H), 2.33-2.26 (m, 1H), 1.78-1.64 (m, 4H), 1.03 (s, 6H), 0.89 (d, 3H), 0.81-0.74 (m, 1H), 0.65-0.57 (m, 1H).

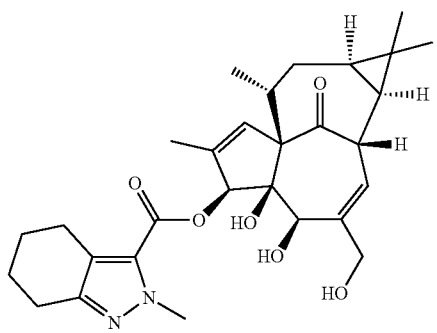 [SMILES: CC1=C[C@]23C(=O)[C@@H](C=C(CO)[C@@H](O)[C@]2(O)[C@H]1OC(=O)c1c2c(nn1C)CCCC2)[C@H]1[C@@H](C[C@H]3C)C1(C)C]

Example 563

Ingenol 3-(2-methyl-4,5,6,7-tetrahydroindazole-3-carboxylate) (Compound 563)

Compound 563 was prepared according to Procedure e.
Starting material: Compound 663.

$^1$H NMR (300 MHz, CDCl$_3$) 6.12-6.10 (m, 1H), 6.08-6.06 (m, 1H), 5.72 (s, 1H), 4.71 (s, 1H), 4.23-4.11 (m, 7H), 3.71 (s, 1H), 2.71-2.57 (m, 6H), 2.34-2.24 (m, 1H), 1.84 (d, 3H), 1.81-1.70 (m, 5H), 1.07 (s, 3H), 1.05 (s, 3H), 1.00 (d, 3H), 0.96-0.88 (m, 1H), 0.74-0.66 (m, 1H).

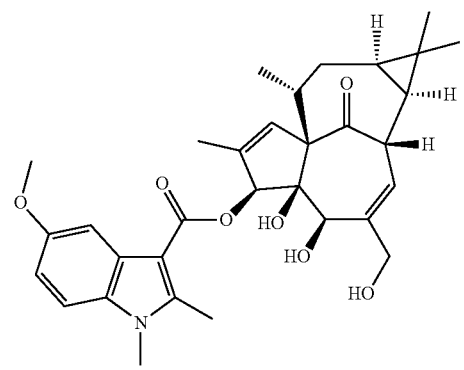

Example 565

Ingenol 3-(5-methoxy-1,2-dimethyl-indole-3-carboxylate) (Compound 565)

Compound 565 was prepared according to Procedure e.
Starting material: Compound 665.

$^1$H NMR (300 MHz, CDCl$_3$) 7.56 (d, 1H), 7.19 (d, 1H), 6.88 (dd, 1H), 6.13-6.11 (m, 1H), 6.07-6.06 (m, 1H), 5.69 (s, 1H), 4.66 (d, 1H), 4.18-4.13 (m, 4H), 3.83 (s, 1H), 3.82 (s, 3H), 3.65 (s, 3H), 2.73 (s, 3H), 2.72-2.62 (m, 2H), 2.29-2.20 (m, 1H), 1.90 (d, 3H), 1.76-1.69 (m, 1H), 1.05 (s, 3H), 1.03 (s, 3H), 1.02 (d, 3H), 0.99-0.92 (m, 1H), 0.72-0.64 (m, 1H).

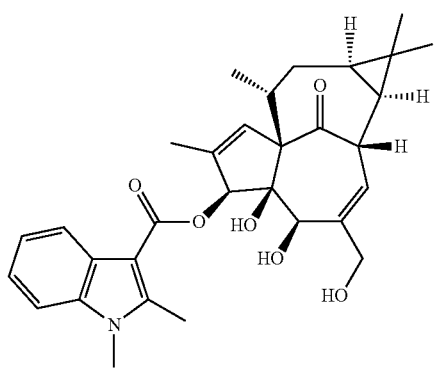 [SMILES: CC1=C[C@]23C(=O)[C@@H](C=C(CO)[C@@H](O)[C@]2(O)[C@H]1OC(=O)c1c(C)n(C)c2ccccc12)[C@H]1[C@@H](C[C@H]3C)C1(C)C]

Example 564

Ingenol 3-(1,2-dimethylindole-3-carboxylate) (Compound 564)

Compound 564 was prepared according to Procedure e.
Starting material: Compound 664.

$^1$H NMR (300 MHz, CDCl$_3$) 8.04-8.01 (m, 1H), 7.33-7.19 (m, 3H), 6.13-6.11 (m, 1H), 6.07-6.05 (m, 1H), 5.72 (s, 1H), 4.62 (d, 1H), 4.19-4.13 (m, 4H), 3.81 (s, 1H), 3.68 (s, 3H), 2.76-2.65 (m, 5H), 2.29-2.20 (m, 1H), 1.89 (d, 3H), 1.76-1.67 (m, 1H), 1.05-1.03 (m, 9H), 0.99-0.91 (m, 1H), 0.72-0.64 (m, 1H).

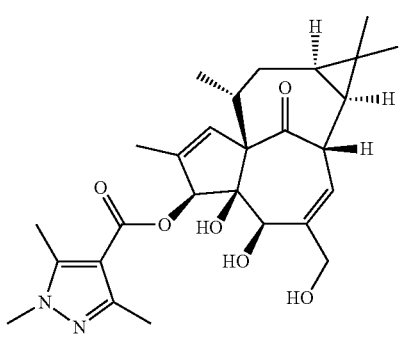

Example 566

Ingenol 3-(1,3,5-trimethylpyrazole-4-carboxylate) (Compound 566)

Compound 566 was prepared according to Procedure e.
Starting material: Compound 630.

$^1$H NMR (300 MHz, CDCl$_3$) 6.08-6.05 (m, 2H), 5.62 (s, 1H), 6.07 (d, 1H), 4.19-4.10 (m, 4H), 3.73 (s, 3H), 3.71 (s, 1H), 3.73 (t, 1H), 2.62-2.57 (m, 1H), 2.50 (s, 3H), 2.38 (s, 3H), 2.32-2.22 (m, 1H), 1.83 (d, 3H), 1.78-1.69 (m, 1H), 1.06 (s, 3H), 1.05 (s, 3H), 0.99 (d, 3H), 0.97-0.90 (m, 1H), 0.73-0.65 (m, 1H).

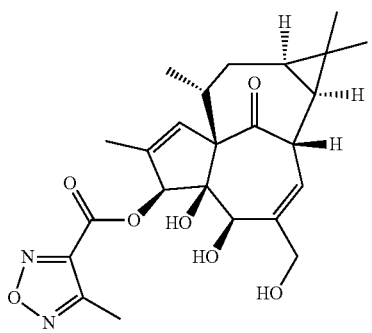 [SMILES: CC1=C[C@]23C(=O)[C@@H](C=C(CO)[C@@H](O)[C@]2(O)[C@H]1OC(=O)c1nonc1C)[C@H]1[C@@H](C[C@H]3C)C1(C)C]

Example 567

Ingenol 3-(4-methyl-1,2,5-oxadiazole-3-carboxylate) (Compound 567)

Compound 567 was prepared according to Procedure e. Starting material: Compound 667.

$^1$H NMR (300 MHz, CDCl$_3$) 6.18-6.17 (m, 1H), 6.09-6.07 (m, 1H), 5.88 (s, 1H), 4.67 (d, 1H), 4.23-4.10 (m, 4H), 3.71 (s, 1H), 2.66-2.60 (m, 4H), 2.31-2.21 (m, 2H), 1.86 (d, 3H), 1.84-1.74 (m, 1H), 1.07 (s, 3H), 1.04 (s, 3H), 1.02 (d, 3H), 0.96-0.89 (m, 1H), 0.75-0.67 (m, 1H).

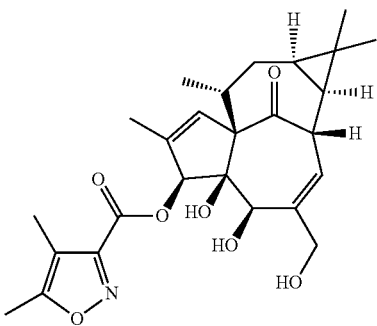

Example 569

Ingenol 3-(4,5-dimethylisoxazole-3-carboxylate) (Compound 569)

Compound 569 was prepared according to Procedure e. Starting material: Compound 669.

$^1$H NMR (300 MHz, CDCl$_3$) 6.11-6.10 (m, 1H), 6.06-6.04 (m, 1H), 5.84 (s, 1H), 4.34 (d, 1H), 4.23-4.13 (m, 3H), 4.05 (d, 1H), 3.89 (s, 1H), 2.65-2.59 (m, 2H), 2.39 (s, 3H), 2.30-2.21 (m, 1H), 2.14 (s, 3H), 1.85 (d, 3H), 1.82-1.73 (m, 1H), 1.07 (s, 3H), 1.05 (s, 3H), 1.00 (d, 3H), 0.96-0.88 (m, 1H), 0.74-0.66 (m, 1H).

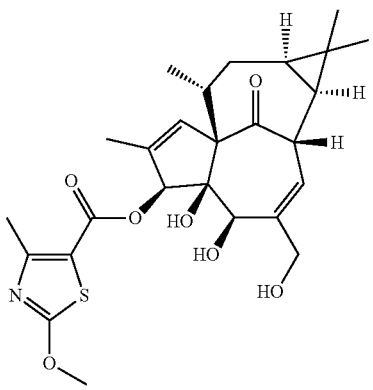

Example 568

Ingenol 3-(2-methoxy-4-methyl-thiazole-5-carboxylate) (Compound 568)

Compound 568 was prepared according to Procedure e. Starting material: Compound 668.

$^1$H NMR (300 MHz, CDCl$_3$) 6.08-6.05 (m, 2H), 5.65 (s, 1H), 4.53 (bs, 1H), 4.22-4.13 (m, 3H), 4.06 (s, 1H), 3.58 (s, 1H), 3.33 (s, 3H), 2.60 (s, 3H), 2.59-2.52 (m, 1H), 2.41 (bs, 1H), 2.31-2.22 (m, 1H), 1.81 (d, 3H), 1.78-1.73 (m, 1H), 1.07 (s, 3H), 1.05 (s, 3H), 0.99 (d, 3H), 0.96-0.89 (m, 1H), 0.74-0.67 (m, 1H).

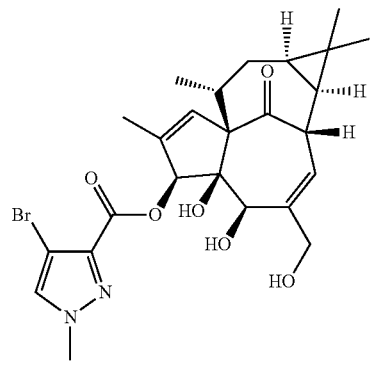 [SMILES: CC1=C[C@]23C(=O)[C@@H](C=C(CO)[C@@H](O)[C@]2(O)[C@H]1OC(=O)c1nn(C)cc1Br)[C@H]1[C@@H](C[C@H]3C)C1(C)C]

Example 570

Ingenol 3-(4-bromo-1-methyl-pyrazole-3-carboxylate) (Compound 570)

Compound 570 was prepared according to Procedure e. Starting material: Compound 670.

$^1$H NMR (300 MHz, CDCl$_3$) 7.50 (s, 1H), 6.11-6.09 (m, 1H), 6.08-6.06 (m, 1H), 5.81 (s, 1H), 4.18-4.11 (m, 3H), 4.04 (d, 1H), 3.98 (s, 3H), 3.88 (s, 1H), 3.75 (d, 1H), 2.73-2.68 (m, 1H), 2.30-2.21 (m, 2H), 1.88 (d, 3H), 1.82-1.73 (m, 1H), 1.09 (s, 3H), 1.06 (s, 3H), 1.01 (d, 3H), 0.99-0.92 (m, 1H), 0.75-0.67 (m, 1H).

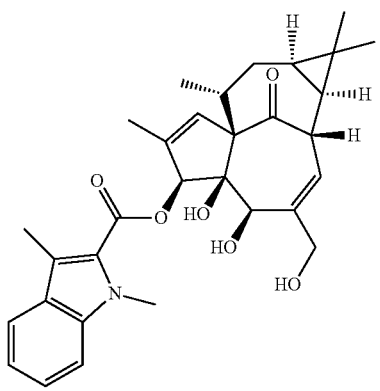 [SMILES: CC1=C[C@]23C(=O)[C@@H](C=C(CO)[C@@H](O)[C@]2(O)[C@H]1OC(=O)c1c(C)c2ccccc2n1C)[C@H]1[C@@H](C[C@H]3C)C1(C)C]

Example 571

Ingenol 3-(1,3-dimethylindole-2-carboxylate) (Compound 571)

Compound 571 was prepared according to Procedure e. Starting material: Compound 671.

$^1$H NMR (300 MHz, CDCl$_3$) 7.68-7.65 (m, 1H), 7.40-7.32 (m, 2H), 7.17-7.12 (m, 1H), 6.14-6.13 (m, 1H), 6.08-6.06 (m, 1H), 5.79 (s, 1H), 4.60 (bs, 1H), 4.23-4.13 (m, 4H), 4.01 (s, 3H), 3.76 (s, 1H), 2.69-2.64 (m, 1H), 2.59 (s, 3H), 2.54-2.49 (m, 1H), 2.32-2.23 (m, 1H), 1.88 (d, 3H), 1.78-1.67 (m, 1H), 1.06 (s, 3H), 1.05 (s, 3H), 1.02 (d, 3H), 0.97-0.88 (m, 1H), 0.73-0.65 (m, 1H).

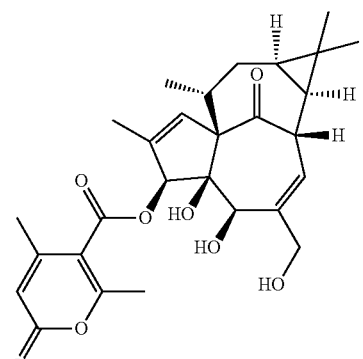

Example 573

Ingenol 3-(2,4-dimethyl-6-oxo-pyran-3-carboxylate) (Compound 573)

Compound 573 was prepared according to Procedure e. Starting material: Compound 673.

$^1$H NMR (300 MHz, CDCl$_3$) 6.14-6.13 (m, 1H), 6.10-6.08 (m, 1H), 6.04 (s, 1H), 5.75 (s, 1H), 4.76 (bs, 1H), 4.22-4.18 (m, 3H), 4.12 (s, 1H), 3.76 (s, 1H), 2.51-2.46 (m, 1H), 2.44 (s, 3H), 2.33-2.26 (m, 1H), 2.23 (d, 3H), 2.11 (bs, 1H), 1.82 (d, 3H), 1.79-1.70 (m, 1H), 1.08 (s, 3H), 1.06 (s, 3H), 0.98 (d, 3H), 0.96-0.88 (m, 1H), 0.75-0.67 (m, 1H).

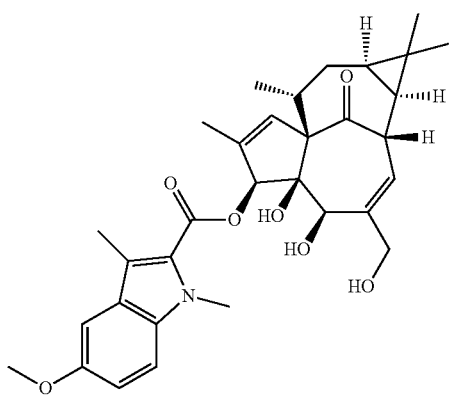

Example 572

Ingenol 3-(5-methoxy-1,3-dimethyl-indole-2-carboxylate) (Compound 572)

Compound 572 was prepared according to Procedure e. Starting material: Compound 672.

$^1$H NMR (300 MHz, CDCl$_3$) 7.26-7.23 (m, 1H), 7.06-7.00 (m, 2H), 6.14-6.12 (m, 1H), 6.08-6.06 (m, 1H), 5.78 (s, 1H), 4.58 (bs, 1H), 4.22-4.14 (m, 4H), 3.99 (s, 3H), 3.87 (s, 3H), 3.75 (s, 1H), 2.68-2.62 (m, 1H), 2.55 (s, 3H), 2.49 (bs, 1H), 2.33-2.23 (m, 1H), 1.88 (d, 3H), 1.78-1.69 (m, 1H), 1.06 (s, 3H), 1.05 (s, 3H), 1.02 (d, 3H), 0.97-0.88 (m, 1H), 0.73-0.65 (m, 1H).

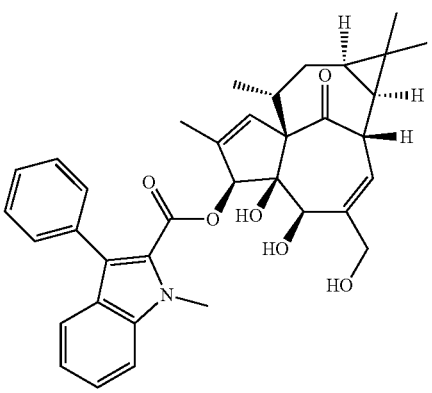 [SMILES: CC1=C[C@]23C(=O)[C@@H](C=C(CO)[C@@H](O)[C@]2(O)[C@H]1OC(=O)c1c(-c2ccccc2)c2ccccc2n1C)[C@H]1[C@@H](C[C@H]3C)C1(C)C]

Example 574

Ingenol 3-(1-methyl-3-phenyl-indole-2-carboxylate) (Compound 574)

Compound 574 was prepared according to Procedure e. Starting material: Compound 674.

$^1$H NMR (300 MHz, CDCl$_3$) 7.46-7.34 (m, 8H), 7.15-7.10 (m, 1H), 6.01-5.99 (m, 1H), 5.89-5.87 (m, 1H), 5.73 (s, 1H), 4.12-4.11 (m, 5H), 3.98-3.91 (m, 2H), 3.81-3.79 (d, 1H), 3.02 (s, 1H), 2.35 (bs, 1H), 1.92-1.83 (m, 1H), 1.70-1.66 (d, 4H), 1.54-1.45 (m, 1H), 1.03 (s, 3H), 1.03 (s, 3H), 0.89-0.82 (m, 1H), 0.74 (d, 3H), 0.64-0.56 (m, 1H).

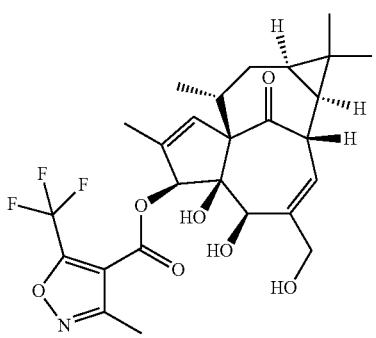 [SMILES: CC1=C[C@]23C(=O)[C@@H](C=C(CO)[C@@H](O)[C@]2(O)[C@H]1OC(=O)c1c(C)noc1C(F)(F)F)[C@H]1[C@@H](C[C@H]3C)C1(C)C]

Example 575

Ingenol 3-(3-methyl-5-(trifluoromethyl)isoxazole-4-carboxylate) (Compound 575)

Compound 575 was prepared according to Procedure e.

Starting material: Compound 675.

$^1$H NMR (300 MHz, CDCl$_3$) 6.16-6.14 (m, 1H), 6.09-6.06 (m, 1H), 5.77 (s, 1H), 4.25-4.14 (m, 3H), 4.10 (s, 1H), 3.08 (bs, 3H), 2.57-2.48 (m, 4H), 2.31-2.22 (m, 1H), 1.81 (d, 3H), 1.78-1.69 (m, 1H), 1.06 (s, 6H), 0.99 (d, 3H), 0.94-0.87 (m, 1H), 0.74-0.66 (m, 1H).

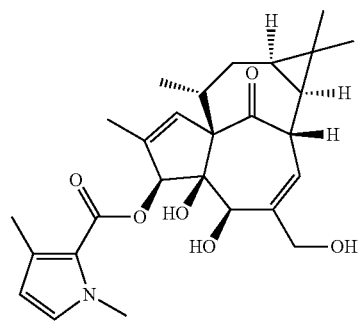

Example 576

Ingenol 3-(1,3-dimethylpyrrole-2-carboxylate) (Compound 576)

Compound 576 was prepared according to Procedure e with the following changes: Tetrahydrofuran was replaced with methanol and the reaction time at room temperature was 0.5 h.

Starting material: Compound 676.

$^1$H NMR (300 MHz, CDCl$_3$) 6.71 (d, 1H), 6.08-6.04 (m, 2H), 5.98 (d, 1H), 5.63 (s, 1H), 4.50 (d, 1H), 4.19-4.09 (m, 4H), 3.87 (s, 3H), 3.72 (s, 1H), 2.64-2.53 (m, 2H), 2.31 (s, 3H), 2.30-2.22 (m, 1H), 1.84 (d, 3H), 1.78-1.71 (m, 1H), 1.07 (s, 3H), 1.05 (s, 3H), 0.99 (d, 3H), 0.95-0.86 (m, 1H), 0.73-0.65 (m, 1H).

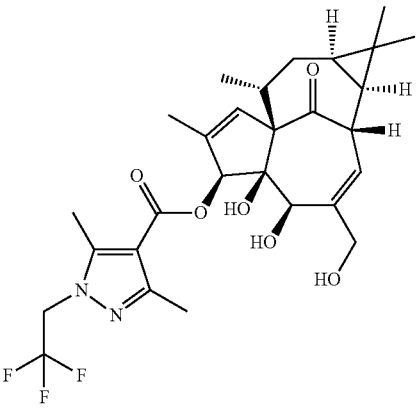 [SMILES: CC1=C[C@]23C(=O)[C@@H](C=C(CO)[C@@H](O)[C@]2(O)[C@H]1OC(=O)c1c(C)nn(CC(F)(F)F)c1C)[C@H]1[C@@H](C[C@H]3C)C1(C)C]

Example 577

Ingenol 3-(3,5-dimethyl-1-(2,2,2-trifluoroethyl)pyrazole-4-carboxylate) (Compound 577)

Compound 577 was prepared according to Procedure e.

Starting material: Compound 677.

$^1$H NMR (300 MHz, CDCl$_3$) 6.09-6.08 (m, 1H), 6.06-6.04 (m, 1H), 5.68 (s, 1H), 4.82 (d, 1H), 4.62 (q, 2H), 4.22-4.12 (m, 4H), 3.77 (s, 1H), 2.97 (bs, 1H), 2.63-2.58 (m, 1H), 2.55 (s, 3H), 2.41 (s, 3H), 2.34-2.24 (m, 1H), 1.83 (d, 3H), 1.79-1.70 (m, 1H), 1.07 (s, 3H), 1.05 (s, 3H), 0.99 (d, 3H), 0.96-0.88 (m, 1H), 0.73-0.65 (m, 1H).

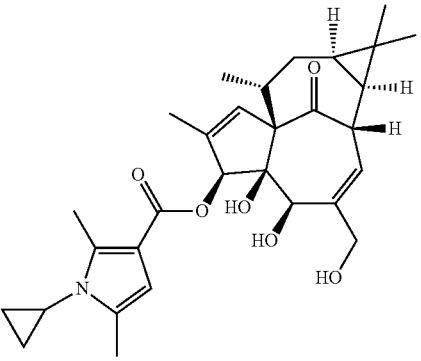 [SMILES: CC1=C[C@]23C(=O)[C@@H](C=C(CO)[C@@H](O)[C@]2(O)[C@H]1OC(=O)c1cc(C)n(C2CC2)c1C)[C@H]1[C@@H](C[C@H]3C)C1(C)C]

Example 578

Ingenol 3-(1-cyclopropyl-2,5-dimethyl-pyrrole-3-carboxylate) (Compound 578)

Compound 578 was prepared according to Procedure e.

Starting material: Compound 678.

$^1$H NMR (300 MHz, CDCl$_3$) 6.18-6.17 (m, 1H), 6.04-6.00 (m, 2H), 5.58 (s, 1H), 4.42 (d, 1H), 4.16-4.05 (m, 4H), 3.60 (s, 1H), 2.93-2.87 (m, 1H), 2.76 (bs, 1H), 2.61-2.56 (m, 4H), 2.28-2.19 (m, 4H), 1.80 (d, 3H), 1.78-1.71 (m, 1H), 1.15-1.08 (m, 2H), 1.06 (s, 3H), 1.03 (s, 3H), 0.99 (d, 3H), 0.95-0.88 (m, 3H), 0.72-0.65 (m, 1H).

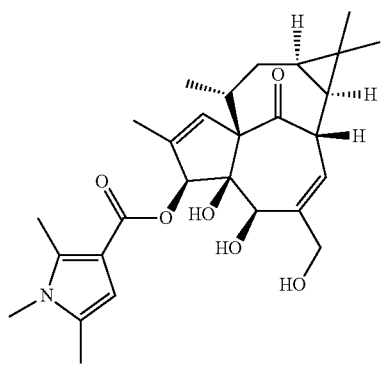

Example 579

Ingenol 3-(1,2,5-trimethylpyrrole-3-carboxylate)
(Compound 579)

Compound 579 was prepared according to Procedure e.
Starting material: Compound 679.

$^1$H NMR (300 MHz, CDCl$_3$) 6.23-6.22 (m, 1H), 6.05-6.00 (m, 2H), 5.57 (s, 1H), 4.31 (d, 1H), 4.16-4.06 (m, 4H), 3.57 (s, 1H), 3.41 (s, 3H), 2.60-2.54 (m, 2H), 2.51 (s, 3H), 2.28-2.19 (m, 4H), 1.81 (d, 3H), 1.79-1.72 (m, 1H), 1.07 (s, 3H), 1.04 (s, 3H), 1.00 (d, 3H), 0.98-0.92 (m, 1H), 0.73-0.65 (m, 1H).

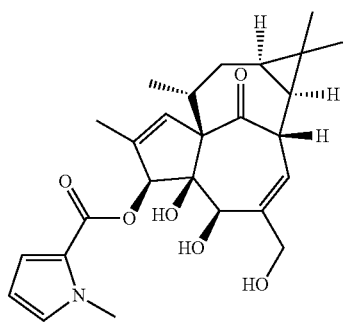

Example 581

Ingenol 3-(1-methylpyrrole-2-carboxylate)
(Compound 581)

Compound 581 was prepared according to Procedure e.
Starting material: Compound 681.

$^1$H NMR (300 MHz, CDCl$_3$) 6.96 (dd, 1H), 6.84 (t, 1H), 6.14 (dd, 1H), 6.06-6.03 (m, 2H), 5.69 (s, 1H), 4.43 (d, 1H), 4.18-4.06 (m, 4H), 3.93 (s, 3H), 3.64 (s, 1H), 2.77 (bs, 1H), 2.62-2.57 (m, 1H), 2.31-2.21 (m, 1H), 1.82 (d, 3H), 1.80-1.73 (m, 1H), 1.07 (s, 3H), 1.05 (s, 3H), 1.01 (d, 3H), 0.97-0.91 (m, 1H), 0.74-0.66 (m, 1H).

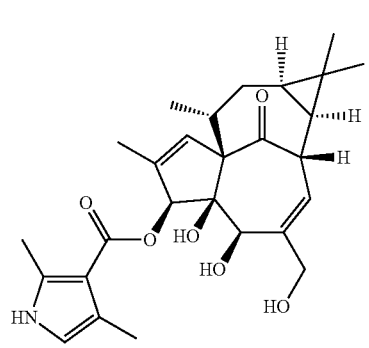

Example 580

Ingenol 3-(2,4-dimethyl-1H-pyrrole-3-carboxylate)
(Compound 580)

Compound 580 was prepared according to Procedure e.
Starting material: Compound 680.

$^1$H NMR (300 MHz, CDCl$_3$) 10.51 (bs, 1H), 6.09-6.05 (m, 2H), 5.95 (d, 1H), 5.83 (s, 1H), 4.89 (bs, 1H), 4.54 (s, 1H), 4.23-4.07 (m, 4H), 3.11 (bs, 1H), 2.59-2.54 (m, 1H), 2.38 (s, 3H), 2.35-2.25 (m, 4H), 1.82 (d, 3H), 1.79-1.74 (m, 1H), 1.09 (s, 3H), 1.06 (s, 3H), 0.98-0.88 (m, 4H), 0.75-0.67 (m, 1H).

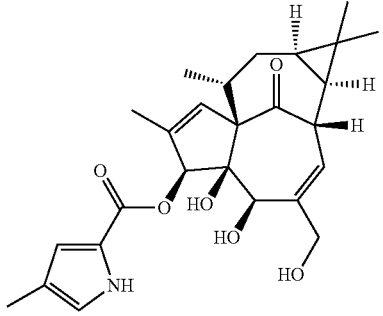

Example 582

Ingenol 3-(4-methyl-1H-pyrrole-2-carboxylate)
(Compound 582)

Compound 582 was prepared according to Procedure e.
Starting material: Compound 682.

$^1$H NMR (300 MHz, CDCl$_3$) 9.54 (s, 1H), 6.77-6.72 (m, 2H), 6.06-6.02 (m, 2H), 5.69 (s, 1H), 4.80 (d, 1H), 4.26-4.07 (m, 4H), 3.80 (s, 1H), 2.79 (t, 1H), 2.62-2.56 (m, 1H), 2.32-2.23 (m, 1H), 2.11 (s, 3H), 1.82-1.73 (m, 4H), 1.05 (s, 3H), 1.04 (s, 3H), 1.01 (d, 3H), 0.96-0.88 (m, 1H), 0.73-0.66 (m, 1H).

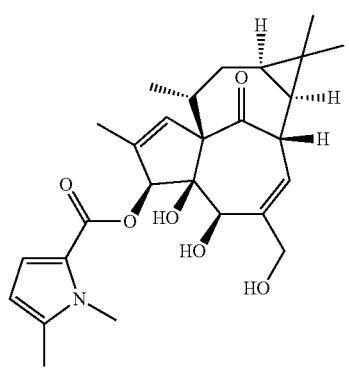 [SMILES: CC1=C[C@]23C(=O)[C@@H](C=C(CO)[C@@H](O)[C@]2(O)[C@H]1OC(=O)c1ccc(C)n1C)[C@H]1[C@@H](C[C@H]3C)C1(C)C]

Example 583

Ingenol 3-(1,5-dimethylpyrrole-2-carboxylate) (Compound 583)

Compound 583 was prepared according to Procedure e.
Starting material: Compound 683.

$^1$H NMR (300 MHz, CDCl$_3$) 6.91 (d, 1H), 6.04-6.02 (m, 2H), 5.94 (d, 1H), 5.67 (s, 1H), 4.39 (d, 1H), 4.17-4.05 (m, 4H), 3.83 (s, 3H), 3.64 (s, 1H), 2.80 (t, 1H), 2.61-2.56 (m, 1H), 2.30-2.21 (m, 4H), 1.81 (d, 3H), 1.79-1.72 (m, 1H), 1.07 (s, 3H), 1.04 (s, 3H), 1.01 (d, 3H), 0.97-0.91 (m, 1H), 0.73-0.65 (m, 1H).

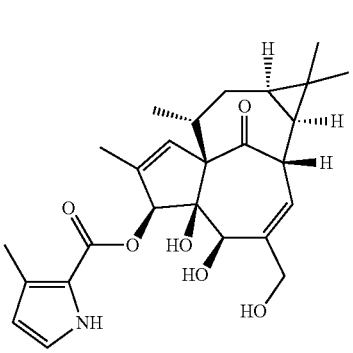

Example 584

Ingenol 3-(3-methyl-1H-pyrrole-2-carboxylate) (Compound 584)

Compound 584 was prepared according to Procedure e.
Starting material: Compound 684.

$^1$H NMR (300 MHz, CDCl$_3$) 9.33 (s, 1H), 6.87 (t, 1H), 6.11 (t, 1H), 6.08-6.04 (m, 2H), 5.66 (s, 1H), 4.76 (d, 1H), 4.23-4.10 (m, 4H), 3.81 (s, 1H), 2.62-2.57 (m, 2H), 2.34-2.23 (m, 4H), 1.81 (d, 3H), 1.79-1.70 (m, 1H), 1.05 (s, 3H), 1.04 (s, 3H), 1.00 (d, 3H), 0.96-0.88 (m, 1H), 0.73-0.65 (m, 1H).

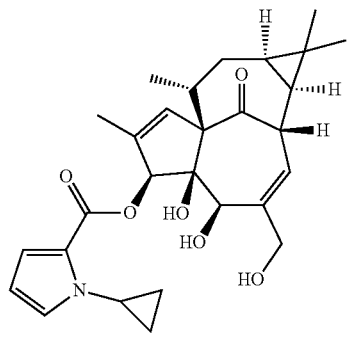 [SMILES: CC1=C[C@]23C(=O)[C@@H](C=C(CO)[C@@H](O)[C@]2(O)[C@H]1OC(=O)c1cccn1C1CC1)[C@H]1[C@@H](C[C@H]3C)C1(C)C]

Example 585

Ingenol 3-(1-cyclopropylpyrrole-2-carboxylate) (Compound 585)

Compound 585 was prepared according to Procedure e.
Starting material: Compound 685.

$^1$H NMR (300 MHz, CDCl$_3$) 6.95 (dd, 1H), 6.91 (t, 1H), 6.09 (dd, 1H), 6.05-6.03 (m, 2H), 5.70 (s, 1H), 4.40 (d, 1H), 4.18-4.07 (m, 4H), 3.73 (m, 1H), 3.64 (s, 1H), 2.74 (t, 1H), 2.62-2.57 (m, 1H), 2.31-2.21 (m, 1H), 1.83 (d, 3H), 1.81-1.72 (m, 1H), 1.07 (s, 3H), 1.05 (s, 3H), 1.03-0.91 (m, 8H), 0.73-0.66 (m, 1H).

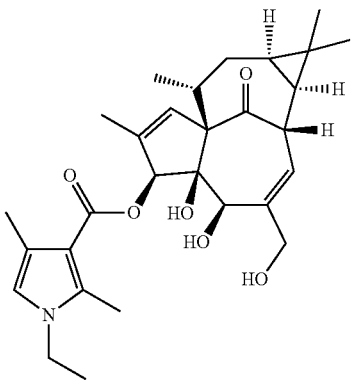

Example 586

Ingenol 3-(1-ethyl-2,4-dimethyl-pyrrole-3-carboxylate) (Compound 586)

Compound 586 was prepared according to Procedure e.
Starting material: Compound 686.

$^1$H NMR (300 MHz, CDCl$_3$) 6.34-6.33 (m, 1H), 6.05-6.02 (m, 2H), 5.58 (s, 1H), 4.60 (d, 1H), 4.17-4.08 (m, 4H), 3.81 (q, 2H), 3.73 (s, 1H), 2.77 (bs, 1H), 2.64-2.59 (m, 1H), 2.48 (s, 3H), 2.30-2.21 (m, 1H), 2.19 (d, 3H), 1.83 (d, 3H), 1.77-1.68 (m, 1H), 1.33 (t, 3H), 1.06 (s, 3H), 1.04 (s, 3H), 0.98 (d, 3H), 0.97-0.91 (m, 1H), 0.72-0.64 (m, 1H).

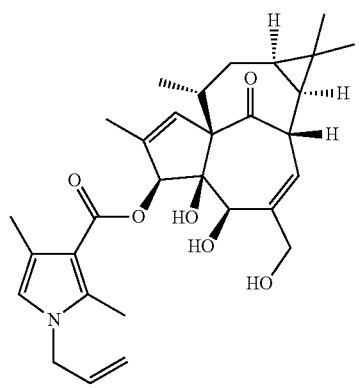

Example 587

Ingenol 3-(1-allyl-2,4-dimethyl-pyrrole-3-carboxylate) (Compound 587)

Compound 587 was prepared according to Procedure e.
Starting material: Compound 687.
$^1$H NMR (300 MHz, CDCl$_3$) 6.32 (q, 1H), 6.05-6.03 (m, 2H), 5.94-5.81 (m, 1H), 5.60 (s, 1H), 5.23-5.18 (m, 1H), 5.03-4.96 (m, 1H), 4.62 (d, 1H), 4.39-4.36 (m, 2H), 4.17-4.08 (m, 4H), 3.74 (s, 1H), 2.81 (bs, 1H), 2.64-2.59 (m, 1H), 2.45 (s, 3H), 2.31-2.22 (m, 1H), 2.19 (d, 3H), 1.83 (d, 3H), 1.77-1.68 (m, 1H), 1.07 (s, 3H), 1.04 (s, 3H), 0.98 (d, 3H), 0.97-0.90 (m, 1H), 0.72-0.64 (m, 1H).

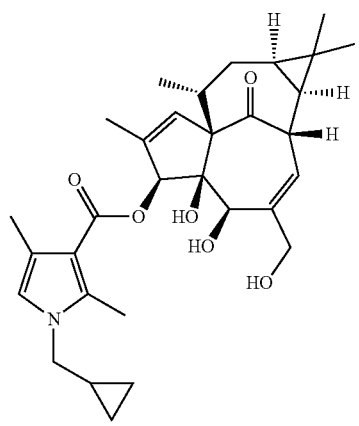

Example 588

Ingenol 3-(1-(cyclopropylmethyl)-2,4-dimethyl-pyrrole-3-carboxylate) (Compound 588)

Compound 588 was prepared according to Procedure e.
Starting material: Compound 688.
$^1$H NMR (300 MHz, CDCl$_3$) 6.42 (q, 1H), 6.05-6.03 (m, 2H), 5.58 (s, 1H), 4.58 (d, 1H), 4.17-4.08 (m, 4H), 3.73 (s, 1H), 3.63 (d, 2H), 2.74 (s, 1H), 2.64-2.59 (m, 1H), 2.50 (s, 3H), 2.30-2.24 (m, 1H), 2.20 (d, 3H), 1.83 (d, 3H), 1.77-1.68 (m, 1H), 1.13-1.08 (m, 1H), 1.07 (s, 3H), 1.04 (s, 3H), 0.98 (d, 3H), 0.97-0.91 (m, 1H), 0.72-0.59 (m, 3H), 0.34-0.29 (m, 2H).

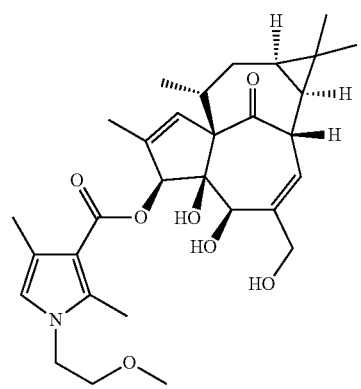

Example 589

Ingenol 3-(1-(2-methoxyethyl)-2,4-dimethyl-pyrrole-3-carboxylate) (Compound 589)

Compound 589 was prepared according to Procedure e.
Starting material: Compound 689.
$^1$H NMR (300 MHz, CDCl$_3$) 6.37 (s, 1H), 6.05-6.03 (m, 2H), 5.57 (s, 1H), 4.54 (d, 1H), 4.16-4.08 (m, 4H), 3.94 (t, 2H), 3.71 (s, 1H), 3.58 (t, 2H), 3.33 (s, 3H), 2.70-2.58 (m, 2H), 2.49 (s, 3H), 2.30-2.21 (m, 1H), 2.19 (s, 3H), 1.83 (d, 3H), 1.77-1.68 (m, 1H), 1.07 (s, 3H), 1.04 (s, 3H), 0.98 (d, 3H), 0.97-0.91 (m, 1H), 0.72-0.64 (m, 1H).

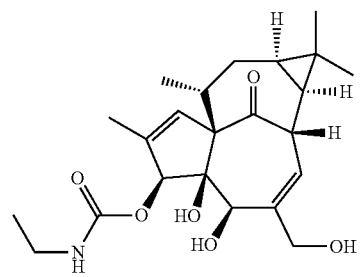 [SMILES: CCNC(=O)O[C@H]1C(C)=C[C@]23C(=O)[C@@H](C=C(CO)[C@@H](O)[C@]12O)[C@H]1[C@@H](C[C@H]3C)C1(C)C]

Example 701

Ingenol 3-(N-ethyl-carbamate) (Compound 701)

Compound 701 was prepared according to Procedure e.
Starting material: Compound 801.
$^1$H NMR (300 MHz, DMSO-d$_6$) δ 6.98 (t, 1H), 5.86-5.83 (m, 2H), 5.37 (s, 1H), 5.20 (bs, 1H), 4.85 (s, 1H), 4.19-4.15 (m, 1H), 3.95-3.84 (m, 2H), 3.57-3.5 (m, 2H) (coincided with water absorption), 3.05-3.00 (m, 2H), 2.5 (m, 1H) (coincided with solvent absorption), 2.31-2.23 (m, 1H), 1.71 (d, 3H), 1.68-1.63 (m, 1H), 1.05 (s, 3H), 1.03 (t, 3H), 1.03 (s, 3H), 0.87 (d, 3H), 0.84-0.74 (m, 1H), 0.65-0.57 (m, 1H).

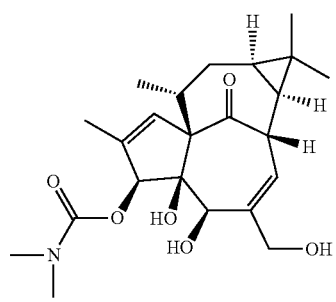

Example 702

Ingenol 3-(N,N-dimethyl-carbamate) (Compound 702)

Compound 702 was prepared according to Procedure e.

Starting material: Compound 802.

$^1$H NMR (300 MHz, DMSO-d$_6$) δ 5.86-5.84 (m, 2H), 5.45 (s, 1H), 5.28 (d, 1H), 4.94 (s, 1H), 4.65 (t, 1H), 4.20-4.15 (m, 1H), 3.97-3.84 (m, 2H), 3.57-3.55 (m, 1H), 2.84 (s, 6H), 2.5 (m, 1H) (coincided with solvent absorption), 2.33-2.24 (m, 1H), 1.70 (d, 3H), 1.68-1.63 (m, 1H), 1.05 (s, 3H), 1.03 (s, 3H), 0.88 (d, 3H), 0.81-0.74 (m, 1H), 0.64-0.57 (m, 1H).

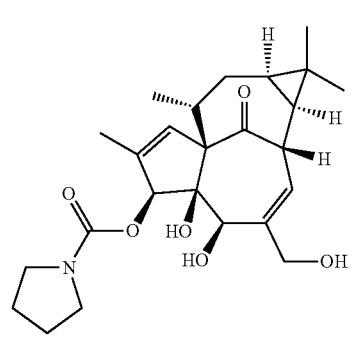

Example 704

Ingenol 3-(pyrrolidine-1-carboxylate) (Compound 704)

Compound 704 was prepared according to Procedure e.

Starting material: Compound 804.

$^1$H NMR (300 MHz, DMSO-d$_6$) δ 5.86-5.83 (m, 2H), 5.45 (s, 1H), 5.24 (d, 1H), 4.95 (s, 1H), 4.60 (t, 1H), 4.19-4.15 (m, 1H), 3.99-3.84 (m, 2H), 3.56 (d, 1H), 3.43-3.39 (m, 1H), 3.30-3.18 (m, 3H), 2.5 (m, 1H) (coincided with solvent absorption), 2.32-2.24 (m, 1H), 1.84-1.76 (m, 4H), 1.72-1.65 (m, 4H), 1.05 (s, 3H), 1.03 (s, 3H), 0.87 (d, 3H), 0.83-0.74 (m, 1H), 0.64-0.56 (m, 1H).

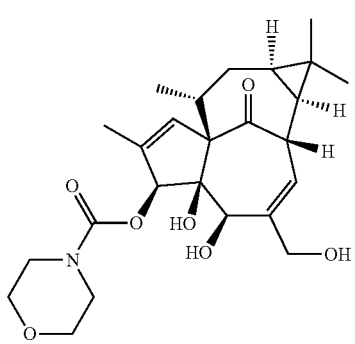 [SMILES: CC1=C[C@]23C(=O)[C@@H](C=C(CO)[C@@H](O)[C@]2(O)[C@H]1OC(=O)N1CCOCC1)[C@H]1[C@@H](C[C@H]3C)C1(C)C]

Example 703

Ingenol 3-(morpholine-4-carboxylate) (Compound 703)

Compound 703 was prepared according to Procedure e.

Starting material: Compound 803.

$^1$H NMR (300 MHz, DMSO-d$_6$) δ 5.86-5.85 (m, 2H), 5.51 (s, 1H), 5.29 (d, 1H), 5.05 (s, 1H), 4.62 (t, 1H), 4.17 (m, 1H), 3.97-3.83 (m, 2H), 3.60-3.53 (m, 5H), 3.40-3.32 (m, 4H), 2.45-2.40 (m, 1H), 2.32-2.23 (m, 1H), 1.70 (d, 3H), 1.68-1.63 (m, 1H), 1.05 (s, 3H), 1.03 (s, 3H), 0.87 (d, 3H), 0.81-0.74 (m, 1H), 0.64-0.56 (m, 1H).

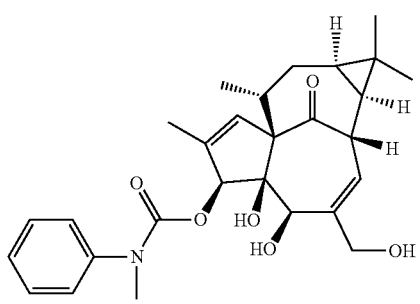 [SMILES: CC1=C[C@]23C(=O)[C@@H](C=C(CO)[C@@H](O)[C@]2(O)[C@H]1OC(=O)N(C)c1ccccc1)[C@H]1[C@@H](C[C@H]3C)C1(C)C]

Example 705

Ingenol 3-(N-methyl-N-phenyl-carbamate) (Compound 705)

Compound 705 was prepared according to Procedure e.
Compound 705 was obtained as an amorphous compound.

Starting material: Compound 805.

$^1$H NMR (300 MHz, DMSO-d$_6$) δ 7.37-7.30 (m, 4H), 7.22-7.16 (m, 1H), 5.85-5.84 (m, 1H), 5.77 (s, 1H), 5.54 (s, 1H), 5.34 (d, 1H), 4.97 (s, 1H), 4.61 (t, 1H), 4.16-4.11 (m, 1H), 3.97-3.82 (m, 2H), 3.57 (d, 1H), 3.24 (s, 3H), 2.24-2.16 (m, 1H), 2.09-1.95 (m, 1H), 1.68 (d, 3H), 1.53-1.45 (m, 1H), 1.03 (s, 3H), 1.02 (s, 3H), 0.76-0.70 (m, 1H), 0.65 (d, 3H), 0.58-0.50 (m, 1H).

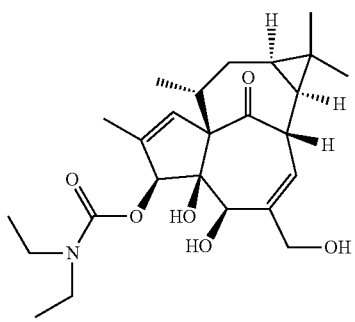 [SMILES: CCN(CC)C(=O)O[C@H]1C(C)=C[C@]23C(=O)[C@@H](C=C(CO)[C@@H](O)[C@]12O)[C@H]1[C@@H](C[C@H]3C)C1(C)C]

Example 706

Ingenol 3-(N,N-diethyl-carbamate) (Compound 706)

Compound 706 was prepared according to Procedure e.

Starting material: Compound 806.

$^1$H NMR (300 MHz, DMSO-$d_6$) δ 5.87-5.84 (m, 2H), 5.49 (s, 1H), 5.27 (d, 1H), 4.94 (s, 1H), 4.60 (t, 1H), 4.21-4.16 (m, 1H), 3.97-3.83 (m, 2H), 3.58 (d, 1H), 3.38-3.10 (m, 4H), 2.5 (m, 1H) (coincided with solvent absorption), 2.34-2.25 (m, 1H), 1.70 (d, 3H), 1.69-1.62 (m, 1H), 1.05 (t, 6H), 1.05 (s, 3H), 1.03 (s, 3H), 0.88 (d, 3H), 0.88-0.74 (m, 1H), 0.64-0.56 (m, 1H).

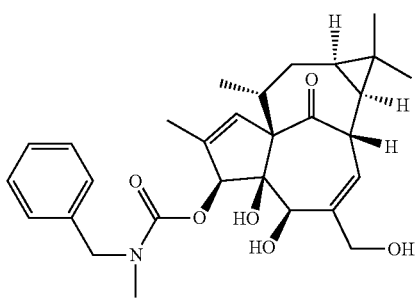

Example 708

Ingenol 3-(N-benzyl-N-methyl-carbamate) (Compound 708)

Compound 708 was prepared according to Procedure e.

Starting material: Compound 808.

$^1$H NMR (300 MHz, DMSO-$d_6$) δ 7.31-7.24 (m, 5H), 5.86-5.82 (m, 2H), 5.53 (s, 1H), 5.34-5.28 (m, 1H), 5.03 (s, 0.4H), 4.91 (s, 0.6H), 4.61 (t, 1H), 4.54-4.32 (m, 2H), 4.24-4.12 (m, 1H), 3.99-3.83 (m, 2H), 3.58 (d, 1H), 2.84 (s, 3H), 2.37-2.18 (m, 2H), 1.73-1.47 (m, 4H), 1.05 (s, 3H), 1.02 (s, 3H), 0.90-0.70 (m, 4H), 0.61-0.53 (m, 1H).

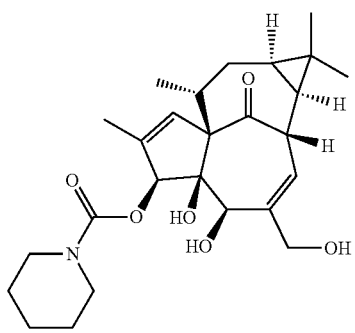 [SMILES: CC1=C[C@]23C(=O)[C@@H](C=C(CO)[C@@H](O)[C@]2(O)[C@H]1OC(=O)N1CCCCC1)[C@H]1[C@@H](C[C@H]3C)C1(C)C]

Example 707

Ingenol 3-(piperidine-1-carboxylate) (Compound 707)

Compound 707 was prepared according to Procedure e.

Starting material: Compound 807.

$^1$H NMR (300 MHz, DMSO-$d_6$) δ 5.86-5.84 (m, 2H), 5.47 (s, 1H), 5.29 (d, 1H), 4.90 (s, 1H), 4.61 (t, 1H), 4.20-4.15 (m, 1H), 3.96-3.83 (m, 2H), 3.57 (d, 1H), 3.38-3.27 (m, 4H), 2.48-2.42 (m, 1H), 2.33-2.24 (m, 1H), 1.70 (d, 3H), 1.68-1.62 (m, 1H), 1.58-1.40 (m, 6H), 1.05 (s, 3H), 1.03 (s, 3H), 0.88 (d, 3H), 0.84-0.75 (m, 1H), 0.64-0.56 (m, 1H).

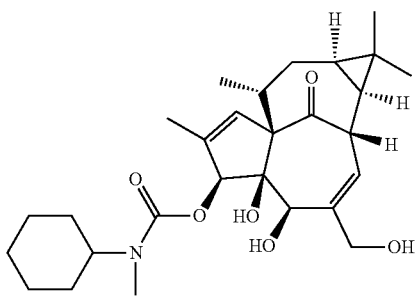 [SMILES: CC1=C[C@]23C(=O)[C@@H](C=C(CO)[C@@H](O)[C@]2(O)[C@H]1OC(=O)N(C)C1CCCCC1)[C@H]1[C@@H](C[C@H]3C)C1(C)C]

Example 709

Ingenol 3-(N-cyclohexyl-N-methyl-carbamate) (Compound 709)

Compound 709 was prepared according to Procedure e.

Starting material: Compound 809.

$^1$H NMR (300 MHz, DMSO-$d_6$) δ 5.86-5.85 (m, 2H), 5.50 (s, 1H), 5.27-5.25 (m, 1H), 4.96-4.92 (m, 1H), 4.61 (t, 1H), 4.21-4.16 (m, 1H), 3.97-3.75 (m, 3H), 3.58 (d, 1H), 2.72 (s, 3H), 2.5 (m, 1H) (coincided with solvent absorption), 2.36-2.26 (m, 1H), 1.78-1.09 (m, 14H), 1.04 (s, 3H), 1.03 (s, 3H), 0.88 (d, 3H), 0.84-0.74 (m, 1H), 0.65-0.57 (m, 1H).

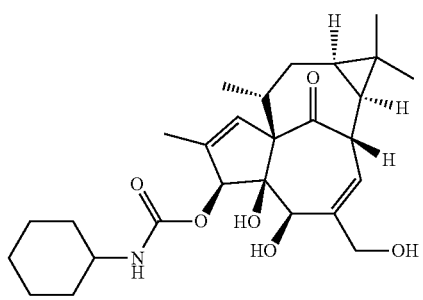 [SMILES: CC1=C[C@]23C(=O)[C@@H](C=C(CO)[C@@H](O)[C@]2(O)[C@H]1OC(=O)NC1CCCCC1)[C@H]1[C@@H](C[C@H]3C)C1(C)C]

Example 710

Ingenol 3-(N-cyclohexyl-carbamate) (Compound 710)

Compound 710 was prepared according to Procedure e.
Starting material: Compound 810.

$^1$H NMR (300 MHz, DMSO-d$_6$) δ 6.90 (d, 1H), 5.85-5.81 (m, 2H), 5.35 (s, 1H), 5.16 (d, 1H), 4.84 (m, 1H), 4.58 (t, 1H), 4.20-4.15 (m, 1H), 3.97-3.81 (m, 2H), 3.50 (d, 1H), 3.25-3.20 (m, 1H), 2.5 (m, 1H) (coincided with solvent absorption), 2.32-2.23 (m, 1H), 1.80-1.52 (m, 10H), 1.30-1.09 (m, 4H), 1.06 (s, 3H), 1.04 (s, 3H), 0.87 (d, 3H), 0.81-0.74 (m, 1H), 0.65-0.57 (m, 1H).

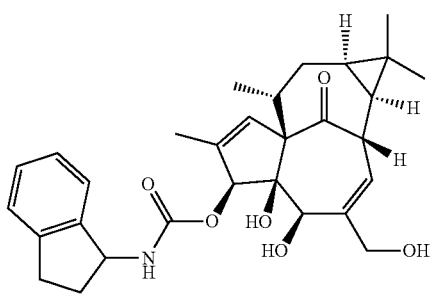

Example 712

Ingenol 3-(N-(indan-1-yl)-carbamate) (Compound 712)

Compound 712 was prepared according to Procedure e.
Starting material: Compound 812.

$^1$H NMR (300 MHz, DMSO-d$_6$) δ 7.43 (d, 1H), 7.26-7.18 (m, 4H), 5.86-5.84 (m, 2H), 5.46 (s, 1H), 5.20 (d, 1H), 5.01 (q, 1H), 4.87 (s, 1H), 4.59 (t, 1H), 4.21-4.15 (m, 1H), 3.99-3.83 (m, 2H), 3.54 (d, 1H), 2.98-2.89 (m, 1H), 2.84-2.73 (m, 1H), 2.47-2.35 (m, 2H), 2.31-2.22 (m, 1H), 1.91-1.79 (m, 1H), 1.78-1.62 (m, 4H), 1.05 (s, 3H), 1.03 (s, 3H), 0.86 (d, 3H), 0.81-0.74 (m, 1H), 0.64-0.57 (m, 1H).

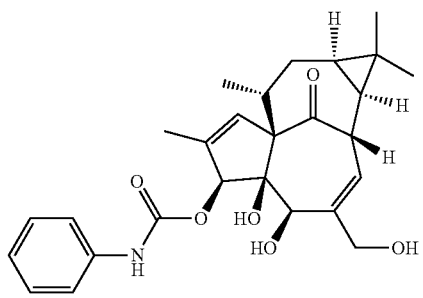 [SMILES: CC1=C[C@]23C(=O)[C@@H](C=C(CO)[C@@H](O)[C@]2(O)[C@H]1OC(=O)Nc1ccccc1)[C@H]1[C@@H](C[C@H]3C)C1(C)C]

Example 711

Ingenol 3-(N-phenyl-carbamate) (Compound 711)

Compound 711 was prepared according to Procedure e.
Starting material: Compound 811.

$^1$H NMR (300 MHz, DMSO-d$_6$) δ 9.44 (s, 1H), 7.50 (d, 2H), 7.29 (t, 2H), 6.99 (t, 1H), 5.91-5.87 (m, 2H), 5.55 (s, 1H), 5.31 (d, 1H), 4.99 (s, 1H), 4.62 (t, 1H), 4.23-4.18 (m, 1H), 3.99-3.84 (m, 2H), 3.60 (d, 1H), 2.60-2.57 (m, 1H), 2.36-2.27 (m, 1H), 1.76 (d, 3H), 1.74-1.66 (m, 1H), 1.05 (s, 3H), 1.04 (s, 3H), 0.91 (d, 3H), 0.82-0.75 (m, 1H), 0.67-0.59 (m, 1H).

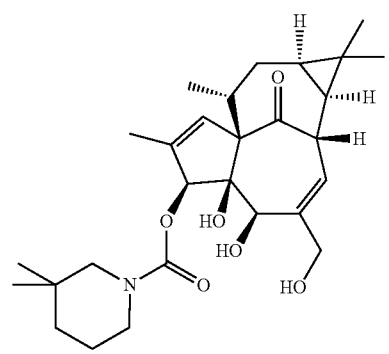

Example 713

Ingenol 3-(3,3-dimethyl-piperidine-1-carboxylate) (Compound 713)

Compound 713 was prepared according to Procedure e.
Starting material: Compound 813.

$^1$H NMR (300 MHz, CDCl$_3$) δ 6.04-6.02 (m, 1H), 5.99 (s, 1H), 5.19-5.17 (m, 1H), 4.78-4.69 (m, 1H), 4.16-4.07 (m, 3H), 4.01 (bs, 1H), 3.85-3.77 (m, 1H), 3.49-3.05 (m, 4H), 2.66 (bs, 1H), 2.51 (m, 1H), 2.29-2.22 (m, 1H), 1.78 (m, 3H), 1.70-1.55 (m, 3H), 1.42-1.31 (m, 2H), 1.10 (s, 3H), 1.04 (s, 3H), 0.99-0.82 (m, 10H), 0.72-0.65 (m, 1H).

153

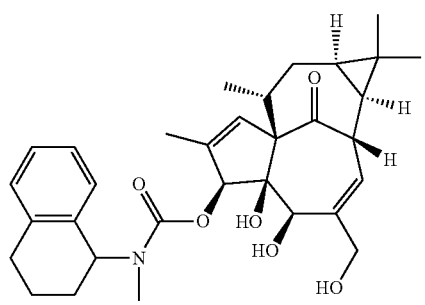 [SMILES: CC1=C[C@]23C(=O)[C@@H](C=C(CO)[C@@H](O)[C@]2(O)[C@H]1OC(=O)N(C)C1CCCc2ccccc21)[C@H]1[C@@H](C[C@H]3C)C1(C)C]

Example 714

Ingenol 3-(N-Methyl-N-tetralin-1-yl-carbamate) (Compound 714)

Compound 714 was prepared according to Procedure e.
Starting material: Compound 814.
$^1$H NMR (300 MHz, CDCl$_3$) δ 7.19-7.10 (m, 4H), 6.06-5.95 (m, 2H), 5.50-5.20 (m, 2H), 4.74-4.50 (2 bs, 1H), 4.18-3.55 (m, 5H), 2.77-1.59 (m, 16H), 1.16-1.05 (m, 6H), 0.97-0.82 (m, 4H), 0.72-0.63 (m, 1H).

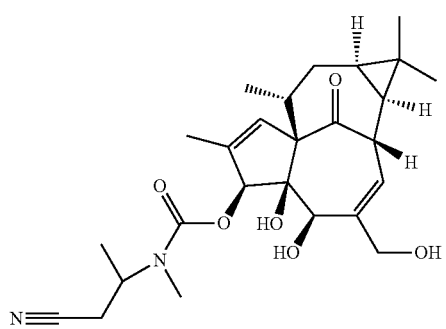 [SMILES: CC1=C[C@]23C(=O)[C@@H](C=C(CO)[C@@H](O)[C@]2(O)[C@H]1OC(=O)N(C)C(C)CC#N)[C@H]1[C@@H](C[C@H]3C)C1(C)C]

Example 715

Ingenol 3-(N-(2-cyano-1-methyl-ethyl)-N-methyl-carbamate) (Compound 715)

Compound 715 was prepared according to Procedure e.
Starting material: Compound 815.
$^1$H NMR (300 MHz, CDCl$_3$) δ 6.05-6.01 (m, 2H), 5.26 (s, 1H), 4.84-4.38 (m, 2H), 4.15-4.09 (m, 3H), 4.03 (m, 1H), 3.89-3.70 (m, 1H), 2.91-2.83 (m, 3H), 2.64-2.42 (m, 3H), 2.31-2.23 (m, 1H), 1.85-1.71 (m, 4H), 1.60 (m, 2H), 1.40-1.35 (m, 2H), 1.11-1.10 (m, 3H), 1.05 (s, 3H), 0.98-0.98 (m, 4H), 0.73-0.65 (m, 1H).

154

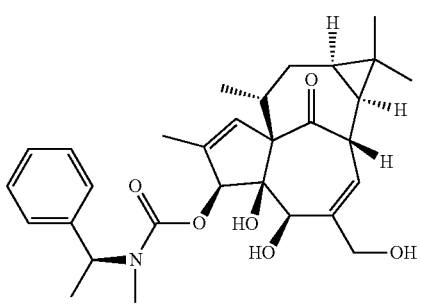 [SMILES: CC1=C[C@]23C(=O)[C@@H](C=C(CO)[C@@H](O)[C@]2(O)[C@H]1OC(=O)N(C)[C@@H](C)c1ccccc1)[C@H]1[C@@H](C[C@H]3C)C1(C)C]

Example 716

Ingenol 3-(N-methyl-N—((S)-1-phenethyl)-carbamate) (Compound 716)

Compound 716 was prepared according to Procedure e.
Starting material: Compound 816.
$^1$H NMR (300 MHz, CDCl$_3$) δ 7.35-7.27 (m, 5H), 6.05-6.04 (m, 1H), 6.00 (s, 1H), 5.57-5.40 (m, 1H), 5.29 (s, 1H), 4.73-4.45 (2 bs, 1H), 4.13-4.08 (m, 3H), 4.03 (s, 1H), 3.76-3.69 (2 bs, 1H), 2.73-2.17 (m, 6H), 1.81 (d, 3H), 1.80-1.54 (m, 4H), 1.11 (s, 3H), 1.05 (s, 3H), 0.95-0.84 (m, 4H), 0.70-0.62 (m, 1H).

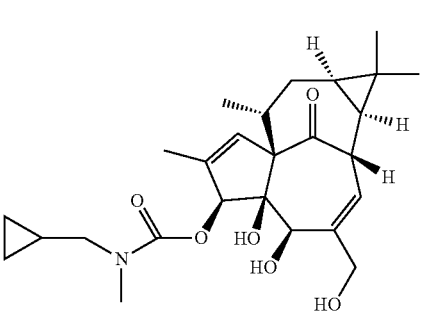 [SMILES: CC1=C[C@]23C(=O)[C@@H](C=C(CO)[C@@H](O)[C@]2(O)[C@H]1OC(=O)N(C)CC1CC1)[C@H]1[C@@H](C[C@H]3C)C1(C)C]

Example 717

Ingenol 3-(N-methyl-N-(cyclopropylmethyl)-carbamate) (Compound 717)

Compound 717 was prepared according to Procedure e.
Starting material: Compound 817.
$^1$H NMR (300 MHz, CDCl$_3$) δ 6.04-6.03 (d, 1H), 5.99 (s, 1H), 5.20-5.17 (m, 1H), 4.73 (bs, 1H), 4.16-4.06 (m, 3H), 4.02 (m, 1H), 3.83-3.77 (m, 1H), 3.29-3.10 (m, 2H), 3.00 (s, 3H), 2.63 (bs, 1H), 2.54-2.50 (m, 1H), 2.30-2.21 (m, 1H), 1.80-1.70 (m, 4H), 1.10 (s, 3H), 1.05 (s, 3H), 0.99-0.88 (m, 5H), 0.73-0.65 (m, 1H), 0.56-0.50 (m, 2H), 0.26-0.19 (m, 2H).

155

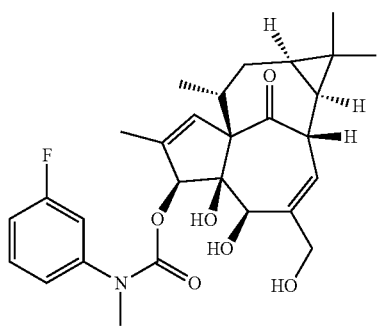 [SMILES: CC1=C[C@]23C(=O)[C@@H](C=C(CO)[C@@H](O)[C@]2(O)[C@H]1OC(=O)N(C)c1cccc(F)c1)[C@H]1[C@@H](C[C@H]3C)C1(C)C]

Example 718

Ingenol 3-(N-(3-fluoro-phenyl)-N-methyl-carbamate) (Compound 718)

Compound 718 was prepared according to Procedure e. Compound 718 was obtained as an amorphous compound.
Starting material: Compound 818.

$^1$H NMR (300 MHz, CDCl$_3$) δ 7.36-7.28 (m, 1H), 7.09-7.02 (m, 2H), 6.99-6.93 (m, 1H), 6.00 (d, 1H), 5.94 (s, 1H), 5.35 (s, 1H), 4.38 (bs, 1H), 4.13-4.05 (m, 3H), 3.99 (d, 1H), 3.59 (s, 1H), 3.32 (s, 3H), 2.45 (t, 1H), 2.19-2.12 (m, 2H), 1.76 (d, 3H), 1.70-1.62 (m, 1H), 1.09 (s, 3H), 1.05 (s, 3H), 0.94-0.88 (m, 1H), 0.79 (d, 3H), 0.70-0.62 (m, 1H).

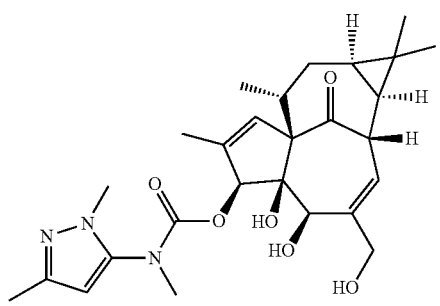

Example 719

Ingenol 3-(N-(2,5-dimethylpyrazol-3-yl)-N-methyl-carbamate) (Compound 719)

Compound 719 was prepared according to Procedure e.
Starting material: Compound 819.

$^1$H NMR (300 MHz, CDCl$_3$) δ 6.02 (bd, 1H), 5.95 (bs, 1H), 5.88 (s, 1H), 5.40 (s, 1H), 4.20-4.04 (m, 4H), 3.96 (m, 1H), 3.62 (s, 3H), 3.41 (bs, 1H), 3.21 (s, 3H), 2.51 (bs, 1H), 2.22 (s, 3H), 2.09-2.00 (m, 1H), 1.80-1.60 (m, 5H), 1.07 (s, 3H), 1.05 (s, 3H), 0.92-0.86 (m, 1H), 0.77 (bd, 3H), 0.69-0.64 (m, 1H).

156

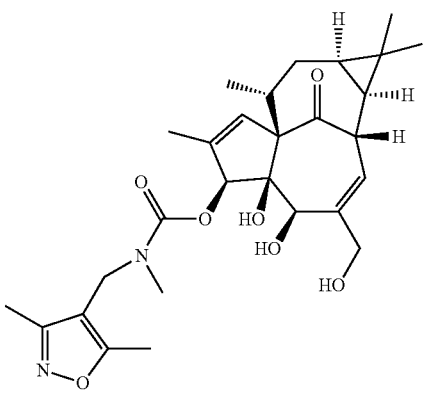

Example 720

Ingenol 3-(N-(3,5-dimethylisoxazol-4-yl)-N-methyl-carbamate) (Compound 720)

Compound 720 was prepared according to Procedure e.
Starting material: Compound 820.

$^1$H NMR (300 MHz, CDCl$_3$) δ 6.05-6.02 (m, 2H), 5.28 (s, 1H), 4.79 (bs, 1H), 4.37-4.24 (m, 2H), 4.14-4.10 (m, 3H), 4.04 (bs, 1H), 3.83 (bs, 1H), 2.80 (s, 4H), 2.49 (bs, 1H), 2.38 (s, 3H), 2.31-2.22 (m, 4H), 1.83-1.69 (m, 4H), 1.09 (s, 3H), 1.05 (s, 3H), 0.97-0.90 (m, 4H), 0.72-0.65 (m, 1H).

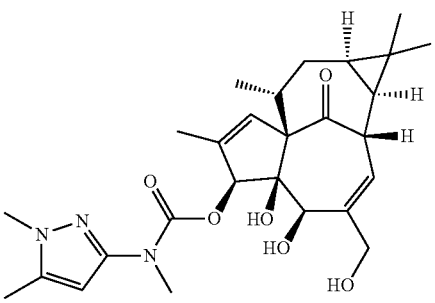

Example 721

Ingenol 3-(N-(1,5-dimethylpyrazol-3-yl)-N-methyl-carbamate) (Compound 721)

Compound 721 was prepared according to Procedure e.
Starting material: Compound 821.

$^1$H NMR (300 MHz, CDCl$_3$) δ 6.20-5.87 (m, 4H), 5.53 (s, 1H), 4.17-4.11 (m, 3H), 3.89 (d, 1H), 3.69 (s, 3H), 3.50 (bs, 1H), 3.28 (s, 3H), 2.51 (bs, 1H), 2.30-2.21 (m, 5H), 1.85 (d, 3H), 1.72-1.63 (m, 1H), 1.13 (s, 3H), 1.06 (s, 3H), 1.00-0.93 (m, 1H), 0.85 (d, 3H), 0.72-0.65 (m, 1H).

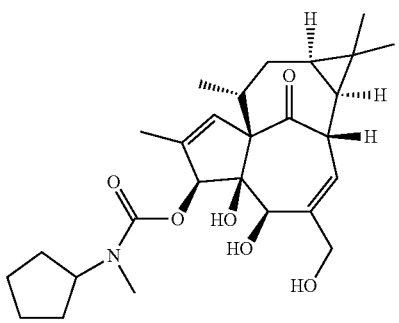 [SMILES: CC1=C[C@]23C(=O)[C@@H](C=C(CO)[C@@H](O)[C@]2(O)[C@H]1OC(=O)N(C)C1CCCC1)[C@H]1[C@@H](C[C@H]3C)C1(C)C]

Example 722

Ingenol 3-(N-cyclopentyl-N-methyl-carbamate)
(Compound 722)

Compound 722 was prepared according to Procedure e.
Starting material: Compound 822.
$^1$H NMR (300 MHz, CDCl$_3$) δ 6.05-6.03 (m, 1H), 5.99-5.98 (bs, 1H), 5.16 (2×s, 1H), 4.70 (bs, 1H), 4.17-4.02 (m, 4H), 3.77 (s, 1H), 3.32-3.27 (m, 1H), 2.81 (s, 3H), 2.53-2.50 (m, 2H), 2.29-2.19 (m, 1H), 1.85-1.70 (m, 8H), 1.33-1.13 (m, 4H), 1.11 (s, 3H), 1.05 (s, 3H), 0.97-0.88 (m, 4H), 0.73-0.65 (m, 1H).

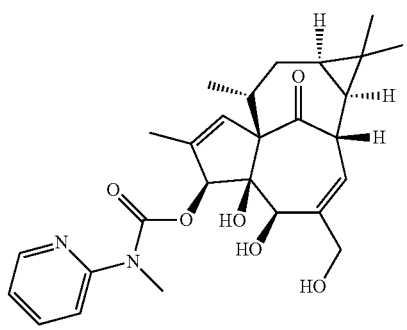

Example 724

Ingenol 3-(N-methyl-N-(2-pyridyl)-carbamate)
(Compound 724)

Compound 724 was prepared according to Procedure e.
Starting material: Compound 824.
$^1$H NMR (300 MHz, CDCl$_3$) δ 8.36-8.34 (m, 1H), 7.81-7.75 (m, 1H), 7.29 (d, 1H), 7.15-7.11 (m, 1H), 6.34 (bs, 1H), 6.04-6.02 (m, 1H), 5.98-5.96 (m, 1H), 5.77 (s, 1H), 4.19-4.13 (m, 3H), 3.90 (d, 1H), 3.61 (d, 1H), 3.44 (s, 3H), 2.49 (t, 1H), 2.34-2.25 (m, 1H), 2.09-2.04 (m, 1H), 1.81 (d, 3H), 1.72-1.64 (m, 1H), 1.18 (s, 3H), 1.08 (s, 3H), 0.99-0.93 (m, 1H), 0.78 (d, 3H), 0.72-0.64 (m, 1H).

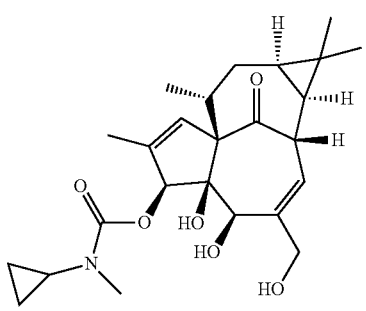 [SMILES: CC1=C[C@]23C(=O)[C@@H](C=C(CO)[C@@H](O)[C@]2(O)[C@H]1OC(=O)N(C)C1CC1)[C@H]1[C@@H](C[C@H]3C)C1(C)C]

Example 723

Ingenol 3-(N-cyclopropyl-N-methyl-carbamate)
(Compound 723)

Compound 723 was prepared according to Procedure e.
Starting material: Compound 823.
$^1$H NMR (300 MHz, CDCl$_3$) δ 6.05-6.03 (m, 1H), 6.00-5.98 (m, 1H), 5.15 (s, 1H), 4.46 (bs, 1H), 4.16-4.02 (m, 4H), 3.72 (s, 1H), 3.36-3.28 (m, 3H), 2.92 (s, 1H), 2.60-2.50 (m, 2H), 2.29-2.20 (m, 1H), 1.81 (d, 3H), 1.80-1.71 (m, 1H), 1.11 (s, 3H), 1.05 (s, 3H), 0.97-0.90 (m, 4H), 0.77-0.65 (m, 5H).

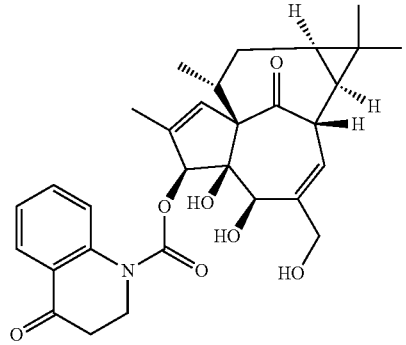 [SMILES: CC1=C[C@]23C(=O)[C@@H](C=C(CO)[C@@H](O)[C@]2(O)[C@H]1OC(=O)N1CCC(=O)c2ccccc21)[C@H]1[C@@H](C[C@H]3C)C1(C)C]

Example 725

Ingenol
3-(4-oxo-2,3-dihydroquinoline-1-carboxylate)
(Compound 725)

Compound 725 was prepared according to Procedure e.
Starting material: Compound 825.
$^1$H NMR (300 MHz, CDCl$_3$) δ 8.02-7.99 (m, 1H), 7.81 (d, 1H), 7.53-7.48 (m, 1H), 7.24-7.19 (m, 1H), 6.06 (d, 1H), 6.00 (d, 1H), 5.53 (s, 1H), 4.89 (d, 1H), 4.36-4.27 (m, 1H), 4.18-4.05 (m, 5H), 3.83 (s, 1H), 2.85-2.75 (m, 3H), 2.40-2.35 (m, 1H), 2.30-2.20 (m, 1H), 1.84 (d, 3H), 1.72-1.63 (m, 1H), 1.06 (s, 3H), 1.04 (s, 3H), 0.93-0.86 (m, 4H), 0.71-0.63 (m, 1H).

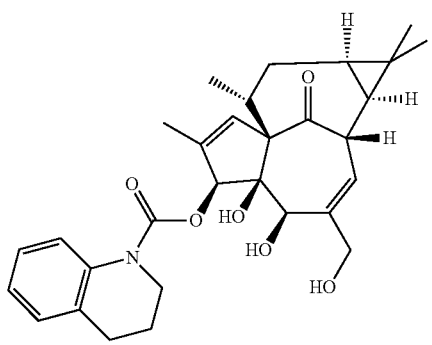 [SMILES: CC1=C[C@]23C(=O)[C@@H](C=C(CO)[C@@H](O)[C@]2(O)[C@H]1OC(=O)N1CCCc2ccccc21)[C@H]1[C@@H](C[C@H]3C)C1(C)C]

Example 726

Ingenol 3-(3,4-dihydro-2H-quinoline-1-carboxylate) (Compound 726)

Compound 726 was prepared according to Procedure e. Starting material: Compound 826.

¹H NMR (300 MHz, CDCl₃) δ 7.68 (bd, 1H), 7.17-7.00 (m, 3H), 6.03-6.01 (m, 1H), 5.98 (d, 1H), 5.43 (s, 1H), 4.64 (bs, 1H), 4.14-4.09 (m, 3H), 4.03 (d, 1H), 3.84-3.72 (m, 3H), 2.80 (t, 2H), 2.67 (bs, 1H), 2.43 (bs, 1H), 2.25-2.19 (m, 1H), 2.02-1.93 (m, 2H), 1.83 (d, 3H), 1.74-1.65 (m, 1H), 1.08 (s, 3H), 1.04 (s, 3H), 0.93-0.86 (m, 4H), 0.71-0.63 (m, 1H).

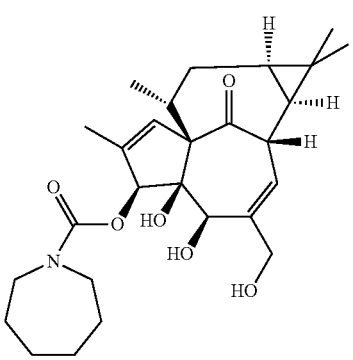

Example 728

Ingenol 3-(azepane-1-carboxylate) (Compound 728)

Compound 728 was prepared according to Procedure e. Starting material: Compound 828.

¹H NMR (300 MHz, CDCl₃) δ 6.04-6.02 (m, 1H), 5.98 (m, 1H), 5.20-5.19 (m, 1H), 5.87-5.85 (m, 1H), 4.13-4.08 (m, 3H), 4.03-4.01 (m, 1H), 3.84-3.81 (m, 1H), 3.47-3.26 (m, 4H), 2.80-2.76 (m, 1H), 2.55-2.50 (m, 1H), 2.30-2.22 (m, 1H), 1.80 (d, 3H), 1.75-1.56 (m, 9H), 1.11 (s, 3H), 1.04 (s, 3H), 0.94 (d, 3H), 0.91-0.86 (m, 1H), 0.72-0.65 (m, 1H).

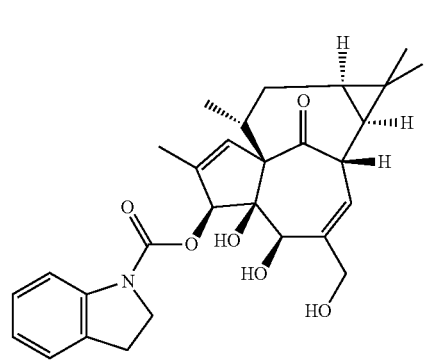 [SMILES: CC1=C[C@]23C(=O)[C@@H](C=C(CO)[C@@H](O)[C@]2(O)[C@H]1OC(=O)N1CCc2ccccc21)[C@H]1[C@@H](C[C@H]3C)C1(C)C]

Example 727

Ingenol 3-(indoline-1-carboxylate) (Compound 727)

Compound 727 was prepared according to Procedure e. Starting material: Compound 827.

¹H NMR (300 MHz, CDCl₃) δ 7.87 (bd, 1H), 7.18 (d, 2H), 6.99 (t, 1H), 6.06-6.05 (m, 2H), 5.41 (s, 1H), 4.62 (s, 1H), 4.17-4.02 (m, 6H), 3.80 (s, 1H), 3.17 (t, 2H), 2.57 (bs, 1H), 2.43 (bs, 1H), 2.31-2.23 (m, 1H), 1.85 (s, 3H), 1.78-1.73 (m, 1H), 1.08 (s, 3H), 1.04 (s, 3H), 0.99 (d, 3H), 0.95-0.90 (m, 1H), 0.73-0.65 (m, 1H).

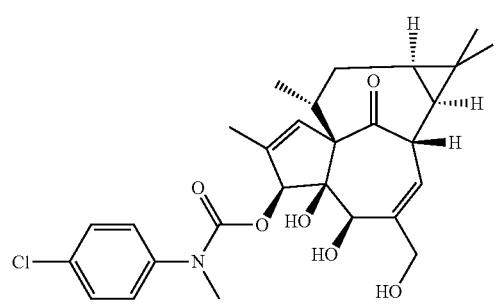 [SMILES: CC1=C[C@]23C(=O)[C@@H](C=C(CO)[C@@H](O)[C@]2(O)[C@H]1OC(=O)N(C)c1ccc(Cl)cc1)[C@H]1[C@@H](C[C@H]3C)C1(C)C]

Example 729

Ingenol 3-(N-(4-chloro-phenyl)-N-methyl-carbamate) (Compound 729)

Compound 729 was prepared according to Procedure e. Starting material: Compound 829.

¹H NMR (300 MHz, CDCl₃) δ 7.35-7.30 (m, 2H), 7.23-7.20 (m, 2H), 6.00 (d, 1H), 5.93 (bs, 1H), 5.34 (s, 1H), 4.48 (bs, 1H), 4.13-4.05 (m, 3H), 3.98 (s, 1H), 3.60 (s, 1H), 3.30 (s, 3H), 2.62 (bs, 1H), 2.15-2.10 (m, 1H), 1.75 (s, 3H), 1.70-1.64 (m, 2H), 1.09 (s, 3H), 1.05 (s, 3H), 0.94-0.86 (m, 4H), 0.70-0.62 (m, 1H).

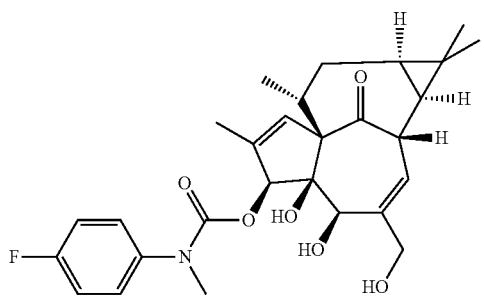 [SMILES: CC1=C[C@]23C(=O)[C@@H](C=C(CO)[C@@H](O)[C@]2(O)[C@H]1OC(=O)N(C)c1ccc(F)cc1)[C@H]1[C@@H](C[C@H]3C)C1(C)C]

Example 730

Ingenol 3-(N-(4-fluoro-phenyl)-N-methyl-carbamate) (Compound 730)

Compound 730 was prepared according to Procedure e.

Starting material: Compound 830.

$^1$H NMR (300 MHz, CDCl$_3$) δ 7.28-7.01 (m, 4H), 6.00-5.98 (m, 1H), 5.91 (bs, 1H), 5.34 (s, 1H), 4.48 (bs, 1H), 4.11-4.04 (m, 3H), 3.97 (d, 1H), 3.59 (bs, 1H), 3.29 (s, 3H), 2.71 (bs, 1H), 2.12 (bs, 1H), 1.74 (s, 3H), 1.60 (bs, 2H), 1.09 (s, 3H), 1.05 (s, 3H), 0.94-0.87 (m, 1H), 0.73 (bs, 3H), 0.69-061 (m, 1H).

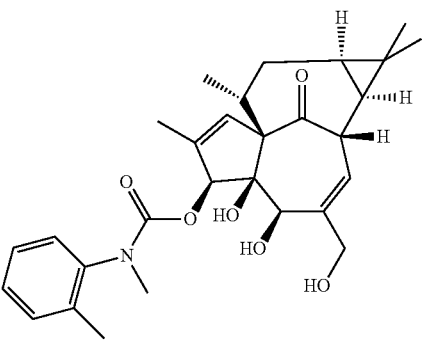

Example 732

Ingenol 3-(N-methyl-N-(2-methyl-phenyl)-carbamate) (Compound 732)

Compound 732 was prepared according to Procedure e.

Starting material: Compound 832.

$^1$H NMR (300 MHz, CDCl$_3$) δ 7.23-7.16 (m, 4H), 6.04-5.80 (m, 2H), 5.41 (s, 1H), 4.11-3.90 (m, 4H), 3.24-3.16 (m, 4H), 2.29-2.19 (m, 4H), 1.77 (s, 3H), 1.72-1.45 (m, 4H), 1.06-1.02 (m, 6H), 0.92-0.83 (m, 1H), 0.64-0.56 (m, 4H).

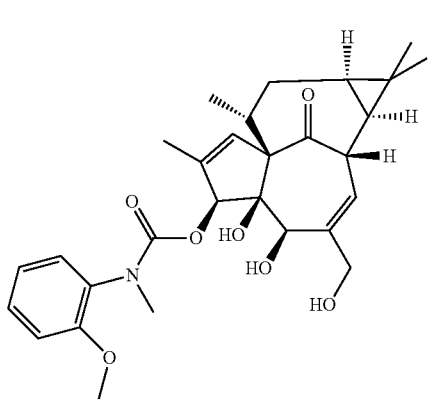 [SMILES: COc1ccccc1N(C)C(=O)O[C@H]1C(C)=C[C@]23C(=O)[C@@H](C=C(CO)[C@@H](O)[C@]12O)[C@H]1[C@@H](C[C@H]3C)C1(C)C]

Example 731

Ingenol 3-(N-methyl-N-(2-methoxy-phenyl)-carbamate) (Compound 731)

Compound 731 was prepared according to Procedure e.

Starting material: Compound 831.

$^1$H NMR (300 MHz, CDCl$_3$) δ 7.32-7.28 (m, 1H), 7.19 (d, 1H), 7.02-6.98 (m, 2H), 5.99 (d, 1H), 5.82 (d, 1H), 5.68 (bs, 1H), 4.24 (s, 1H), 4.12 (s, 2H), 3.98 (d, 1H), 3.88-3.80 (m, 4H), 3.30-3.24 (m, 4H), 2.40 (bs, 1H), 1.95-1.91 (m, 1H), 1.72 (d, 3H), 1.55-1.48 (m, 2H), 1.10 (s, 3H), 1.04 (s, 3H), 0.95-0.87 (m, 1H), 0.64-0.55 (m, 4H).

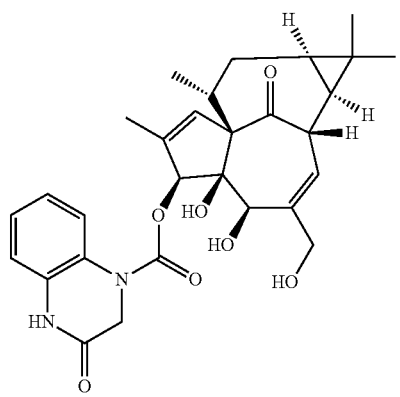 [SMILES: CC1=C[C@]23C(=O)[C@@H](C=C(CO)[C@@H](O)[C@]2(O)[C@H]1OC(=O)N1CC(=O)Nc2ccccc21)[C@H]1[C@@H](C[C@H]3C)C1(C)C]

Example 733

Ingenol 3-(3-oxo-2,4-dihydroquinoxaline-1-carboxylate) (Compound 733)

Compound 733 was prepared according to Procedure e.

Starting material: Compound 833.

$^1$H NMR (300 MHz, CDCl$_3$) δ 8.72 (bs, 1H), 7.68 (bd, 1H), 7.16-7.10 (m, 1H), 7.06-7.03 (m, 1H), 6.90 (dd, 1H), 6.04-6.02 (m, 2H), 5.57 (s, 1H), 4.72 (d, 1H), 4.49 (d, 1H), 4.39 (d, 1H), 4.20-4.11 (m, 3H), 4.02-4.00 (m, 2H), 2.77 (bs, 1H), 2.31-2.17 (m, 2H), 1.82 (d, 3H), 1.68-1.60 (m, 1H), 1.06 (s, 3H), 1.04 (s, 3H), 0.93-0.84 (m, 4H), 0.70-0.62 (m, 1H).

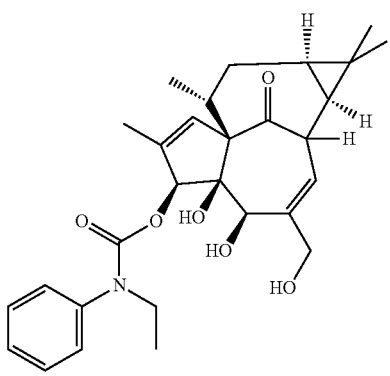 [SMILES: CCN(C(=O)O[C@H]1C(C)=C[C@]23C(=O)C(C=C(CO)[C@@H](O)[C@]12O)[C@H]1[C@@H](C[C@H]3C)C1(C)C)c1ccccc1]

Example 734

Ingenol 3-(N-ethyl-N-phenyl-carbamate)
(Compound 734)

Compound 734 was prepared according to Procedure e.
Starting material: Compound 834.

$^1$H NMR (300 MHz, CDCl$_3$) δ 7.40-7.20 (m, 5H), 5.99-5.97 (d, 1H), 5.88 (bs, 1H), 5.34 (s, 1H), 4.09-3.93 (m, 5H), 3.76-3.66 (dq, 2H), 3.44 (bs, 1H), 2.64 (bs, 1H), 2.01 (bs, 1H), 1.80-1.53 (m, 5H), 1.18 (t, 3H), 1.08 (s, 3H), 1.04 (s, 3H), 0.95-0.89 (m, 1H), 0.72-0.58 (m, 4H).

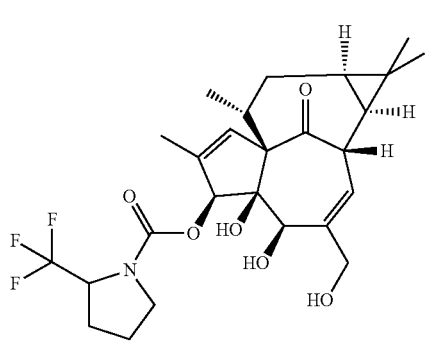 [SMILES: CC1=C[C@]23C(=O)[C@@H](C=C(CO)[C@@H](O)[C@]2(O)[C@H]1OC(=O)N1CCCC1C(F)(F)F)[C@H]1[C@@H](C[C@H]3C)C1(C)C]

Example 735

Ingenol 3-(2-trifluoromethyl-pyrrolidine-1-carboxylate)
(Compound 735)

Compound 735 was prepared according to Procedure e.
Starting material: Compound 835.

$^1$H NMR (300 MHz, CDCl$_3$) δ 6.04-6.00 (m, 2H), 5.31 (s, 1H), 4.84 (bs, 1H), 4.49-4.40 (bd, 1H), 4.16-4.02 (m, 4H), 3.83-3.47 (m, 3H), 2.90 (bs, 1H), 2.49 (bs, 1H), 2.31-2.22 (m, 1H), 2.13-1.91 (m, 4H), 1.80-1.70 (m, 4H), 1.10-1.09 (2×s, 3H), 1.05 (s, 3H), 0.97-0.89 (m, 4H), 0.73-0.65 (m, 1H).

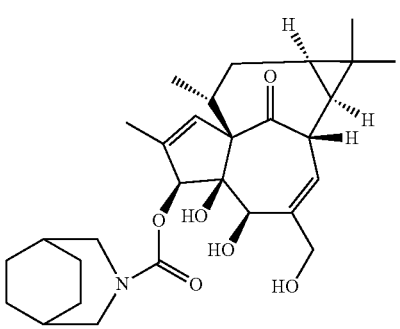 [SMILES: CC1=C[C@]23C(=O)[C@@H](C=C(CO)[C@@H](O)[C@]2(O)[C@H]1OC(=O)N1CC2CCC(CC2)C1)[C@H]1[C@@H](C[C@H]3C)C1(C)C]

Example 736

Ingenol 3-(3-azabicyclo[3.2.2]nonane-3-carboxylate)
(Compound 736)

Compound 736 was prepared according to Procedure e.
Starting material: Compound 836.

$^1$H NMR (300 MHz, CDCl$_3$) δ 6.04-6.03 (m, 1H), 5.99-5.98 (m, 1H), 5.18 (s, 1H), 4.77 (bs, 1H), 4.12-4.07 (m, 3H), 4.03 (s, 1H), 3.84 (s, 1H), 3.74-3.65 (m, 2H), 3.59-3.50 (m, 2H), 2.60 (bs, 1H), 2.55-2.50 (m, 1H), 2.29-2.21 (m, 1H), 2.06-2.01 (bd, 2H), 1.80 (d, 3H), 1.78-1.62 (m, 9H), 1.11 (s, 3H), 1.04 (s, 3H), 0.99-0.90 (m, 4H), 0.72-0.65 (m, 1H).

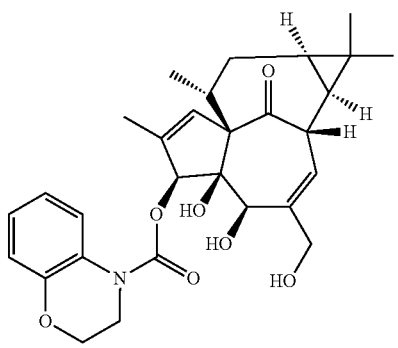 [SMILES: CC1=C[C@]23C(=O)[C@@H](C=C(CO)[C@@H](O)[C@]2(O)[C@H]1OC(=O)N1CCOc2ccccc21)[C@H]1[C@@H](C[C@H]3C)C1(C)C]

Example 737

Ingenol 3-(2,3-dihydro-1,4-benzoxazine-4-carboxylate)
(Compound 737)

Compound 737 was prepared according to Procedure e.
Starting material: Compound 837.

$^1$H NMR (300 MHz, CDCl$_3$) δ 7.81 (bs, 1H), 7.05-6.99 (m, 1H), 6.91-6.84 (m, 2H), 6.06-6.05 (m, 1H), 5.98-5.96 (m, 1H), 5.49 (s, 1H), 4.77 (s, 1H), 4.29 (t, 2H), 4.17-4.11 (m, 3H), 4.05-3.86 (m, 3H), 3.75 (s, 1H), 2.71 (s, 1H), 2.45-2.40 (m, 1H), 2.29-2.20 (m, 1H), 1.83 (d, 3H), 1.73-1.64 (m, 1H), 1.06 (s, 3H), 1.05 (s, 3H), 0.94-0.86 (m, 4H), 0.71-0.63 (m, 1H).

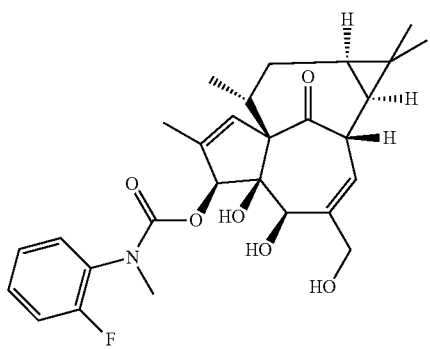 [SMILES: CC1=C[C@]23C(=O)[C@@H](C=C(CO)[C@@H](O)[C@]2(O)[C@H]1OC(=O)N(C)c1ccccc1F)[C@H]1[C@@H](C[C@H]3C)C1(C)C]

Example 738

Ingenol 3-(N-(2-fluoro-phenyl)-N-methyl-carbamate) (Compound 738)

Compound 738 was prepared according to Procedure e.
Starting material: Compound 838.
¹H NMR (300 MHz, CDCl₃) δ 7.31-7.24 (m, 2H), 7.17-7.08 (m, 2H), 6.00-5.98 (m, 1H), 5.85 (s, 1H), 5.44 (s, 1H), 4.18-3.92 (m, 6H), 3.53 (s, 1H), 3.28 (s, 3H), 2.68 (s, 1H), 2.08-2.00 (m, 1H), 1.80 (d, 3H), 1.8-1.7 (m, 1H), 1.08 (s, 3H), 1.04 (s, 3H), 0.93-0.89 (m, 1H), 0.68-0.60 (m, 4H).

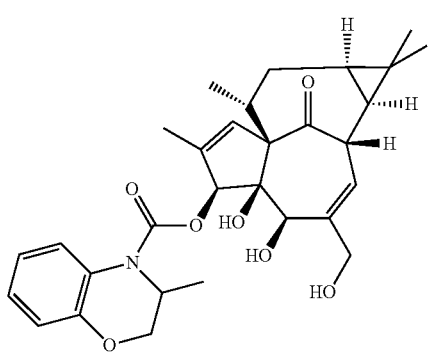 [SMILES: CC1=C[C@]23C(=O)[C@@H](C=C(CO)[C@@H](O)[C@]2(O)[C@H]1OC(=O)N1c2ccccc2OCC1C)[C@H]1[C@@H](C[C@H]3C)C1(C)C]

Example 739

Ingenol 3-(3-methyl-2,3-dihydro-1,4-benzoxazine-4-carboxylate) (Compound 739)

Compound 739 was prepared according to Procedure e.
Starting material: Compound 839.
¹H NMR (300 MHz, CDCl₃) δ 7.98-7.95 (d, 1H), 7.05-6.98 (m, 1H), 6.91-6.85 (m, 2H), 6.08-5.96 (m, 2H), 5.48 (s, 1H), 4.88 (s, 1H), 4.73-4.68 (m, 1H), 4.20-4.04 (m, 6H), 3.83 (s, 1H), 2.75 (s, 1H), 2.54-2.48 (m, 1H), 2.38-2.29 (m, 1H), 1.81 (d, 3H), 1.79-1.72 (m, 1H), 1.25 (d, 3H), 1.09 (s, 3H), 1.06 (s, 3H), 0.97 (d, 3H), 0.91-0.86 (m, 1H), 0.74-0.64 (m, 1H).

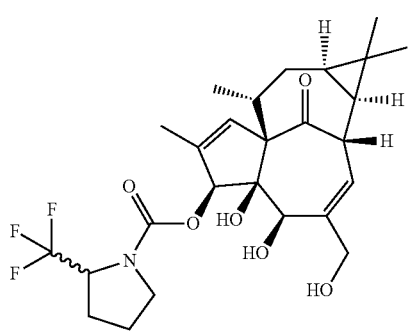 [SMILES: CC1=C[C@]23C(=O)[C@@H](C=C(CO)[C@@H](O)[C@]2(O)[C@H]1OC(=O)N1CCCC1C(F)(F)F)[C@H]1[C@@H](C[C@H]3C)C1(C)C]

Example 740

Ingenol 3-(2-trifluoromethyl-pyrrolidine-1-carboxylate) (ISOMER A) (Compound 740)

Compound 740 was prepared according to Procedure e.
Compound 740 was the first isomer to be collected from the chromatographic purification.
Starting material: Compound 835.
¹H NMR (300 MHz, CDCl₃) δ 6.06-6.02 (m, 2H), 5.26 (s, 1H), 4.51 (s, 1H), 4.39 (s, 1H), 4.14-3.97 (m, 4H), 3.86-3.51 (m, 3H), 2.50-2.02 (m, 7H), 1.81 (s, 3H), 1.80-1.71 (m, 1H), 1.10 (s, 3H), 1.05 (s, 3H), 0.96 (d, 3H), 0.95-0.90 (m, 1H), 0.73-0.66 (m, 1H).

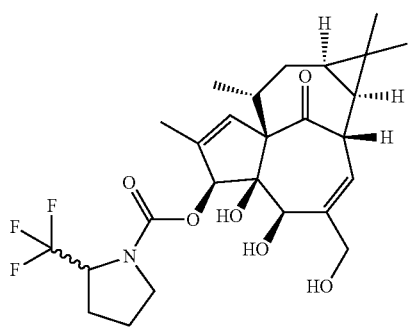 [SMILES: CC1=C[C@]23C(=O)[C@@H](C=C(CO)[C@@H](O)[C@]2(O)[C@H]1OC(=O)N1CCCC1C(F)(F)F)[C@H]1[C@@H](C[C@H]3C)C1(C)C]

Example 741

Ingenol 3-(2-trifluoromethyl-pyrrolidine-1-carboxylate) (ISOMER B) (Compound 741)

Compound 741 was prepared according to Procedure e.
Compound 741 was the second isomer to be collected from the chromatographic purification.
Starting material: Compound 835.
¹H NMR (300 MHz, CDCl₃) δ 6.06-6.00 (m, 2H), 5.25 (s, 1H), 4.59-4.43 (m, 2H), 4.14-4.03 (m, 4H), 3.72-3.52 (m, 3H), 2.50-2.02 (m, 7H), 1.81-1.72 (m, 4H), 1.11 (s, 3H), 1.05 (s, 3H), 0.99-0.93 (m, 4H), 0.71-0.66 (m, 1H).

167

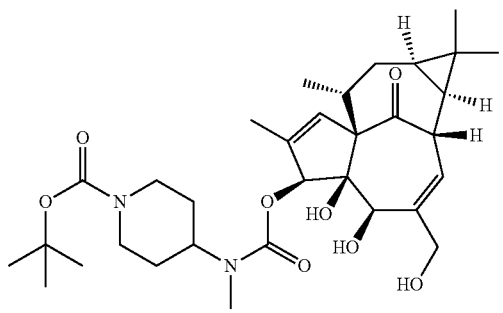 [SMILES: CC1=C[C@]23C(=O)[C@@H](C=C(CO)[C@@H](O)[C@]2(O)[C@H]1OC(=O)N(C)C1CCN(C(=O)OC(C)(C)C)CC1)[C@H]1[C@@H](C[C@H]3C)C1(C)C]

Example 742

Ingenol 3-(N-methyl-N—(N-(tert-butyloxycarbo-nyl)-4-piperidyl)-carbamate) (Compound 742)

Compound 742 was prepared according to Procedure e.

Starting material: Compound 842.

$^1$H NMR (300 MHz, CDCl$_3$) δ 6.05-6.03 (m, 1H), 6.00 (bs, 1H), 5.26-5.22 (m, 1H), 4.75-4.68 (m, 1H), 4.20-4.02 (m, 7H), 3.74 (s, 1H), 2.80-2.51 (m, 7H), 2.29-2.20 (m, 1H), 1.80 (d, 3H), 1.78-1.62 (m, 5H), 1.47 (s, 9H), 1.10 (s, 3H), 1.05 (s, 3H), 0.99-0.93 (m, 4H), 0.73-0.65 (m, 1H).

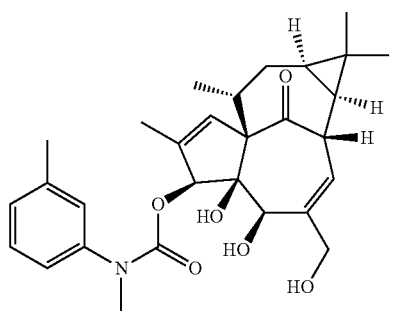 [SMILES: CC1=C[C@]23C(=O)[C@@H](C=C(CO)[C@@H](O)[C@]2(O)[C@H]1OC(=O)N(C)c1cccc(C)c1)[C@H]1[C@@H](C[C@H]3C)C1(C)C]

Example 743

Ingenol 3-(N-methyl-N-(3-methyl-phenyl)-carbamate) (Compound 743)

Compound 743 was prepared according to Procedure e.

Starting material: Compound 843.

$^1$H NMR (300 MHz, CDCl$_3$) δ 7.27-7.22 (m, 1H), 7.09-7.04 (m, 3H), 5.98-5.97 (m, 1H), 5.91 (bs, 1H), 5.33 (s, 1H), 4.11-3.94 (m, 5H), 3.48 (bs, 1H), 3.30 (s, 3H), 2.54 (bs, 1H), 2.35 (s, 3H), 2.03 (bs, 1H), 1.77 (s, 3H), 1.65-1.56 (m, 2H), 1.08 (s, 3H), 1.04 (s, 3H), 0.93-0.75 (m, 4H), 0.67-0.59 (m, 1H).

168

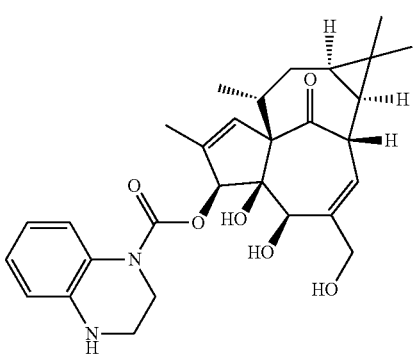 [SMILES: CC1=C[C@]23C(=O)[C@@H](C=C(CO)[C@@H](O)[C@]2(O)[C@H]1OC(=O)N1CCNc2ccccc21)[C@H]1[C@@H](C[C@H]3C)C1(C)C]

Example 744

Ingenol 3-(3,4-dihydro-2H-quinoxaline-1-carboxylate) (Compound 744)

Compound 744 was prepared according to Procedure e.

Starting material: Compound 844.

$^1$H NMR (300 MHz, CDCl$_3$) δ 7.87 (bd, 1H), 7.67 (bd, 1H), 7.23-7.11 (m, 2H), 6.07-6.05 (m, 2H), 5.50 (s, 1H), 4.64 (d, 1H), 4.19-3.96 (m, 9H), 3.78 (s, 1H), 2.39-2.22 (m, 3H), 1.84 (d, 3H), 1.75-1.67 (m, 1H), 1.09 (s, 3H), 1.05 (s, 3H), 0.96-0.85 (m, 4H), 0.72-0.64 (m, 1H).

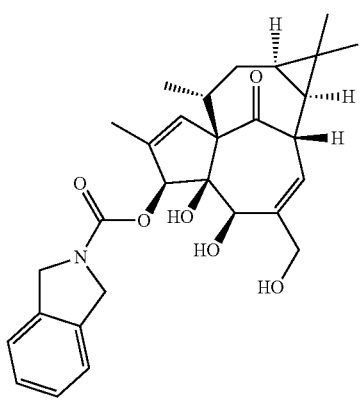 [SMILES: CC1=C[C@]23C(=O)[C@@H](C=C(CO)[C@@H](O)[C@]2(O)[C@H]1OC(=O)N1Cc2ccccc2C1)[C@H]1[C@@H](C[C@H]3C)C1(C)C]

Example 745

Ingenol 3-(isoindoline-2-carboxylate) (Compound 745)

Compound 745 was prepared according to Procedure e.

Starting material: Compound 845.

$^1$H NMR (300 MHz, CDCl$_3$) δ 7.31-7.25 (m, 4H), 6.05-6.03 (m, 2H), 5.36 (s, 1H), 4.89 (bs, 1H), 4.75 (s, 4H), 4.17-4.04 (m, 5H), 3.94 (s, 1H), 2.61-2.56 (m, 1H), 2.33-2.24 (m, 1H), 1.83 (d, 3H), 1.81-1.71 (m, 1H), 1.08 (s, 3H), 1.02 (s, 3H), 1.00 (d, 3H), 0.98-0.90 (m, 1H), 0.73-0.65 (m, 1H).

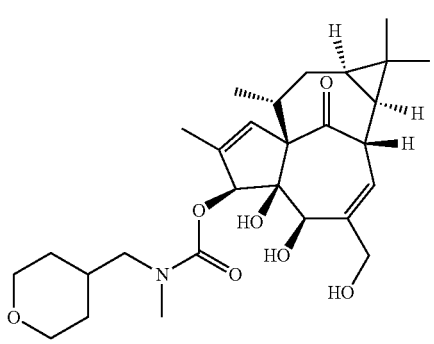 [SMILES: CC1=C[C@]23C(=O)[C@@H](C=C(CO)[C@@H](O)[C@]2(O)[C@H]1OC(=O)N(C)CC1CCOCC1)[C@H]1[C@@H](C[C@H]3C)C1(C)C]

Example 746

Ingenol 3-(N-methyl-N-(tetrahydropyran-4-ylm-ethyl)-carbamate) (Compound 746)

Compound 746 was prepared according to Procedure e.
Starting material: Compound 846.

$^1$H NMR (300 MHz, CDCl$_3$) δ 6.05-6.01 (m, 2H), 5.20 (d, 1H), 4.74 (s, 1H), 4.11-3.95 (m, 6H), 3.78 (d, 1H), 3.41-3.31 (m, 2H), 3.23-3.11 (m, 2H), 2.96 (s, 3H), 2.67 (bs, 1H), 2.53-2.51 (m, 1H), 2.29-2.19 (m, 1H), 1.94-1.86 (m, 1H), 1.80-1.70 (m, 4H), 1.59-1.54 (m, 2H), 1.40-1.27 (m, 2H), 1.09 (s, 3H), 1.05 (s, 3H), 0.98-0.88 (m, 4H), 0.73-0.65 (m, 1H).

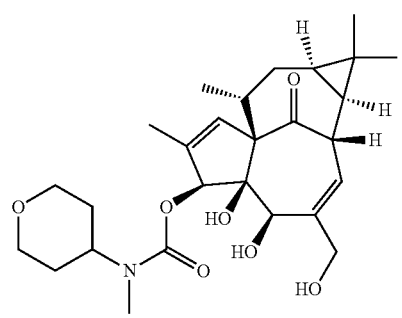 [SMILES: CC1=C[C@]23C(=O)[C@@H](C=C(CO)[C@@H](O)[C@]2(O)[C@H]1OC(=O)N(C)C1CCOCC1)[C@H]1[C@@H](C[C@H]3C)C1(C)C]

Example 747

Ingenol 3-(N-methyl-N-(tetrahydropyran-4-yl)-carbamate) (Compound 747)

Compound 747 was prepared according to Procedure e.
Starting material: Compound 847.

$^1$H NMR (300 MHz, CDCl$_3$) δ 6.05-6.03 (m, 1H), 6.00 (bs, 1H), 5.23 (bs, 1H), 4.73 (bs, 1H), 4.25 (bs, 1H), 4.13-4.01 (m, 6H), 3.75 (s, 1H), 3.50-3.39 (m, 2H), 2.83 (s, 3H), 2.68 (bs, 1H), 2.52 (bs, 1H), 2.29-2.20 (m, 1H), 1.82-1.65 (m, 8H), 1.10 (s, 3H), 1.05 (s, 3H), 0.99-0.92 (m, 4H), 0.73-0.65 (m, 1H).

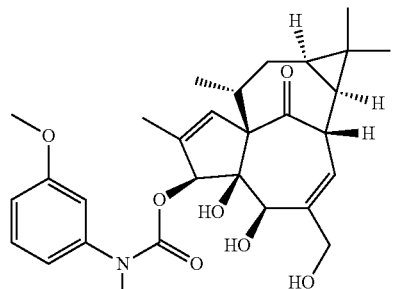

Example 748

Ingenol 3-(N-methyl-N-(3-methoxy-phenyl)-carbamate) (Compound 748)

Compound 748 was prepared according to Procedure e.
Starting material: Compound 848.

$^1$H NMR (300 MHz, CDCl$_3$) δ 7.29-7.24 (m, 1H), 6.86-6.80 (m, 3H), 5.98-5.96 (m, 1H), 5.92 (bs, 1H), 5.36 (s, 1H), 4.16-3.93 (m, 5H), 3.80 (s, 3H), 3.52 (bs, 1H), 3.31 (s, 3H), 2.63 (bs, 1H), 2.05 (bs, 2H), 1.80-1.57 (m, 4H), 1.08 (s, 3H), 1.04 (s, 3H), 0.95-0.89 (m, 1H), 0.75 (bs, 3H), 0.67-0.59 (m, 1H).

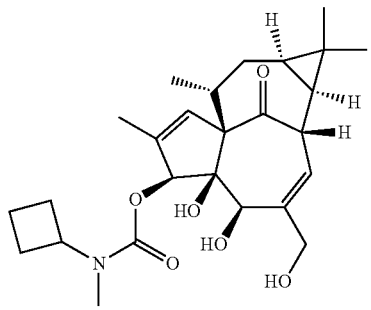 [SMILES: CC1=C[C@]23C(=O)[C@@H](C=C(CO)[C@@H](O)[C@]2(O)[C@H]1OC(=O)N(C)C1CCC1)[C@H]1[C@@H](C[C@H]3C)C1(C)C]

Example 749

Ingenol 3-(N-cyclobutyl-N-methyl-carbamate) (Compound 749)

Compound 749 was prepared according to Procedure e.
Starting material: Compound 849.

$^1$H NMR (300 MHz, CDCl$_3$) δ 6.04-6.03 (d, 1H), 5.99-5.98 (m, 1H), 5.18 (s, 1H), 4.81-4.73 (m, 1H), 4.60-4.35 (bs, 1H), 4.12-4.00 (m, 4H), 3.79 (s, 1H), 2.89 (s, 3H), 2.68 (bs, 1H), 2.55-2.50 (m, 1H), 2.30-2.22 (m, 1H), 2.19-2.09 (m, 4H), 1.79 (d, 3H), 1.78-1.62 (m, 3H), 1.10 (s, 3H), 1.04 (s, 3H), 0.99-0.92 (m, 4H), 0.72-0.65 (m, 1H).

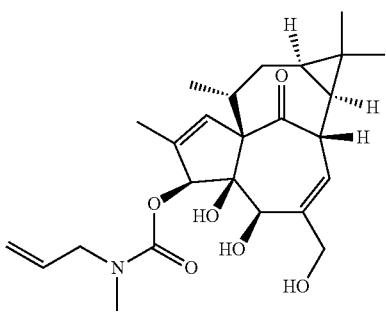 [SMILES: C=CCN(C)C(=O)O[C@H]1C(C)=C[C@]23C(=O)[C@@H](C=C(CO)[C@@H](O)[C@]12O)[C@H]1[C@@H](C[C@H]3C)C1(C)C]

Example 750

Ingenol 3-(N-allyl-N-methyl-carbamate) (Compound 750)

Compound 750 was prepared according to Procedure e.
Starting material: Compound 850.
$^1$H NMR (300 MHz, CDCl$_3$) δ 6.05-6.03 (m, 1H), 6.00-5.98 (m, 1H), 5.83-5.73 (m, 1H), 5.25-5.14 (m, 3H), 4.46 (bs, 1H), 4.12-3.76 (m, 7H), 2.94 (s, 3H), 2.56-2.50 (m, 2H), 2.28-2.21 (m, 1H), 1.80 (d, 3H), 1.78-1.70 (m, 1H), 1.10 (s, 3H), 1.05 (s, 3H), 0.97-0.88 (m, 4H), 0.73-0.65 (m, 1H).

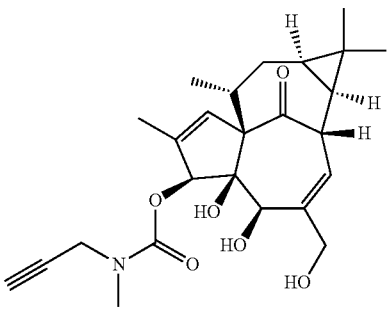 [SMILES: C#CCN(C)C(=O)O[C@H]1C(C)=C[C@]23C(=O)[C@@H](C=C(CO)[C@@H](O)[C@]12O)[C@H]1[C@@H](C[C@H]3C)C1(C)C]

Example 751

Ingenol 3-(N-methyl-N-prop-2-ynyl-carbamate) (Compound 751)

Compound 751 was prepared according to Procedure e.
Starting material: Compound 851.
$^1$H NMR (300 MHz, CDCl$_3$) δ 6.05-6.02 (m, 2H), 5.38 (bs, 1H), 4.21-4.01 (m, 7H), 3.80 (bs, 1H), 3.02 (s, 3H), 2.51 (bs, 2H), 2.30-2.21 (m, 2H), 1.81 (d, 3H), 1.78-1.71 (m, 1H), 1.10 (s, 3H), 1.05 (s, 3H), 0.99-0.90 (m, 4H), 0.73-0.65 (m, 1H).

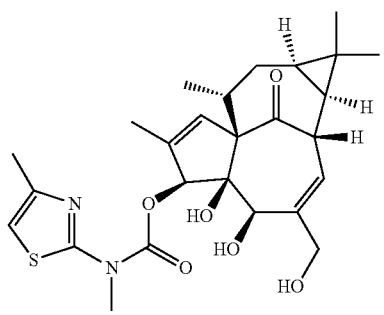 [SMILES: CC1=C[C@]23C(=O)[C@@H](C=C(CO)[C@@H](O)[C@]2(O)[C@H]1OC(=O)N(C)c1nc(C)cs1)[C@H]1[C@@H](C[C@H]3C)C1(C)C]

Example 752

Ingenol 3-(N-methyl-N-(4-methylthiazol-2-yl)-carbamate) (Compound 752)

Compound 752 was prepared according to Procedure e.
Starting material: Compound 852.
$^1$H NMR (300 MHz, CDCl$_3$) δ 6.53-6.52 (m, 1H), 6.11-6.10 (m, 1H), 6.07-6.05 (m, 1H), 5.52 (s, 1H), 4.41 (bs, 1H), 4.19-4.05 (m, 5H), 3.61 (s, 3H), 2.56-2.51 (m, 1H), 2.35 (d, 3H), 2.34-2.25 (m, 2H), 1.85 (d, 3H), 1.83-1.71 (m, 1H), 1.08 (s, 3H), 1.05 (s, 3H), 0.98 (d, 3H), 0.96-0.90 (m, 1H), 0.74-0.66 (m, 1H).

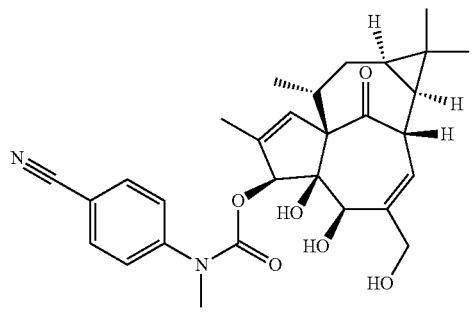 [SMILES: CC1=C[C@]23C(=O)[C@@H](C=C(CO)[C@@H](O)[C@]2(O)[C@H]1OC(=O)N(C)c1ccc(C#N)cc1)[C@H]1[C@@H](C[C@H]3C)C1(C)C]

Example 753

Ingenol 3-(N-(4-cyano-phenyl)-N-methyl-carbamate) (Compound 753)

Compound 753 was prepared according to Procedure e.
Starting material: Compound 853.
$^1$H NMR (300 MHz, CDCl$_3$) δ 7.66-7.62 (m, 2H), 7.49-7.44 (m, 2H), 6.02-6.00 (m, 1H), 5.99-5.97 (m, 1H), 5.41 (s, 1H), 4.76 (d, 1H), 4.15-4.09 (m, 3H), 4.03-4.01 (m, 1H), 3.75 (s, 1H), 3.37 (s, 3H), 2.73 (t, 1H), 2.28-2.19 (m, 2H), 1.77 (d, 3H), 1.71-1.62 (m, 1H), 1.09 (s, 3H), 1.06 (s, 3H), 0.95-0.82 (m, 4H), 0.72-0.64 (m, 1H).

Example 1

Neutrophil Oxidative Burst

PMN's (polymorphonuclear leukocytes) were isolated and purified from fresh buffy coats by sequential sedimentation, density centrifugation and lysis of contaminating erythrocytes. Buffy coats were incubated with 2% methocel for 30-45 min to differentially sediment red blood cells. The leukocyte-rich supernatant was transferred to lymphoprep tubes to remove mononuclear cells by density centrifugation (400×g, 30 min). The pellet was resuspended and any remaining erythrocytes lysed using 0.2% NaCl for 30 sec before restoring isotonicity by the addition of 1.2% NaCl. This step was repeated until the cell pellet appears relatively free of red blood cells. Cells were resuspended in DPBS (Dulbecco's Phosphate Buffered Saline) (w.o. $Ca^{2+}$, $Mg^{2+}$) and the concentration adjusted to $1.4\times10^6$ cells/ml in HBSS (Hanks Balanced Salt solution) (w $Ca^{2+}$, $Mg^{2\pm}$) containing 0.1% BSA (Bovine Serum Albumin) and 5 mM glucose just prior to assay initiation. Titrated reference and test compounds were pre-mixed with HE (Hydroethidine) (10 μM final assay concentration) before addition to 96-well plates containing $2.5\times10^5$ cells. Following 40 min incubation at RT, changes in the respiratory burst was estimated by measuring fluorescence at 579 nm (excitation: 485 nm) using an Envision plate reader.

Test compound titration curves were fitted to a four-parameter sigmoidal curve after normalizing the effect of the test compound to the effect of the positive control ($5\times10^{-7}$ M PEP0005). Rel $EC_{50}$ denotes the concentration of test compound producing an effect that is midway between the fitted top and bottom. Abs $EC_{50}$ is the concentration of test compound that provokes a response corresponding to 50% of the maximal effect associated with the positive control ($5\times10^{-7}$ M PEP0005).

Example 2

HeKa Cytokine Release (IL-8)

Primary human epidermal keratinocytes, HeKa, were seeded (10.000 cells/well) in 96-well plates the day before the assay. Test compounds were diluted in DMSO (dimethyl sulfoxide) and further diluted in assay medium and pipetted into wells of 96 well-plates containing HeKa cells. The plates were incubated for 6 h at 37° C. in humidified air with 5% $CO_2$. Plates were centrifuged briefly to spin down cells at 4° C., the supernatant was removed and analysed by Meso Scale Discovery (MSD) 4-spot cytokine assay (Pro-inflammatory II Ultra Sensitive kit, MSD, MD, USA). The MSD assay employs a sandwich immunoassay format where capture antibodies are coated in a patterned array on the bottom of the wells of a 4-Spot-Multi-MSD plate. Standard samples were incubated in the MULTI-SPOT plates as well, and the cytokine (IL-8) binds to its corresponding capture antibody spot. The cytokine level was quantitated on a SECTOR™ Imager using a cytokine-specific Detection Antibody labelled with MSD SULFO-TAG™ reagent.

Test compound titration curves were fitted to a four-parameter sigmoidal curve after normalizing the effect of the test compound to the effect of the positive control ($1.5\times10^{-7}$ M PEP0005). Rel $EC_{50}$ denotes the concentration of test compound producing an effect that is midway between the fitted top and bottom. Abs $EC_{50}$ is the concentration of test compound that provokes a response corresponding to 50% of the maximal effect associated with the positive control ($1.5\times10^{-7}$ M PEP0005).

Example 3

Necrosis Assay

HeLa cells (ATCC CCL-002) were grown in minimal essential medium (Invitrogen catalog no. 42360) containing 10% fetal bovine serum, 100 IU/ml penicillin and 100 μg/ml streptomycin. 4,000-6,000 cells were seeded into 96-well black ViewPlates-plates, clear bottom, (Perkin Elmer) in 100 μl medium and incubated overnight. Compounds were dissolved and pre-diluted in DMSO in 96-well polypropylene plates (Greiner) in a concentration range of 15 μM to 600 μM. At the time of the experiment cell plates were placed on heating blocks at 37° C., medium was removed and 40 μl fresh, pre-warmed medium was added per well. Cells were incubated for 15 min before addition of compounds. In parallel, 3 μl of compounds were diluted with 197 μl growth medium on a Tecan freedom-EVO pipetting station using 250 μl/s pipetting speed, in order to ensure effective mixing of the highly concentrated compound solutions with the aqueous phase. These pre-dilution plates were then equilibrated on heating blocks at 37° C. for 10 min. 80 μl pre-diluted compound were transferred manually to the corresponding wells containing HeLa cells yielding compound concentrations of 10 μM to 400 μM. Control conditions were 1% DMSO in growth medium (100% viability) and 400 μM ingenol mebutate in growth medium (0% viability). Plates were incubated on the heating blocks at 37° C. for 30 min. At the end of the incubation 10 μl PrestoBlue reagent (Invitrogen) were added to each well, plates were sealed with black seal, followed by incubation at 37° C. for 10 min with gentle shaking (150 rpm). Subsequently, plates were placed at room temperature for 20-30 min. Plates were read immediately after on an Envision Fluorescence reader (Perkin Elmer) with excitation at 535 nm and emission at 630 nm. Test compound titration curves were fitted to a four-parameter sigmoidal curve after normalizing the effect of the test compound to the effect of the positive control ($4 \cdot 10^{-4}$ M PEP0005/ingenol mebutate). $AbsEC_{50}$ denotes the concentration of test compound producing 50% effect.

Compounds of the present invention were tested in the neutrophil oxidative burst assay according to the description in example 1, in the HeKa cytokine release assay according to the description in example 2 and in the necrosis assay according to the description in example 3.

Compounds of the present invention display Rel $EC_{50}$ values below 10000 nM in the neutrophil oxidative burst assay and Rel $EC_{50}$ values below 10000 nM in the HeKa cytokine release assay.

Neutrophil oxidative burst Rel $EC_{50}$ ranges

* indicates that Rel $EC_{50}$ values are 100 nM
** indicates that Rel $EC_{50}$ values are 20 nM and <100 nM
*** indicates that Rel $EC_{50}$ values are <20 nM HeKa cytokine release (IL-8) Rel $EC_{50}$ ranges

* indicates that Rel $EC_{50}$ values are ≥100 nM
** indicates that Rel $EC_{50}$ values are ≥20 nM and <100 nM
*** indicates that Rel $EC_{50}$ values are <20 nM HeLa Necrosis $EC_{50}$ ranges

* indicates that $EC_{50}$ values are ≥350 μM
** indicates that $EC_{50}$ values are ≥150 μM and <350 μM
*** indicates that $EC_{50}$ values are <150 μM Results are shown in the table below.

| Compound name and number | Neutrophil oxidative burst Rel EC$_{50}$ range | HeKa cytokine release (IL-8) Rel EC$_{50}$ range | HeLa necrosis EC$_{50}$ range |
|---|---|---|---|
| Ingenol 3-(5-methyl-3-(2-chloro-6-fluoro-phenyl)-isoxazole-4-carboxylate) (Compound 501) | ** | *** | *** |
| Ingenol 3-(5-methyl-3-phenyl-isoxazole-4-carboxylate) (Compound 502) | *** | *** | *** |
| Ingenol 3-(1S-camphanate) (Compound 503) | ** | — | — |
| Ingenol 3-(3-phenyltriazole-4-carboxylate) (Compound 504) | ** | ** | — |
| Ingenol 3-(2-phenylpyrazole-3-carboxylate) (Compound 505) | *** | *** | *** |
| Ingenol 3-(1-methylindazole-3-carboxylate) (Compound 506) | *** | *** | *** |
| Ingenol 3-(3-ethyl-5-methyl-isoxazole-4-carboxylate) (Compound 507) | *** | *** | ** |
| Ingenol 3-(3-methyl-5-methyl-isoxazole-4-carboxylate) (Compound 508) | *** | *** | ** |
| Ingenol 3-(1-methylindole-3-carboxylate) (Compound 509) | *** | *** | — |
| Ingenol 3-(3-phenylthiophene-2-carboxylate) (Compound 510) | ** | *** | *** |
| Ingenol 3-(5-phenylisoxazole-3-carboxylate) (Compound 511) | ** | — | *** |
| Ingenol 3-(isoquinoline-1-carboxylate) (Compound 512) | ** | — | *** |
| Ingenol 3-(quinoline-4-carboxylate) (Compound 513) | *** | — | *** |
| Ingenol 3-(cinnoline-4-carboxylate) (Compound 514) | * | * | *** |
| Ingenol 3-(3-phenylimidazole-4-carboxylate) (Compound 515) | *** | — | *** |
| Ingenol 3-(5-phenyloxazole-4-carboxylate) (Compound 516) | *** | ** | *** |
| Ingenol 3-(1,2-benzoxazole-3-carboxylate) (Compound 517) | ** | * | *** |
| Ingenol 3-(3-isopropyl-5-methyl-isoxazole-4-carboxylate) (Compound 518) | *** | *** | *** |
| Ingenol 3-(3-(2-methoxyphenyl)-5-methyl-isoxazole-4-carboxylate) (Compound 519) | *** | *** | *** |
| Ingenol 3-(4-bromo-2-methyl-pyrazole-3-carboxylate) (Compound 520) | *** | — | — |
| Ingenol 3-(4-bromo-2-ethyl-pyrazole-3-carboxylate) (Compound 521) | *** | *** | *** |
| Ingenol 3-(4-chloro-2-methyl-pyrazole-3-carboxylate) (Compound 522) | *** | *** | ** |
| Ingenol 3-(5-bromopyrimidine-4-carboxylate) (Compound 523) | ** | * | * |
| Ingenol 3-(3-bromopyridine-2-carboxylate) (Compound 524) | ** | — | ** |
| Ingenol 3-(5-methylthiazole-4-carboxylate) (Compound 525) | ** | * | * |
| Ingenol 3-(4-chloro-1-methyl-pyrazole-3-carboxylate) (Compound 526) | ** | * | * |
| Ingenol 3-(2,4-dimethylthiazole-5-carboxylate) (Compound 527) | *** | ** | ** |
| Ingenol 3-(2,5-dimethyloxazole-4-carboxylate) (Compound 528) | ** | * | * |
| Ingenol 3-(2,4-dimethylfuran-3-carboxylate) (Compound 529) | *** | *** | *** |
| Ingenol 3-(3,5-diethylisoxazole-4-carboxylate) (Compound 530) | *** | *** | *** |
| Ingenol 3-(1H-indole-7-carboxylate) (Compound 531) | ** | *** | *** |
| Ingenol 3-(2-tert-butyl-5-methyl-pyrazole-3-carboxylate) (Compound 532) | ** | *** | *** |
| Ingenol 3-(5-tert-butyl-2-methyl-pyrazole-3-carboxylate) (Compound 533) | *** | *** | *** |
| Ingenol 3-(6-methylimidazo[2,1-b]thiazole-5-carboxylate) (Compound 534) | *** | *** | ** |

-continued

| Compound name and number | Neutrophil oxidative burst Rel EC$_{50}$ range | HeKa cytokine release (IL-8) Rel EC$_{50}$ range | HeLa necrosis EC$_{50}$ range |
|---|---|---|---|
| Ingenol 3-(2-methylimidazo[1,2-a]pyridine-3-carboxylate) (Compound 535) | *** | — | ** |
| Ingenol 3-(2,4,5-trimethylfuran-3-carboxylate) (Compound 536) | *** | *** | ** |
| Ingenol 3-(3-methylthiophene-2-carboxylate) (Compound 537) | *** | *** | ** |
| Ingenol 3-(2-methyl-4-(1-piperidyl)pyrazole-3-carboxylate) (Compound 538) | *** | ** | ** |
| Ingenol 3-(2-chloro-5-isopropyl-thiazole-4-carboxylate) (Compound 539) | ** | *** | *** |
| Ingenol 3-(4-chloro-2,5-dimethyl-pyrazole-3-carboxylate) (Compound 540) | *** | *** | *** |
| Ingenol 3-(1,2,4-trimethylpyrrole-3-carboxylate) (Compound 541) | *** | *** | ** |
| Ingenol 3-(1,3,5-trimethylpyrrole-2-carboxylate) (Compound 542) | *** | *** | *** |
| Ingenol 3-(1-ethyl-3,5-dimethylpyrrole-2-carboxylate) (Compound 543) | *** | — | *** |
| Ingenol 3-(1-tert-butyloxycarbonyl-3,3-dimethylpyrrolidine-2-carboxylate) (Compound 544) | * | * | ** |
| Ingenol 3-((2S)-1-phenylpyrrolidine-2-carboxylate) (Compound 545) | ** | — | ** |
| Ingenol 3-(1-isopropyl-3,5-dimethyl-pyrazole-4-carboxylate) (Compound 546) | *** | *** | ** |
| Ingenol 3-(5-ethyl-3-isopropyl-isoxazole-4-carboxylate) (Compound 547) | ** | *** | *** |
| Ingenol 3-(2-methylindazole-3-carboxylate) (Compound 548) | ** | *** | ** |
| Ingenol 3-(5-methyl-3-tert-butyl-isoxazole-4-carboxylate) (Compound 549) | *** | *** | — |
| Ingenol 3-(2-methyl-3-oxo-4-oxaspiro[4.5]dec-1-ene-1-carboxylate) (Compound 550) | *** | *** | *** |
| Ingenol 3-(1-tert-butyl-3,5-dimethyl-pyrazole-4-carboxylate) (Compound 551) | *** | *** | — |
| Ingenol 3-(3,5-dimethylisothiazole-4-carboxylate) (Compound 552) | ** | ** | ** |
| Ingenol 3-(5-iodo-3-methyl-isothiazole-4-carboxylate) (Compound 553) | *** | *** | ** |
| Ingenol 3-(4-(4-methoxyphenyl)-2-methyl-pyrazole-3-carboxylate) (Compound 554) | *** | *** | *** |
| Ingenol 3-(4-(2-methylphenyl)-2-methyl-pyrazole-3-carboxylate) (Compound 555) | *** | *** | *** |
| Ingenol 3-(2-methyl-4-(4-methylsulfonylphenyl)pyrazole-3-carboxylate) (Compound 556) | ** | ** | ** |
| Ingenol 3-(2-methyl-4-phenyl-pyrazole-3-carboxylate) (Compound 557) | *** | *** | *** |
| Ingenol 3-(3,5-dimethyl-1-phenyl-pyrazole-4-carboxylate) (Compound 558) | *** | *** | *** |
| Ingenol 3-(1,5-dimethyl-3-phenyl-pyrazole-4-carboxylate) (Compound 559) | *** | *** | ** |
| Ingenol 3-(1-benzyl-3,5-dimethyl-pyrazole-4-carboxylate) (Compound 560) | *** | *** | *** |
| Ingenol 3-(3,5-dimethyl-1-(tetrahydropyran-4-ylmethyl)pyrazole-4-carboxylate) (Compound 561) | ** | — | ** |

-continued

| Compound name and number | Neutrophil oxidative burst Rel EC$_{50}$ range | HeKa cytokine release (IL-8) Rel EC$_{50}$ range | HeLa necrosis EC$_{50}$ range |
|---|---|---|---|
| Ingenol 3-(4-methyl-2-oxo-3H-thiazole-5-carboxylate) (Compound 562) | ** | — | * |
| Ingenol 3-(2-methyl-4,5,6,7-tetrahydroindazole-3-carboxylate) (Compound 563) | *** | *** | *** |
| Ingenol 3-(1,2-dimethylindole-3-carboxylate) (Compound 564) | *** | *** | *** |
| Ingenol 3-(5-methoxy-1,2-dimethyl-indole-3-carboxylate) (Compound 565) | *** | *** | *** |
| Ingenol 3-(1,3,5-trimethylpyrazole-4-carboxylate) (Compound 566) | ** | ** | * |
| Ingenol 3-(4-methyl-1,2,5-oxadiazole-3-carboxylate) (Compound 567) | ** | * | * |
| Ingenol 3-(2-methoxy-4-methyl-thiazole-5-carboxylate) (Compound 568) | ** | ** | ** |
| Ingenol 3-(4,5-dimethylisoxazole-3-carboxylate) (Compound 569) | ** | — | ** |
| Ingenol 3-(4-bromo-1-methyl-pyrazole-3-carboxylate) (Compound 570) | ** | * | ** |
| Ingenol 3-(1,3-dimethylindole-2-carboxylate) (Compound 571) | *** | *** | *** |
| Ingenol 3-(5-methoxy-1,3-dimethyl-indole-2-carboxylate) (Compound 572) | *** | *** | *** |
| Ingenol 3-(2,4-dimethyl-6-oxo-pyran-3-carboxylate) (Compound 573) | ** | ** | — |
| Ingenol 3-(1-methyl-3-phenyl-indole-2-carboxylate) (Compound 574) | *** | *** | *** |
| Ingenol 3-(3-methyl-5-(trifluoromethyl)isoxazole-4-carboxylate) (Compound 575) | *** | *** | *** |
| Ingenol 3-(1,3-dimethylpyrrole-2-carboxylate) (Compound 576) | *** | *** | *** |
| Ingenol 3-(3,5-dimethyl-1-(2,2,2-trifluoroethyl)pyrazole-4-carboxylate) (Compound 577) | ** | *** | ** |
| Ingenol 3-(1-cyclopropyl-2,5-dimethyl-pyrrole-3-carboxylate) (Compound 578) | *** | *** | *** |
| Ingenol 3-(1,2,5-trimethylpyrrole-3-carboxylate) (Compound 579) | *** | *** | ** |
| Ingenol 3-(2,4-dimethyl-1H-pyrrole-3-carboxylate) (Compound 580) | * | * | ** |
| Ingenol 3-(1-methylpyrrole-2-carboxylate) (Compound 581) | *** | *** | ** |
| Ingenol 3-(4-methyl-1H-pyrrole-2-carboxylate) (Compound 582) | *** | *** | ** |
| Ingenol 3-(1,5-dimethylpyrrole-2-carboxylate) (Compound 583) | *** | *** | ** |
| Ingenol 3-(3-methyl-1H-pyrrole-2-carboxylate) (Compound 584) | *** | *** | ** |
| Ingenol 3-(1-cyclopropylpyrrole-2-carboxylate) (Compound 585) | *** | *** | *** |
| Ingenol 3-(1-ethyl-2,4-dimethyl-pyrrole-3-carboxylate) (Compound 586) | *** | *** | *** |
| Ingenol 3-(1-allyl-2,4-dimethyl-pyrrole-3-carboxylate) (Compound 587) | *** | *** | *** |
| Ingenol 3-(1-(cyclopropylmethyl)-2,4-dimethyl-pyrrole-3-carboxylate) (Compound 588) | *** | *** | *** |
| Ingenol 3-(1-(2-methoxyethyl)-2,4-dimethyl-pyrrole-3-carboxylate) (Compound 589) | ** | *** | *** |
| Ingenol 3-(N-ethyl-carbamate) (Compound 701) | ** | — | — |
| Ingenol 3-(N,N-dimethyl-carbamate) (Compound 702) | ** | * | — |
| Ingenol 3-(morpholine-4-carboxylate) (Compound 703) | ** | * | — |
| Ingenol 3-(pyrrolidine-1-carboxylate) (Compound 704) | ** | * | — |

| Compound name and number | Neutrophil oxidative burst Rel EC$_{50}$ range | HeKa cytokine release (IL-8) Rel EC$_{50}$ range | HeLa necrosis EC$_{50}$ range |
|---|---|---|---|
| Ingenol 3-(N-methtyl-N-phenyl-carbamate) (Compound 705) | *** | *** | ** |
| Ingenol 3-(N,N-diethyl-carbamate) (Compound 706) | *** | ** | * |
| Ingenol 3-(piperidine-1-carboxylate) (Compound 707) | *** | ** | — |
| Ingenol 3-(N-benzyl-N-methyl-carbamate) (Compound 708) | ** | *** | — |
| Ingenol 3-(N-cyclohexyl-N-methyl-carbamate) (Compound 709) | *** | *** | ** |
| Ingenol 3-(N-cyclohexyl-carbamate) (Compound 710) | *** | ** | — |
| Ingenol 3-(N-phenyl-carbamate) (Compound 711) | ** | *** | — |
| Ingenol 3-(N-(indan-1-yl)-carbamate) (Compound 712) | ** | ** | — |
| Ingenol 3-(3,3-dimethyl-piperidine-1-carboxylate) (Compound 713) | ** | *** | ** |
| Ingenol 3-(N-Methyl-N-tetralin-1-yl-carbamate) (Compound 714) | * | *** | *** |
| Ingenol 3-(N-(2-cyano-1-methyl-ethyl)-N-methyl-carbamate) (Compound 715) | * | — | * |
| Ingenol 3-(N-methyl-N-((S)-1-phenethyl)-carbamate) (Compound 716) | ** | *** | *** |
| Ingenol 3-(N-methyl-N-(cyclopropylmethyl)-carbamate) (Compound 717) | *** | *** | * |
| Ingenol 3-(N-(3-fluoro-phenyl)-N-methyl-carbamate) (Compound 718) | *** | *** | ** |
| Ingenol 3-(N-(2,5-dimethylpyrazol-3-yl)-N-methyl-carbamate) (Compound 719) | * | — | * |
| Ingenol 3-(N-(3,5-dimethylisoxazol-4-yl)-N-methyl-carbamate) (Compound 720) | ** | — | * |
| Ingenol 3-(N-(1,5-dimethylpyrazol-3-yl)-N-methyl-carbamate) (Compound 721) | ** | ** | * |
| Ingenol 3-(N-cyclopentyl-N-methyl-carbamate) (Compound 722) | *** | ** | * |
| Ingenol 3-(N-cyclopropyl-N-methyl-carbamate) (Compound 723) | *** | ** | * |
| Ingenol 3-(N-methyl-N-(2-pyridyl)-carbamate) (Compound 724) | — | ** | * |
| Ingenol 3-(4-oxo-2,3-dihydroquinoline-1-carboxylate) (Compound 725) | *** | — | ** |
| Ingenol 3-(3,4-dihydro-2H-quinoline-1-carboxylate) (Compound 726) | ** | *** | *** |
| Ingenol 3-(indoline-1-carboxylate) (Compound 727) | *** | *** | *** |
| Ingenol 3-(azepane-1-carboxylate) (Compound 728) | ** | ** | — |
| Ingenol 3-(N-(4-chloro-phenyl)-N-methyl-carbamate) (Compound 729) | *** | *** | ** |
| Ingenol 3-(N-(4-fluoro-phenyl)-N-methyl-carbamate) (Compound 730) | — | — | ** |
| Ingenol 3-(N-methyl-N-(2-methoxy-phenyl)-carbamate) (Compound 731) | ** | — | ** |
| Ingenol 3-(N-methyl-N-(2-methyl-phenyl)-carbamate) (Compound 732) | *** | *** | ** |
| Ingenol 3-(3-oxo-2,4-dyhidroquinoxaline-1-carboxylate) (Compound 733) | * | — | ** |
| Ingenol 3-(N-ethyl-N-phenyl-carbamate) (Compound 734) | ** | *** | ** |
| Ingenol 3-(2-trifluoromethyl-pyrrolidine-1-carboxylate) (Compound 735) | *** | — | ** |
| Ingenol 3-(3-azabicyclo[3.2.2]nonane-3-carboxylate) (Compound 736) | *** | *** | ** |
| Ingenol 3-(2,3-dihydro-1,4-benzoxazine-4-carboxylate) (Compound 737) | *** | *** | *** |

| Compound name and number | Neutrophil oxidative burst Rel EC$_{50}$ range | HeKa cytokine release (IL-8) Rel EC$_{50}$ range | HeLa necrosis EC$_{50}$ range |
|---|---|---|---|
| Ingenol 3-(N-(2-fluoro-phenyl)-N-methyl-carbamate) (Compound 738) | *** | ** | ** |
| Ingenol 3-(3-methyl-2,3-dihydro-1,4-benzoxazine-4-carboxylate) (Compound 739) | *** | *** | *** |
| Ingenol 3-(2-trifluoromethyl-pyrrolidine-1-carboxylate) (ISOMER A) (Compound 740) | *** | ** | — |
| Ingenol 3-(2-trifluoromethyl-pyrrolidine-1-carboxylate) (ISOMER B) (Compound 741) | ** | ** | * |
| Ingenol 3-(N-methyl-N-(N-(tert-butyloxycarbonyl)-4-piperidyl)-carbamate) (Compound 742) | ** | — | ** |
| Ingenol 3-(N-methyl-N-(3-methyl-phenyl)-carbamate) (Compound 743) | *** | *** | ** |
| Ingenol 3-(3,4-dihydro-2H-quinoxaline-1-carboxylate) (Compound 744) | ** | ** | ** |
| Ingenol 3-(isoindoline-2-carboxylate) (Compound 745) | *** | *** | ** |
| Ingenol 3-(N-methyl-N-(tetrahydropyran-4-ylmethyl)-carbamate) (Compound 746) | ** | * | * |
| Ingenol 3-(N-methyl-N-(tetrahydropyran-4-yl)-carbamate) (Compound 747) | ** | * | * |
| Ingenol 3-(N-methyl-N-(3-methoxy-phenyl)-carbamate) (Compound 748) | *** | ** | ** |
| Ingenol 3-(N-cyclobutyl-N-methyl-carbamate) (Compound 749) | *** | — | * |
| Ingenol 3-(N-allyl-N-methyl-carbamate) (Compound 750) | *** | — | * |
| Ingenol 3-(N-methyl-N-prop-2-ynyl-carbamate) (Compound 751) | ** | — | * |
| Ingenol 3-(N-methyl-N-(4-methylthiazol-2-yl)-carbamate) (Compound 752) | *** | *** | ** |
| Ingenol 3-(N-(4-cyano-phenyl)-N-methyl-carbamate) (Compound 753) | ** | ** | ** |
| Ingenol mebutate, ingenol-3-angelate | *** | *** | ** |

Example 4

B16-F0 Mouse Melanoma Model for Evaluation of Anti-Tumor Efficacy

B16-F0 mouse melanoma cells (ATCC® number CRL-6322™) were cultured in RPMI-1640 glutaMAX (Invitrogen, catalogue number 61870-010) supplemented with 10% fetal bovine serum and 1% pencillin-Streptomysin (Invitrogen, catalogue number 15140-122) at 37° C. in humidified air with 5% $CO_2$. At day 0 of the experiment, B16-F0 cells (70-90% confluent) were harvested by trypsinization with TrypLE (Invitrogen, catalogue number 12605-010), washed, resuspended in RPMI-1640 glutaMAX and kept on ice. Within 30 minutes, a volume of 50 µl containing 0.5×10$^6$ viable B16-F0 cells were injected intradermally into shaved flanks of 10-week-old female C57BL/6JBomTac mice, one injection per mouse. At experimental day 4, tumors were measured with a digital caliper (Mahr 16 Ex H100207), and the tumor volumes were estimated using the formula: Tumor volume=½*(longest diameter)*(orthogonale diameter)^2. Mice with tumors ranging from 9 to 60 mm$^3$ were included in the study and stratified into treatment groups according to tumor size. The tumors were treated topically with 20 µl solution containing 0.1% test compound once daily for 2 consecutive days. Vehicle was included in each experiment as negative control. Tumors were measured daily, and mice were euthanized when tumors exceed an estimated volume of 250 mm$^3$. Mice with ulcerating tumors or compromised well-being were euthanized regardless of tumor size and were included in the data analysis as censored objects. The experiment was terminated at experimental day 90, and mice with tumors below 250 mm$^3$ at this day were included in the data analysis as censored objects as well. Kaplan Meier survival curves with tumor >250 mm$^3$ as surrogate death event were generated, and comparison of survival curves were performed by Log-rank test. Specifically, tumor growth in each treatment group was compared to tumor growth in the vehicle group, to evaluate the efficacy of each compound to cure tumors or delay tumor growth. P-values below 0.05 were considered significant.

Some compounds of the present invention were tested in the B16-F0 mouse melanoma model. Compounds possessing an effect which was significantly better than vehicle are listed in the table below.

Compounds with an effect significantly better than vehicle in the B16-F0 mouse melanoma model Ingenol 3-(3,5-diethylisoxazole-4-carboxylate) (Compound 530)
Ingenol 3-(2,4-dimethylfuran-3-carboxylate) (Compound 529)

-continued

Compounds with an effect significantly better than vehicle in the B16-F0 mouse melanoma model Ingenol 3-(3-ethyl-5-methyl-isoxazole-4-carboxylate) (Compound 507)
Ingenol 3-(N-methyl-N-phenyl-carbamate) (Compound 705)
Ingenol 3-(indoline-1-carboxylate) (Compound 727)
Ingenol 3-(2,4,5-trimethylfuran-3-carboxylate) (Compound 536)
Ingenol 3-(5-methyl-3-phenyl-isoxazole-4-carboxylate) (Compound 502)
Ingenol 3-(pyrrolidine-1-carboxylate) (Compound 704)
Ingenol 3-(N-(3-fluoro-phenyl)-N-methyl-carbamate) (Compound 718)

The invention claimed is:
1. A compound of the general formula I

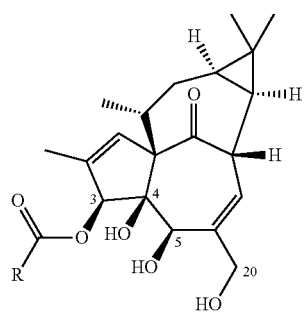

I wherein R is heterocycloalkyl or heterocycloalkenyl, wherein said heterocycloalkyl or heterocycloalkenyl are optionally substituted by one or more substituents independently selected from R8;
or R is X;
R8 represents halogen, cyano or hydroxyl;
or R8 represents ($C_1$-$C_4$)alkyl, ($C_2$-$C_4$)alkenyl, aryl, heteroaryl, ($C_3$-$C_7$)-cycloalkyl or heterocycloalkyl, wherein said $C_1$-$C_4$)alkyl, ($C_2$-$C_4$)alkenyl, aryl, heteroaryl, ($C_3$-$C_7$)-cycloalkyl or heterocycloalkyl are optionally substituted by one or more substituents independently selected from R10;
or R8 represents —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O, =N—ORa, —O—N=CRaRb, NRaRb or —C(O)N(Ra)O—Rb;
R10 represents halogen, cyano, hydroxy, ($C_1$-$C_4$)-alkyl, ($C_1$-$C_4$)alkoxy, halo($C_1$-$C_4$)alkyl, halo($C_1$-$C_4$)alkoxy, hydroxy($C_1$-$C_4$)alkyl, cyano($C_1$-$C_4$)alkyl, aryl, heteroaryl, cycloalkyl, heterocycloalkyl, —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa or =O;
Ra and Rb represent hydrogen, ($C_1$-$C_4$)alkyl, halo($C_1$-$C_4$) alkyl, ($C_1$-$C_4$)alkoxy($C_1$-$C_4$)alkyl, hydroxy($C_1$-$C_4$) alkyl, cyano($C_1$-$C_4$)alkyl, aryl, heteroaryl, cycloalkyl or heterocycloalkyl;
Rc represents hydrogen, ($C_1$-$C_4$)alkyl, halo($C_1$-$C_4$)alkyl, ($C_1$-$C_4$)alkoxy($C_1$-$C_4$)alkyl, hydroxy($C_1$-$C_x$)alkyl, cyano($C_1$-$C_x$)alkyl, aryl, heteroaryl, cycloalkyl or heterocycloalkyl;
X represents —NR11R12;
wherein R11 and R12 independently represent hydrogen, or wherein R11 and R12 independently represents ($C_1$-$C_6$) alkyl, ($C_2$-$C_6$)alkenyl or ($C_2$-$C_6$)alkynyl, cycloalkyl, cycloalkenyl, aryl, heteroaryl, heterocycloalkyl, heterocycloalkenyl, cycloalkylalkyl, cycloalkenylalkyl, arylalkyl, heteroarylalkyl, heterocycloalkylalkyl, heterocycloalkenylalkyl, alkylcycloalkyl, alkylcycloalkenyl, alkylaryl, alkylheteroaryl or alkylheterocycloalkyl, wherein said ($C_1$-$C_6$)alkyl, ($C_2$-$C_6$)alkenyl or ($C_2$-$C_6$)alkynyl, cycloalkyl, cycloalkenyl, aryl, heteroaryl, heterocycloalkyl, heterocycloalkenyl, cycloalkylalkyl, cycloalkenylalkyl, arylalkyl, heteroarylalkyl, heterocycloalkylalkyl, heterocycloalkenylalkyl, alkylcycloalkyl, alkylcycloalkenyl, alkylaryl, alkylheteroaryl or alkylheterocycloalkyl are optionally substituted by one or more substituents independently selected from R13;
R13 represents halogen, cyano or hydroxyl,
or R13 represents ($C_1$-$C_4$)alkyl, ($C_2$-$C_4$)alkenyl, aryl, ($C_3$-$C_7$)cycloalkyl, heteroaryl or heterocycloalkyl, wherein said ($C_1$-$C_4$)alkyl, ($C_2$-$C_4$)alkenyl, aryl, ($C_3$-$C_7$)cycloalkyl, heteroaryl or heterocycloalkyl are optionally substituted by one or more substituents selected from R14,
or R13 represents —NRdCORe, —COORf, —OCORd, —CONRdRe, —OCONRdRe, —NRdCOORe, —NRdCONRdRe, —NRdSO2Re, —NRdSO2NRdRe, —SO2NRdRe, —SO2Rd, —S(O)Rd, —ORd, —SRd, =O, =N—ORd, —O—N=CRdRe, —NRdRe or —C(O)N(Rd)—ORe
wherein Rd and Re independently represents hydrogen, ($C_1$-$C_4$)alkyl, halo($C_1$-$C_4$)alkyl, ($C_1$-$C_4$)alkoxy($C_1$-$C_4$) alkyl, hydroxy($C_1$-$C_4$)alkyl, cyano($C_1$-$C_4$)alkyl, aryl, heteroaryl, cycloalkyl or heterocycloalkyl;
Rf represents hydrogen, ($C_1$-$C_4$)alkyl, halo($C_1$-$C_4$)alkyl, ($C_1$-$C_4$)alkoxyl($C_1$-$C_4$)alkyl, hydroxy($C_1$-$C_4$)alkyl, cyano($C_1$-$C_4$)alkyl, aryl, heteroaryl, cycloalkyl or heterocycloalkyl;
R14 represents halogen, hydroxyl, cyano, ($C_1$-$C_4$)alkyl, ($C_1$-$C_4$)alkoxy, halo($C_1$-$C_4$)alkyl, halo($C_1$-$C_4$)alkoxy, hydroxy($C_1$-$C_4$)alkyl, cyano($C_1$-$C_4$)alkyl, aryl, heteroaryl, cycloalkyl, heterocycloalkyl, —NRdCORe, —COORf, —OCORd, —CONRdRe, —OCONRdRe, —NRdCOORe, —NRdCONRdRe, —NRdSO2Re, —NRdSO2NRdRe, —SO2NRdRe, —SO2Rd, —S(O) Rd, —ORd, —SRd or =O; and
pharmaceutically acceptable salts, hydrates and solvates thereof.
2. A compound according to claim 1, wherein
R is heterocycloalkyl or heterocycloalkenyl, each of which may optionally be substituted by one or more substituents independently selected from R8;
R8 represents halogen, cyano, hydroxyl;
or R8 represents ($C_1$-$C_4$)-alkyl, ($C_2$-$C_4$)alkenyl, aryl, heteroaryl, ($C_3$-$C_7$)-cycloalkyl, heterocycloalkyl, each of which is optionally substituted by one or more substituents independently selected from R10,
or R8 represents —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O;
R10 represents halogen, cyano, hydroxy, ($C_1$-$C_4$)-alkyl, halo($C_1$-$C_4$)alkyl, —NRaCORb, —COORc, —OCORa, —CONRaRb, —OCONRaRb, —NRaCO-ORb, —NRaCONRaRb, —NRaSO2NRaRb, —NRaSO2Rb, —SO2NRaRb, —SO2Ra, —S(O)Ra, —ORa, —SRa, =O;

Ra and Rb represents hydrogen, $(C_1-C_4)$alkyl, halo$(C_1-C_4)$alkyl, $(C_1-C_4)$alkoxy$(C_1-C_4)$alkyl, hydroxy$(C_1-C_4)$alkyl, cyano$(C_1-C_4)$alkyl; and Rc represents $(C_1-C_4)$alkyl, halo$(C_1-C_4)$alkyl, $(C_1-C_4)$alkoxy$(C_1-C_4)$alkyl, hydroxy$(C_1-C_4)$alkyl, cyano$(C_1-C_4)$alkyl.

3. A compound according to claim 1, wherein heterocycloalkyl or heterocycloalkenyl is pyrrolidinyl, piperidinyl, morpholinyl, 5-oxabicyclo[2.2.2]octanyl, oxaspiro[4.5]dec-1-enyl, oxo-thiazolyl, dihydrothiazolyl, oxo-pyranyl, azepanyl, azabicyclo[3.2.2]nonanyl, benzoxazinyl, quinoxalinyl, isoindolinyl, dihydroquinolinyl, indolinyl or dihydroquinoxalinyl.

4. A compound according to claim 1, wherein R8 is $(C_1-C_4)$alkyl, aryl or =O.

5. A compound according to claim 4, wherein R8 is methyl, phenyl or =O.

6. A compound according to claim 1, wherein R10 represents halogen.

7. A compound according to claim 1, wherein R is —NR11R12.

8. A compound according to claim 1, wherein R11 and R12 independently represents hydrogen, $(C_1-C_6)$alkyl, aryl, cycloalkyl, arylalkyl, heteroaryl, cycloalkylalkyl, heteroarylalkyl, heterocycloalkyl, heterocycloalkylalkyl, $(C_2-C_6)$alkenyl or $(C_2-C_6)$alkynyl.

9. A compound according to claim 1, wherein R11 and R12 independently represents hydrogen, methyl, ethyl, isopropyl, phenyl, benzyl, cyclohexyl, indanyl, tetralinyl, phenylethyl, cyclopropylmethyl, pyrazolyl, isoxazolylmethyl, cyclopentyl, cyclopropyl, pyridyl, piperidyl, tetrahydropyranylmethyl, tetrahydropyranyl, cyclobutyl, allyl, propynyl or thiazolyl.

10. A compound according to claim 1, wherein R13 represents $(C_1-C_4)$alkyl, cyano, halogen, =O, —ORa or —COORf.

11. A compound according to claim 10, wherein R13 represents methyl, cyano, F, =O, —OCH$_3$ or —COOC(CH$_3$)$_3$.

12. A compound according to claim 1, wherein R11 or R12 independently represent hydrogen.

13. A compound according to claim 1 said compound being selected from the group consisting of:
Ingenol 3-(1S-camphanate),
Ingenol 3-(N-ethyl-carbamate),
Ingenol 3-(N,N-dimethyl-carbamate),
Ingenol 3-(morpholine-4-carboxylate),
Ingenol 3-(pyrrolidine-1-carboxylate),
Ingenol 3-(N-methyl-N-phenyl-carbamate),
Ingenol 3-(N,N-diethyl-carbamate),
Ingenol 3-(piperidine-1-carboxylate),
Ingenol 3-(N-benzyl-N-methyl-carbamate),
Ingenol 3-(N-cyclohexyl-N-methyl-carbamate),
Ingenol 3-(N-cyclohexyl-carbamate),
Ingenol 3-(N-phenyl-carbamate),
Ingenol 3-(N-(indan-1-yl)-carbamate),
Ingenol 3-(3,3-dimethyl-piperidine-1-carboxylate),
Ingenol 3-(N-Methyl-N-tetralin-1-yl-carbamate),
Ingenol 3-(N-(2-cyano-1-methyl-ethyl)-N-methyl-carbamate),
Ingenol 3-(N-methyl-N-((S)-1-phenethyl)-carbamate),
Ingenol 3-(N-methyl-N-(cyclopropylmethyl)-carbamate,
Ingenol 3-(N-(3-fluoro-phenyl)-N-methyl-carbamate),
Ingenol 3-(N-(2,5-dimethylpyrazol-3-yl)-N-methyl-carbamate),
Ingenol 3-(1-tert-butyloxycarbonyl-3,3-dimethylpyrrolidine-2-carboxylate),
Ingenol 3-((2S)-1-phenylpyrrolidine-2-carboxylate),
Ingenol 3-(2-methyl-3-oxo-4-oxaspiro[4.5]dec-1-ene-1-carboxylate),
Ingenol 3-(4-methyl-2-oxo-3H-thiazole-5-carboxylate),
Ingenol 3-(N-(3,5-dimethylisoxazol-4-yl)-N-methyl-carbamate),
Ingenol 3-(N-(1,5-dimethylpyrazol-3-yl)-N-methyl-carbamate),
Ingenol 3-(N-cyclopentyl-N-methyl-carbamate),
Ingenol 3-(N-cyclopropyl-N-methyl-carbamate),
Ingenol 3-(N-methyl-N-(2-pyridyl)-carbamate),
Ingenol 3-(4-oxo-2,3-dihydroquinoline-1-carboxylate),
Ingenol 3-(3,4-dihydro-2H-quinoline-1-carboxylate),
Ingenol 3-(indoline-1-carboxylate),
Ingenol 3-(azepane-1-carboxylate),
Ingenol 3-(N-(4-chloro-phenyl)-N-methyl-carbamate),
Ingenol 3-(N-(4-fluoro-phenyl)-N-methyl-carbamate),
Ingenol 3-(N-methyl-N-(2-methoxy-phenyl)-carbamate),
Ingenol 3-(N-methyl-N-(2-methyl-phenyl)-carbamate),
Ingenol 3-(3-oxo-2,4-dihydroquinoxaline-1-carboxylate),
Ingenol 3-(N-ethyl-N-phenyl-carbamate),
Ingenol 3-(2-trifluoromethyl-pyrrolidine-1-carboxylate),
Ingenol 3-(3-azabicyclo[3.2.2]nonane-3-carboxylate),
Ingenol 3-(2,3-dihydro-1,4-benzoxazine-4-carboxylate),
Ingenol 3-(N-(2-fluoro-phenyl)-N-methyl-carbamate),
Ingenol 3-(3-methyl-2,3-dihydro-1,4-benzoxazine-4-carboxylate),
Ingenol 3-(2-trifluoromethyl-pyrrolidine-1-carboxylate) (ISOMER A),
Ingenol 3-(2-trifluoromethyl-pyrrolidine-1-carboxylate) (ISOMER B),
Ingenol 3-(N-methyl-N-(N-(tert-butyloxycarbonyl)-4-piperidyl)-carbamate),
Ingenol 3-(N-methyl-N-(3-methyl-phenyl)-carbamate),
Ingenol 3-(3,4-dihydro-2H-quinoxaline-1-carboxylate),
Ingenol 3-(isoindoline-2-carboxylate),
Ingenol 3-(N-methyl-N-(tetrahydropyran-4-ylmethyl)-carbamate),
Ingenol 3-(N-methyl-N-(tetrahydropyran-4-yl)-carbamate),
Ingenol 3-(N-methyl-N-(3-methoxy-phenyl)-carbamate),
Ingenol 3-(N-cyclobutyl-N-methyl-carbamate),
Ingenol 3-(N-allyl-N-methyl-carbamate),
Ingenol 3-(N-methyl-N-prop-2-ynyl-carbamate),
Ingenol 3-(N-methyl-N-(4-methylthiazol-2-yl)-carbamate) or
Ingenol 3-(N-(4-cyano-phenyl)-N-methyl-carbamate).

14. A pharmaceutical composition comprising a compound according to claim 1 or a pharmaceutically acceptable stereoisomer, or salt thereof together with a pharmaceutically acceptable vehicle or excipient.

15. A pharmaceutical composition according to claim 14, wherein the composition is suitable for topical administration.

16. A pharmaceutical composition comprising a compound according to claim 1 or a pharmaceutically acceptable stereoisomer or salt thereof in combination with one or more other therapeutically active agents.

17. The compound Ingenol 3-(N-methyl-N-phenyl-carbamate).

18. The compound Ingenol 3-(N-(3-fluoro-phenyl)-N-methyl-carbamate).

19. The compound Ingenol 3-(pyrrolidine-1-carboxylate).

20. The compound Ingenol 3-(indoline-1-carboxylate).

* * * * *